(12) United States Patent
Ladner

(10) Patent No.: US 8,466,091 B2
(45) Date of Patent: *Jun. 18, 2013

(54) FOCUSED LIBRARIES OF GENETIC PACKAGES

(75) Inventor: Robert Charles Ladner, Ijamsville, MD (US)

(73) Assignee: Dyax Corp., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/161,445

(22) Filed: Jun. 15, 2011

(65) Prior Publication Data

US 2012/0028841 A1    Feb. 2, 2012

Related U.S. Application Data

(63) Continuation of application No. 12/762,051, filed on Apr. 16, 2010, which is a continuation of application No. 11/416,460, filed on May 1, 2006, now abandoned, which is a continuation of application No. 10/026,925, filed on Dec. 18, 2001, now abandoned.

(60) Provisional application No. 60/256,380, filed on Dec. 18, 2000.

(51) Int. Cl.
*C40B 40/02* (2006.01)

(52) U.S. Cl.
USPC .................................................. 506/14

(58) Field of Classification Search
None
See application file for complete search history.

(56) References Cited

U.S. PATENT DOCUMENTS

| | | |
|---|---|---|
| 5,118,605 A | 6/1992 | Urdea |
| 5,223,409 A | 6/1993 | Ladner et al. |
| 5,380,833 A | 1/1995 | Urdea |
| 5,565,332 A | 10/1996 | Hoogenboom et al. |
| 5,618,920 A | 4/1997 | Robinson et al. |
| 5,658,727 A | 8/1997 | Barbas et al. |
| 5,688,666 A | 11/1997 | Bass et al. |
| 5,723,323 A | 3/1998 | Kauffman et al. |
| 5,733,743 A | 3/1998 | Johnson et al. |
| 5,739,281 A | 4/1998 | Thøgersen et al. |
| 5,750,373 A | 5/1998 | Garrard et al. |
| 5,780,279 A | 7/1998 | Matthews et al. |
| 5,798,208 A | 8/1998 | Crea |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,830,663 A | 11/1998 | Embleton et al. |
| 5,837,242 A | 11/1998 | Holliger et al. |
| 5,840,479 A | 11/1998 | Little et al. |
| 5,846,765 A | 12/1998 | Matthews et al. |
| 5,858,657 A | 1/1999 | Winter et al. |
| 5,858,671 A | 1/1999 | Jones |
| 5,871,907 A | 2/1999 | Winter et al. |
| 5,872,215 A | 2/1999 | Osbourne et al. |
| 5,885,793 A | 3/1999 | Griffiths et al. |
| 5,917,018 A | 6/1999 | Thøgersen et al. |
| 5,935,831 A | 8/1999 | Quax et al. |
| 5,962,255 A | 10/1999 | Griffiths et al. |
| 5,969,108 A | 10/1999 | McCafferty et al. |
| 5,976,862 A | 11/1999 | Kauffman et al. |
| 5,994,519 A | 11/1999 | Osbourn et al. |
| 6,010,884 A | 1/2000 | Griffiths et al. |
| 6,017,732 A | 1/2000 | Jespers et al. |
| 6,040,136 A | 3/2000 | Garrard et al. |
| 6,057,098 A | 5/2000 | Buechler et al. |
| 6,140,471 A | 10/2000 | Johnson et al. |
| 6,172,197 B1 | 1/2001 | McCafferty et al. |
| 6,180,336 B1 | 1/2001 | Osbourn et al. |
| 6,225,447 B1 | 5/2001 | Winter et al. |
| 6,248,516 B1 | 6/2001 | Winter et al. |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,291,650 B1 | 9/2001 | Winter et al. |
| 6,300,064 B1 | 10/2001 | Knappik et al. |
| 6,319,690 B1 | 11/2001 | Little et al. |
| 6,342,588 B1 | 1/2002 | Osbourn et al. |
| 6,420,113 B1 | 7/2002 | Buechler et al. |
| 6,489,123 B2 | 12/2002 | Osbourn et al. |
| 6,492,107 B1 | 12/2002 | Kauffman et al. |
| 6,492,123 B1 | 12/2002 | Holliger et al. |
| 6,492,160 B1 | 12/2002 | Griffiths et al. |
| 6,521,404 B1 | 2/2003 | Griffiths et al. |
| 6,531,580 B1 | 3/2003 | Huse et al. |
| 6,544,731 B1 | 4/2003 | Griffiths et al. |
| 6,545,142 B1 | 4/2003 | Winter et al. |
| 6,555,313 B1 | 4/2003 | Griffiths et al. |
| 6,569,641 B1 | 5/2003 | Kauffman et al. |
| 6,582,915 B1 | 6/2003 | Griffiths et al. |
| 6,589,527 B1 | 7/2003 | Winter et al. |
| 6,593,081 B1 | 7/2003 | Griffiths et al. |
| 6,680,192 B1 | 1/2004 | Lerner et al. |

(Continued)

FOREIGN PATENT DOCUMENTS

| | | |
|---|---|---|
| DE | 19624562 A1 | 1/1998 |
| WO | WO-92/01047 A1 | 1/1992 |

(Continued)

OTHER PUBLICATIONS

Brezinschek et al. (May 1997) Journal of Clinical Investigation vol. 99 pp. 2488 to 2501.*

(Continued)

*Primary Examiner* — Ardin Marschel
*Assistant Examiner* — Christian Boesen
(74) *Attorney, Agent, or Firm* — Wolf, Greenfield & Sacks, P.C.

(57) ABSTRACT

Focused libraries of vectors or genetic packages that display, display and express, or comprise a member of a diverse family of antibody peptides, polypeptides or proteins and collectively display, display and express, or comprise at least a portion of the focused diversity of the family. The libraries have length and sequence diversities that mimic that found in native human antibodies.

22 Claims, No Drawings

U.S. PATENT DOCUMENTS

| | | |
|---|---|---|
| 6,696,245 B2 | 2/2004 | Winter et al. |
| 6,696,248 B1 | 2/2004 | Knappik et al. |
| 6,706,484 B1 | 3/2004 | Knappik et al. |
| 6,753,136 B2 | 6/2004 | Lohning |
| 6,806,079 B1 | 10/2004 | McCafferty et al. |
| 6,828,422 B1 | 12/2004 | Achim et al. |
| 6,846,634 B1 | 1/2005 | Tomlinson et al. |
| 6,916,605 B1 | 7/2005 | McCafferty et al. |
| 6,969,586 B1 | 11/2005 | Lerner et al. |
| 7,063,943 B1 | 6/2006 | McCafferty et al. |
| 7,189,841 B2 | 3/2007 | Lerner et al. |
| 2001/0008759 A1 | 7/2001 | Marks et al. |
| 2002/0004215 A1 | 1/2002 | Osbourn et al. |
| 2002/0016445 A1 | 2/2002 | Persson et al. |
| 2003/0044772 A1 | 3/2003 | Watkins et al. |
| 2003/0114659 A1 | 6/2003 | Winter et al. |
| 2003/0130496 A1 | 7/2003 | Winter et al. |
| 2003/0148372 A1 | 8/2003 | Tomlinson et al. |
| 2003/0190674 A1 | 10/2003 | Griffiths et al. |
| 2003/0232333 A1 | 12/2003 | Ladner et al. |
| 2003/0232395 A1 | 12/2003 | Hufton |
| 2004/0038921 A1 | 2/2004 | Kreutzer et al. |
| 2004/0110941 A2 | 6/2004 | Winter et al. |
| 2004/0157214 A1 | 8/2004 | McCafferty et al. |
| 2004/0157215 A1 | 8/2004 | McCafferty et al. |
| 2005/0202512 A1 | 9/2005 | Tomlinson et al. |
| 2006/0003334 A1 | 1/2006 | Achim et al. |
| 2006/0019260 A1 | 1/2006 | Lerner et al. |
| 2006/0166252 A1 | 7/2006 | Ladner et al. |
| 2006/0257937 A1 | 11/2006 | Ladner |
| 2007/0031879 A1 | 2/2007 | Ley et al. |
| 2009/0181855 A1 | 7/2009 | Vasquez et al. |
| 2010/0292103 A1 | 11/2010 | Ladner |

FOREIGN PATENT DOCUMENTS

| | | |
|---|---|---|
| WO | WO-94/07922 A1 | 4/1994 |
| WO | WO-97/08320 A1 | 3/1997 |
| WO | WO-97/20923 A1 | 6/1997 |
| WO | WO-97/49809 A1 | 12/1997 |
| WO | WO-99/06834 A2 | 2/1999 |
| WO | WO-99/20749 A1 | 4/1999 |
| WO | WO-99/36569 A1 | 7/1999 |
| WO | WO-99/55367 A1 | 11/1999 |
| WO | WO-00/18905 A1 | 4/2000 |
| WO | WO-01/79481 A2 | 10/2001 |
| WO | WO-02/02641 A1 | 1/2002 |

OTHER PUBLICATIONS

Guo et al. (Jul. 1, 1999) Clinical and Experimental Immunology vol. 117 pp. 19 to 29.*

Bahler et al., Clonal salivary gland infiltrates associated with myoepithelial sialadenitis (Sjögren's syndrome) begin as nonmalignant antigen-selected expansions. Blood. Mar. 15, 1998;91(6):1864-72.

Bakkus et al., Evidence that multiple myeloma Ig heavy chain VDJ genes contain somatic mutations but show no intraclonal variation. Blood. Nov. 1, 1992;80(9):2326-35.

Barbas et al., Molecular profile of an antibody response to HIV-1 as probed by combinatorial libraries. J Mol Biol. Apr. 5, 1993;230(3):812-23.

Boder et al., Directed evolution of antibody fragments with monovalent femtomolar antigen-binding affinity. Proc Natl Acad Sci U S A. Sep. 26, 2000;97(20):10701-5.

Carroll et al., Absence of Ig V region gene somatic hypermutation in advanced Burkitt's lymphoma. J Immunol. Jul. 15, 1989;143(2):692-8.

Davi et al., High frequency of somatic mutations in the VH genes expressed in prolymphocytic leukemia. Blood. Nov. 15, 1996;88(10):3953-61.

Dipietro et al., Limited number of immunoglobulin VH regions expressed in the mutant rabbit "Alicia". Eur J Immunol. Jun. 1990;20(6):1401-4.

Esposito et al., Phage display of a human antibody against *Clostridium tetani* toxin. Gene. Oct. 11, 1994;148(1):167-8.

Huang et al., A majority of Ig H chain cDNA of normal human adult blood lymphocytes resembles cDNA for fetal Ig and natural autoantibodies. J Immunol. Nov. 15, 1993;151(10):5290-300.

Ivanovski et al., Somatic hypermutation, clonal diversity, and preferential expression of the VH 51p1/VL kv325 immunoglobulin gene combination in hepatitis C virus-associated immunocytomas. Blood. Apr. 1, 1998;91(7):2433-42.

Lieber et al., Lymphoid V(D)J recombination: nucleotide insertion at signal joints as well as coding joints. Proc Natl Acad Sci U S A. Nov. 1988;85(22):8588-92.

Lieber, Site-specific recombination in the immune system. FASEB J. Nov. 1991;5(14):2934-44.

Liu et al., Normal human IgD+IgM− germinal center B cells can express up to 80 mutations in the variable region of their IgD transcripts. Immunity. Jun. 1996;4(6):603-13.

Matolcsy et al., Molecular characterization of IgA− and/or IgG-switched chronic lymphocytic leukemia B cells. Blood. Mar. 1, 1997;89(5):1732-9.

McCafferty et al., Phage antibodies: filamentous phage displaying antibody variable domains. Nature. Dec. 6, 1990;348(6301):552-4.

McIntosh et al., Analysis of immunoglobulin G kappa antithyroid peroxidase antibodies from different tissues in Hashimoto's thyroiditis. J Clin Endocrinol Metab. Nov. 1997;82(11):3818-25.

Mouquet et al., Enhanced HIV-1 neutralization by antibody heteroligation. Proc Natl Acad Sci U S A. Jan. 17, 2012;109(3):875-80. Epub Jan. 4, 2012. (With Supporting Information).

Patrick et al., User-friendly algorithms for estimating completeness and diversity in randomized protein-encoding libraries. Protein Eng. Jun. 2003;16(6):451-7.

Sahota et al., Ig VH gene mutational patterns indicate different tumor cell status in human myeloma and monoclonal gammopathy of undetermined significance. Blood. Jan. 15, 1996;87(2):746-55.

Shimoda et al., Natural polyreactive immunoglobulin A antibodies produced in mouse Peyer's patches. Immunology. May 1999;97(1):9-17.

Welschof et al., Amino acid sequence based PCR primers for amplification of rearranged human heavy and light chain immunoglobulin variable region genes. J Immunol Methods. Feb. 27, 1995;179(2):203-14.

Wen et al., T cells recognize the VH complementarity-determining region 3 of the idiotypic protein of B cell non-Hodgkin's lymphoma. Eur J Immunol. Apr. 1997;27(4):1043-7.

Winkler et al., Analysis of immunoglobulin variable region genes from human IgG anti-DNA hybridomas. Eur J Immunol. Jul. 1992;22(7):1719-28.

Winter, Synthetic human antibodies and a strategy for protein engineering. FEBS Lett. Jun. 23, 1998;430(1-2):92-4.

Zeng et al., CD146, an epithelial-mesenchymal transition inducer, is associated with triple-negative breast cancer. Proc Natl Acad Sci U S A. Jan. 24, 2012;109(4):1127-32. Epub Dec. 30, 2011. (With Supporting Information).

Cook et al., The human immunoglobulin VH repertoire. Immunol Today. May 1995;16(5):237-42.

De Wildt et al., Antibody arrays for high-throughput screening of antibody-antigen interactions. Nat Biotechnol. Sep. 2000;18(9):989-94.

De Wildt et al., Characterization of human variable domain antibody fragments against the U1 RNA-associated A protein, selected from a synthetic and patient-derived combinatorial V gene library. Eur J Immunol. Mar. 1996;26(3):629-39.

De Wildt et al., Heavy chain CDR3 optimization of a germline encoded recombinant antibody fragment predisposed to bind the U1A protein. Protein Eng. Jul. 1997;10(7):835-41.

Ge, Upa, a universal protein array system for quantitative detection of protein-protein, protein-DNA, protein-RNA and protein-ligand interactions. Nucleic Acids Res. Jan. 15, 2000;28(2):e3.

Hoogenboom et al., Natural and designer binding sites made by phage display technology. Immunol Today. Aug. 2000;21(8):371-8.

Hughes-Jones et al., Synthesis of Rh Fv phage-antibodies using VH and VL germline genes. Br J Haematol. Jun. 1999;105(3):811-6.

Leclerc et al., Selection and characterization of single chain Fv fragments against murine recombinant prion protein from a synthetic human antibody phage display library. Hum Antibodies. 2000;9(4):207-14.

Leung et al., A method for random mutagenesis of a defined DNA segment using a modified polymerase chain reaction. Technique. Aug. 1989;1(1):11-5.

Lueking et al., Protein microarrays for gene expression and antibody screening. Anal Biochem, May 15, 1999;270(1):103-11.

Macbeath et al., Printing proteins as microarrays for high-throughput function determination. Science. Sep. 8, 2000;289(5485):1760-3.

Mattheakis et al., An in vitro polysome display system for identifying ligands from very large peptide libraries. Proc Natl Acad Sci USA. Sep. 13, 1994;91(19):9022-6.

Nissim et al., Antibody fragments from a 'single pot' phage display library as immunochemical reagents. EMBO J. Feb. 1, 1994;13(3):692-8.

Reidhaar-Olson et al., Random mutagenesis of protein sequences using oligonucleotide cassettes. Methods Enzymol, 1991;208:564-86.

Sjölander et al., Integrated fluid handling system for biomolecular interaction analysis. Anal Chem. Oct. 15, 1991;63(20)2338-45.

Stemmer, Rapid evolution of a protein in vitro by DNA shuffling. Nature. Aug. 4, 1994;370(6488):389-91.

Szabo et al., Surface plasmon resonance and its use in biomolecular interaction analysis (BIA). Curr Opin Struct Biol. Oct. 1995;5(5):699-705.

Van Den Brink et al., Human antibodies with specificity for the C2 domain of factor VIII are derived from VH1 germline genes. Blood. Jan. 15, 2000;95(2):558-63.

Vaughan et al., Human antibodies with sub-nanomolar affinities isolated from a large non-immunized phage display library. Nat Biotechnol. Mar. 1996;14(3):309-14.

Zoller et al., Oligonucleotide-directed mutagenesis using M13-derived vectors: an efficient and general procedure for the production of point mutations in any fragment of DNA. Nucleic Acids Res. Oct. 25, 1982;10(20):6487-500.

Abbas et al., Cellular and Molecular Immunology. 4th Ed. W.B. Saunders Company. 2000:p. 133.

Akamatsu et al., Construction of a human Ig combinatorial library from genomic V segments and synthetic CDR3 fragments. J Immunol. Nov. 1, 1993;151(9):4651-9.

Alt et al., Joining of immunoglobulin heavy chain gene segments: implications from a chromosome with evidence of three D-JH fusions. Proc Natl Acad Sci U S A. Jul. 1982;79(13):4118-22.

Alves et al., Accuracy of the EcoRV restriction endonuclease: binding and cleavage studies with oligodeoxynucleotide substrates containing degenerate recognition sequences. Biochemistry. Sep. 5, 1995;34(35):11191-7.

Arden, Conserved motifs in T-cell receptor CDR1 and CDR2: implications for ligand and CD8 co-receptor binding. Curr Opin Immunol. Feb. 1998;10(1):74-81.

Aujame et al., High affinity human antibodies by phage display. Hum Antibodies. 1997;8(4):155-68.

Balint et al., Antibody engineering by parsimonious mutagenesis. Gene. Dec. 27, 1993;137(1):109-18.

Barbas et al., Assembly of combinatorial antibody libraries on phage surfaces: the gene III site. Proc Natl Acad Sci U S A. Sep. 15, 1991;88(18):7978-82.

Barbas et al., Human autoantibody recognition of DNA. Proc Natl Acad Sci U S A. Mar. 28, 1995;92(7):2529-33.

Barbas et al., Semisynthetic combinatorial antibody libraries: a chemical solution to the diversity problem. Proc Natl Acad Sci U S A. May 15, 1992;89(10):4457-61.

Basu et al., Synthesis of compositionally unique DNA by terminal deoxynucleotidyl transferase. Biochem Biophys Res Commun. Mar. 29, 1983;111(3):1105-12.

Blakesley et al., Duplex regions in "single-stranded" phiX174 DNA are cleaved by a restriction endonuclease from *Haemophilus aegyptius*. J Biol Chem. Oct. 25, 1977;252(20):7300-6.

Boder et al., Optimal screening of surface-displayed polypeptide libraries. Biotechnol Prog. Jan.-Feb. 1998;14(1):55-62.

Brezinschek et al., Analysis of the human VH gene repertoire. Differential effects of selection and somatic hypermutation on human peripheral CD5(+)/IgM+ and CD5(-/IgM+ B cells. J Clin Invest. May 15, 1997;99(10):2488-501.

Chang et al., A general method for facilitating heterodimeric pairing between two proteins: application to expression of alpha and beta T-cell receptor extracellular segments. Proc Natl Acad Sci USA. Nov. 22, 1994;91(24):11408-12.

Chothia et al., Canonical structures for the hypervariable regions of immunoglobulins. J Mol Biol. Aug. 20, 1987;196(4):901-17.

Chothia et al., Conformations of immunoglobulin hypervariable regions. Nature. Dec. 21-28, 1989;342(6252):877-83.

Chothia et al., Structural repertoire of the human VH segments. J Mol Biol. Oct. 5, 1992;227(3):799-817.

Clackson et al., In vitro selection from protein and peptide libraries. Trends Biotechnol. May 1994;12(5):173-84.

Corbett et al., Sequence of the human immunoglobulin diversity (D) segment locus: a systematic analysis provides no evidence for the use of DIR segments, inverted D segments, "minor" D segments or D-D recombination. J Mol Biol. Jul. 5, 1997;270(4):587-97.

Courtney et al., A phage display vector with improved stability, applicability and ease of manipulation. Gene. Nov. 7, 1995;165(1):139-40.

Crameri et al., Cloning *Aspergillus fumigatus* allergens by the pJuFo filamentous phage display system. Int Arch Allergy Immunol. May 1996;110(1):41-5.

Crameri et al., Display of biologically active proteins on the surface of filamentous phages: a cDNA cloning system for selection of functional gene products linked to the genetic information responsible for their production. Gene. Dec. 27, 1993;137(1):69-75.

Cwirla et al., Peptides on phage: a vast library of peptides for identifying ligands. Proc Natl Acad Sci U S A. Aug. 1990;87(16):6378-82.

Davies et al., Affinity improvement of single antibody VH domains: residues in all three hypervariable regions affect antigen binding. Immunotechnology. Sep. 1996;2(3):169-79.

De Haard et al., A large non-immunized human Fab fragment phage library that permits rapid isolation and kinetic analysis of high affinity antibodies. J Biol Chem. Jun. 25, 1999;274(26):18218-30.

De Kruif et al., Selection and application of human single chain Fv antibody fragments from a semi-synthetic phage antibody display library with designed CDR3 regions. J Mol Biol. Apr. 21, 1995;248(1):97-105.

Extended European Search Report dated May 26, 2010 for European Application No. 10156326.0.

Fan et al., Three-dimensional structure of an Fv from a human IgM immunoglobulin. J Mol Biol. Nov. 5, 1992;228(1):188-207.

Feldhaus et al., Oligonucleotide-conjugated beads for transdominant genetic experiments. Nucleic Acids Res. Jan. 15, 2000;28(2):534-43.

Fields et al., The two-hybrid system: an assay for protein-protein interactions. Trends Genet. Aug. 1994;10(8):286-92.

Gietz et al., Improved method for high efficiency transformation of intact yeast cells. Nucleic Acids Res. Mar. 25, 1992;20(6):1425.

Gilfillan et al., Efficient immune responses in mice lacking N-region diversity. Eur J Immunol. Nov. 1995;25(11):3115-22.

Griffiths et al., Human anti-self antibodies with high specificity from phage display libraries. EMBO J. Feb. 1993;12(2):725-34.

Griffiths et al., Isolation of high affinity human antibodies directly from large synthetic repertoires. EMBO J. Jul. 15, 1994;13(14):3245-60.

Grimes et al., Achilles' heel cleavage: creation of rare restriction sites in lambda phage genomes and evaluation of additional operators, repressors and restriction/modification systems. Gene. May 31, 1990;90(1):1-7.

Gushiken et al., Polymorphism of beta2-glycoprotein I at codons 306 and 316 in patients with systemic lupus erythematosus and antiphospholipid syndrome. Arthritis Rheum. Jun. 1999;42(6):1189-93.

Hanes et al., Picomolar affinity antibodies from a fully synthetic naive library selected and evolved by ribosome display. Nat Biotechnol. Dec. 2000;18(12):1287-92.

Hasan et al., Control of cloned gene expression by promoter inversion in vivo: construction of improved vectors with a multiple cloning site and the Ptac promoter. Gene. 1987;56(1):145-51.

Heddle et al., Dog immunoglobulins. I. immunochemical characterization of dog serum, parotid saliva, colostrum, milk and small bowel fluid. Immunology. Jul. 1975;29(1):185-95.

Hoet et al., Generation of high-affinity human antibodies by combining donor-derived and synthetic complementarity-determining-region diversity. Nat Biotechnol. Mar. 2005;23(3):344-8. Epub Feb. 20, 2005.

Hoet et al., The importance of the light chain for the epitope specificity of human anti-U1 small nuclear RNA autoantibodies present in systemic lupus erythematosus patients. J Immunol. Sep. 15, 1999;163(6):3304-12.

Hoogenboom et al., Antibody phage display technology and its applications. Immunotechnology. Jun. 1998;4(1):1-20.

Hoogenboom et al., By-passing immunisation. Human antibodies from synthetic repertoires of germline VH gene segments rearranged in vitro. J Mol Biol. Sep. 20, 1992;227(2):381-8.

Hoogenboom et al., Designing and optimizing library selection strategies for generating high-affinity antibodies. Trends Biotechnol. Feb. 1997;15(2):62-70.

Hoogenboom et al., Multi-subunit proteins on the surface of filamentous phage: methodologies for displaying antibody (Fab) heavy and light chains. Nucleic Acids Res. Aug. 11, 1991;19(15):4133-7.

Horwitz et al., Secretion of functional antibody and Fab fragment from yeast cells. Proc Natl Acad Sci U S A. Nov. 1988;85(22):8678-82.

Hrncír et al., [Anticardiolipin antibodies in diffuse connective tissue diseases with IgG, IgM and IgA isotypes]. Vnitr Lek. Nov. 1990;36(11):1041-9. Czech. Translation (provided by USPTO).

Jirholt et al., Exploiting sequence space: shuffling in vivo formed complementarity determining regions into a master framework. Gene. Jul. 30, 1998;215(2):471-6.

Juul et al., The normally expressed kappa immunoglobulin light chain gene repertoire and somatic mutations studied by single-sided specific polymerase chain reaction (PCR); frequent occurrence of features often assigned to autoimmunity. Clin Exp Immunol. Jul. 1997;109(1):194-203.

Kaczorowski et al., Genomic DNA sequencing by SPEL-6 primer walking using hexamer ligation. Gene. Nov. 26, 1998;223(1-2):83-91.

Kieke et al., Isolation of anti-T cell receptor scFv mutants by yeast surface display. Protein Eng. Nov. 1997;10(11):1303-10.

Kieke et al., Selection of functional T cell receptor mutants from a yeast surface-display library. . Proc Natl Acad Sci U S A. May 11, 1999;96(10):5651-6.

Kim et al., Cleaving DNA at any predetermined site with adapter-primers and class-IIS restriction enzymes. Science. Apr. 22, 1988;240(4851):504-6.

Kim et al., Structural requirements for FokI-DNA interaction and oligodeoxyribonucleotide-instructed cleavage. J Mol Biol. May 17, 1996;258(4):638-49.

Klein et al., Expressed human immunoglobulin kappa genes and their hypermutation. Eur J Immunol. Dec. 1993;23(12):3248-62.

Knappik et al., Fully synthetic human combinatorial antibody libraries (HuCAL) based on modular consensus frameworks and CDRs randomized with trinucleotides. J Mol Biol. Feb. 11, 2000;296(1):57-86.

Koiwai et al., Isolation and characterization of bovine and mouse terminal deoxynucleotidyltransferase cDNAs expressible in mammalian cells. Nucleic Acids Res. Jul. 25, 1986;14(14):5777-92.

Koob et al., Cleaving yeast and *Escherichia coli* genomes at a single site. Science. Oct. 12, 1990;250(4978):271-3.

Koob et al., Conferring new specificity upon restriction endonucleases by combining repressor-operator interaction and methylation. Gene. Dec. 25, 1988;74(1) 165-7.

Koob et al., Conferring operator specificity on restriction endonucleases. Science. Aug. 26, 1988;241(4869):1084-6.

Koob et al., RecA-AC: single-site cleavage of plasmids and chromosomes at any predetermined restriction site. Nucleic Acids Res. Nov. 11, 1992;20(21):5831-6.

Kur et al., A novel method for converting common restriction enzymes into rare cutters: integration host factor-mediated Achilles' cleavage (IHF-AC). Gene. Jan. 2, 1992;110(1):1-7.

Liu et al., Rapid construction of recombinant DNA by the univector plasmid-fusion system. Methods Enzymol. 2000;328:530-49.

Lowman et al., Affinity maturation of human growth hormone by monovalent phage display. J Mol Biol. Dec. 5, 1993;234(3):564-78.

MacCallum et al., Antibody-antigen interactions: contact analysis and binding site topography. J Mol Biol. Oct. 11, 1996;262(5):732-45.

Marks et al., By-passing immunization. Human antibodies from V-gene libraries displayed on phage. J Mol Biol. Dec. 5, 1991;222(3):581-97.

Martin et al., Structural families in loops of homologous proteins: automatic classification, modelling and application to antibodies. J Mol Biol. Nov. 15, 1996;263(5):800-15.

Martin, Accessing the Kabat antibody sequence database by computer. Proteins. May 1996;25(1):130-3.

Matsuda et al., The complete nucleotide sequence of the human immunoglobulin heavy chain variable region locus. J Exp Med. Dec. 7, 1998;188(11):2151-62.

Mattila et al., Extensive allelic sequence variation in the J region of the human immunoglobulin heavy chain gene locus. Eur J Immunol. Sep. 1995;25(9):2578-82.

Moll et al., Designed heterodimerizing leucine zippers with a ranger of pIs and stabilities up to 10(-15) M. Protein Sci. Mar. 2001;10(3):649-55.

Nishigaki et al., Type II restriction endonucleases cleave single-stranded DNAs in general. Nucleic Acids Res. Aug. 26, 1985;13(16):5747-60.

Ornstein et al., An optimized potential function for the calculation of nucleic acid interaction energies. Biopolymers. 1978;17:2341-60.

Pearson et al., Construction of PCR-ligated long flanking homology cassettes for use in the functional analysis of six unknown open reading frames from the left and right arms of *Saccharomyces cerevisiae* chromosome XV. Yeast. Mar. 15, 1998;14(4):391-9.

Phizicky et al., Protein-protein interactions: methods for detection and analysis. Microbiol Rev. Mar. 1995;59(1):94-123.

Pini et al., Design and use of a phage display library. Human antibodies with subnanomolar affinity against a marker of angiogenesis eluted from a two-dimensional gel. J Biol Chem. Aug. 21, 1998;273(34):21769-76.

Podhajska et al., Conferring new specificities on restriction enzymes: cleavage at any predetermined site by combining adapter oligodeoxynucleotide and class-IIS enzyme. Methods Enzymol. 1992;216:303-9.

Podhajska et al., Conversion of the FokI endonuclease to a universal restriction enzyme: cleavage of phage M13mp7 DNA at predetermined sites. Gene. 1985;40(2-3):175-82.

Powell et al., Construction, assembly and selection of combinatorial antibody libraries. Genetic Engineering with PCR: vol. 5 in The Current Innovations in Molecular Biology series. Horton and Tait, Eds. Horizon Scientific Press. 1998:155-72.

Pu et al., Dimerization of leucine zippers analyzed by random selection. Nucleic Acids Res. Sep. 11, 1993;21(18):4348-55.

Pósfai et al., A simple method for locating methylated bases in DNA using class-IIS restriction enzymes. Gene. Dec. 25, 1988;74(1):179-81.

Qi et al., Restriction of single-stranded M13 DNA using synthetic oligonucleotides: the structural requirement of restriction enzymes. Biochem Cell Biol. Jan. 1987;65(1):50-5.

Roitt et al., Immunology 6th Edition. New York. Mosby. 2001:67-70, 80.

Ruiz et al., The human immunoglobulin heavy diversity (IGHD) and joining (IGHJ) segments. Exp Clin Immunogenet. 1999;16(3):173-84.

Ryu et al., Recent progress in biomolecular engineering. Biotechnol Prog. Jan.-Feb. 2000;16(1):2-16.

Saviranta et al., Engineering the steroid-specificity of an anti-17beta-estradiol Fab by random mutagenesis and competitive phage panning. Protein Eng. Feb. 1998;11(2):143-52.

Scaviner et al., Protein displays of the human immunoglobulin heavy, kappa and lambda variable and joining regions. Exp Clin Immunogenet. 1999;16(4):234-40.

Schoonbroodt et al., Oligonucleotide-assisted cleavage and ligation: a novel directional DNA cloning technology to capture cDNAs. Application in the construction of a human immune antibody phage-display library. Nucleic Acids Res. May 19, 2005;33(9):e81.

Schäble et al., The variable genes of the human immunoglobulin kappa locus. Biol Chem Hoppe Seyler. Nov. 1993;374(11):1001-22.

Seed, Developments in expression cloning. Curr Opin Biotechnol. Oct. 1995;6(5):567-73.

Sheets et al., Efficient construction of a large nonimmune phage antibody library: the production of high-affinity human single-chain antibodies to protein antigens. Proc Natl Acad Sci U S A. May 26, 1998;95(11):6157-62.

Short et al., Contribution of antibody heavy chain CDR1 to digoxin binding analyzed by random mutagenesis of phage-displayed Fab 26-10. J Biol Chem. Dec. 1, 1995;270(48):28541-50.

Smith et al., Phage Display. Chem Rev. Apr. 1, 1997;97(2):391-410.

Solderlind et al., The immune diversity in a test tube—non-immunised antibody libraries and functional variability in defined protein scaffolds. Comb Chem High Throughput Screen. Aug. 2001;4(5):409-16.

Stewart et al., High-frequency representation of a single VH gene in the expressed human B cell repertoire. J Exp Med. Feb. 1, 1993;177(2):409-18.

Suzuki et al., Light chain determines the binding property of human anti-dsDNA IgG autoantibodies. Biochem Biophy Res Commun. Apr. 29, 2000;271(1):240-3.

Szybalski et al., Class-IIS restriction enzymes—a review. Gene. Apr. 1991;100:13-26. Review.

Szybalski et al., Nobel prizes and restriction enzymes. Gene. Nov. 1978;4(3):181-2.

Szybalski, Reasons and risks to study restriction/modification enzymes form extreme thermophiles: chilly coldrooms, 13th sample, and 13-codon overlap. Gene. Mar. 1, 1992;112(1):1-2.

Szybalski, Universal restriction endonucleases: designing novel cleavage specificities by combining adapter oligodeoxynucleotide and enzyme moieties. Gene. 1985;40(2-3):169-73.

Söderlind et al., Domain libraries: synthetic diversity for de novo design of antibody V-regions. Gene. Jul. 28, 1995;160(2):269-72.

Thielking et al., Accuracy of the EcoRI restriction endonuclease: binding and cleavage studies with oligodeoxynucleotide substrates containing degenerate recognition sequences. Biochemistry. May 15, 1990;29(19):4682-91.

Tomlinson et al., The repertoire of human germline VH sequences reveals about fifty groups of VH segments with different hypervariable loops. J Mol Biol. Oct. 5, 1992;227(3):776-98.

Virnekäs et al., Trinucleotide phosphoramidites: ideal reagents for the synthesis of mixed oligonucleotides for random mutagenesis. Nucleic Acids Res. Dec. 25, 1994;22(25):5600-7.

Walhout et al., Gateway recombinational cloning: application to the cloning of large numbers of open reading frames or ORFeomes. Methods Enzymol. 2000;328:575-92.

Xu et al., Diversity in the CDR3 region of V(H) is sufficient for most antibody specificities. Immunity. Jul. 2000;13(1):37-45.

Yang et al., CDR walking mutagenesis for the affinity maturation of a potent human anti-HIV-1 antibody into the picomolar range. J Mol Biol. Dec. 1, 1995;254(3):392-403.

Zhu, Oligodeoxynucleotide-directed cleavage and repair of a single-stranded vector: a method of site-specific mutagenesis. Anal Biochem. Feb. 15, 1989;177(1):120-4.

Zucconi et al., Domain repertoires as a tool to derive protein recognition rules. FEBS Lett. Aug. 25, 2000;480(1):49-54.

* cited by examiner

FOCUSED LIBRARIES OF GENETIC PACKAGES

This application is a continuation of U.S. application Ser. No. 12/762,051, filed on Apr. 16, 2010, now published, which is a continuation of U.S. application Ser. No. 11/416,460, filed on May 1, 2006, now abandoned, which is a continuation of U.S. application Ser. No. 10/026,925, filed on Dec. 18, 2001, now abandoned, which claims the benefit under 35 USC §120 of U.S. provisional application 60/256,380, filed Dec. 18, 2000 the entire content of each of which is herein incorporated by reference. The provisional application and the Tables attached to it are specifically incorporated by reference herein.

The present invention relates to focused libraries of genetic packages that each display, display and express, or comprise a member of a diverse family of peptides, polypeptides or proteins and collectively display, display and express, or comprise at least a portion of the focused diversity of the family. The focused diversity of the libraries of this invention comprises both sequence diversity and length diversity. In a preferred embodiment, the focused diversity of the libraries of this invention is biased toward the natural diversity of the selected family. In more preferred embodiment, the libraries are biased toward the natural diversity of human antibodies and are characterized by variegation in their heavy chain and light chain complementarity determining regions ("CDRs").

The present invention further relates to vectors and genetic packages (e.g., cells, spores or viruses) for displaying, or displaying and expressing a focused diverse family of peptides, polypeptides or proteins. In a preferred embodiment the genetic packages are filamentous phage or phagemids or yeast. Again, the focused diversity of the family comprises diversity in sequence and diversity in length.

The present invention further relates to methods of screening the focused libraries of the invention and to the peptides, polypeptides and proteins identified by such screening.

BACKGROUND OF THE INVENTION

It is now common practice in the art to prepare libraries of genetic packages that individually display, display and express, or comprise a member of a diverse family of peptides, polypeptides or proteins and collectively display, display and express, or comprise at least a portion of the amino acid diversity of the family. In many common libraries, the peptides, polypeptides or proteins are related to antibodies (e.g., single chain Fv (scFv), Fv, Fab, whole antibodies or minibodies (i.e., dimers that consist of $V_H$ linked to $V_L$)). Often, they comprise one or more of the CDRs and framework regions of the heavy and light chains of human antibodies.

Peptide, polypeptide or protein libraries have been produced in several ways in the prior art. See e.g., Knappik et al., J. Mol. Biol., 296, pp. 57-86 (20004, which is incorporated herein by references. One method is to capture the diversity of native donors, either naive or immunized. Another way is to generate libraries having synthetic diversity. A third method is combination of the first two. Typically, the diversity produced by these methods is limited to sequence diversity, i.e., each member of the library differs from the other members of the family by having different amino acids or variegation at a given position in the peptide, polypeptide or protein chain. Naturally diverse peptides, polypeptides or proteins, however, are not limited to diversity only in their amino acid sequences. For example, human antibodies are not limited to sequence diversity in their amino acids, they are also diverse in the lengths of their amino acid chains.

For antibodies, diversity in length occurs, for example, during variable region rearrangements. See e.g., Corbett et al., J. Mol. Biol., 270, pp. 587-97 (1997). The joining of V genes to J genes, for example, results in the inclusion of a recognizable D segment in CDR3 in about half of the heavy chain antibody sequences, thus creating regions encoding varying lengths of amino-acids. The following also may occur during joining of antibody gene segments: (i) the end of the V gene may have zero to several base deleted or changed; (ii) the end of the D segment may have zero to many bases removed or changed; (iii) a number of random bases may be inserted between V and D or between D and J; and (iv) the 5' end of J may be edited to remove or to change several bases. These rearrangements result in antibodies that are diverse both in amino acid sequence and in length.

Libraries that contain only amino acid sequence diversity are, thus disadvantaged in that they do not reflect the natural diversity of the peptide, polypeptide or protein that the library is intended to mimic. Further, diversity in length may be important to the ultimate functioning of the protein, peptide or polypeptide. For example, with regard to a library comprising antibody regions, many of the peptides, polypeptides, proteins displayed, displayed and expressed, or comprised by the genetic packages of the library may not fold properly or their binding to an antigen may be disadvantaged, if diversity both in sequence and length are not represented in the library.

An additional disadvantage of prior art libraries of genetic packages that display, display and express, or comprise peptides, polypeptides and proteins is that they are not focused on those members that are based on natural occurring diversity and thus on members that are most likely to be functional. Rather, the prior art libraries, typically, attempt to include as much diversity or variegation at every amino acid residue as possible. This makes library construction time-consuming and less efficient than possible. The large number of members that are produced by trying to capture complete diversity also makes screening more cumbersome than it needs to be This is particularly true given that many members of the library will not be functional.

SUMMARY OF THE INVENTION

One objective of this invention is focused libraries of vectors or genetic packages that encode members of a diverse family of peptides, polypeptides or proteins wherein the libraries encode populations that are diverse in both length and sequence. The diverse length comprising components contain motifs that are likely to fold and function in the context of the parental peptide, polypeptide or protein.

Another object of this invention is focused libraries of genetic packages that display, display and express, or comprise a member of a diverse family of peptides, polypeptides and proteins and collectively display, display and express, or comprise at least a portion of the focused diversity of the family. These libraries are diverse not only in their amino acid sequences, but also in their lengths. And, their diversity is focused so as to more closely mimic or take into account the naturally-occurring diversity of the specific family that the library represents.

Another object of this invention is diverse, but focused, populations of DNA sequences encoding peptides, polypeptides or proteins suitable for display or display and expression using genetic packages (such as phage or phagemids) or other regimens that allow selection of specific binding components of a library.

A further object of this invention is focused libraries comprising the CDRs of human antibodies that are diverse in both their amino acid sequence and in their length (examples of such libraries include libraries of single chain Fv(scFv), Fv, Fab, whole antibodies or minibodies (i.e., dimers that consist of $V_H$ linked to $V_L$). Such regions may be from the heavy or light chains or both and may include one or, more of the CDRs of those chains. More preferably, they diversity or variegation occurs in all of the heavy chain and light chain CDRs.

It is another object of this invention to provide methods of making and screening the above libraries and the peptides, polypeptides and proteins obtained in such screening.

Among the preferred embodiments of this invention are the following:

1. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a heavy chain CDR1 selected from the group consisting of:
    (1) $<1>_1 Y_2 <1>_3 M_4 <1>_5$ (SEQ ID NO:100), wherein $<1>$ is an equimolar mixture of each of amino acid residues A, D, E, F, G, H, I, K, L, M, N, P, Q, R, S, T, V, W, and Y;
    (2) $(S/T)_1 (S/G/X)_2 (S/G/X)_3 Y_4 Y_5 W_6 (S/G/X)_7$ (SEQ ID NO:101) wherein (S/T) is a 1:1 mixture of S and T residues, (S/G/X) is a mixture of 0.2025 S, 0.2025 G and 0.035 of each of amino acid residues A, D, E, F, H, I, K, L, H, N, P, Q, R, T, V, W, and Y;
    (3) $V_1 S_2 G_3 G_4 S_5 I_6 S_7 <1>_8 <1>_9 <1>_{10} Y_{11} Y_{12} W_{13} <1>_{14}$ (SEQ ID NO:1), wherein $<1>$ is an equimolar mixture of each of amino acid residues A, D, E, F, G, H, I, K, L, M, N, P, Q, R, S, T, V, W, and Y; and
    (4) mixtures of vectors or genetic packages characterized by any of the above DNA sequences, preferably in the ratio: HC CDR1s (1):(2):(3)::0.80:0.17:0.02.

2. A focused library of vectors or genetic packages that display, display and express, or comprise a member of a diverse family of human antibody related peptides, polypeptides and proteins and collectively display, display and express or comprise at least a portion of the diversity of the antibody facility, the vectors or genetic packages being characterized by variegated DNA sequences that encode a heavy chain CDR2 selected from the group consisting of:
    (1) $<2>I<2><3>SGG<1>T<1>YADSVKG$ (SEQ ID NO:2), wherein $<1>$ is an equimolar mixture of each of amino acid residues $2^1 1$, 0, E, F, G, H, I, K, L, M, N, P, 0, P, S, T, V, W, and Y; $<2>$ is an equimolar mixture of each of amino acid residues Y, R, W, V, G, and S; and $<3>$ is an equimolar mixture of each of amino acid residues P, S, and G or an equimolar mixture of P and S;
    (2) $<1>I<4><1><1><G><5><1><1><1>YADSVKG$ (SEQ ID NO:3), wherein $<1>$ is an equimolar mixture of each of amino acid residues A, D, E, F, G, H, I, K, L, M, N, P, Q, R, S, T, V, W, and Y; $<4>$ is an equimolar mixture of residues D, I, N, S, W, Y; and $<5>$ is an equimolar mixture of residues S, G, D and N;
    (3) $<1>I<4><1><1>G<5><1><1>$ YNPSLKG (SEQ ID NO:4), wherein $<1>$ is an equimolar mixture of each of amino acid residues A, D, E, F, G, H, I, K, L, M, N; P, Q, R, S, T, V, W and Y, and $<4>$ and $<5>$ are as defined above;
    (4) $<1>I<8>S<1><1><1>GGYY<1>YAASVKG$ (SEQ ID NO:5), wherein $<1>$ is an equimolar mixture of each amino acid residues A, D, E, F, Gill, I, K, L, M, N, P, Q, R, S, T, V, and Y; $<8>$ is 0.27 R and 0.027 of each of ADEFGHIKLMNPQSTVWY; and
    (5) mixtures of vectors or genetic packages characterized by any of the above DNA sequences, preferably in the ratio: HC CDR2s:(1)/(2) (equimolar):(3):(4)::0.54:0.43: 0.03.

3. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a heavy chain CDR3 was selected from the group consisting of:
    (1) YYCA21111YFDYWG (SEQ ID NO:6), Wherein 1 is an equimolar mixture of each amino acid residues A, D, E, F, G, H, I, K, L, M, N, P, Q, R, S, T, V, W and Y; and 2 is an equimolar mixture of K and R;
    (2) YYCA2111111YFDYWG (SEQ ID NO:7), wherein 1 is an equimolar mixture of each amino acid residues A, D, E, F, G, H, K, L, M, N, P, Q, R, S, T, V, W and Y; and 2 is an equimolar mixture of K and R;
    (3) YYCA211111111YFDAYTG (SEQ ID NO:8), wherein 1 is an equimolar mixture of each amino acid residues A, D, E, F, G, H, 1, K, L, M, N, P, Q, R, S, T, V, W and Y; and 2 is an equimolar mixture of K and R;
    (4) YYCAR111S2S3111YFDYWG (SEQ ID NO:9), wherein 1 is an equimolar mixture of each amino acid residues A, D, E, G, H, I, K, L, M, N, P, Q, R, S, T, V, W and Y; and 2 is an equimolar mixture of S and G; and 3 is an equimolar mixture of Y and W;
    (5) YYCA2111CSG11CY1YFDYWG (SEQ ID NO:10), wherein 1 is an equimolar mixture of each amino acid residues A, D, E, F, G, H, I, K, L, M, N, P, Q, R, S, T, V, W and Y; and 2 is an equimolar mixture of K and R;
    (6) YYCA211S1TIFG11111YFDYWG (SEQ ID NO:11), wherein 1 is an equimolar mixture of each amino acid residues A, D, E, F, G, H, I, K, L, M, N, P, Q, R, S, T, V, W and Y; and 2 is an equimolar mixture of K and R.
    (7) YYCAR111YY2S3344111YFDYWG (SEQ ID NO:12), wherein 1 is an equimolar mixture of each amino acid residues A, D, E, F, G, H, I, K, L, M, N, P, Q, R, S, T, V, W and Y; 2 is an equimolar mixture of D and S; and 3 is an equimolar mixture of S and G;
    (8) YYCAR1111YC2231CY111YFDYWG (SEQ ID NO:13), wherein 1 is an equimolar mixture of each amino acid residues A, D, E, F, G, H, I, K, L, M, N, P, Q, R, S, T, V, W and Y; 2 is an equimolar mixture of S and G; and 3 is an equimolar mixture of T, D and G; and
    (9) mixtures of vectors or genetic packages characterized by any of the above DNA sequences, preferably the HC CDR3s (1) through (8) are in the following proportions in the mixture:
    (1) 0.10
    (2) 0.14
    (3) 0.25
    (4) 0.13
    (5) 0.13
    (6) 0.11
    (7) 0.04 and
    (8) 0.10; and more preferably the HC CDR3s (1) through (8) are in the following proportions in the mixture:
    (1) 0.02
    (2) 0.14
    (3) 0.25
    (4) 0.14
    (5) 0.14

(6) 0.12
(7) 0.08 and
(8) 0.11.
Preferably, 1 in one or all of HC CDR3s (1) through (8) is 0.095 of each of G and Y and 0.048 of each of A, D, E, F H, 1, K, L, M, N, P, Q, R, S, T, V, and W.

4. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encodes a kappa light chain CDR1 selected from the group consisting of:
   (1) RASQ<1>V<2><2><3>LA (SEQ ID NO:14)
   (2) RASQ<1>V<2><2><2><3>LA (SEQ ID NO:15); wherein <1> is an equimolar mixture of amino acid residues ADEFGHIKLMNPQRSTVWY; <2> is 0.2 S and 0.044 of each of ADEFGHIKLMNPQRTVWY; and <3> is 0.2Y and 0.044 each of ADEFGHIKLMNPQRTVW and S; and
   (3) mixtures of vectors or genetic packages characterized by any of the above DNA sequences, preferably in the ratio CDR1s (1):(2)::0.68:0.32.

5. A focused library of vectors or genetic packages that display, display and express, or comprise a member of a diverse family of human antibody related peptides, polypeptides and proteins and collectively display, display and express, or comprise at least a portion of the diversity of the-antibody family the vectors or genetic packages being characterized by variegated DNA sequences that encode a kappa light-chain CDR2 having the sequence:
   <1>AS<2>R<4><1> (SEQ ID NO:102),
wherein <1> is an equimolar mixture of amino acid residues ADEFGHIKLMNPQRSTVWY; <2> is 0.2 S and 0.044 of each of ADEFGHIKLMNPQRTVWY; and <4> is 0.2.A and 0.044 each of DEFGHIKLMNPQRSTVWY.

6. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a kappa light chain CDR3 selected from the groups consisting of:
   (1) QQ<3><1><1><1>P<1>T (SEQ ID NO:16), wherein <1> is an equimolar mixture of amino acid residues ADEFGHIKLMNPQRSTVWY; <3> is 0.2Y and 0.044 each of ADEFGHIKIMNPQRTVW;
   (2) QQ33111P (SEQ ID NO:103), wherein 1 and 3 are as defined in (1) above;
   (3) QQ3211PP1T (SEQ ID NO:17), wherein 1 and 3 are as defined in (1) above and 2 is 0.2 S and 0.044 each of ADEFGHIKLMNPQRTVWY; and
   (4) mixtures of vectors or genetic packages characterized by any of the above DNA sequences, preferably in the ratio CDA3s (1):(2):(3)::0.65:0.1:0.25.

7. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a lambda light chain CDR1 selected from the group consisting of:
   (1) TG<1>SS<2>VG<1><3><2><3>VS (SEQ ID NO:18), wherein <1> is 0.27 T, 0.27 G and 0.027 each of ADEFRIKLMNPQRSVWY: <2> is 0.27 D, 0.27 N and 0.027 each of AEFGHIKLMPQRSTVWY, and <3> is 0.36Y and 0.036 each of ADEFGHIKLMNPQRSTVW;
   (2) G<2><4>L<4><4><4><3><4><4> (SEQ ID NO:104), wherein <2> is as defined in (1) above and <4> is an equimolar mixture of amino acid residues ADEFGHIKIMNPQRSTVWY; and
   (3) mixtures of vectors or genetic packages characterized by any of the above DNA sequences, preferably in the ratio CDR1 (1):(2)::0.67:0.33;

8. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a lambda light chain CDR2 has the sequence:
   <4><4><4><2>RPS (SEQ ID NO:105)
wherein <2> is 0.27 D, 0.27 N, and 0.027 each of AEFGHIKIMPQRSTVWY and <4> is an equimolar mixture of amino acid residues ADEFGHIKLONPQRSTVW.

9. A focused library of vectors or genetic packages that display, display and express, or comprise a member of a diverse family of human antibody related peptides, polypeptides and proteins and collectively display, display and express, or comprise at least a portion of the diversity of the antibody family, the vectors or genetic packages being characterized by variegated DNA sequences that encode a lambda light chain CDR3 selected from the group consisting of:
   (1) <4><5><4><2><4>S<4><4><4><4>V (SEQ ID NO:106), wherein <2> is 0.27 D, 0.27 N, and 0.027 each of AEFGHIKIMPQRSTVWY; <4> is an equimolar mixture of amino acid residues ADEFGHIKLM-VPQRSTVW; and <5> is 0.36 S and 0.6355 each of ADEFGHIKLMNPQRTVWY;
   (2) <5>SY<1><5>S<5><1><4>V (SEQ ID NO:19), wherein <1> is an equimolar mixture of ADEFGHIKLMNPQRSTVWY; and <4> and 5 <5> are as defined in (1) above; and
   (3) mixtures of vectors or genetic packages characterized by any of the above DNA sequences, preferably in the ratio CDR3s 10. A focused library comprising variegated-DNA sequences that encode a heavy chain CDR selected from the group consisting of:
   (1) one or more of the heavy chain CDR's of paragraph 1 above;
   (2) one or more of the heavy chin CDR2s of paragraph 2 above;
   (3) one or more of the heavy chain CDR3s of paragraph 3 above; and
   (4) mixtures of vectors or genetic-packages characterized by (1), (2) and (3).

11. The focused library comprising one or more of the variegated DNA sequences that encodes a heavy chain CDR of paragraphs 1, 2 and 3 and further comprising variegated DNA sequences that encodes a light chain CDR selected from the group consisting of (1) one or more the kappa light chain CDR1s of paragraph 4;
   (2) the kappa light chain. CDR2 of paragraph 5;
   (3) one or more of the kappa light chain CDR3s of paragraph 6;
   (4) one or more of the kappa light chain CDR1s of paragraph 7;
   (5) the lambda light chain 'CDR2' of paragraph 8
   (6) one or more of the lambda light chain CDR3s of paragraph. 9; and (7) mixtures of vectors and genetic packages characterized by one or more of (1) through (6).
12. A population of variegated DNA sequences as. described in paragraphs 1-11 above.
13. A population of vectors comprising the variegated DNA sequences as described in paragraphs 1-11 above.

DETAILED DESCRIPTION OF THE PREFERRED EMBODIMENTS

Antibodies ("Ab") concentrate their diversity into those regions that are involved in determining affinity and specificity of the Ab for particular targets. These regions may be diverse in sequence or in length. Generally, they are diverse In both ways. However, within families of human antibodies the diversities, both in sequence and in length, are not truly random. Rather, some amino acid residues are preferred at certain positions of the CDRs and some CDR lengths are preferred. These preferred diversities account for the natural diversity of the antibody family.

According to this invention, and as more fully described below, libraries of vectors and genetic packages that more closely mirror the natural diversity, both in sequence and in length, of antibody families, or portions thereof are prepared and used.

Human Antibody Heavy Chain Sequence and Length Diversity (a) Framework

The heavy chain ("HC") Germ-Line Gene (GLG) 3-23 (also known as 1/1)-47) accounts for about 12% of all human Abs and is preferred as the framework in the preferred embodiment of the invention. It should, however, be understood that other well-known frameworks, such as 4-34, 3-30, 3-30.3 and 4-30.1, may also be used without departing from the principles of the focused diversities of this invention.

In addition, JH4(YFDYWGQGTLVTVSS; SEQ ID NO:20) occurs more often than JH3 in native antibodies. Hence, it is preferred for the focused libraries of this invention. However, JH3 (AFDIWGQGTMVTVSS; SEQ ID NO:21) could as well be used.

(b) Focused Length Diversity: CDR1, 2 and 3

(i) CDR1

For CDR1, GLGs provide CDR1s only Of the lengths 5, 6, and 7. Mutations during the maturation of the v-domain gene, however, can lead to CDR1s having lengths as short as 2 and as long as 16. Nevertheless, length 5, predominates. Accordingly, in the preferred embodiment of this invention the preferred HC CDR1 is 5 amino acids, with less preferred CDR1s having lengths of 7 and 14. In the most preferred libraries of this invention, all three lengths are used in proportions similar to those found in natural antibodies.

(ii) CDR2

GLGs provide CDR2s only of the lengths 15:19, but mutations during maturation may result in CDR2s of lengths from 16 to 28 amino acids. The lengths 16 and 17 predominate in mature Ab genes. Accordingly, length 17 is the preferred length for HC CDR2 of the present invention. Less preferred HC CDR2s of this invention have lengths 16 and 19. In the most preferred focused libraries of this invention, all three lengths are included in proportions similar to those found in natural antibody families.

(iii) CDR3

HC CDR3s vary in length. About half of human HCs consist of the components: V::nz::D::ny::JHn where V is a V gene, nz is a series of bases (mean 12) that are essentially random, D is a D segment, often with heavy editing at both ends, ny is a series of bases (mean 6) that are essentially random, and JH is one of the six JH segments, often with heavy editing at the 5' end. The D segments appear to provide spacer segments that allow folding of the IgG. The greatest diversity is at the junctions of y with D and of D with JH.

In the preferred-libraries of this invention both types of HC CDR3s are used. In HC CDR3s that have no identifiable D segment, the structure is V::nz::JHn where JH is usually edited at the 5' end. In HC CDR3s that have an identifiable D segment, the structure is V::nz::D::ny::JHn.

(c) Focused Sequence Diversity: CDR1, 2 and 3

(i) CDR1

In 5 amino acid length CDR1, examination of a 3D model of a humanized Ab showed that the side groups of residues 1, 3, and 5 were directed toward the combining pocket. Consequently, in the focused libraries of this invention, each of these positions may be selected from any of the native amino acid residues, except cysteine ("C"). Cysteine can form disulfide bonds, which are an important component of the canonical Ig fold. Having free thiol groups Could, thus, interfere with proper folding of the HC and could lead to problems in production or manipulation of selected Abs. Thus, in the focused libraries of this invention cysteine is excluded from positions 1; 3 and 5 of the preferred 5 amino acid CDR1s. The other 19 natural amino acids residues may be used at positions 1, 3 and 5. Preferably, each is present in equimolar ratios in the variegated libraries of this invention.

3D modeling also suggests that the side groups of residue 2 in a 5 amino acid CDR1 are directed away from the combining pocket. Although this position shows substantial diversity, both in GLG and mature genes, in the focused libraries of this invention this residue is preferably Tyr (Y) because it occurs in 681/820 mature antibody genes. However, any of the other native amino acid residues, except Cys (C), could also be used at this position.

For position 4, there is also some diversity in GLG and mature antibody genes. However, almost all mature genes have uncharged hydrophobic amino acid residues: A, G, L, P, F, M, W, I, V, at this position. Inspection of a 3D model also shows that the side group of residue 4 is packed into the innards of the HC. Thus, in the preferred embodiment of this invention which uses framework 3-23, residue 4 is preferably Met because it Is likely to fit very well into the framework of 3-23. With other frameworks, a similar fit consideration is used to assign residue 4.

Thus, the most preferred HC CDR1 of this invention consists of the amino acid sequence <1>Y<1>M<1> where <1> can be any one of amino acid residues: A, D, E, G, H, I, K, L, M, N, R, Q, S, T, V, W, Y (not C), preferably present at each position in an equimolar amount. This diversity is shown in the context of a framework 3-23:JH4 in Table 1. It has a diversity of 6859-fold.

The two less preferred HC CDR1s of this invention have length 7 and length 14. For length 7, a preferred variegation is (S/T) (S/G/<1>)$_2$(S/G/<1>)$_3$Y$_4$Y$_5$W$_6$ (S/G/<1>)$_7$ (SEQ ID NO:107); where (S/T) indicates an equimolar mixture of Ser and Thr codons; (S/G/<1>) indicates a mixture Of 0.2025 S, 0.2025 G, and 0.035 for each of A, D, E, F, H, I, K, L, M, N, P, Q, R, T, V, W, Y. This design gives a predominance of Ser and Gly at positions 2, 3, and 7, as occurs in mature HC genes. For length 14, a preferred variegation is VSGGSIS<1><1><1>YYW<1> (SEQ ID NO:108), where <1> is an equimolar mixture of the 19 native amino acid residues, except Cys (C).

The DNA that encodes these preferred HC CDR1s is preferably synthesized using trinucleotide building blocks so that each amino acid residue ii present in essentially equimolar or other described amounts. The preferred codons for the <1> amino acid residues are gct, gat, gag, ttt, ggt, cat, att, aag, ctt, atg, aat, cct, cag, cgt, tct, act, gtt, tgg, and tat. Of course, other codons for the chosen amino acid residue could also be used.

The diversity oligonucleotide (ON) is preferably synthesized from BspEI to BstXI (as shown in Table 1) and can, therefore, be incorporated either by PCR synthesis using overlapping ONs or introduced by ligation of BspEI/BstXI-cut fragments. Table 2 shows the oligonucleotides that embody the specified variegations of the preferred length 5 HC CDR1s of this invention. PCR using ON-R1V1vg, ON-R1top, and ON-R1bot gives a dsDNA product of 73 base-pairs, cleavage with 14spEI and BstXI trims 11 and 13 bases from the ends and provides cohesive ends that can be ligated to similarly cut vector having the 3-23 domain shown in Table 1. Replacement of ON-R1V1vg with either ONR1V2vg or ONR1V3vg (see Table 2) allows synthesis of the two alternative diversity patterns—the 7 residue length and the 14 residue length HC CDR1.

The more preferred libraries of this invention comprise the 3 preferred HC CDR1 length diversities. Most preferably, the 3 lengths should be incorporated in approximately the ratios in which they are observed in antibodies selected without reference to the length of the CDRs. For example, one sample of 1095 HC genes have the three lengths present in the ratio: L=5:L=7:L=14::820:175:23::0.80:0.17:0.02. This is the preferred ratio in accordance with this invention.

(ii) CDR2

Diversity in HC CDR2 was designed with the same considerations as for HC CORI: GLG sequences, mature sequences and 3D structure. A preferred length for CDR2 is 17, as shown in Table 1. For this preferred 17 length CDR2, the preferred variegation in accordance with the invention is: <2>I<2><3>SGG<1>T<1>YADSVKG (SEQ ID NO:2), where <2> indicates any amino acid residue selected from the group of Y, R, W, V, G and S (equimolar mixture), <3> is P, S and G or P and S only (equimolar mixture), and <1> is any native amino acid residue except C (equimolar mixture).

ON-R2V1vg shown in Table 3 embodies this diversity pattern. It is preferably synthesized so that fragments of dsDNA containing the BstXI and XbaI site can be generated by PCR. PCR with ON-R2V1vg, ON-R2top, and ONR2bot gives a dsDNA product of 122 base pairs. Cleavage with BstXI and XbaI removes about 10 bases from each end and produces cohesive ends that can be ligated to similarly cut vector that contains the 3-23 gene-shown in Table 1.

In an alternative embodiment for a 17 length HC CDR2, the following variegation may be used; <1>I<4><1><1>G<5><1><1><1>YADSVKG (SEQ ID NO:3), where <1> is as described above for the more preferred alternative of HC CDR2; <4> indicates an equimolar mixture of DINSWY, and <5> indicates an equimolar mixture of SGDN. This diversity pattern is embodied in ON-R2V2vg shown in Table 3. Preferably, the two embodiments are used in equimolar mixtures in the libraries of this invention.

Other preferred HC CDR2s have lengths 16 and 19. Length 16: <1>I<4><1><1>G<5><1><1>YNPSLKG (SEQ ID NO:4); Length:19: <1>I<8>S<1><1><1> GGYY<1>YAASVKG (SEQ ID NO:5), wherein <1> is an equimolar mixture of all native amino acid residues except C; <4> is a equimolar mixture of DINSWY; <5> is an equimolar mixture of SGDN; and <8> is 0.27 R and 0:0 7 of each of residues ADEFGHIKLMNPQSTVWY. Table 3 shows ON-R2V3vg which embodies a preferred aDR2 variegation of length 16 and ON7R2V4vg which embodies a preferred CDR2 variegation of length 19. To prepare these variegations ON-R2V3vg may be PCR amplified with ON-A2top and ON-R2bo3 and ON-R2V4vg may be PCR amplified with ON-R2top and ON-R2-bo4. See Table 3. In the most preferred embodiment of this invention, all three HC CDR2 lengths are used. Preferably, they are present in a ratio 17:16:19::579:464:31::0.54:0.43:0.03.

(iii) CDR3

The preferred libraries of this invention comprise several BC CDR3 components. Some of these will have only sequence diversity. Others will have sequence diversity with embedded D segments to extend the length, while also incorporating sequences known to allow Igs to fold. The HC CDR3 components of the preferred libraries of this invention and their diversities are depicted in Table 4: Components 1-8.

This set of components was chosen after studying the sequences of 1383 human BC sequences. The proposed components are meant to fulfill the following goals:

1) approximately the same distribution of lengths as seen in native Ab genes;

2) high level of sequence diversity at places having high diversity in native Ab genes; and 3) incorporation of constant sequences often seen in native Ab genes.

Component 1 represents all the genes having lengths 0 to 8 (counting from the YYCAR motif at the end of FR3 to the WG dipeptide motif near the start of the J region, i.e., FR4). Component 2 corresponds the all the genes having lengths 9 or 10. Component 3. corresponds to the genes having lengths 11 or 12 plus half the genes having length 13. Component 4 corresponds to those having length 14 plus half those having length 13. Component 5 corresponds to the genes having length 15 and half of those having length 16. Component. 6 corresponds to genes of length 17 plus half of those with length 16. Component 7 corresponds to those with length 18. Component 8 corresponds to those having length 19 and greater. See Table 4.

For each HC CDR3 residue having the diversity <1>, equimolar ratios are preferably not used. Rather, the following ratios are used 0.095 [G and Y] and 0.048 [A, D, E, F, H, I, K, L, M, N, P, Q, R, S, T, V, and W]. Thus, there is a double dose of G and Y with the other residues being in equimolar ratios. For the other diversities, e.g., KR or SG, the residues are present in equimolar mixtures.

In the preferred libraries of this invention the eight components are present in the following fractions: 1 (0.10), 2 (0.14), 3 (0.25), 4 (0.13), 5 (0.13), 6 (0.11), 7 (0.04) and 8 (0.10). See Table 4.

In the more preferred embodiment of this invention, the amounts of the eight components is adjusted because the first component is not complex enough to justify including it as 10% of the library. For example, if the final library were to have $1\times10^9$ members, then $1\times10^8$ sequences would come from component 1, but it has only $2.6\times10^5$ CDR3 sequences so that each one would occur in ~385 CDR1/2 contexts. Therefore, the more preferred amounts of the eight components are 1(0.02), 2(0.14), 3(0.25), 4(0.14), 510.14), 6(0.12), 7(0.68), 8(0.11). In accordance with the more preferred embodiment component 1 occurs in ~77 CDR1/2 contexts and the other, longer CDR3s occur more often.

Table 5 shows vgDNA that embodies each of the eight HC CDR3 components shown in Table 4. In Table 5, the oligonucleotides (ON) Ctop25, CtprmA, C8prmB, and CBot25 allow PCR amplification of each of the variegated ONs (vgDNA): C1t08, C2t10, C3t12, C4t14, C5t15, C6t17, C7t18, and C8t19. After amplification, the dsDNA can be cleaved with AfiII and BstEII (or KpnI) and ligated to similarly cleaved vector that contains the remainder of the 3-23 domain. Preferably, this vector already contains diversity in one, or both, of CDR1 and CDR2 as disclosed herein. Most preferably, it contains diversity in both the CDR1 and CDR2 regions. It is, of course, to be understood that the various diversities can be incorporated into the vector in any order.

Preferably, the recipient vector originally contains a stuffer in place of CDR1, CDR2 and CDR3 so that there will be no parental sequence that would then occur in the resulting library. Table 6 shows a version of the V3-23 gene segment with each CDR replaced by a short segment that contains both stop codons and restriction sites that will allow specific cleavage of any vector that does not have the stuffer removed. The stuffer can either be short and contain a restriction enzyme site that will not occur in the finished library, allowing removal of vectors that are not cleaved by both AfiII and BstEII (or AionI) and religated. Alternatively, the stuffer could be 200-400 bases long so that uncleaned or once-cleaved vector can be readily separated from doubly cleaved vector.

Human Antibody Light Chain: Sequence and Length Diversity (i) Kappa Chain (a) Framework In the preferred embodiment of this invention, the kappa light chain is built in an A27 framework with a JK1 region. These are the most common V and J regions in the native genes. Other frameworks, such as 012, L2, and All, and other J regions, such as JK4, however, may be used without departing from the scope of this invention.

(b) CDR1

In native human kappa chains, CDR1s with lengths of 11, 12, 13, 16, and 17 were observed with length 11 being predominant and length 12 being well represented. Thus, in the preferred embodiments of this invention LC CDR1s of length 11 and 12 are used in an and mixture similar to that observed in native antibodies), length 11 being most preferred. Length 11 has the following sequence: RASQ<1>V<2><2><3>LA (SEQ ID NO:14) and Length 12 hag the following sequence: RASQ<1>V<25<2><2><3>LA (SEQ ID NO:15), wherein <1> is an equimolar mixture of ill of the native-amino acid residues, except C, <2> is 0.2 S and 0.044 of each of ADEFGHIKLMNPQRTVWY, and <3> is 0.2.Y and 0.044 each of A, D, E, F, G, H, 1, K, L, M, N, Q, R, T, V, W and S. In the most preferred embodiment of this invention, both CDR1. lengths are used. Preferably, they are present in a ratio of 11:12::154:73::0.68:0.32.

(c) CDR2

In native kappa, CDR2 exhibits only length 7. This length is used in the preferred embodiments of-this invention. It has the sequence <1>AS<2>R<4><1>, wherein <1> is an-equimolar mixture of amino acid residues ADEFGHIKLMNPQRSTVWY; <2> is 0.2 S and 0.004 of each of ADEFGHIKLMNPQRTVWY; and <4> is 0.2 A and 0.044 of each of DEFGHIKLMNPQRSTUWY.

(d) CDR3

In native kappa, CDR3 exhibits lengths of 4, 6, 7; 8, 9, 10, 11, 12, 13, 0.0 . . . and 19. While any of these lengths and mixtures of them can be employed in this invention, we prefer lengths 8, 9 and 10, length 9 being more preferred. For the preferred Length 9, the sequence is, QQ<3><1><1><1>P<1>T, wherein <1> is an equimolar mixture of amino acid residues ADEFGHIKLMN-PQRSTVWY and <3> is 0.2? and 0.044 each of ADEFGHIKLWQRSVW. Length 8 is preferably QQ33111P and Length 10 is Preferably QQ3211PP1T, wherein 1 and 3 are as defined for Length 9 and 2 is S (0.2) and 0.044 each of ADEFGHIKLMNPQRTVWY. A mixture of all 3 lengths being most preferred (ratios as in native antibodies), i.e., 8:9:10i28:166:63::0.1:0.65:0.25.

Table 7 shows a kappa chain gene of this invention, including a PlacZ promoter a ribosome-binding site, and signal sequence (MI3 III signal). The DNA sequence encodes the GLG amino acid sequence but does not comprise the GLG DNA sequence. Restriction sites are designed to fall within each framework region so that diversity can be cloned into the CDRs. XmaI and Espl are in FR1, SexAI is in FR2, RsrII is in FR3, and KpnI (or Acc65I), are in FR4. Additional sites are provided in the constant kappa chain to facilitate construction of the gene.

Table 7 also shows a suitable scheme of variegation for kappa. In CDR1, the most preferred length 11 is depicted. However, most preferably both lengths 11 and 12 are used. Length 12 in CDR1 can be construed by introducing codon 51 as <2> (i.e. a Ser-biased mixture). CDR2 of kappa is always 7 codons. Table 7 shows a preferred variegation scheme for CDR2. Table 7 Shows a variegation scheme for the most preferred CDR3 (length 9). Similar variegations can be lied for CDRs of length 8 and 10. In the preferred embodiment of this invention, those three lengths (8, 9 and 10) are included in the libraries of this invention in the native ratios, as described above.

Table 9 shows series of diversity oligonucleotides and primers that may be used to construct the kappa chain diversities depicted in Table 7.

(ii) Lambda Chain (a) Framework

The lambda chain is preferably built in a 2a2 framework with an L2J region. These are the most common V and J regions in the native genes. Other frameworks, such as 31, 4b, la and 6a, and other J regions, such as L1J, L3J and L7J, however, may be used without departing from the scope of this invention.

(b) CDR1

In native human lambda chains, CDR1s with length 14 predominate, lengths 11, 12 and 13 also occur. While any of these can be used in this invention, lengths 11 and 14 are preferred. For length 11 the sequence is: TG<2><4>L<4><4><4><3><4><4> (SEQ ID NO:22) and for Length 14 the sequence is: TG<1>SS<2>VG<1><3><2><3>VS (SEQ ID NO:18), wherein <1> is 0.27 T, 0.21 G and 0.027 each of ADEF-HIKLMNPQRSVWY; <2> is 0.27 D, 0.27 N and 0.027 each of AEFGHIKLMNPQRSTVWY; <3> is 0.36 Y and 0.0355 each of ADEFGHIKLMNPQRSTVW; and <4> is an equimolar mixture of amino acid residues ADEFGHIKLM-NPQRSTVWY. Most preferably, Mixtures (similar to those occurring in native antibodies) preferably, the ratio is 11:14::23:46::0.33:0.67 of the three lengths are used.

(c) CDR2

In native human lambda chains₄.CDR2s with length 7 are by far the most common. This length is preferred in this invention. The sequence of this Length 7 CDR2 is <4><4><4><2>RPS, wherein <2> is 0.27 D, 0.27 N, and 0.027 each of AEFGHIKLMPQRTVWY and <4> is an equimolar mixture of amino acid residues ADEFGHIKLM-NPQRSTVW.

(d) CDR3

In native human lambda chains, CDR3s of length 10 and 11 predominate, while length 9 is also common. Any of these three lengths can be used in the invention. Length 11 is preferred and mixtures of 10 and 11 more preferred. The sequence of Length 11 is <4><5><4><2><4>S<4><4><4><4>V, where <2> and <4> are as defined for the lambda CORI and <5> is 0.36 S and 0.0355 each of ADFFGHIKLMNFORTVWY. The sequence of Length 10 is <5>SY<1><5>S<5><1><4>V (SEQ ID NO:19), wherein <1> is an equimolar mixture of ADEF-GHIKLMNPQRSTVWY; and <4> and <5> are as defined for Length 11. The preferred mixtures of this invention comprise an equimolar mixture of Length 10 and Length 11. Table 8 shows a preferred focused lambda light chain diversity in accordance with this invention.

Table 9 shows a series of diversity oligonucleotides and primers that may be used to construct 10 the lambda chain diversities depicted in Table 7.

Method of Construction of the Genetic Package

The diversities of heavy chain and the kappa and lambda light chains are best constructed in separate vector's. First a synthetic gene is designed to embody each of the synthetic variable domains. The light chains are bounded by restriction sites for ApaLI (positioned at the very end of the signal sequence) and AscI (positioned after the stop codon). The heavy chain is bounded by SfiI (positioned within the PelB signal sequence) and NotI (positioned in the linker between CH1 and the anchor protein). Signal sequences other than PelB may also need, e.g., a M13 pIII signal sequence.

The initial genes are made with "stuffer" sequences in place of the desired CDRs. A "stuffer" is a sequence that is to be cut away and replaced by diverse DNA but which does not allow expression 'of a functional antibody gene. For example, the stuffer may contain several stop codons and restriction sites that will not occur in the correct finished library vector. For example, in Table 10, the stuffer for CDR1 of kappa A27 contains a StuI site. The vgDNA for CDR1 is introduced as a cassette from EspI, XmaI, or AflII to dither SexAI or KasI. After the ligation, the DNA is cleaved with StiI; there should be no StuI sites in the desired vectors.

The sequences of the heavy chain gene with stuffers is depicted in Table 6. The sequences of the kappa light chain gene with stuffers is depicted in Table 10. The sequence of the lambda light chain gene with stuffers is depicted in Table 11.

In another embodiment of the present invention the diversities of heavy chain and the kappa or lambda light chains are constructed in a single vector or genetic packages (e.g., for display or display and expression) having appropriate restriction sites that allow cloning of these chains. The processes to construct such vectors are well known and widely used in the art. Preferably, a heavy chain and Kappa light Chain library and a heavy chain and lambda light chain library would be prepared separately. The two libraries, most preferably, will then be mixed in equimolar amounts to attain maximum diversity.

Most preferably, the display is had on the surface of a derivative of M13 phage. The most preferred vector contains all the genes of M13, an antibiotic resistance-gene, and the display cassette. The preferred vector is provided with restriction sites that allow introduction and excision of members of the diverse family of genes, as cassettes. The preferred vector is stable against rearrangement under the growth conditions used to amplify phage.

In another embodiment of this invention, the diversity captured by the methods of the present invention may be displayed and/or expressed in a phagemid vector (e.g., pCES1) that displays and/or expresses the peptide, polypeptide or protein. Such vectors may also be used to store the diversity for subsequent display and/or expression using other vectors or phage.

In another embodiment of this invention, the diversity captured by the methods of the present invention may be displayed and/or expressed in a yeast vector.

TABLE 1

3-23:JH4 CDR1/2 diversity = 1.78 x 10$^8$

```
                            FR1(VP47/V3-23)---------------
                  20  21  22              23  24  25  26  27  28  29  30
                   A   M   A               E   V   Q   L   L   E   S   G  (SEQ ID NO: 99)
        ctgtctgaac  cc  atg gcc           gaa|gtt|caa|ttg|tta|gag|tct|ggt|
        Scab......  NcoI....                            MfeI --------------FR1----------------------------------------
31  32  33  34  35  36  37  38  39  40  41  42  43  44  45
 G   G   L   V   Q   P   G   G   S   L   R   L   S   C   A
|ggc|ggt|ctt|gtt|cag|cct|ggt|ggt|tct|tta|cgt|ctt|tct|tgc|gct|

Sites of variegation     <1>      <1> <1> <1>                   6859-fold diversity
----FR1-------------------->|.....CDR1..................|---FR2------
46  47  48  49  50  51  52   53  54   55  56  57  58  59  60
 A   S   G   F   T   F   S    -   Y    -   M   -   W   V   R
|gct|tcc|gga|ttc|act|ttc|tct|  - |tac|  - |atg|  - |tgg|gtt|cgc|
    BspEI                      BsiWI                      BstXI.

Sites of variegation-><2>       <2> <3>
-------FR2---------------------------->|...CDR2.........
61  62  63  64  65  66  67  68  69  70  71  72  73  74  75
 Q   A   P   G   K   G   L   E   W   V   S   -   I   -   -
|caa|gct|cct|ggt|aaa|ggt|ttg|gag|tgg|gtt|tct|  - |atc|  - |  - |
...BstXI <1>      <1>  25992-fold diversity in CDR2
.....CDR2 .......................................|---FR3---
 76  77  78  79  80  81  82  83  84  85  86  87  88  89  90
  S   G   G   -   T   -   Y   A   D   S   V   K   G   R   F
|tct|ggt|ggc|  - |act|  - |tat|gct|gac|tcc|gtt|aaa|ggt|cgc|ttc|

-- - - FR3--------------------------------------------
  91  92  93  94  95  96  97  98  99 100 101 102 103 104 105
   T   I   S   R   D   N   S   K   N   T   L   Y   L   Q   M
 |act|atc|tct|aga|gac|aac|tct|aag|aat|act|ctc|tac|ttg|cag|atg|
          XbaI
```

TABLE 1-continued 3-23:JH4 CDR1/2 diversity = 1.78 × 10⁸

```
---FR3-----------------------------------------------------
106 107 108 109 110 111 112 113 114 115 116 117 118 119 120
 N   S   L   R   A   E   D   T   A   V   Y   Y   C   A   K
|aac|agc|tta|agg|gct|gag|gac|acc|gct|gtc|tac|tac|tgc|gcc|aaa|
        AflII ......CDR3.................| Replaced by the various components!
121 122 123 124 125 126 127
 D   Y   E   G   T   G   Y  (SEQ ID NO: 24)
|gac|tat|gaa|ggt|act|ggt|tat| (SEQ ID NO: 23)

|---------- FR4 ---(JH4)------------------------------------
 Y   F   D   Y   W   G   Q   G   T   L   V   T   V   S   S  (SEQ ID NO: 26)
|tat|ttc|gat|tat|tgg|ggt|caa|ggt|acc|ctg|gtc|acc|gtc|tct|agt|. (SEQ ID NO: 25)
                            KpnI            BstEII
```

<1> = Codons for ADEFGHIKLMNPQRSTVWY (equimolar mixture)
<2> = Codons for YRWVGS (equimolar mixture)
<3> = Codons for PS or PS and G (equimolar mixture)

TABLE 2

Oligonucleotides used to variegate CDR1 of human HC

CDR1 - 5 residues (ON-R1V1vg):  5'-ct|tcc|gga|ttc|act|ttc|tct|<1>|tac|<1>|atg|<1>|tgg|gtt|cgc|caa|
              gct|cct|gg-3' (SEQ ID NO: 27)
<1> = Codons of ADEFGHIKLMNPQRSTVWY 1:1
(ON-R1top):   5'-cctactgtct|tcc|gga|ttc|act|ttc|tct-3' (SEQ ID NO: 28)
(ON-R1bot) [RC]: 5'-tgg|gtt|cgc|caa|gct|cct|ggttgctcactc-3' (SEQ ID NO: 29)

CDR1 - 7 residues (ON-R1V2vg):  5'-ct|tcc|gga|ttc|act|ttc|tct|<6>|<7>|<7>|tac|tac|tgg|<7>|tgg|
              gtt|cgc|caa|gct|cct|gg-3' (SEQ ID NO: 30)
<6> = Codons for ST, 1:1
<7> = 0.2025(Codons for SG) + 0.035(Codons for ADEFHIKLMNPQRTVWY)

CDR1 - 14 residues (ON-R1V3vg):  5'-ct|tcc|gga|ttc|act|ttc|tct|atc|agc|ggt|ggt|tct|atc|tcc|<1>|<1>|<1>|-
              tac|tac|tgg|<1>|tgg|gtt|cgc|caa|gct|cct|gg-3' (SEQ ID NO: 31)
<1> = Codons for ADEFGHIKLMNPQRSTVWY 1:1

TABLE 3

Oligonucleotides used to variegate CDR2 of human HC

CDR2 - 17 residues (ON-R2V1vg):  5'-ggt|ttg|gag|tgg|gtt|tct|<2>|atc|<2>|<3>|tct|ggt|ggc|<1>|act|<1>|tat|gct|-
              gac|tcc|gtt|aaa|gg-3' (SEQ ID NO: 32)
(ON-R2top):   5'-ct|tgg|gtt|cgc|caa|gct|cct|ggt|aaa|ggt|ttg|gag|tgg|gtt|tct-3' (SEQ ID NO: 33)
(ON-R2bot) [RC]: 5'-tat|gct|gac|tcc|gtt|aaa|ggt|cgc|ttc|act|atc|tct|aga|ttcctgtcac-3' (SEQ ID NO: 34)
<1> = Codons for A, D, E, F, G, H, I, K, L, M, N, P, Q, R, S, T, V, W and Y
(equimolar mixture)
<2> = Codons for Y, R, W, V, G and S (equimolar mixture)
<3> = Codons for P and S (equimolar mixture) or P, S and G (equimolar mixture)

(ON-R2V2vg):  5'-ggt|ttg|gag|tgg|gtt|tct|<1>|atc|<4>|<1>|<1>|ggt|<5>|<1>|<1>|<1>|tat|gct|-
              gac|tcc|gtt|aaa|gg-3' (SEQ ID NO: 35)
<4> = Codons for DINSWY (equimolar mixture)
<5> = Codons for SGDN, (equimolar mixture)

CDR2 - 16 residues (ON-R2V3vg):  5'-ggt|ttg|gag|tgg|gtt|tct|<1>|atc|<4>|<1>|<1>|ggt|
              <5>|<1>|<1>|tat|aac|cct|tcc|ctt|aag|gg-3' (SEQ ID NO: 36)
(ON-R2bo3) [RC]: 5'-tat|aac|cct|tcc|ctt|aag|ggt|cgc|ttc|act|atc|tct|aga|ttcctgtcac-3' (SEQ ID NO: 37)

TABLE 3-continued

Oligonucleotides used to variegate CDR2 of human HC

CDR2 - 19 residues (ON-R2V4vg):    5'-ggt|ttg|gag|tgg|gtt|tct|<1>|atc|<8>|agt|<1>|<1>|
                <1>|ggt|ggt|act|act|<1>|tat|gcc|gct|tcc|gtt|aag|gg-3' (SEQ ID NO: 38)
(ON-R2bo4) [RC]: 5'-tat|gcc|gct|tcc|gtt|aag|ggt|cgc|ttc|act|atc|tct|aga|ttcctgtcac-3' (SEQ ID NO: 39)
<1>, <2>, <3>, <4> and <5> are as defined above
<8> is 0.27 R and 0.027 each of ADEFGHIKLMNPQSTVWY

TABLE 4

Preferred Components of HC CDR3

| Component | | Length | Complexity | Fraction of Library | Preferred Adjusted Fraction |
|---|---|---|---|---|---|
| 1 | YYCA21111YFDYWG. (SEQ ID NO: 6) (1 = any amino acid residue, except C; 2 = K and R) | 8 | $2.6 \times 10^5$ | .10 | .02 |
| 2 | YYCA2111111YFDYWG. (SEQ ID NO: 7) (1 = any amino acid residue, except C; 2 = K and R) | 10 | $9.4 \times 10^7$ | .14 | .14 |
| 3 | YYCA211111111YFDYTG. (SEQ ID NO: 8) (1 = any amino acid residue, except C; 2 = K and R) | 12 | $3.4 \times 10^{10}$ | .25 | .25 |
| 4 | YYCAR111S2S3111YFDYWG. (SEQ ID NO: 9) (1 = any amino acid residue, except C; 2 = S and G  3 = Y and W) | 14 | $1.9 \times 10^8$ | .13 | .14 |
| 5 | YYCA2111CSG11CY1YFDYWG. (SEQ ID NO: 10) (1 = any amino acid residue, except C; 2 = K and R) | 15 | $9.4 \times 10^7$ | .13 | .14 |
| 6 | YYCA211S1TIFG11111YFDYWG. (SEQ ID NO: 11) (1 = any amino acid residue, except C; 2 = K and R) | 17 | $1.7 \times 10^{10}$ | .11 | .12 |
| 7 | YYCAR111YY2S33YY111YFDYWG. (SEQ ID NO: 12) (1 = any amino acid residue, except C; 2 = D or G; 3 = S and G) | 18 | $3.8 \times 10^8$ | .04 | .08 |
| 8 | YYCAR1111YC2231CY111YFDYWG. (SEQ ID NO: 13) (1 = any amino acid residue, except C; 2 = S and G; 3 = T, D and G) | 19 | $2.0 \times 10^{11}$ | .10 | .11 |

TABLE 5

Oligonucleotides used to variegate the eight components of HC CDR3

(Ctop25):    5'-gctctggtcaac|tta|agg|gct|gag|g-3' (SEQ ID NO: 40)
(CtprmA):    5'-gctctggtcaac|tta|agg|gct|gag|gac|acc|gct|gtc|tac|tac|tgc|gcc-3' (SEQ ID NO: 41)
             AflII...
(CBprmB) [RC]: 5'-|tac|ttc|gat|tac|tgg|ggc|caa|ggt|acc|ctg|gtc|acc|tcgctccacc-3' (SEQ ID NO: 42)
                                                  BstEII...
(CBot25) [RC]: 5'-|ggt|acc|ctg|gtc|acc|tcgctccacc-3' (SEQ ID NO: 43)
The 20 bases at 3' end of CtprmA are identical to the most 5' 20 bases
of each of the vgDNA molecules.
Ctop25 is identical to the most 5' 25 bases of CtprmA.
The 23 most 3' bases of CBprmB are the reverse complement of the
most 3' 23 bases of each of the vgDNA molecules.
CBot25 is identical to the 25 bases at the 5' end of CBprmB.

Component 1

(C1t08):    5'-cc|gct|gtc|tac|tac|tgc|gcc|<2>|<1>|<1>|<1>|<1>|tac|ttc|gat|tac|tgg|ggc|caa|gg-3'
            (SEQ ID NO: 44)

TABLE 5-continued

Oligonucleotides used to variegate the eight components of HC CDR3

<1> = 0.095 Y + 0.095 G + 0.048 each of the residues ADEFHIKLMNPQRSTVW, no C; <2> = K and R (equimolar mixture)

Component 2

(C2t10): 5'-cc|gct|gtc|tac|tac|tgc|gcc|<2>|<1>|<1>|<1>|<1>|<1>|<1>|tac|ttc|gat|tac|tgg| ggc|caa|gg-3' (SEQ ID NO: 45)
<1> = 0.095 Y + 0.095 G + 0.048 each of ADEFHIKLMNPQRSTVW, no C; <2> = K and R (equimolar mixture)

Component 3

(C3t12): 5'-cc|gct|gtc|tac|tac|tgc|gcc|<2>|<1>|<1>|<1>|<1>|<1>|<1>|<1>|tac|ttc|gat|tac|- tgg|ggc|caa|gg-3' (SEQ ID NO: 46)
<1> = 0.095 Y + 0.095 G + 0.048 each of ADEFHIKLMNPQRSTVW, no C; <2> = K and R (equimolar mixture)

Component 4

(C4t140): 5'-cc|gct|gtc|tac|tac|tgc|gcc|cgt|<1>|<1>|<1>|tct|<2>|tct|<3>|<1>|<1>|<1>|tac|ttc|gat|- tac|tgg|ggc|caa|gg-3' (SEQ ID NO: 47)
<1> = 0.095 Y + 0.095 G + 0.048 each of ADEFHIKLMNPQRSTVW, no C; <2> = S and G (equimolar mixture); <3> = Y and W (equimolar mixture)

Component 5

(C5t15): 5'-cc|gct|gtc|tac|tac|tgc|gcc|<2>|<1>|<1>|<1>|tgc|tct|ggt|<1>|<1>|tgc|tat|<1>|tac|- ttc|gat|tac|tgg|ggc|caa|gg-3' (SEQ ID NO: 48)
<1> = 0.095 Y + 0.095 G + 0.048 each of ADEFHIKLMNPQRSTVW, no C; <2> = K and R (equimolar mixture)

Component 6

(C6t17): 5'-cc|gct|gtc|tac|tac|tgc|gcc|<2>|<1>|<1>|tct|<1>|act|atc|ttc|ggt|<1>|<1>|<1>|<1>|- <1>|tac|ttc|gat|tac|tgg|ggc|caa|gg-3' (SEQ ID NO: 49)
<1> = 0.095 Y + 0.095 G + 0.048 each of ADEFHIKLMNPQRSTVW, no C; <2> = K and R (equimolar mixture)

Component 7

(C7t18): 5'-cc|gct|gtc|tac|tac|tgc|gcc|cgt|<1>|<1>|<1>|tat|tac|<2>|tct|<3>|<3>|tac|tat|- <1>|<1>|<1>|tac|ttc|gat|tac|tgg|ggc|caa|gg-3' (SEQ ID NO: 50)
<1> = 0.095 Y + 0.095 G + 0.048 each of ADEFHIKLMNPQRSTVW, no C; <2> = D and G (equimolar mixture); <3> = S and G (equimolar mixture)

Component 8

(c8t19): 5'-cc|gct|gtc|tac|tac|tgc|gcc|cgt|<1>|<1>|<1>|<1>|tat|tgc|<2>|<2>|<3>|<1>|tgc|tat|- <1>|<1>|<1>|tac|ttc|gat|tac|tgg|ggc|caa|gg-3' (SEQ ID NO: 51)
<1> = 0.095 Y + 0.095 G + 0.048 each of ADEFHIKLMNPQRSTVW, no C; <2> = S and G (equimolar mixture); <3> = TDG (equimolar mixture);

TABLE 6

3-23::JH4 Stuffers in place of CDRs

```
                              FR1(DP47/V3-23)---------------
         20  21  22           23  24  25  26  27  28  29  30
          A   M   A            E   V   Q   L   L   E   S   G
ctgtctgaac  cc  atg  gcc      gaa|gtt|caa|ttg|tta|gag|tct|ggt|
(SEQ ID NO: 99)
Scab.....  NcoI....                       MfeI ---------------FR1--------------------------------------
 31  32  33  34  35  36  37  38  39  40  41  42  43  44  45
  G   G   L   V   Q   P   G   G   S   L   R   L   S   C   A
|ggc|ggt|ctt|gtt|cag|cct|ggt|ggt|tct|tta|cgt|ctt|tct|tgc|gct|

----FR1-------------------->|...CDR1 stuffer....|---FR2------
 46  47  48  49  50  51  52  53  54  55  56  57  58  59  60
  A   S   G   F   T   F   S   S   Y   A           W   V   R
|gct|tcc|gga|ttc|act|ttc|tct|tcg|tac|gct|tag|taa|tgg|gtt|cgc|
     BspEI                       BsiWI                BstXI.
```

TABLE 6-continued

3-23::JH4 Stuffers in place of CDRs

```
-------FR2-------------------------->|...CDR2 stuffer.
 61  62  63  64  65  66  67  68  69  70  71  72  73  74  75
  Q   A   P   G   K   G   L   E   W   V   S   |   p   r   |
|caa|gct|cct|ggt|aaa|ggt|ttg|gag|tgg|gtt|tct|taa|cct|agg|tag|
...BstXI                                          AvrII..

.....CDR2 stuffer...................................|---FR3---
     91  92  93  94  95  96  97  98  99 100 101 102 103 104 105
      T   I   S   R   D   N   S   K   N   T   L   Y   L   Q   M
|act|atc|tct|aga|gac|aac|tct|aag|aat|act|ctc|tac|ttg|cag|atg|
        XbaI ---FR3----------..> CDR3 Stuffer------------->|
 106 107 108 109 110
  N   S   L   R   A      (SEQ ID NO: 53)
|aac|agc|tta|agg|gct|tag taa agg cct taa     (SEQ ID NO: 52)
        AflII           StuI...

|----- FR4 ---(JH4)----------------------------------------
  Y   F   D   Y   W   G   Q   G   T   L   V   T   V   S      (SEQ ID NO: 26)
|tat|ttc|gat|tat|tgg|ggt|caa|ggt|acc|ctg|gtc|acc|gtc|tct|agt|... (SEQ ID NO: 25)
                            KpnI            BstEII
```

TABLE 7

A27:JH1 Human Kappa light chain gene

```
gaggacc attgggcccc ctccgagact ctcgagcgca
Scab...... EcoO109I       XhoI..
         ApaI.

acgcaattaa tgtgagttag ctcactcatt aggcacccca ggctttacac tttatgcttc
    ..-35..             Plac                 ..-10.

cggctcgtat gttgtgtgga attgtgagcg gataacaatt tcacacagga aacagctatg accatgatta cgccaagctt tggagccttt tttttggaga ttttcaac (SEQ ID NO: 54)
   pflMI.......
       Hind III M13 III signal sequence (AA seq)---------------------------->
  1   2   3   4   5   6   7   8   9  10  11  12  13  14  15
  M   K   K   L   L   F   A   I   P   L   V   V   P   F   Y
 gtg aag aag ctc cta ttt gct atc ccg ctt gtc gtt ccg ttt tac --Signal-->FR1------------------------------------------>
 16  17  18  19  20  21  22  23  24  25  26  27  28  29  30
  S   H   S   A   Q   S   V   L   T   Q   S   P   G   T   L
|agc|cat|agt|gca|caa|tcc|gtc|ctt|act|caa|tct|cct|ggc|act|ctt|
            ApaLI...

----- FR1 ------------------------------------>| CDR1------>
 31  32  33  34  35  36  37  38  39  40  41  42  43  44  45
  S   L   S   P   G   E   R   A   T   L   S   C   R   A   S      (SEQ ID NO: 55)
|tcg|cta|agc|ccg|ggt|gaa|cgt|gct|acc|tta|agt|tgc|cgt|gct|tcc|  (SEQ ID NO: 54; Cont'd)
    EspI.....                              AflII...
        XmaI....
```

For CDR1:

<1> ADEFGHIKLMNPQRSTVWY 1:1
<2> S(0.2) ADEFGHIKLMNPQRTVWY (0.044 each)
<3> Y(0.2) ADEFGHIKLMNPQRSTVW (0.044 each)

(CDR1 installed as AflII-(SexAI or KasI) cassette.)
 For the most preferred 11 length codon 51
(XXX) is omitted; for the preferred 12 length this codon is <2>

```
------- CDR1 -------------------->|--- FR2 ---------------->
     <1>        <2> <2> xxx <3>
 46  47  48  49  50  51  52  53  54  55  56  57  58  59  60
  Q   -   V   -   -   -   -   L   A   W   Y   Q   Q   K   P      (SEQ ID NO: 55; Cont'd)
|cag| - |gtt| - | - | - | - |ctt|gct|tgg|tat|caa|cag|aaa|cct|   (SEQ ID NO: 54; Cont'd)
                                        SexAI...
```

TABLE 7-continued

A27:JH1 Human Kappa light chain gene

For CDR2:

<1> ADEFGHIKLMNPQRSTVWY 1:1
<2> S(0.2) ADEFGHIKLMNPQRTVWY (0.044 each)
<4> A(0.2) DEFGHIKLMNPQRSTVWY (0.044 each)

CDR2 installed as (SexAI or KasI) to (BamHI or RsrII) cassette.)

```
----- FR2 ---------------------->|------ CDR2 ---------->
                                    <1>       <2>      <4>
  61  62  63  64  65  66  67  68  69  70  71  72  73  74  75
   G   Q   A   P   R   L   L   I   Y   -   A   S   -   R   -   (SEQ ID NO: 55; Cont'd)
|ggt|cag|gcg|ccg|cgt|tta|ctt|att|tat| - |gct|tct| - |cgc| - | (SEQ ID NO: 54; Cont'd)
SexAI.... KasI....

CDR2-->|--- FR3 ----------------------------------------------->
<1>
  76  77  78  79  80  81  82  83  84  85  86  87  88  89  90
   -   G   I   P   D   R   F   S   G   S   G   S   G   T   D
| - |ggg|atc|ccg|gac|cgt|ttc|tct|ggc|tct|ggt|tca|ggt|act|gac|
        BamHI...
                RsrII.....

------ FR3 ------------------------------------------------>
  91  92  93  94  95  96  97  98  99 100 101 102 103 104 105
   F   T   L   T   I   S   R   L   E   P   E   D   F   A   V   (SEQ ID NO: 55' Cont'd)
|ttt|acc|ctt|act|att|tct|aga|ttg|gaa|cct|gaa|gac|ttc|gct|gtt| (SEQ ID NO: 54; Cont'd)
                        XbaI...
```

For CDR3 (Length 9):

<1> ADEFGHIKLMNPQRSTVWY 1:1
<3> Y(0.2) ADEFGHIKLMNPQRTVW (0.044 each)

For CDR3 (Length 8): QQ33111P
1 and 3 as defined for Length 9
For CDR3 (Length 10): QQ3211PP1T
1 and 3 as defined for Length 9
2 S(0.2) and 0.044 each of ADEFGHIKLMNPQRTVWY
CDR3 installed as XbaI to (StyI or BsiWI) cassette.

```
----------->|----CDR3-------------------------->|-----FR4--->
              <3> <1> <1> <1>      <1>
 106 107 108 109 110 111 112 113 114 115 116 117 118 119 120
   Y   Y   C   Q   Q   -   -   -   -   P   -   T   F   G   Q   (SEQ ID NO: 55; Cont'd)
|tat|tat|tgc|caa|cag| - | - | - | - |cct| - |act|ttc|ggt|caa| (SEQ ID NO: 54; Cont'd)
            BstXI..........

-----FR4------------------>|   <------- Ckappa -----------
 121 122 123 124 125 126 127   128 129 130 131 132 133 134
   G   T   K   V   E   I   K     R   T   V   A   A   P   S
|ggt|acc|aag|gtt|gaa|atc|aag| |cgt|acg|gtt|gcc|gct|cct|agt|
        StyI....                BsiWI..

135 136 137 138 139 140 141 142 143 144 145 146 147 148 149
   V   F   I   F   P   P   S   D   E   Q   L   K   S   G   T
|gtg|ttt|atc|ttt|cct|cct|tct|gac|gaa|caa|ttg|aag|tca|ggt|act|
                            MfeI...

150 151 152 153 154 155 156 157 158 159 160 161 162 163 164
   A   S   V   V   C   L   L   N   N   F   Y   P   R   E   A   (SEQ ID NO: 55; Cont'd)
|gct|tct|gtc|gta|tgt|ttg|ctc|aac|aat|ttc|tac|cct|cgt|gaa|gct| (SEQ ID NO: 54; Cont'd)
                                                BssSI...

165 166 167 168 169 170 171 172 173 174 175 176 177 178 179
   K   V   Q   W   K   V   D   N   A   L   Q   S   G   N   S
|aaa|gtt|cag|tgg|aaa|gtc|gat|aac|gcg|ttg|cag|tcg|ggt|aac|agt|
                            MluI....

180 181 182 183 184 185 186 187 188 189 190 191 192 193 194
   Q   E   S   V   T   E   Q   D   S   K   D   S   T   Y   S
|caa|gaa|tcc|gtc|act|gaa|cag|gat|agt|aag|gac|tct|acc|tac|tct|

195 196 197 198 199 200 201 202 203 204 205 206 207 208 209
   L   S   S   T   L   T   L   S   K   A   D   Y   E   K   H
|ttg|tcc|tct|act|ctt|act|tta|tca|aag|gct|gat|tat|gag|aag|cat|

210 211 212 213 214 215 216 217 218 219 220 221 222 223 224
   K   V   Y   A   C   E   V   T   H   Q   G   L   S   S   P   (SEQ ID NO: 55; Cont'd)
```

TABLE 7-continued

A27:JH1 Human Kappa light chain gene

```
|aag|gtc|tat|GCt|TGC|gaa|gtt|acc|cac|cag|ggt|ctg|agc|tcc|cct| (SEQ ID NO: 54; Cont'd)
                                                   SacI....

225 226 227 228 229 230 231 232 233 234
 V   T   K   S   F   N   R   G   E   C  (SEQ ID NO: 55; Cont'd)
|gtt|acc|aaa|agt|ttc|aac|cgt|ggt|gaa|tgc|taa|tag ggcgcgcc
              DsaI....                          AscI....
                                                BssHII acgcatctctaa gcggccgc aacaggaggag (SEQ ID NO: 54; Cont'd)
            NotI....
```

TABLE 8

2a2:JH2 Human lambda-chain gene

```
gaggaccatt gggcccc   ttactccgtgac
ScaB...... EcoO109I
         ApaI..

-----------FR1-------------------------------------->
            1   2   3   4   5   6   7   8   9  10  11  12  13  14  15
            S   A   Q   S   A   L   T   Q   P   A   S   V   S   G   P   G  (SEQ ID NO: 57)
           agt|gca|caa|tcc|gct|ctc|act|cag|cct|gct|agc|gtt|tcc|ggg|tca|cct|ggt| (SEQ ID NO: 56)
           ApaLI...                         NheI...              BstEII...
                                                                    SexAI....

For CDR1 (length 14):

<1> = 0.27 T, 0.27 G, 0.027 each of ADEFHIKLMNPQRSVWY, no C
<2> = 0.27 D, 0.27 N, 0.027 each of AEFGHIKLMPQRSTVWY, no C
<3> = 0.36 Y, 0.0355 each of ADEFGHIKLMNPQRSTVW, no C
                            T   G  <1>  S   S  <2>  V   G
------FR1------------------>  |-----CDR1--------------------
 16  17  18  19  20  21  22   23  24  25  26  27  28  29  30
  Q   S   I   T   I   S   C    T   G   -   S   S   -   V   G
|caa|agt|atc|act|att|tct|tgt|aca|ggt| - |tct|tct| - |gtt|ggc|
                            BsrGI..

<1> <3> <2> <3>  V   S  = vg Scheme #1, length = 14
-----CDR1-------------->|--------FR2---------------------
 31  32  33  34  35  36   37  38  39  40  41  42  43  44  45
  -   -   -   -   V   S    W   Y   Q   Q   H   P   G   K   A  (SEQ ID NO: 57; Cont'd)
|  - |  - |  - |  - |gtt|tct|tgg|tat|caa|caa|cac|ccg|ggc|aag|gcg| (SEQ ID NO: 56; Cont'd)
                                     XmaI....    KasI.....
                                     AvaI....

A second Vg scheme for CDR1 gives segments of length 11:
T22G<2><4>L<4><4><4><3><4><4> where
<4> = equimolar mixture of each of ADEFGHIKLMNPQRSTVWY, no C
<3> = as defined above for the alternative CDR1

For CDR2:

<2> and <4> are the same variegation as for CDR1
                <4> <4> <4> <2>  R   P   S
--FR2------------->|------CDR2-------------->|-----FR3-
 46  47  48  49  50  51  52  53  54  55  56  57  58  59  60
  P   K   L   M   I   Y   -   -   -   -   R   P   S   G   V
|ccg|aag|ttg|atg|atc|tac|  - |  - |  - |  - |cgt|cct|tct|ggt|gtt|
KasI....

-------FR3---------------------------------------------
 61  62  63  64  65  66  67  68  69  70  71  72  73  74  75
  S   N   R   F   S   G   S   K   S   G   N   T   A   S   L  (SEQ ID NO: 57; Cont'd)
|agc|aat|cgt|ttc|tcc|gga|tct|aaa|tcc|ggt|aat|acc|gca|agc|tta| (SEQ ID NO: 56; Cont'd)
              BspEI..                              HindIII.
                BsaBI........(blunt)

-------FR3---------------------------------------->|
 76  77  78  79  80  81  82  83  84  85  86  87  88  89  90
  T   I   S   G   L   Q   A   E   D   E   A   D   Y   Y   C  (SEQ ID NO: 57; Cont'd)
|act|atc|tct|ggt|ctg|cag|gct|gaa|gac|gag|gct|gac|tac|tat|tgt| (SEQ ID NO: 56; Cont'd)
              PstI...
```

TABLE 8-continued

2a2:JH2 Human lambda-chain gene

CDR3 (Length 11):

<2> and <4> are the same variegation as for CDR1
<5> = 0.36 S, 0.0355 each of ADEFGHIKLMNPQRTVWY no C CDR3 (Length 10): <5> SY <1> <5> S <5> <1> <4> V
<1> is an equimolar mixture of ADEFGHIKLMNPQRSTVWY, no C
<4> and <5> are as defined for Length 11
  <4> <5> <4> <2> <4> S <4> <4> <4> <4> V

```
-----CDR3-------------------------->|---FR4---------
 91  92  93  94  95  96  97  98  99 100 101 102 103 104 105
  -   -   -   -   -   S   -   -   -   -   V   F   G   G   G
| - | - | - | - | - |tct| - | - | - | - |gtc|ttc|ggc|ggt|ggt|
                                                     KpnI...

-------FR4-------------->
106 107 108 109 110 111 112 113 114 115 116 117 118 119 120
  T   K   L   T   V   L   G   Q   P   K   A   A   P   S   V
|acc|aaa|ctt|act|gtc|ctc|ggt|caa|cct|aag|gct|gct|cct|tcc|gtt|
KpnI...                      HincII..
                                  Bsu36I...

121 122 123 124 125 126 127 128 129 130 131 132 133 134 135
  T   L   F   P   P   S   S   E   E   L   Q   A   N   K   A    (SEQ ID NO: 57; Cont'd)
|act|ctc|ttc|cct|cct|agt|tct|gaa|gag|ctt|caa|gct|aac|aag|gct|  (SEQ ID NO: 56; Cont'd)
                          SapI.....

136 137 138 139 140 141 142 143 144 145 146 147 148 149 150
  T   L   V   C   L   I   S   D   F   Y   P   G   A   V   T
|act|ctt|gtt|tgc|ttg|atc|agt|gac|ttt|tat|cct|ggt|gct|gtt|act|
              BclI....

151 152 153 154 155 156 157 158 159 160 161 162 163 164 165
  V   A   W   K   A   D   S   S   P   V   K   A   G   V   E
|gtc|gct|tgg|aaa|gcc|gat|tct|tct|cct|gtt|aaa|gct|ggt|gtt|gag|
                                                      BsmBI...

166 167 168 169 170 171 172 173 174 175 176 177 178 179 180
  T   T   T   P   S   K   Q   S   N   N   K   Y   A   A   S
|acg|acc|act|cct|tct|aaa|caa|tct|aac|aat|aag|tac|gct|gcg|agc|
BsmBI....                                         SacI....

181 182 183 184 185 186 187 188 189 190 191 192 193 194 195
  S   Y   L   S   L   T   P   E   Q   W   K   S   H   K   S    (SEQ ID NO: 57; Cont'd)
|tct|tat|ctt|tct|ctc|acc|cct|gaa|caa|tgg|aag|tct|cat|aaa|tcc|  (SEQ ID NO: 56; Cont'd)
SacI...

196 197 198 199 200 201 202 203 204 205 206 207 208 209 210
  Y   S   C   Q   V   T   H   E   G   S   T   V   E   K   T
|tat|tcc|tgt|caa|gtt|act|cat|gaa|ggt|tct|acc|gtt|gaa|aag|act|
                              BspHI...

211 212 213 214 215 216 217 218 219
  V   A   P   T   E   C   S   .   .
|gtt|gcc|cct|act|gag|tgt|tct|tag|tga|ggcgcgcc
                              AscI....
                                  BssHII aacgatgttc aag gcggccgc aacaggaggag   (SEQ ID NO: 56; Cont'd)
           NotI.... Scab.......
```

TABLE 9

Oligonucleotides For Kappa and Lambda Light Chain Variegation

| | |
|---|---|
| (Ctop25): | 5'-gctctggtcaac\|tta\|agg\|gct\|gag\|g-3' (SEQ ID NO: 58) |
| (CtprmA): | 5'-gctctggtcaac\|tta\|agg\|gct\|gag\|gac\|acc\|gct\|gtc\|tac\|tac\|tgc\|gcc-3' (SEQ ID NO: 59) |
| |                 AflII... |
| (CBprmB) [RC]: | 5'-\|tac\|ttc\|gat\|tac\|ttg\|ggc\|caa\|ggt\|acc\|ctg\|gtc\|acc\|tcgctccacc-3' (SEQ ID NO: 60) |
| |                                                                       BstEII... |
| (CBot25) [RC]: | 5'-\|ggt\|acc\|ctg\|gtc\|acc\|tcgctccacc-3' (SEQ ID NO: 61) |

TABLE 9-continued

Oligonucleotides For Kappa and Lambda Light Chain Variegation

Kappa chains:        CDR1 ("1"), CDR2 ("2"), CDR3 ("3")

CDR1

| | |
|---|---|
| (Ka1Top610): | 5'-ggtctcagttg\|cta\|agc\|ccg\|ggt\|gaa\|cgt\|gct\|acc\|tta\|agt\|tgc\|<br>cgt\|gct\|tcc\|cag-3' (SEQ ID NO: 62) |
| (Ka1STp615): | 5'-ggtctcagttg\|cta\|agc\|ccg\|ggt\|g-3' (SEQ ID NO: 63) |
| (Ka1Bot620) [RC]: | 5'-ctt\|gct\|tgg\|tat\|caa\|cag\|aaa\|cct\|ggt\|cag\|gcg\|ccaagtcgtgtc-3' (SEQ ID NO: 64) |
| (Ka1SB625) [RC]: | 5'-cct\|ggt\|cag\|gcg\|ccaagtcgtgtc-3' (SEQ ID NO: 65) |
| (Ka1vg600): | 5'-gct\|acc\|tta\|agt\|tgc\|cgt\|gct\|tcc\|cag-<br>\|<1>\|gtt\|<2>\|<2>\|<3>\|ctt\|gct\|tgg\|tat\|caa\|cag\|aaa\|cc-3' (SEQ ID NO: 66) |
| (Ka1vg600-12): | 5'-gct\|acc\|tta\|agt\|tgc\|cgt\|gct\|tcc\|cag-<br>\|<1>\|gtt\|<2>\|<2>\|<2>\|<3>\|ctt\|gct\|tgg\|tat\|caa\|cag\|aaa\|cc-3' (SEQ ID NO: 67) |

CDR2

| | |
|---|---|
| (Ka2Tshort657): | 5'-cacgagtccta\|cct\|ggt\|cag\|gc-3' (SEQ ID NO: 68) |
| (Ka2Tlong655): | 5'-cacgagtccta\|cct\|ggt\|cag\|gcg\|ccg\|cgt\|tta\|ctt\|att\|tat-3' (SEQ ID NO: 69) |
| (Ka2Bshort660): [RC]: | 5'-\|gac\|cgt\|ttc\|tct\|ggt\|tctcacc-3' (SEQ ID NO: 70) |
| (Ka2vg650): | 5'-cag\|gcg\|ccg\|cgt\|tta\|ctt\|att\|tat\|<1>\|gct\|tct\|<2>\|-<br>\|cgc\|<4>\|<1>\|ggg\|atc\|gac\|cgt\|ttc\|tct\|ggt\|tctcacc-3' (SEQ ID NO: 71) |

CDR3

| | |
|---|---|
| (Ka3Tlon672): | 5'-gacgagtccttct\|aga\|ttg\|gaa\|cct\|gaa\|gac\|ttc\|gct\|gtt\|tat\|tat\|tgc\|caa\|c-3'<br>(SEQ ID NO: 72) |
| (Ka3BotL682) [RC]: | 5'-act\|ttc\|ggt\|caa\|ggt\|acc\|aag\|gtt\|gaa\|atc\|aag\|cgt\|acg\|tcacaggtgag-3'<br>(SEQ ID NO: 73) |
| (Ka3Bsho694) [RC]: | 5'-gaa\|atc\|aag\|cgt\|acg\|tcacaggtgag-3' (SEQ ID NO: 74) |
| (Ka3vg670): | 5'-gac\|ttc\|gct\|gtt\|-<br>\|tat\|tat\|tgc\|caa\|cag\|<3>\|<1>\|<1>\|<1>\|cct\|<1>\|act\|ttc\|ggt\|caa\|-<br>\|ggt\|acc\|aag\|gtt\|g-3' (SEQ ID NO: 75) |
| (Ka3vg670-8): | 5'-gac\|ttc\|gct\|gtt\|-<br>\|tat\|tat\|tgc\|caa\|cag\|<3>\|<3>\|<1>\|<1>\|<1>\|cct\|ttc\|ggt\|caa\|-<br>\|ggt\|acc\|aag\|gtt\|g-3' (SEQ ID NO: 76) |
| (Ka3vg670-10): | 5'-gac\|ttc\|gct\|gtt\|tat\|-<br>\|tat\|tgc\|caa\|cag\|<3>\|<2>\|<1>\|<1>\|cct\|cct\|<1>\|act\|ttc\|ggt\|caa\|-<br>\|ggt\|acc\|aag\|gtt\|g-3' (SEQ ID NO: 77) |

Lambda Chains:        CDR1 ("1"), CDR2 ("2"), CDR3 ("3")

CDR1

| | |
|---|---|
| (Lm1TPri75): | 5'-gacgagtcctgg\|tca\|cct\|ggt\|-3' (SEQ ID NO: 78) |
| (Lm1tlo715): | 5'-gacgagtcctgg\|tca\|cct\|ggt\|caa\|agt\|atc\|act\|att\|tct\|tgt\|aca\|ggt-3' (SEQ ID NO: 79) |
| (Lm1blo724) [rc]: | 5'-gtt\|tct\|tgg\|tat\|caa\|caa\|cac\|ccg\|ggc\|aag\|gcg\|agatcttcacaggtgag-3' (SEQ ID NO: 80) |
| (Lm1bsh737) [rc]: | 5'-gc\|aag\|gcg\|agatcttcacaggtgag-3' (SEQ ID NO: 81) |
| (Lm1vg710b): | 5'-gt\|atc\|act\|att\|tct\|tgt\|aca\|ggt\|<2>\|<4>\|ctc\|<4>\|<4>\|<4>\|-<br>\|<3>\|<4>\|<4>\|tgg\|tat\|caa\|caa\|cac\|cc-3' (SEQ ID NO: 82) |
| (Lm1vg710): | 5'-gt\|atc\|act\|att\|tct\|tgt\|aca\|ggt\|<1>\|tct\|tct\|<2>\|gtt\|ggc\|-<br>\|<1>\|<3>\|<2>\|<3>\|gtt\|tct\|tgg\|tat\|caa\|caa\|cac\|cc-3' (SEQ ID NO: 83) |

CDR2

| | |
|---|---|
| (Lm2TSh757): | 5'-gagcagaggac\|ccg\|ggc\|aag\|gc-3' (SEQ ID NO: 84) |
| (Lm2TLo753): | 5'-gagcagaggac\|ccg\|ggc\|aag\|gcg\|ccg\|aag\|ttg\|atg\|atc\|tac-3' (SEQ ID NO: 85) |
| (Lm2BLo762) [RC]: | 5'-cgt\|cct\|tct\|ggt\|gtc\|agc\|aat\|cgt\|ttc\|tcc\|gga\|tcacaggtgag-3' (SEQ ID NO: 86) |
| (Lm2BSh765) [RC]: | 5'-cgt\|ttc\|tcc\|gga\|tcacaggtgag-3' (SEQ ID NO: 87) |
| (Lm2vg750): | 5'-g\|ccg\|aag\|ttg\|atg\|atc\|tac\|-<br><4>\|<4>\|<4>\|<2>\|cgt\|cct\|tct\|ggt\|gtc\|agc\|aat\|c-3' (SEQ ID NO: 88) |

CDR3

| | |
|---|---|
| (Lm3TSh822): | 5'-ctg\|cag\|gct\|gaa\|gac\|gag\|gct\|gac-3' (SEQ ID NO: 89) |
| (Lm3TLo819): | 5'-ctg\|cag\|gct\|gaa\|gac\|gag\|gct\|gac\|tac\|tat\|tgt\|-3' (SEQ ID NO: 90) |
| (Lm3BLo825) [RC]: | 5'-gtc\|ttc\|ggc\|ggt\|ggt\|acc\|aaa\|ctt\|act\|gtc\|ctc\|ggt\|caa\|cct\|aag\|g-<br>acacaggtgag-3' (SEQ ID NO: 91) |
| (Lm3BSh832) [RC]: | 5'-c\|ggt\|caa\|cct\|aag\|gacacaggtgag-3' (SEQ ID NO: 92) |
| (Lm3vg817): | 5'-gac\|gag\|gct\|gac\|tac\|tat\|tgt\|-<br>\|<4>\|<5>\|<4>\|<2>\|<4>\|tct\|<4>\|<4>\|<4>\|-<br>Gtc\|ttc\|ggc\|ggt\|ggt\|acc\|aaa\|ctt\|ac-3' (SEQ ID NO: 93) |
| (Lm3vg817-10): | 5'-gac\|gag\|gct\|gac\|tac\|tat\|tgt\|-<br>\|<5>\|agc\|tat\|<1>\|<5>\|tct\|<5>\|<1>\|<4>\|gtc\|ttc\|ggc\|ggt\|ggt\|-<br>\|acc\|aaa\|ctt\|ac-3' (SEQ ID NO: 94) |

TABLE 10

A27:JH1 Kappa light chain gene with stuffers in place of CDRs

Each stuffer contains at least one stop codon and a
restriction site that will be unique within the diversity vector.

```
gaggacc attgggcccc ctccgagact ctcgagcgca
  Scab.....EcoO109I
         ApaI.
                                XhoI..

acgcaattaa tgtgagttag ctcactcatt aggcacccca ggctttacac tttatgcttc
    ..-35..           Plac                         ..-10.

cggctcgtat gttgtgtgga attgtgagcg gataacaatt tcacacagga aacagctatgac catgatta cgccaagctt tggagccttt tttttggaga ttttcaac  (SEQ ID NO: 95)
         PflMI.......
            Hind3.
```

M13 III signal sequence (AA seq)-------------------------->

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| M | K | K | L | L | F | A | I | P | L  | V  | V  | P  | F  | Y  |

```
gtg aag aag ctc cta ttt gct atc ccg ctt gtc gtt ccg ttt tac
```

--Signal--> FR1---------------------------------------->

| 16 | 17 | 18 | 19 | 20 | 21 | 22 | 23 | 24 | 25 | 26 | 27 | 28 | 29 | 30 |
|----|----|----|----|----|----|----|----|----|----|----|----|----|----|----|
| S  | H  | S  | A  | Q  | S  | V  | L  | T  | Q  | S  | P  | G  | T  | L  |

```
|agc|cat|agt|gca|caa|tcc|gtc|ctt|act|caa|tct|cct|ggc|act|ctt|
             ApaLI...
```

----- FR1 ---------------------------->|-------Stuffer->

| 31 | 32 | 33 | 34 | 35 | 36 | 37 | 38 | 39 | 40 | 41 | 42 | 43 |
|----|----|----|----|----|----|----|----|----|----|----|----|----|
| S  | L  | S  | P  | G  | E  | R  | A  | T  | L  | S  |    |    |

```
|tcg|cta|agc|ccg|ggt|gaa|cgt|gct|acc|tta|agt|tag|taa|gct|ccc|  (SEQ ID NO: 95; Cont'd)
   EspI.....              AflII...
       XmaI....
```
(SEQ ID NO: 96)

- Stuffer for CDR1--> FR2 ------- FR2 ------>|-----------Stuffer for CDR2

|    |    |    | 59 | 60 | 61 | 62 | 63 | 64 | 65 | 66 |
|----|----|----|----|----|----|----|----|----|----|----|
|    |    |    | K  | P  | G  | Q  | A  | P  | R  |    |

```
|agg|cct|ctt|tga|tct|g|aaa|cct|ggt|cag|gcg|ccg|cgt|taa|tga|aagcgctaatggccaacagtg
  StuI...       SexAI... KasI....                 AfeI.. MscI..
```

Stuffer-->|--- FR3 ---------------------------------------->

| 76 | 77 | 78 | 79 | 80 | 81 | 82 | 83 | 84 | 85 | 86 | 87 | 88 | 89 | 90 |
|----|----|----|----|----|----|----|----|----|----|----|----|----|----|----|
| T  | G  | I  | P  | D  | R  | F  | S  | G  | S  | G  | S  | G  | T  | D  |

```
|act|ggg|atc|ccg|gac|cgt|ttc|tct|ggc|tct|ggt|tca|ggt|act|gac|  (SEQ ID NO: 95; Cont'd)
      BamHI...
          RsrII.....
```
(SEQ ID NO: 96; Cont'd)

------ FR3 ----->----------------STUFFER for CDR3------------------>

| 91 | 92 | 93 | 94 | 95 | 96 | 97 |
|----|----|----|----|----|----|----|
| F  | T  | L  | T  | I  | S  | R  |

```
|ttt|acc|ctt|act|att|tct|aga|taa|tga| gttaac tag acc tacgta acc tag
                       XbaI...    HpaI..      SnaBI.
```

-----------------CDR3 stuffer------------------>|-----FR4--->

|    |    |    | 118 | 119 | 120 |
|----|----|----|-----|-----|-----|
|    |    |    | F   | G   | Q   |

```
                              |ttc|ggt|caa|
```

-----FR4-------------------->|     <------- Ckappa ------------

| 121 | 122 | 123 | 124 | 125 | 126 | 127 | 128 | 129 | 130 | 131 | 132 | 133 | 134 |
|-----|-----|-----|-----|-----|-----|-----|-----|-----|-----|-----|-----|-----|-----|
| G   | T   | K   | V   | E   | I   | K   | R   | T   | V   | A   | A   | P   | S   |

```
|ggt|acc|aag|gtt|gaa|atc|aag|   |cgt|acg|gtt|gcc|gct|cct|agt|  (SEQ ID NO: 95; Cont'd)
       StyI....                  BsiWI..
```
(SEQ ID NO: 96; Cont'd)

| 135 | 136 | 137 | 138 | 139 | 140 | 141 | 142 | 143 | 144 | 145 | 146 | 147 | 148 | 149 |
|-----|-----|-----|-----|-----|-----|-----|-----|-----|-----|-----|-----|-----|-----|-----|
| V   | F   | I   | F   | P   | P   | S   | D   | E   | Q   | L   | K   | S   | G   | T   |

```
|gtg|ttt|atc|ttt|cct|cct|tct|gac|gaa|caa|ttg|aag|tca|ggt|act|    (SEQ ID NO: 95; Cont'd)
                           MfeI...

acgcatctctaa gcggccgc aacaggaggag
         NotI....
           EagI..
```

TABLE 11

2a2:JH2 Human lambda-chain gene with stuffers in place of CDRs

```
gaggaccatt gggcccc   ttactccgtgac
ScaB...... EcoO109I
         ApaI..

-----------FR1-------------------------------------->
           1   2   3   4   5   6   7   8   9  10  11  12  13  14  15
         S   A   Q   S   A   L   T   Q   P   A   S   V   S   G   S   P   G
        agt|gca|caa|tcc|gct|ctc|act|cag|cct|gct|agc|gtt|tcc|ggg|tca|cct|ggt|
         ApaLI...                       NheI...           BstEII...
                                                                   SexAI....

-------FR1------------------->  |-----stuffer for CDR1---------
 16  17  18  19  20  21  22  23
  Q   S   I   T   I   S   C   T (SEQ ID NO: 98)
|caa|agt|atc|act|att|tct|tgt|aca|tct tag tga ctc (SEQ ID NO: 97)
                             BsrGI..

-----Stuffer--------------------------->-------FR2---------->
 31  32  33  34  35  36  37  38  39  40  41  42  43  44  45
  R   S   |   |   P   |                   H   P   G   K   A
aga tct taa tga ccg tag                 cac|ccg|ggc|aag|gcg|
 BglII                                      XmaI....   KasI.....
                                            AvaI....

--|-------------Stuffer for CDR2 ------------------------------------->
  P
|ccg|taa|tga|atc tcg tac g                              ct|ggt|gtt|
 KasI....           BsiWI...

--------FR3-------------------------------------------
 61  62  63  64  65  66  67  68  69  70  71  72  73  74  75
  S   N   R   F   S   G   S   K   S   G   N   T   A   S   L (SEQ ID NO: 98; Cont'd)
|agc|aat|cgt|ttc|tcc|gga|tct|aaa|tcc|ggt|aat|acc|gca|agc|tta| (SEQ ID NO: 97;
 Cont'd)
                 BspEI..                         HindIII.
                    BsaBI........(blunt)

-------FR3------------->|--Stuffer for CDR3----------------->|
 76  77  78  79  80  81  82  83  84  85  86  87  88  89  90
  T   I   S   G   L   Q
|act|atc|tct|ggt|ctg|cag|gtt ctg tag ttc caattg ctt tag tga ccc
                 PstI...          MfeI..

-----Stuffer-------------------------->|---FR4---------
                                        103 104 105
                                          G   G   G
                                        |ggc|ggt|ggt|
                                                KpnI...

-------FR4-------------->
 106 107 108 109 110 111 112 113 114 115 116 117 118 119 120
  T   K   L   T   V   L   G   Q   P   K   A   A   P   S   V (SEQ ID NO: 98; Cont'd)
|acc|aaa|ctt|act|gtc|ctc|ggt|caa|cct|aag|gct|gct|cct|tcc|gtt| (SEQ ID NO: 97;
 Cont'd)
 KpnI...                 HincII..
                            Bsu36I...

121 122 123 124 125 126 127 128 129 130 131 132 133 134 135
  T   L   F   P   P   S   S   E   E   L   Q   A   N   K   A
|act|ctc|ttc|cct|cct|agt|tct|gaa|gag|ctt|caa|gct|aac|aag|gct|
                             SapI.....

136 137 138 139 140 141 142 143 144 145 146 147 148 149 150
  T   L   V   C   L   I   S   D   F   Y   P   G   A   V   T (SEQ ID NO: 98; Cont'd)
|act|ctt|gtt|tgc|ttg|atc|agt|gac|ttt|tat|cct|ggt|gct|gtt|act| (SEQ ID NO: 97;
 Cont'd)
                 BclI....
```

The invention relates to generation of useful diversity in synthetic antibody (Ab) gene, especially to Ab genes having frameworks derived from human Abs.

BACKGROUND OF THE INVENTION

Antibodies are highly useful molecules because of their ability to bind almost any substance with high specificity and affinity and their ability to remain in circulation in blood for prolonged periods as therapeutic or diagnostic agents. For treatment of humans, Abs derived from human Abs are much preferred to avoid immune response to the Ab. For example, murine Abs very often cause Human Anti Mouse Antibodies (HAMA) which at a minimum prevent the therapeutic effects of the murine Ab. For many medical applications, monoclonal Abs are preferred. Nowadays the preferred method of obtaining a human Ab having a particular binding specificity is to select the Ab from a library of human-derived Abs displayed on a genetic package, such as filamentous phage.

Libraries of phage-displayed Fabs and scFvs have been produced in several ways. One method is to capture the diversity of donors, either naive or immunized. Another way is to generate libraries having synthetic diversity. The present invention relates to methods of generating useful diversity in human Ab scaffolds.

As is well known, typical Abs consist of two heavy chains (HC) and two light chains (LC). There are several types of HCs: gamma, mu, epsilon, delta, etc. Each type has an N-terminal V domain followed by three or more constant domains. The LCs comprise an N-terminal V domain followed by a constant domain. LCs come in two types: kappa and lambda.

Within each V domain (LC or HC) there are seven canonical regions, named FR1, CDR1, FR2, CDR2, FR3, CDR3, and FR4, where "FR" stands for "Framework Region" and "CDR" stands for "Complementarity Determining Region". For LC and HC, the FR and CDR GLGs have been selected over time to be secretable, stable, non-antigenic and these properties should be preserved as much as possible. Actual Ab genes contain mutations in the FR regions and some of these mutations contribute to binding, but such useful FR mutations are rare and are not necessary to obtain high-affinity binding. Thus, the present invention will concentrate diversity in the CDR regions.

In LC, FR1 up to FR3 and part of CDR3 comes from a genomic collection of genes called "V-genes". The remainder of CDR3 and FR4 comes from a genomic collection of genes called "J-genes". The joining may involve a certain degree of mutation, allowing diversity in CDR3 that is not present in the genomic sequences. After the LC gene is formed, somatic mutations can give rise to mature, rearranged LC genes that have higher affinity for an antigen (Ag) than does any LC encoded by genomic sequences. A large fraction of somatic mutations occur in CDRs.

The HC V region is more complicated. A V gene is joined to a J gene with the possible inclusion of a D segment. About half of HC Abs sequences contain a recognizable D segment in CDR3. The joining is achieved with an amazing degree of molecular sloppiness. Roughly, the end of the V gene may have zero to several bases deleted or changed, the D segment may have zero to many bases removed or changed at either end, a number of random bases may be inserted between V and D or between D and J, and the 5' end of J may be edited to remove or change several bases. Withal, it is amazing that human heavy chains work, but they do. The upshot is that the CDR3 is highly diverse both in encoded amino-acid sequences and in length. In designing synthetic libraries, there is the temptation to just throw in a high degree of synthetic diversity and let the phage sort it out. Nevertheless, D regions serve a function. They cause the Ab repertoire to be rich in sequences that a) allow Abs to fold correctly, and b) are conducive to binding to biological molecules, i.e. antigens.

One purpose of the present invention is to show how a manageable collection of diversified sequences can confer these advantages on synthetic Ab libraries. Another purpose of the present invention is to disclose analysis of known mature Ab sequences that lead to improved designs for diversity in the CDR1 and CDR2 of HC and the three CDRs of lambda and kappa chains.

BRIEF STATEMENT OF THE INVENTION

The invention is directed to methods of preparing synthetically diverse populations of Ab genes suitable for display on genetic packages (such as phage or phagemids) or for other regimens that allow selection of specific binding. Said populations concentrate the diversity into regions of the Ab that are likely to be involved in determining affinity and specificity of the Ab for particular targets. In particular, a collection of actual Ab genes has been analyzed and the sites of actual diversity have been identified. In addition, structural considerations were used to determine whether the diversity is likely to greatly influence the binding activity of the Ab. Schemes of variegation are presented that encode populations in which the majority of members will fold correctly and in which there is likely to be a plurality of members that will bind to any given Ag. Specifically, a plan of variegation is presented for each CDR of the human heavy chain, kappa light chain, and lambda light chain. The variegated CDRs are presented in synthetic HC and LC frameworks.

In one embodiment, the invention involves variegation of human HC variable domains based on a synthetic 3-23 domain joined to a JH4 segment in which the variability in CDR1 and CDR2 comprises sequence variation of segments of fixed length while in CDR3 there are several components such that the population has lengths roughly corresponding to lengths seen in human Abs and having embedded D segments in a portion of the longer segments. In the light chains, the kappa chain is built in an A27 framework and a JK1 while lambda is built in a 2a2 framework with an L2 J region.

EXAMPLES

Choice of a Heavy-Chain V Domain

The HC Germ-Line Gene (GLG) 3-23 (also known as VP-47) accounts for about 12% of all human Abs and it suitable for the framework of the library. Certain types of Ags elicit Abs having particular types of VH genes; in some cases, the types elicited are otherwise rarely found. This apparent Ag/Ab type specificity has been ascribed to possible structural differences between the various families of V genes. It is also possible that the selection has to do with the availability of particular AA types in the GLG CDRs. Suppose, for example, that the sequence YR at positions 4 and 5 of CDR2 is particularly effective in binding a particular type of Ag. Only the V gene 6-1 provides this combination. Most Abs specific for the Ag will come from GLG 6-1. If Y4-R5 were provided in other frameworks, then other frameworks are likely to be as effective in binding the Ag.

Analysis of HC CDR1 and CDR2:

In CDR1 and CDR2 of HCs, the GLGs provide limited length diversity as shown in Table 15P. Note that GLGs provide CDR1s only of the lengths 5, 6, and 7. Mutations during the maturation of the V-domain gene leads to CDR1s having lengths as short as 2 and as long as 16. Nevertheless, length 5 predominates. The preferred length for the present invention is 5 AAs in CDR1 with a possible supplemental components having lengths of 7 and 14.

GLGs provide CDR2s only of the lengths 15-19, but mutations during maturation result in CDR2s of length from 16 to 28 AAs. The lengths 16 and 17 predominate in mature Ab genes and length 17 is the most preferred length for the present invention. Possible supplementary components of length 16 and 19 may also be incorporated.

Table 20P shows the AA sequences of human GLG CDR1s and CDR2. Table 21P shows the frequency of each amino-acid type at each position in the GLGs. The GLGs as shown in Table 20P have been aligned by inserting gaps near the middle of the segment so that the ends align.

The 1398 mature V-domain genes used in studying D segments (vide infra) were scanned for examples in which CDR1 and CDR2 could be readily identified. Of this sample 1095 had identifiable CDR1, 2, and 3. The CDRs were identified by finding subsequences of the GLGs in an open reading frame. There are 51 human HC V genes. At the end of FR1, there are 20 different 9-mers. At the start of FR2, there are 11 different 9-mers. At the end of FR2 there are 14 different 9-mers. At the start of FR3, there are 14 different 9-mers. At the end of FR3, there are 13 different 9-mers. At the start of JH, there are three different 9-mers. These motifs were compared to the reported gene in frame and a match, at the site of maximum similarity, of seven out of nine was deemed acceptable. Only when all three CDRs were identified were any of the CDRs included in the analysis. In addition, the type of the gene was determined by comparing the framework regions to the GLG frameworks; the results are shown in Table 22P.

Design of HC CDR1 and CDR2 Diversity.

Diversity in CDR1 and CDR2 was designed from: a) the diversity of the GLGs, b) observed diversity in mature HC genes, and c) structural considerations. In CDR1, examination of a 3D model of a humanized Ab showed that the side groups of residues 1, 3, and 5 were directed toward the combining pocket. Consequently, we allow each of these positions to be any amino-acid type except cysteine. Cysteine can form disulfide bonds. Disulfide bonds are an important component of the canonical Ig fold. Having free thiol groups could interfere with proper folding of the HC and could lead to problems in production or manipulation of selected Abs. Thus, I exclude cysteine from the menu. The side groups of residue 2 is directed away from the combining pocket. Although this position shows substantial diversity, both in GLG and mature genes, I fixed this residue as Tyr because it occurs in 681/820 mature genes (Table 21P). Position 4 is fixed as Met. There is some diversity here, but almost all mature genes have uncharged hydrophobic AA types: M, W, I, V, etc. (Table 21P). Inspection of a 3D model shows that the side group of residue 4 is packed into the innards of the HC. Since we are using a single framework (3-23), we retain the Met that 3-23 has because it is likely to fit very well into the framework of 3-23. Thus, the most preferred CDR1 library consists of XYXMX (SEQ ID NO:109) where X can be any one of [A,D,E,F,G,H,I,K,L,M,N,P,Q,R,S,T,V,W,Y] (no C). The DNA that encodes this is preferably synthesized using trinucleotide building blocks so that each AA type is present in essentially equimolar amounts. Specifically, the X codons are synthesized using a mixture of the codons [gct, gat, gag, ttt, ggt, cat, att, aag, atg, aat, cct, cag, cgt, tct, act, gtt, tgg, tat]. This diversity is shown in the context of a synthetic 3-23 gene in Table 18P. The diversity oligonucleotide (ON) is synthesized from BspEI to BstXI and can be incorporated either by PCR synthesis using overlapping ONs or introduced by ligation of BspEI/BstXI-cut fragments. Table 22P shows ONs that embody the specified variegation. PCR using ON-R1V1vg, ON-R1top, and ON-R1bot gives a dsDNA product of 73 base pairs, cleavage with BspEI and BstXI trims 11 and 13 bases from the ends and provides cohesive ends that can be ligated to similarly cut vector having the synthetic 3-23 domain shown in Table 18P. Replacement of ON-R1V1vg with either ONR1V2vg or ONR1V3vg allows synthesis of the two alternative diversity patterns given below.

Alternatively, one can include CDR1s of length 7 and/or 14. For length 7, a preferred diversity is $(S/T)_1(S/G/x)_2(S/G/x)_3Y_4Y_5W_6(S/G/x)_7$ (SEQ ID NO:107); where (S/T) indicates an equimolar mixture of Ser and Thr codons; (S/G/x) indicates a mixture of 0.2025 S, 0.2025 G, and 0.035 for each of A, D, E, F, H, I, K, L, M, N, P, Q, R, T, V, W, Y. Other proportions could be used. The design gives a predominance of Ser and Gly at positions 2, 3, and 7, as occurs in mature HC genes. For length 14, a preferred pattern of diversity is VSGG-SISXXXYYWX (SEQ ID NO:1) where X can be any AA type except Cys. This pattern appears to arise by insertions into the GLG sequences (SGGYYWS; SEQ ID NO:110, (4-30.1 and 4-31) and similar sequences. There is a preference for a hydrophobic residue at position 1 (V or C) with a second insertion of SISXXX (SEQ ID NO:111) between GG and YY. Diversity ONs having CDR1s of length 7 or 14 are synthesized from BspEI to BstXI and introduced into the library in appropriate proportions to the CDR1 of length 5. The components should be incorporated in approximately the ratios in which they are observed in antibodies selected without reference to the length of the CDRs. For example, the sample of 1095 HC genes examined here have them in the ratios (L=5:L=7:L=14::820:175:23::0.80:0.17:0.02).

CDR2

Diversity at CDR2 was designed with the same considerations: GLG sequences, mature sequences and 3D structure. A preferred length for CDR2 is 17, as shown in Table 18P. Examination of a 3D model suggests that the residues shown as varied in Table 18P are the most likely to interact directly with Ag. Thus a preferred pattern of variegation is: <2>I<2><3>SGG<1>T<1>YADSVKG (SEQ ID NO:2), where <2> indicates a mixture of YRWVGS, <3> is a mixture of P and S, and <1> is a mixture of ADEFGHIKLMN-PQRSTVWY (no C). ON-R2V1vg shown in Table 22P embodies this diversity pattern. PCR with ON-R2V1vg, ON-R2top, and ONR2bot gives a dsDNA product of 122 base pairs. Cleavage with BstXI and XbaI removes about 10 bases from each end and produces cohesive ends that can be ligated to similarly cut vector that contains the 3-23 gene shown in Table 18P.

An alternative pattern would include the variability seen in mature CDR2s as shown in Table 21P: <1>I<4><1><1>G<5><1><1><1>YADSVKG (SEQ ID NO:3), where <4> indicates a mixture of DINSWY, and <5> indicates a mixture of SGDN. This diversity pattern is embodied in ON-R2V2vg shown in Table 22P. For either case, the variegated ONs would be synthesized so that fragments of dsDNA containing the BstXI and XbaI site can be generated by PCR. ON-R2V2vg embodies this diversity pattern.

Alternatively, one can allow shorter or longer CDR2s. Table 22P shows ON-R2V3vg which embodies a CDR2 of length 16 and ON-R2V4vg which embodies a CDR2 of length 19. Table 22P shows ON-R2V3vg is PCR amplified with ON-R2top and ON-R2bo3 while ON-R2V4vg is amplified with ON-R2top and ONR2-bo4.

Analysis of HC CDR3:

CDR3s of HC vary in length and in sequence. About half of human HCs consist of the components: V::nz::D::ny::JHn where V is a V gene, nz is a series of bases (mean 12) that are essentially random, D is a D segment, often with heavy editing at both ends, ny is a series of bases (mean 6) that are essentially random, and JH is one of the six JH segments, often with heavy editing at the 5' end. In HCs that have no identifiable D segment, the structure is V::nz::JHn where JH is usually edited at the 5' end. Our goal is to mimic the diversity of CDR3, but not to duplicate it (which would be impossible). The D segments appear to provide spacer segments that allow folding of the IgG. The greatest diversity is at the junctions of V with D and of D with JH. The planned CDR3 library will consist of several components. Some of these will have only sequence diversity. Others will have sequence diversity with embedded D segments to extend the length while incorporating sequences known to allow Igs to fold.

There are many papers on D segments. Corbett et al. (1997) show which D segments are used in which reading frames. My analysis basically confirms their findings. They did not report, however, the level of editing of each D segment and this information is needed for design of an effective library.

The following diversified sequences would be incorporated in the indicated proportions: "1" stands for 0.095 [G, Y] and 0.048 [A, D, E, F, H, I, K, L, M, N, P, Q, R, S, T, V, W]; double dose of Gly and Tyr plus all other AAs except Cys at equal level.

The amount of each component is assigned from the tabulation of lengths of the collection of natural VH genes. Component 1 represents all the genes having length 0 to 8 (counting from the YYCAR (SEQ ID NO:112) motif to the WG dipeptide motif). Component 2 corresponds the all the chains having length 9 or 10. Component 3 corresponds to the genes having length 11 or 12 plus half the genes having length 13. Component 4 corresponds to those having length 14 plus half those having length 13. Component 5 corresponds to the genes having length 15 and half of those having length 16. Component 6 corresponds to genes of length 17 plus half of those with length 16. Component 7 corresponds to those with length 18. Component 8 corresponds to those having length 19 and greater.

The composition has been adjusted because the first component is not complex enough to justify including it as 10% of the library. If the final library were to be 1. E 9, then 1. E 8 sequences would come from component 1, but it has only 2.6 E 5 CDR3 sequences so that each one would occur in ~385 CDR1/2 contexts. I think it better to have this short CDR3 diversity occur in ~77 CDR1/2 contexts and have the other, longer CDR3s occur more often.

The ONs would be PCR amplified with the primers CtprmA and CBprmB, cut with AflII and BstEII, and ligated to similarly cut V3-23.

This set of components was designed after studying the sequences of 1383 human HC sequences as described below. The proposed components are meant to fulfill the goals:
1) approximately the same distribution of lengths as seen in real Ab genes,
2) high level of sequence diversity at places having high diversity in real Ab genes, and
3) incorporation of constant sequences often seen in real Ab genes.

Note that the design uses JH4 (YFDYWGQGTLVTVSS; SEQ ID NO:20), which is found more often, instead of JH3 (AFDIWGQGTMVTVSS; SEQ ID NO:21). This involves three changes in AA sequence, shown as double underscored bold. An alternative JH segment is shown.

How the Library Components were Designed:

The processing of sequence data was accomplished by a series of custom-written FORTRAN programs, each of which carries out a fairly simple transformation on the data and writes its results as one or more ASCII files. The next program then uses these files as input.

A set of 2049 human heavy-chain genes was selected from the version of GenBank that was available at Dyax on the Sun server on 26 Jun. 2000. A program named "Reformat" changed the format of the files to that of GenBank from the GCG format, creating one file per sequence. A second program named "IDENT_CDR3" processed each of these files as follows. Files were tested for duplication by previous entries, duplicates were discarded. Each reading frame was tested. Most entries had a single open reading frame (ORF), none had two, and some had none. Entries with multiple stops in every reading frame were discarded because this indicates poor quality of sequencing. The sequence was written in triplets in the ORF or in all three reading frames if no ORF was found. The sequence was examined for three motifs: a) AA sequence="YYCxx", b) DNA sequence="tgg ggc (=WG)", and DNA sequence="g gtc acc (=BstEII)". FR3 ends with a conserved motif YYCAR or a close approximation. When writing the DNA sequence, IDENT_CDR3 prints the DNA mostly in lower case. Cysteine codons (TGT or TGC) are printed in uppercase. When the motif "tay tay tgy" is found, IDENT_CDR3 starts a new line that contains "< > xxx xxx xxx xxx xxx" where the xxx's stand for the actual five codons that encode YYC and the next two codons (most often AR or AK). The following DNA is printed in triplets on new lines. A typical processed entry appears as in Table 1P.

Following the YYC motif, IDENT_CDR3 seeks the sequence "TGG GGC" (the "WG" motif) in the correct reading frame, 5/6 bases is counted as a hit. If found, the DNA is made uppercase. Following the WG motif (if found) or the YYC motif (if no WG found), IDENT_CDR3 seeks the sequence "G GTC ACC" (the BstEII site) in the correct reading frame, 6/7 bases is counted as a hit. If found, the bases are made upper case. If either the WG or BstEII motif are not found, a note is inserted saying that the feature was not identified. The output of IDENT_CDR3 was processed by hand. In many cases, the lacking YYC motif could be seen as a closely related sequence, such as YFC, FYC, or HYC. When this was supported by an appropriately positioned WG and/or BstEII site, the effective YYC site was marked and the sequence retained for further analysis. If the YYC motif could not be identified or if the WG or BstEII sites could not be found, the entry was discarded. For example, the entry in Table 2P had no YYC motif.

The double underscored sequence encodes YHCAS and is taken as the end of FR3. Note that there is a WG motif at bases 403-408 (bold upper case) and a BstEII site at bases 420-426 (bold upper case). Using WordPerfect, I first made all occurrences of TGC and TGT bold. I then searched for "YYC not found". If I could see the "YYC"-related sequence quickly, I edited the entry so that a YYC was shown. The entry above would be converted to that shown in Table 3P. This processing reduced the list of entries to 1669.

A third program named "New_DJ" processed the output of IDENT_CDR3. The end of the YYC motif (including the two codon following TGy=Cys) was taken as the end of FR3. The WG motif was taken as the end of the region that might contain a D segment. If WG was not observed and BstEII was, the WG site was assumed to be 17 bases upstream of BstEII. Using the WG motif for alignment, the sequence was compared to each human GLG JH segment (1-6) and the best one identified (New_DJ always assigned a JH segment). Starting from the WG motif of JH and moving toward the 5' end, the program looked for the first codon having more than one mismatch. The region from YYCxx (SEQ ID NO:113) to this codon was taken as the region that might contain a D segment.

The region that might contain a D segment was tested against all the germ-line genes (GLGs) of human D segments and the best D segment was identified. The scoring involved matching the observed sequence to the GLG sequence in all possible ways. Starting at each base, multiply by 4 for a match and divide by 4 for a mismatch. Record the maximum value obtained for this function. The match was deemed significant if 7/7, 8/9, 9/11, etc. or more bases matched. Of the 1383 sequences examined for D segments, "Assign_D" processes the output of New_DJ. For each sequence that had a significant match with a GLG D segment, a file was written containing the putative D segment, the DJ segment, the identified GLG D segment, the identified JH segment, the phase of the match between observed and GLG gene. For example, "D1_1-01_Phz0_hsa239356.txt" is a file recording the match of entry hsa239356 with D1-01 in phase 0. The file contains the information shown in Table 4P. The final DV of the second sequence immediately precedes the WG in JH and is ascribed to JH3. Other files that begin D1_1-01_Phz0 match the same GLG D segment and these can be aligned by sliding amino-acid sequences across each other.

Table 5P shows how sequence hs6d4xb7 is first assigned to JH4 and then to D3-22. Note that the DNA sequence TGGGGG is aligned to the TGG GGC of the GLG and that the sequence is truncated on the left to fit. The program finds that JH4 has the best fit (5 misses and 18 correct out of 23). From the right, the program sees that DYWGQ (underscored) come from JH, but then the match drops off and the rest of the sequence on the left comes either from added bases or a D segment.

The lower part of Table 5P shows that the possible D segment matches D#13 (3-23) is a very good match.

Of 1383 files accepted by Assign_D, 757 had identifiable D segments. The tally of JHs in Table 6P shows that JH4 is by far the most common.

JH4 is most common, JH6 next, followed by JH3 and JH5. JH1 and JH2 are seldom used. Table 7P shows the length distributions of each JH class; they do not differ significantly class to class. These lengths count only amino-acids that are not accounted for by JH and so are shorter that the lengths given in Table 8P which cover from YYCAR (SEQ ID NO:112) to WG.

Table 8P contains the distribution of lengths for a) all the CDR3 segments, b) the CDR3 segments with identified D segments, and c) the CDR3 segments having no identifiable D segment. The CDR3s with identifiable D segments (13.9) are systematically longer than are those that lack D segments (11.2).

The identified CDR3 segments can be collated in two ways: aligned to the left (looking for a pattern following YYCAR; SEQ ID NO:112) or aligned to the right (looking for a pattern preceding WG). Table 9P shows the collation of left-aligned sequences while Table 10P shows the right-aligned sequences. For each position, I have tabulated the frequency of each AA type (A-M in the first block and N-Y in the second). The column headed "#" shows how many sequences have some AA at that position. The final column shows all of the AA types seen at that position with the most frequent first and the least frequent last. In the left-aligned sequences, we see that Gly is highly over-represented in the first seven positions while Tyr is over-represented at positions 8-16.

In Table 11P, I have tabulated the AA frequencies for the sequences having between 7 and 15 AAs between YYCAR (SEQ ID NO:112) and WG. The last four positions can be viewed as coming from JH and so would be given lower levels of diversity than would earlier positions. From these tabulations, I conclude that most AA types are allowed at all the positions, but there is a fairly strong tendency to have Gly at the early positions and to end in Asp-Tyr (DY). We could use these tendencies in designing a pattern of variegation. I would not exclude any AA except Cys, but I might increase the frequency of Gly in the first several positions and Tyr in the last few.

There are 80 sequences (5.8%) having a pair of cysteines in CDR3. It is more surprising that 53 (3.8%) have a single Cys in CDR3.

MS-DOS was used to make a list of the files written by Assign_D. "Filter" converts the output of MS-DOS Dir into a form that can be read into WordPerfect and sorted to bring a files belonging to the same D region together.

"Filter2" collects the sequences and produces a draft table of sequences, grouped by the D-segment used, and written so that the sequences can be aligned. The output of Filter2 were edited by hand. For each group, the translation of the GLG was inserted and the collection of observed sequences was aligned to the conserved part of the GLG. "Filter3" collated the aligned sequences. Table 12P shows an example of an alignment and the tabulation of AA types. The entries are as follows: "Entry" is the name used in the data base, "Seq1" is the sequence from the YYCAR (SEQ ID NO:112) motif to the first amino acid not assigned to JH and "L1" is the length of the segment. The segments are shown aligned to the identified D segment. Seq2 is the sequence from the YYCAR (SEQ ID NO:112) motif to the WG motif (i.e. including part of JH) and "L2" is the length of that sequence. JH is the identified JH segment for this sequence. "P" is the phase of the match. For positive values of P, P bases are found in the observed sequence that do not correspond to any from the GLG, i.e. the observed sequence has had that many bases inserted. For negative values of P, there are |P| bases in the GLG sequence for which there are no corresponding bases in the observed sequence. "Score" is approximately 1/(probability of accidental match). This is calculated by looking at all possible alignments. For each alignment, the score is first set to 1.0. Base by base, the score is multiplied by 4. if the bases match and divided by 4. if they do not. This is done for all starting points and ending points and the maximum value is recorded.

Table 13P is a summary of how often each D segment was identified and in which reading frame. I have not been consistent with Corbett et al. in assigning the phases of the GLG D segments. The MRC Web page that I took the GLGs from did not have D segments D1-14, D4-11, D5-18, or D6-25. None of these contribute to any great extent and this omission is unlikely to have any serious effect on the conclusions. The column headed "%" contains the percentage of the sequences examined here. The column headed "C %" contains the percentage reported by Corbett et al. I assume that the data used in Corbett et al. is mostly included in my collection. Nevertheless, the observed frequencies differ in detail. For example, my compilation shows that 10.7% of the collection contains a D segment encoding two cysteines while they have only 4.16% in this category. In D3 phase "0", I see 19.4% of the collection while they report 11.8%.

The most common actual D segments were further analyzed. The GLGs are heavily edited at either end. The aligned sequences were aligned. For each D-segment having more than seven examples, Filter3 produced a table of the frequency of each amino-acid type at each position. From these tabulations, library components shown in Table 17P were designed. At each position where at least half the examples have an amino acid, I entered either the dominant AA type or "x". An AA type was "dominant" if it occurred more than 50% of the time. L is the length and f is the number of sequences observed that have related sequences.

Table 14P shows possible library components for a library of CDR3's. "L" is the length of the insert and "f" is the frequency of the motif in the assayed collection. Table 17P shows vgDNA that embodies each of the components shown in Table 14P. In Table 17P, the oligonucleotides (ON) Ctop25, CtprmA, CBprmB, and CBot25 allow PCR amplification of each of the variegated ONs (vgDNA): C1t08, C2t10, C3t12, C4t14, C5t15, C6t17, C7t18, and c8t19. After amplification, the dsDNA can be cleaved with AflII and BstEII (or KpnI) and ligated to similarly cleaved vector that contains the remainder of the 3-23 synthetic domain. Preferably, this vector already contains diversity in CDR1 and CDR2 as disclosed herein. Preferably, the recipient vector contains a stuffer in place of CDR3 so that there will be no parental sequence that would then occur in the resulting library. Table 50P shows a version of the V3-23 gene segment with each CDR replaced by a short segment that contains both stop codons and restriction sites that will allow specific cleavage of any vector that does not have the stuffer removed. The stuffer can either be short and contain a restriction enzyme site that will not occur in the finish library, allowing removal of vectors that are not cleaved by both AflII and BstEII (or KpnI) and religated. Alternatively, the stuffer could be 200-400 bases long so that uncleaved or once cleaved vector can be readily separated from doubly cleaved vector.

In the vgDNA for HC CDR3, <1> means a mixture comprising 0.27 Y, 0.27 G, and 0.027 of each of the amino-acid codons {A, D, E, F, H, I, K, L, M, N, P, Q, R, S, T, V, W}; <2> means an equimolar mixture of K and R; and <3> means an equimolar mixture of S and G.

Analysis of Human Kappa Light Chains and Preferred Variegation Scheme:

A collection of 285 human kappa chains was assembled from the public data base. Table 27 shows the names of the entries used. The GLG sequences of nine bases at each end of the framework regions were used to find the FR/CDR junctions. Only in cases where all six junctions could be found was the sequences included. Table 25P shows the distribution of lengths in CDRs in human kappas. CDR1s with lengths of 11, 12, 13, 16, and 17 were observed with 11 being predominant and 12 well represented. CDR2 exhibits only length 7. CDR3 exhibits lengths of 1, 4, 6, 7, 8, 9, 10, 11, 12, 13, and 19. Essentially all examples are in the 8, 9, or 10 length groups.

Table 26P shows the distribution of V and J genes seen in the sample. A27 is the most common V and JK1 is the most common J. Thus, a suitable synthetic kappa gene comprises A27 joined to JK1. Table 30P shows a suitable synthetic kappa chain gene, including a PlacZ promoter, ribosome-binding site, and signal sequence (M13 III signal). The DNA sequence encodes the GLG amino-acid sequence, but does not comprise the GLG DNA sequence. Restriction sites are designed to fall within each framework region so that diversity can be cloned into the CDRs. XmaI and EspI are in FR1, SexAI is in FR2, RsrII is in FR3, and KpnI (or Acc65I) are in FR4. Additional sites are provided in the constant kappa chain to facilitate construction of the gene.

Table 30P also shows a suitable scheme of variegation for kappa. In CDR1, a preferred length is 11 codons. The A27 GLG has a CDR1 of 12 codons, but the sample of mature kappa chains has length 11 predominating. One could also introduce a component of kappas having length 12 in CDR1 by introducing codon 52 as <2> (i.e. a Ser-biased mixture). CDR2 of kappa is always 7 codons. Table 31P shows a tally of 285 CDR2s and a preferred variegation scheme for CDR2. The predominant length of CDR3 in kappa chains is 9 codons. Table 32P shows a tally of 166 CDR3s from human kappas and a preferred variegation scheme (which is also shown in Table 30P).

Analysis of Lambda Chains and Preferred Variegation Scheme:

A collection of 158 lambda sequences was obtained from the public data base. Of these 93 contained sequences in which the FR/CDR boundaries could be identified automatically. Table 33P shows the distribution of lengths of CDRs.

Method of Construction:

The diversity of HC, kappa, and lambda are best constructed in separate vectors. First a synthetic gene is designed to embody each of the synthetic variable domains. The light chains are bounded by restriction sites for ApaLI (positioned at the very end of the signal sequence) and AscI (positioned afer the stop codon). The heavy chain is bounded by SfiI (positioned within the PelB signal sequence) and NotI (positioned in the linker between CH1 and the anchor protein. The initial genes are made with "stuffer" sequences in place of the desired CDRs. A "Stuffer" is a sequence the is to be cut away and replaced by diverse DNA but which does not allow expression of a functional antibody gene. For example, the stuffer may contain several stop codons and restriction sites that will not occur in the correct finished library vector. In Table 40P, the stuffer for CDR1 of kappa A27 contains a StuI site. The vgDNA for CDR1 is introduced as a cassette from Espl, XmaI, or AflII to either SexAI or KasI. After the ligation, the DNA is cleaved with StuI; there should be no StuI sites in the desired vectors.

REFERENCES

Corbett, SJ, Tomlinson, I M, Sonnhammer, ELL, Buck, D, Winter, G. "Sequences of the Human Immunoglobulin Diversity (D) Segment Locus: A Systematic Analysis Provides No Evidence for the Use of DIR Segments, Inverted D Segments, 'Minor' D Segments or D-D Recombination". *J Molec Biol* (1997) 270:587-597.

TABLE 1P

Typical entry in which YYC motif is found.
++++C:\tmp\haj10335.txt

```
LOCUS       HAJ10335        306 bp    mRNA           PRI      18-AUG-1998
DEFINITION  Homo sapiens mRNA for immunoglobulin heavy chain variable region,
            clone ELD16/6.
ACCESSION   AJ010335
VERSION     AJ010335.1 GI: 3445266
  Ngene =   306

Stop codons in reading frame 1
    49 115 124 253 277

No stops in reading frame 2
 Stop codons in reading frame 3
    12 60 81 147 204 213

1    t ttg ggg tcc ctg aga ctc tcc TGT gca gcc tct gga ttc acc
```

TABLE 1P-continued

Typical entry in which YYC motif is found.
++++C:\tmp\haj10335.txt

```
 44 gtc agt agc aac tac atg acc tgg gtc cgc cag gct cta ggg aag 89 ggg ctg gag tgg gtc tca gtt att tat agc ggt ggt agc aca tac 134 tac gca gac tcc gtg aag ggc gga ttc acc atc tcc aga gac aat 179 tcc aag aac aca ctg tat ctt caa atg aac agc ctg aga ccc gag 224 gac acg gct gtg <      > TAT TAC TGT gcg aca 251 ggt aat cgc ctg gaa atg gct gca att aac TGG GGC caa gga acc 263 ctG GTC ACC aa (SEQ ID NO: 113)
```

TABLE 2P entry in which YYC motif was not automatically identified
++C:\tmp\hs202g3.txt

```
!!NA_SEQUENCE 1.0
LOCUS       HS202G3    522 bp    mRNA       PRI    03-AUG-1995
DEFINITION  H. sapiens mRNA for immunoglobulin variable region (clone 202-G3).
ACCESSION   Z47259
VERSION     Z47259.1 GI: 619470
  Ngene =   522

No stops in reading frame 1
Stop codons in reading frame 2
    89 110 305 314

Stop codons in reading frame 3
    84 192 321 351 369

1 atg gac tgg acc tgg agg ttc ctc ttt gtg gtg gca gca gct aca 46 ggt gtc cag tcc cag gtg cag ctg gtg cag tct ggg gct gag gtg 91 aag aag cct ggg tcc tcg gtg aag gtc tcc TGC aag gct tct gga 136 ggc acc ttc agc agc tat gct atc agc tgg gtg cga cag gcc cct 181 gga caa ggg ctt gag tgg atg gga ggg atc atc cct atc ttt ggt 226 aca gca aac tac gca cag aag ttc cag ggc aga gtc acg att acc 271 gcg gac gaa tcc acg agc aca gcc tac atg gag ctg agc agc ctg 316 aga tct gag gac acg gcc gtg tat cac TGT gcg agt gag gga tgg 361 gag agt TGT agt ggt ggt ggc TGC tac gac ggt atg gac gtc TGG 406 GGC caa ggg acc acG GTC ACC gtc tcc tca gct tcc acc aag ggc 451 cca tcg gtc ttc ccc ctg gcg ccc TGC tcc agg agc acc tct ggg 496 ggc aca gcg gcc ctg ggc TGC ctg
```

YYC not found !!!

TABLE 3P

Entry of Table 2P after editting.
++C:\tmp\hs202g3.txt

```
!!NA_SEQUENCE 1.0
LOCUS       HS202G3 522 bp mRNA PRI 03-AUG-1995
DEFINITION  H. sapiens mRNA for immunoglobulin variable region (clone 202-G3).
ACCESSION   Z47259
VERSION     Z47259.1 GI: 619470
```

TABLE 3P-continued

Entry of Table 2P after editting.
++C:\tmp\hs202g3.txt

```
Ngene = 522
No stops in reading frame 1
Stop codons in reading frame 2
89 110 305 314
Stop codons in reading frame 3
84 192 321 351 369

1       atg gac tgg acc tgg agg ttc ctc ttt gtg gtg gca gca gct aca 46       ggt gtc cag tcc cag gtg cag ctg gtg cag tct ggg gct gag gtg 91       aag aag cct ggg tcc tcg gtg aag gtc tcc TGC aag gct tct gga 136       ggc acc ttc agc agc tat gct atc agc tgg gtg cga cag gcc cct 181       gga caa ggg ctt gag tgg atg gga ggg atc atc cct atc ttt ggt 226       aca gca aac tac gca cag aag ttc cag ggc aga gtc acg att acc 271       gcg gac gaa tcc acg agc aca gcc tac atg gag ctg agc agc ctg 316       aga tct gag gac acg gcc gtg <YHCAS>   tat cac TGT gcg agt
          (SEQ ID NO: 115)
          gag gga tgg 361       gag agt TGT agt ggt ggt ggc TGC tac gac ggt atg gac gtc TGG 406       GGC caa ggg acc acG GTC ACC gtc tcc tca gct tcc acc aag ggc 451       cca tcg gtc ttc ccc ctg gcg ccc TGC tcc agg agc acc tct ggg 496       ggc aca gcg gcc ctg ggc TGC ctg (SEQ ID NO: 115)

YYC       not found !!!
```

TABLE 4P contents of file D1_1-01_Phz0_hsa239356.txt

DRGGKYQLAPKGGM (SEQ ID NO: 117)

DRGGKYQLAPKGGMDV (SEQ ID NO: 118)

JH3 D# 1 Phase 15 Score 6.55D+04

TABLE 5P alignment of a CDR3::JH segment to GLG JHs and D-segments.
+c:\tmp\hs6d4xb7.txt

```
                    1         1    2    2    3    3    3
          1234567890         5    0    5    0    5    9
Observed tatgatagtagtgggtcatactccgactacTGGGGGcag (SEQ ID NO: 119)
JH1      -----------gctgaatacttccagcactggggccagggcaccctggtcaccgtctcctcag--(SEQ ID NO:
         120)
         Miss =  9 Nt = 27

JH2      -----------ctactggtacttcgatctctggggccgtggcaccctggtcactgtctcctcag--(SEQ ID NO:
         121)
         Miss = 13 Nt = 28

JH3      --------------tgatgcttttgatatctggggccaagggacaatggtcaccgtctcttcag--(SEQ ID NO:
         122)
         Miss = 14 Nt = 25

JH4      ----------------actactttgactactggggccagggaaccctggtcaccgtctcctcag--(SEQ ID NO:
         123)
         Miss =  5 Nt = 23

JH5      -------------acaactggttcgacccctggggccagggaaccctggtcaccgtctcctcag--(SEQ ID NO:
         124)
```

TABLE 5P-continued alignment of a CDR3::JH segment to GLG JHs and D-segments.
+c:\tmp\hs6d4xb7.txt

```
            Miss = 11 Nt = 26
JH6    -attactactactacggtatggacgtctggggccaagggaccacggtcaccgtctcctcag--(SEQ ID NO:
       125)
            Miss = 23 Nt = 38

4 tat gat agt agt ggg tca TAC Tcc GAC TAC TGG GGg CAG (SEQ ID NO: 126)
     Y   D   S   S   G   S   Y   S   D   Y   W   G   Q    (SEQ ID NO: 127)

JH4 --- --- --- --- --- -ac tac ttt gac tac tgg ggc cag gga ac-
      c ctg gtc acc gtc tcc tca g--
    (SEQ ID NO: 128)
     -   -   -   -   -   -   Y   F   D   Y   W   G   Q   G   T   L   V   T   V   S   S   -
    (SEQ ID NO: 129)

Fract = 0.783 = 18/23
Matching the rest to D segments:
D#13 --------gtattactatgatagtagtggttattactac    GLG (SEQ ID NO: 130)
     gatcgccacaattactatgatagtagtgggtcatactcc    Observed (SEQ ID NO: 131)

--------gt..................t.at....a.    . = match
D#13 Phase = 9 Score = 4.3980E+12
```

TABLE 6P

Number of sequences identified as having JH derived from GLG JHn

| | JH | | | | | |
|---|---|---|---|---|---|---|
| | 1 | 2 | 3 | 4 | 5 | 6 |
| # sequences | 17 | 40 | 198 | 707 | 160 | 261 |

TABLE 7P

Distribution of CDR3 fragments that might contain D segments.

For JH1

| 0 | 1 | 2 | 3 | 4 | 5 | 6 | 7 | 8 | 9 | 10 | 11 | 12 | 13 |
|---|---|---|---|---|---|---|---|---|---|---|---|---|---|
| 0 | 0 | 1 | 1 | 3 | 1 | 1 | 2 | 0 | 3 | 1 | 1 | 1 | 2 |

Total = 17 Median = 8.0

For JH2

| 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 0 | 0 | 0 | 2 | 4 | 6 | 2 | 6 | 3 | 4 | 5 | 2 | 3 |  |
| 15 | 16 | 17 | 18 |  |  |  |  |  |  |  |  |  |  |  |
| 2 | 0 | 0 | 1 |  |  |  |  |  |  |  |  |  |  |  |

Total = 40 Median = 9.0

For JH3

| 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 0 | 2 | 6 | 16 | 12 | 17 | 17 | 15 | 22 | 20 | 20 | 18 | 13 | 4 |

TABLE 7P-continued

| 15 | 16 | 17 | 18 | 19 |
|---|---|---|---|---|
| 8 | 3 | 2 | 1 | 2 |

Total = 198 Median = 8.6

For JH4

| 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 0 | 7 | 15 | 19 | 40 | 63 | 82 | 81 | 77 | 81 | 53 | 57 | 44 | 30 |
| 15 | 16 | 17 | 18 | 19 | 20 | 21 | 22 | 23 | 24 | 25 | 26 | 27 | 28 | 29 |
| 15 | 23 | 8 | 3 | 5 | 2 | 0 | 1 | 0 | 0 | 0 | 0 | 0 | 0 | 0 |
| 30 | 31 | 32 | 33 | 34 | 35 |  |  |  |  |  |  |  |  |  |
| 0 | 0 | 0 | 0 | 0 | 1 |  |  |  |  |  |  |  |  |  |

Total = 707 Median = 8.6

For JH5

| 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 0 | 0 | 0 | 3 | 4 | 6 | 13 | 19 | 12 | 14 | 22 | 18 | 10 | 18 | 10 |
| 15 | 16 | 17 | 18 | 19 | 20 | 21 | 22 | 23 | 24 | 25 | 26 | 27 | 28 | 29 |
| 5 | 1 | 1 | 0 | 0 | 1 | 1 | 0 | 0 | 0 | 0 | 0 | 0 | 0 | 0 |
| 30 | 31 | 32 | 33 | 34 | 35 | 36 | 37 | 38 | 39 | 40 | 41 | 42 | 43 | 44 |
| 0 | 0 | 0 | 0 | 0 | 0 | 0 | 0 | 0 | 0 | 0 | 0 | 1 | 0 | 0 |
| 45 | 46 |  |  |  |  |  |  |  |  |  |  |  |  |  |
| 0 | 1 |  |  |  |  |  |  |  |  |  |  |  |  |  |

Total = 160 Median = 9.4

For JH6

| 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 2 | 0 | 1 | 2 | 5 | 15 | 20 | 18 | 22 | 29 | 29 | 28 | 23 | 16 | 10 |
| 15 | 16 | 17 | 18 | 19 | 20 |  |  |  |  |  |  |  |  |  |
| 14 | 9 | 9 | 4 | 2 | 3 |  |  |  |  |  |  |  |  |  |

Total = 261 Median = 9.6

TABLE 8P

Lengths of CDR3 segments from YYCAR to WG.

Distribution of lengths from end of FR3 to WG motif all sequences.

| | L | | | | | | | | | |
|---|---|---|---|---|---|---|---|---|---|---|
| | 0 | 1 | 2 | 3 | 4 | 5 | 6 | 7 | 8 | 9 |
| N | 6 | 0 | 0 | 4 | 2 | 9 | 13 | 38 | 61 | 88 |
| Sum(N) | 6 | 6 | 6 | 10 | 12 | 21 | 34 | 72 | 133 | 221 |
| f | .004 | .004 | .004 | .007 | .009 | .015 | .025 | .052 | .096 | .160 |

TABLE 8P-continued

Lengths of CDR3 segments from YYCAR to WG.

| | \multicolumn{10}{c}{L} |
| | 10 | 11 | 12 | 13 | 14 | 15 | 16 | 17 | 18 | 19 |
|---|---|---|---|---|---|---|---|---|---|---|
| N | 101 | 118 | 154 | 150 | 118 | 125 | 105 | 84 | 61 | 46 |
| SN | 322 | 440 | 594 | 744 | 862 | 987 | 1092 | 1176 | 1237 | 1283 |
| f | .233 | .318 | .430 | .538 | .623 | .714 | .790 | .850 | .894 | .928 |

| | \multicolumn{10}{c}{L} |
| | 20 | 21 | 22 | 23 | 24 | 25 | 26 | 27 | 28 | 29 |
|---|---|---|---|---|---|---|---|---|---|---|
| N | 42 | 16 | 17 | 7 | 9 | 2 | 1 | 0 | 2 | 1 |
| SN | 1325 | 1341 | 1358 | 1365 | 1374 | 1376 | 1377 | 1377 | 1379 | 1380 |
| f | .958 | .970 | .982 | .987 | .993 | .995 | .996 | .996 | .997 | .998 |

| | \multicolumn{10}{c}{L} |
| | 30 | 31 | 32 | 33 | 34 | 35 | 36 | 37 | 38 | 39 |
|---|---|---|---|---|---|---|---|---|---|---|
| N | 0 | 0 | 0 | 0 | 0 | 0 | 0 | 1 | 0 | 0 |
| SN | 1380 | 1380 | 1380 | 1380 | 1380 | 1380 | 1380 | 1381 | 1381 | 1381 |
| f | .998 | .998 | .998 | .998 | .998 | .998 | .998 | .999 | .999 | .999 |

| | \multicolumn{7}{c}{L} |
| | 40 | 41 | 42 | 43 | 44 | 45 | 46 |
|---|---|---|---|---|---|---|---|
| N | 0 | 0 | 1 | 0 | 0 | 0 | 1 |
| SN | 1381 | 1381 | 1382 | 1382 | 1382 | 1382 | 1383 |
| f | .999 | .999 | .999 | .999 | .999 | .999 | 1.0 |

Median = 12.65

Distribution of lengths from end of FR3 to WG motif with assigned D.

| | \multicolumn{10}{c}{L} |
| | 0 | 1 | 2 | 3 | 4 | 5 | 6 | 7 | 8 | 9 |
|---|---|---|---|---|---|---|---|---|---|---|
| N | 3 | 0 | 0 | 0 | 0 | 0 | 3 | 9 | 21 | 15 |
| SN | 3 | 3 | 3 | 3 | 3 | 3 | 6 | 15 | 36 | 51 |
| f | .004 | .004 | .004 | .004 | .004 | .004 | .008 | .019 | .046 | .065 |

| | \multicolumn{10}{c}{L} |
| | 10 | 11 | 12 | 13 | 14 | 15 | 16 | 17 | 18 | 19 |
|---|---|---|---|---|---|---|---|---|---|---|
| N | 39 | 64 | 77 | 97 | 72 | 77 | 75 | 63 | 45 | 35 |
| SN | 90 | 154 | 231 | 328 | 400 | 477 | 552 | 615 | 660 | 695 |
| f | .115 | .196 | .294 | .418 | .510 | .608 | .703 | .783 | .841 | .885 |

| | \multicolumn{10}{c}{L} |
| | 20 | 21 | 22 | 23 | 24 | 25 | 26 | 27 | 28 | 29 |
|---|---|---|---|---|---|---|---|---|---|---|
| N | 38 | 15 | 15 | 6 | 9 | 2 | 1 | 0 | 1 | 1 |
| SN | 733 | 748 | 763 | 769 | 778 | 780 | 781 | 781 | 782 | 783 |
| f | .934 | .953 | .972 | .980 | .991 | .994 | .995 | .995 | .996 | .997 |

| | \multicolumn{10}{c}{L} |
| | 30 | 31 | 32 | 33 | 34 | 35 | 36 | 37 | 38 | 39 |
|---|---|---|---|---|---|---|---|---|---|---|
| N | 0 | 0 | 0 | 0 | 0 | 0 | 0 | 1 | 0 | 0 |
| SN | 783 | 783 | 783 | 783 | 783 | 783 | 783 | 784 | 784 | 784 |
| f | .997 | .997 | .997 | .997 | .997 | .997 | .997 | .999 | .999 | .999 |

| | \multicolumn{7}{c}{L} |
| | 40 | 41 | 42 | 43 | 44 | 45 | 46 |
|---|---|---|---|---|---|---|---|
| N | 0 | 0 | 0 | 0 | 0 | 0 | 1 |
| SN | 784 | 784 | 784 | 784 | 784 | 784 | 785 |
| f | .999 | .999 | .999 | .999 | .999 | .999 | 1.0 |

Median = 13.90

TABLE 8P-continued

Lengths of CDR3 segments from YYCAR to WG.

Distribution of lengths from end of FR3 to WG motif with no assigned D.

| | | | | | L | | | | |
|---|---|---|---|---|---|---|---|---|---|
| | 0 | 1 | 2 | 3 | 4 | 5 | 6 | 7 | 8 | 9 |
| N | 3 | 0 | 0 | 4 | 2 | 9 | 10 | 29 | 40 | 73 |
| SN | 3 | 3 | 3 | 7 | 9 | 18 | 28 | 57 | 97 | 170 |
| f | .005 | .005 | .005 | .012 | .015 | .030 | .047 | .095 | .162 | .284 |

| | | | | | L | | | | |
|---|---|---|---|---|---|---|---|---|---|
| | 10 | 11 | 12 | 13 | 14 | 15 | 16 | 17 | 18 | 19 |
| N | 62 | 54 | 77 | 53 | 46 | 48 | 30 | 21 | 16 | 11 |
| SN | 232 | 286 | 363 | 416 | 462 | 510 | 540 | 561 | 577 | 588 |
| f | .388 | .478 | .607 | .696 | .773 | .853 | .903 | .938 | .965 | .983 |

| | | | | | L | | | | |
|---|---|---|---|---|---|---|---|---|---|
| | 20 | 21 | 22 | 23 | 24 | 25 | 26 | 27 | 28 | 29 |
| N | 4 | 1 | 2 | 1 | 0 | 0 | 0 | 0 | 1 | 0 |
| SN | 592 | 593 | 595 | 596 | 596 | 596 | 596 | 596 | 597 | 597 |
| f | .990 | .992 | .995 | .997 | .997 | .997 | .997 | .997 | .998 | .998 |

| | | | | | L | | | | |
|---|---|---|---|---|---|---|---|---|---|
| | 30 | 31 | 32 | 33 | 34 | 35 | 36 | 37 | 38 | 39 |
| N | 0 | 0 | 0 | 0 | 0 | 0 | 0 | 0 | 0 | 0 |
| SN | 597 | 597 | 597 | 597 | 597 | 597 | 597 | 597 | 597 | 597 |
| f | .998 | .998 | .998 | .998 | .998 | .998 | .998 | .998 | .998 | .998 |

| | L | | | |
|---|---|---|---|---|
| | 40 | 41 | 42 | |
| N | 0 | 0 | 1 | |
| SN | 597 | 597 | 598 | |
| f | .998 | .998 | 1.0 | Median = 11.17 |

L is the length
N is the number of examples
Sum(N) = SN is the sum of the Ns
f is the cumulative fraction seen

TABLE 9P

Tally of left-aligned CDR3 sequences

| | A | C | D | E | F | G | H | I | K | L | M | # | |
|---|---|---|---|---|---|---|---|---|---|---|---|---|---|
| 1 | 74 | 6 | 278 | 109 | 11 | 319 | 50 | 18 | 11 | 60 | 8 | 1383 | GDERVASLHTNQPIWYFKMCX |
| 2 | 50 | 9 | 64 | 32 | 29 | 249 | 43 | 42 | 41 | 109 | 22 | 1377 | GRPSLDVYTANHIQKEFMWCX |
| 3 | 81 | 18 | 74 | 39 | 25 | 214 | 29 | 42 | 16 | 83 | 19 | 1377 | GSYRTVLADPIWEQHNFMCK\| |
| 4 | 70 | 23 | 92 | 49 | 50 | 228 | 23 | 58 | 21 | 70 | 16 | 1373 | GSYDRVALTIPFEWNCHQKMX |
| 5 | 86 | 28 | 106 | 32 | 59 | 217 | 21 | 41 | 16 | 72 | 19 | 1371 | GYSDAVTLRFIPWNECHMQK\|X |
| 6 | 88 | 17 | 104 | 28 | 94 | 171 | 17 | 48 | 12 | 50 | 17 | 1362 | GYSDFATVRWPLINEQCHMK\| |
| 7 | 69 | 15 | 110 | 21 | 89 | 176 | 22 | 50 | 15 | 81 | 12 | 1349 | GSYDFVLTAPRWINHEQCKM\|X |
| 8 | 53 | 19 | 141 | 17 | 90 | 150 | 18 | 47 | 17 | 68 | 11 | 1311 | YSGDFLTVWAPIRNCHEKQM\| |
| 9 | 44 | 21 | 120 | 24 | 102 | 174 | 24 | 36 | 20 | 71 | 11 | 1250 | YGSDFLNVRTAWPIEHCKQM\| |
| 10 | 39 | 31 | 129 | 23 | 124 | 116 | 23 | 42 | 9 | 58 | 32 | 1162 | YDFGSLIARPTVWNMCEHQK |
| 11 | 36 | 12 | 158 | 17 | 137 | 83 | 13 | 18 | 10 | 40 | 21 | 1061 | YDFGSPLVANWMTRIEHCKQX |
| 12 | 34 | 11 | 164 | 10 | 82 | 74 | 34 | 30 | 1 | 31 | 20 | 943 | YDFGPSVAHLINMRTWCEQKX |

TABLE 9P-continued

Tally of left-aligned CDR3 sequences

| | | | | | | | | | | | | | |
|---|---|---|---|---|---|---|---|---|---|---|---|---|---|
| 13 | 32 | 2 | 121 | 6 | 84 | 56 | 10 | 26 | 7 | 43 | 32 | 789 | YDFGLSPVAMIWRTHNKQEC |
| 14 | 23 | | 131 | 5 | 59 | 65 | 10 | 16 | 4 | 25 | 34 | 639 | YDGFMVLAPISWNRHTQEKX |
| 15 | 15 | 4 | 107 | 5 | 43 | 42 | 1 | 23 | | 20 | 34 | 521 | YDFGVMILWAPRSENCQTH\| |
| 16 | 4 | 2 | 80 | 3 | 33 | 26 | 4 | 5 | 1 | 10 | 29 | 396 | YDVFMGPSLNTRIWAHECQ\|K |
| 17 | 3 | 1 | 63 | | 19 | 19 | 9 | 13 | | 12 | 21 | 291 | DYVMFGILHPSTWAQRCNX |
| 18 | 3 | | 47 | | 16 | 13 | 1 | 4 | | 7 | 23 | 207 | DYVMFGPSLTIAHN |
| 19 | 5 | 1 | 39 | 1 | 4 | 13 | 3 | 3 | | 1 | 14 | 146 | DYVMGAFHINRSCELPQW |
| 20 | 2 | | 17 | | 4 | 5 | | 3 | | 4 | 12 | 100 | VYDMGFLIPSARWQ |
| 21 | | | 17 | | 3 | 8 | 1 | 1 | | | 4 | 58 | DVGYMPHINTW |
| 22 | 1 | | 7 | | 6 | 1 | | 1 | | | 5 | 42 | VDFMYSAGITW |
| 23 | | | 9 | | | 1 | | 1 | | 1 | 1 | 25 | DVYGILMPS |
| 24 | 1 | | 2 | | | | 1 | | | 1 | 1 | 18 | VYDAHLMPT |
| 25 | | | 1 | | | 3 | | | | | | 9 | GVDPSY |
| 26 | | | | | | 2 | | | | | 2 | 7 | GMSTV |
| 27 | | | 2 | | | | | 1 | | | 1 | 6 | DKMST |
| 28 | 1 | | 1 | | | 1 | | | | | | 6 | VADGS |
| 29 | | | 1 | | | | | | | | | 4 | DPSV |
| 30 | | | | | 1 | | | | | | | 3 | FST |
| 31 | | | | | | | | 1 | | 1 | | 3 | KLV |
| 32 | | | | | 1 | 1 | | | | | | 3 | FGP |
| 33 | | | | | | 1 | | | | | | 3 | PG |
| 34 | | | | | | | 1 | | | 1 | | 3 | HLS |
| 35 | 1 | | | | | | | | | | | 3 | AVW |
| 36 | | | 1 | | 1 | | | | | | | 3 | DFP |
| 37 | | | | | | | | | | | | 3 | PSY |
| 38 | | | | | | | | | | 1 | | 2 | LS |
| 39 | 1 | | | | | | | 1 | | | | 2 | AK |
| 40 | | | | | | | | | | | | 2 | PS |
| 41 | | | | | | | | | | | | 2 | ST |
| 42 | | | | | | | | | | | | 2 | S |
| 43 | | | | | | | | | | 1 | | 1 | K |
| 44 | | | | | | | | | | | | 1 | S |
| 45 | | | | | | | | | | | | 1 | T |
| 46 | | | | | | | | | | | | 1 | S |
| | 816 | 220 | 2186 | 421 | 1166 | 2428 | 358 | 568 | 205 | 920 | 421 | | |

| | N | P | Q | R | S | T | V | W | Y | \| | X | # | |
|---|---|---|---|---|---|---|---|---|---|---|---|---|---|
| 1 | 35 | 23 | 31 | 108 | 63 | 50 | 94 | 16 | 13 | | 6 | 1383 | GDERVASLHTNQPIWYFKMCX |
| 2 | 44 | 114 | 42 | 169 | 114 | 59 | 62 | 21 | 60 | | 2 | 1377 | GRPSLDVYTANHIQKEFMWCX |
| 3 | 26 | 73 | 37 | 110 | 140 | 97 | 89 | 42 | 122 | 1 | | 1377 | GSYRTVLADPIWEQHNFMCK\| |

TABLE 9P-continued

Tally of left-aligned CDR3 sequences

| | | | | | | | | | | | | |
|---|---|---|---|---|---|---|---|---|---|---|---|---|
| 4 | 48 | 51 | 22 | 79 | 141 | 65 | 77 | 49 | 139 | | 2 | 1373 | GSYDRVALTIPFEWNCHQKMX |
| 5 | 37 | 41 | 18 | 61 | 157 | 75 | 85 | 38 | 158 | 2 | 2 | 1371 | GYSDAVTLRFIPWNECHMQK\|X |
| 6 | 32 | 54 | 23 | 67 | 152 | 80 | 78 | 64 | 165 | 1 | | 1362 | GYSDFATVRWPLINEQCHMK\| |
| 7 | 44 | 59 | 18 | 58 | 157 | 73 | 85 | 54 | 139 | 1 | 1 | 1349 | GSYDFVLTAPRWINHEQCKM\|X |
| 8 | 38 | 48 | 14 | 41 | 167 | 68 | 59 | 59 | 185 | 1 | | 1311 | YSGDFLTVWAPIRNCHEKQM\| |
| 9 | 52 | 40 | 14 | 47 | 123 | 45 | 48 | 41 | 192 | 1 | | 1250 | YGSDFLNVRTAWPIEHCKQM\| |
| 10 | 33 | 37 | 12 | 39 | 73 | 36 | 36 | 35 | 235 | | | 1162 | YDFGSLIARPTVWNMCEHQK |
| 11 | 33 | 49 | 7 | 20 | 68 | 21 | 37 | 29 | 251 | | 1 | 1061 | YDFGSPLVANWMTRIEHCKQX |
| 12 | 30 | 53 | 10 | 19 | 45 | 19 | 42 | 18 | 215 | | 1 | 943 | YDFGPSVAHLINMRTWCEQKX |
| 13 | 10 | 34 | 7 | 22 | 40 | 15 | 33 | 25 | 184 | | | 789 | YDFGLSPVAMIWRTHNKQEC |
| 14 | 13 | 22 | 6 | 12 | 15 | 10 | 26 | 14 | 148 | | 1 | 639 | YDGFMVLAPISWNRHTQEKX |
| 15 | 5 | 12 | 3 | 12 | 12 | 3 | 40 | 20 | 119 | 1 | | 521 | YDFGVMILWAPRSENCQTH\| |
| 16 | 10 | 24 | 2 | 6 | 12 | 7 | 49 | 5 | 82 | 2 | | 396 | YDVFMGPSLNTRIWAHECQ\|K |
| 17 | 1 | 8 | 2 | 2 | 8 | 5 | 42 | 4 | 58 | | 1 | 291 | DYVMFGILHPSTWAQRCNX |
| 18 | 1 | 13 | | | 8 | 5 | 31 | | 35 | | | 207 | DYVMFGPSLTIAHN |
| 19 | 2 | 1 | 1 | 2 | 2 | | 24 | 1 | 29 | | | 146 | DYVMGAFHINRSCELPQW |
| 20 | | 3 | 1 | 2 | 3 | | 23 | 2 | 19 | | | 100 | VYDMGFLIPSARWQ |
| 21 | 1 | | | | 1 | | 14 | 1 | 7 | | | 58 | DVGYMFHINTW |
| 22 | | | | 2 | 1 | | 12 | 1 | 5 | | | 42 | VDFMYSAGITW |
| 23 | | 1 | | | 1 | | 5 | | 5 | | | 25 | DVYGILMPS |
| 24 | | 1 | | | 1 | | 5 | | 5 | | | 18 | VYDAHLMPT |
| 25 | | 1 | | | 1 | | 2 | | 1 | | | 9 | GVDPSY |
| 26 | | | | | 1 | | 1 | | 1 | | | 7 | GMSTV |
| 27 | | | | | 1 | | 1 | | | | | 6 | DKMST |
| 28 | | | | | 1 | | 2 | | | | | 6 | VADGS |
| 29 | | 1 | | | 1 | | 1 | | | | | 4 | DPSV |
| 30 | | | | | 1 | 1 | | | | | | 3 | FST |
| 31 | | | | | | | 1 | | | | | 3 | KLV |
| 32 | | 1 | | | | | | | | | | 3 | FGP |
| 33 | | 2 | | | | | | | | | | 3 | PG |
| 34 | | | | | 1 | | | | | | | 3 | HLS |
| 35 | | | | | | | 1 | 1 | | | | 3 | AVW |
| 36 | | 1 | | | | | | | | | | 3 | DFP |
| 37 | | 1 | | | 1 | | | | 1 | | | 3 | PSY |
| 38 | | | | | 1 | | | | | | | 2 | LS |
| 39 | | | | | | | | | | | | 2 | AK |
| 40 | | 1 | | | 1 | | | | | | | 2 | PS |
| 41 | | | | | 1 | 1 | | | | | | 2 | ST |
| 42 | | | | | 2 | | | | | | | 2 | S |

TABLE 9P-continued

Tally of left-aligned CDR3 sequences

| | A | C | D | E | F | G | H | I | K | L | M | # | |
|---|---|---|---|---|---|---|---|---|---|---|---|---|---|
| 43 | | | | | | | | | 1 | | | 1 | K |
| 44 | | | 1 | | | | | | | | | 1 | S |
| 45 | | | | | 1 | | | | | | | 1 | T |
| 46 | | | | | 1 | | | | | | | 1 | S |
| | 495 | 769 | 270 | 876 | 1518 | 741 | 1104 | 540 | 2572 | 10 | 17 | 18621 | |

TABLE 10P

Tally of right-aligned sequences

| | A | C | D | E | F | G | H | I | K | L | M | # | |
|---|---|---|---|---|---|---|---|---|---|---|---|---|---|
| 5 | | | | | | 1 | | | | 1 | | 1 | G |
| 6 | | | | | | | | | | 1 | | 1 | S |
| 7 | | | | | | 1 | | | | 1 | | 1 | G |
| 8 | | | | | | 1 | | | | 1 | | 1 | G |
| 9 | | | | | | | | | | 2 | | 2 | RV |
| 10 | | | | | | | | | | 2 | | 2 | RV |
| 11 | | | | | | 1 | | 1 | | 2 | | 2 | GI |
| 12 | | | | | | | | | | 2 | | 2 | V |
| 13 | | | | | | | | | | 2 | | 2 | TY |
| 14 | | | 1 | | | 1 | | | | 3 | | 3 | DGN |
| 15 | | | | | | | | 1 | | 3 | | 3 | ISY |
| 16 | | | 1 | | | | | | | 3 | | 3 | DSY |
| 17 | 1 | | | | | | | | | 3 | | 3 | APY |
| 18 | | | 1 | | 1 | | | | | 3 | 1 | 3 | DFM |
| 19 | | | 2 | | | 1 | | | | 3 | | 3 | DG |
| 20 | | | | | | | | 1 | | 3 | 1 | 3 | ILV |
| 21 | | | | | | | | | | 3 | | 3 | WP |
| 22 | | | | | | 3 | | | | 4 | | 4 | GS |
| 23 | | | | | | 2 | 1 | | | 6 | | 6 | GHQSV |
| 24 | 1 | | | | | 3 | | | | 6 | 1 | 6 | GALR |
| 25 | 1 | | 2 | | | | | 1 | | 7 | | 7 | DTAIS |
| 26 | 1 | 1 | 1 | | | 1 | | | 1 | 9 | 1 | 9 | ACDGKLMST |
| 27 | 2 | | 5 | 1 | | 2 | | 1 | | 18 | 1 | 18 | DAGVEILNQRS |
| 28 | | | 2 | 2 | | 3 | | 1 | | 25 | 2 | 25 | TGQSDELPRIV |
| 29 | 3 | | 5 | 6 | | 7 | | | 1 | 42 | 1 | 42 | GEDVAPQRSKLMTY |
| 30 | 2 | | 9 | 1 | | 9 | 1 | 4 | | 58 | 5 | 58 | DGRLSIVPAMQTFHNY |
| 31 | 4 | 2 | 19 | 9 | 2 | 18 | 1 | 2 | 1 | 100 | 3 | 100 | DGSERVYALPTCFINHKW |
| 32 | 10 | 5 | 18 | 5 | 3 | 16 | 3 | 3 | 2 | 146 | 14 | 146 | DGLRVAPYSTCEQFHINWKM |
| 33 | 20 | | 18 | 10 | 7 | 34 | 7 | 8 | 2 | 207 | 6 | 207 | GARDPSYTEVIFHLQWKM |

TABLE 10P-continued

Tally of right-aligned sequences

| | N | P | Q | R | S | T | V | W | Y | \| | X | # | |
|---|---|---|---|---|---|---|---|---|---|---|---|---|---|
| 34 | 13 | 4 | 31 | 18 | 9 | 37 | 8 | 16 | 4 | 14 | 4 | 291 | GDRYPVEILASTFHQWCKMNX\| |
| 35 | 17 | 5 | 32 | 23 | 10 | 70 | 12 | 10 | 6 | 25 | 1 | 396 | GRSDYLEVTPAHNFIWKCQM\| |
| 36 | 23 | 6 | 51 | 21 | 9 | 79 | 19 | 15 | 14 | 36 | 9 | 521 | GDSYRLTVPAEHIKNFMWCQ\| |
| 37 | 35 | 12 | 56 | 23 | 15 | 110 | 14 | 17 | 5 | 24 | 4 | 639 | GYDVRSTAPLEIFHNCWQKMX\| |
| 38 | 28 | 19 | 68 | 27 | 29 | 133 | 26 | 31 | 12 | 43 | 7 | 789 | GSYDVRLPTIFAEHCNWKQM |
| 39 | 51 | 25 | 80 | 27 | 33 | 162 | 16 | 30 | 18 | 55 | 15 | 943 | GSDRYVLATPFWIECKHMQNX |
| 40 | 44 | 14 | 73 | 36 | 46 | 161 | 27 | 32 | 17 | 59 | 8 | 1061 | GSRDYVTLPFAEIWHQNKCM |
| 41 | 54 | 21 | 74 | 25 | 23 | 178 | 23 | 52 | 15 | 57 | 11 | 1162 | GSYTDRVLPAIWNQEFHCKMX\| |
| 42 | 57 | 13 | 82 | 40 | 42 | 190 | 14 | 39 | 15 | 82 | 15 | 1250 | GSYDLVRTANPFEIWQKMHC\| |
| 43 | 75 | 18 | 54 | 25 | 35 | 242 | 13 | 29 | 18 | 49 | 12 | 1311 | GYSTARVPDLWNFIQECKHM\| |
| 44 | 63 | 17 | 79 | 15 | 43 | 197 | 20 | 38 | 14 | 76 | 8 | 1349 | YGSTDLRAPVWNFIQHCEKM |
| 45 | 59 | 16 | 69 | 35 | 55 | 165 | 26 | 23 | 23 | 75 | 9 | 1362 | YGSLRTDNAFPVWEHIKCQM |
| 46 | 41 | 19 | 125 | 26 | 27 | 208 | 31 | 14 | 16 | 38 | 8 | 1371 | YGDSNRWATLPHFEVQCKIM |
| 47 | 160 | 10 | 24 | 13 | 53 | 332 | 36 | 16 | 11 | 40 | 10 | 1373 | GYAWPSFRLHTVNDIEKCMQX |
| 48 | 21 | 4 | 8 | 5 | 680 | 27 | 4 | 44 | 5 | 145 | 288 | 1377 | FMLISGVYPAWTDNQREKCHX |
| 49 | 23 | 2 | 1181 | 29 | 1 | 30 | 15 | 4 | 2 | 8 | 1 | 1377 | DGEAHNQSYVLPTIRCKW\|FMX |
| 50 | 7 | 7 | 15 | | 42 | 3 | 41 | 135 | 3 | 59 | 4 | 1383 | YVIPSLFHNDTACXMGKQRW\| |
| | 816 | 220 | 2186 | 421 | 1166 | 2428 | 358 | 568 | 205 | 920 | 421 | | |

| | N | P | Q | R | S | T | V | W | Y | \| | X | # | |
|---|---|---|---|---|---|---|---|---|---|---|---|---|---|
| 5 | | | | | | | | | | | | 1 | G |
| 6 | | | | | 1 | | | | | | | 1 | S |
| 7 | | | | | | | | | | | | 1 | G |
| 8 | | | | | | | | | | | | 1 | G |
| 9 | | | | 1 | | | 1 | | | | | 2 | RV |
| 10 | | | | 1 | | | 1 | | | | | 2 | RV |
| 11 | | | | | | | | | | | | 2 | GI |
| 12 | | | | | | | 2 | | | | | 2 | V |
| 13 | | | | | | 1 | | | 1 | | | 2 | TY |
| 14 | 1 | | | | | | | | | | | 3 | DGN |
| 15 | | | | | 1 | | | | 1 | | | 3 | ISY |
| 16 | | | | | 1 | | | | 1 | | | 3 | DSY |
| 17 | | 1 | | | | | | | 1 | | | 3 | APY |
| 18 | | | | | | | | | | | | 3 | DFM |
| 19 | | | | | | | | | | | | 3 | DG |
| 20 | | | | | | | 1 | | | | | 3 | ILV |
| 21 | | 1 | | | | | | 2 | | | | 3 | WP |
| 22 | | | | | 1 | | | | | | | 4 | GS |
| 23 | | | | 1 | 1 | 1 | | | | | | 6 | GHQSV |
| 24 | | | | | 1 | | | | | | | 6 | GALR |

TABLE 10P-continued

Tally of right-aligned sequences

| | | | | | | | | | | | | |
|---|---|---|---|---|---|---|---|---|---|---|---|---|
| 25 | | | | 1 | 2 | | | | | | 7 | DTAIS |
| 26 | | | | 1 | 1 | | | | | | 9 | ACDGKLMST |
| 27 | 1 | | 1 | 1 | 1 | | 2 | | | | 18 | DAGVEILNQRS |
| 28 | | 2 | 3 | 2 | 3 | 4 | 1 | | | | 25 | TGQSDELPRIV |
| 29 | | 3 | 3 | 2 | 2 | 1 | 5 | | 1 | 1 | 42 | GEDVAPQRSKLMTY\| |
| 30 | 1 | 3 | 2 | 7 | 5 | 2 | 4 | | 1 | | 58 | DGRLSIVPAMQTFHNY |
| 31 | 2 | 3 | | 7 | 10 | 3 | 7 | 1 | 6 | | 100 | DGSERVYALPTCFINHKW |
| 32 | 3 | 9 | 4 | 12 | 8 | 6 | 12 | 3 | 9 | | 146 | DGLRVAPYSTCEQFHINWKM |
| 33 | | 16 | 6 | 19 | 15 | 12 | 10 | 3 | 13 | | 207 | GARDPSYTEVIFHLQWKM |
| 34 | 2 | 20 | 5 | 31 | 12 | 12 | 20 | 5 | 23 | 1 | 2 | 291 | GDRYPVEILASTFHQWCKMNX\| |
| 35 | 12 | 18 | 5 | 39 | 35 | 19 | 23 | 7 | 26 | 1 | | 396 | GRSDYLEVTPAHNFIWKCQM\| |
| 36 | 11 | 24 | 6 | 42 | 47 | 29 | 28 | 7 | 44 | 1 | | 521 | GDSYRLTVPAEHIKNFMWCQ\| |
| 37 | 14 | 33 | 9 | 54 | 52 | 37 | 55 | 11 | 58 | | 1 | 639 | GYDVRSTAPLEIFHNCWQKMX\| |
| 38 | 18 | 33 | 12 | 46 | 77 | 32 | 58 | 17 | 73 | | | 789 | GSYDVRLPTIFAEHCNWKQM |
| 39 | 11 | 38 | 12 | 70 | 94 | 42 | 61 | 33 | 68 | | 2 | 943 | GSDRYVLATPFWIECKHMQNX |
| 40 | 24 | 52 | 27 | 74 | 140 | 61 | 66 | 29 | 71 | | | 1061 | GSRDYVTLPFAEIWHQNKCM |
| 41 | 31 | 55 | 29 | 70 | 156 | 76 | 61 | 51 | 97 | 1 | 2 | 1162 | GSYTDRVLPAIWNQEFHCKMX\| |
| 42 | 48 | 47 | 24 | 68 | 171 | 68 | 70 | 39 | 125 | 1 | | 1250 | GSYDLVRTANPFEIWQKMHC\| |
| 43 | 38 | 58 | 28 | 73 | 164 | 76 | 66 | 43 | 194 | 1 | | 1311 | GYSTARVPDLWNFIQECKHM\| |
| 44 | 48 | 60 | 24 | 69 | 131 | 86 | 57 | 52 | 252 | | | 1349 | YGSTDLRAPVWNFIQHCEKM |
| 45 | 62 | 51 | 16 | 75 | 116 | 74 | 50 | 39 | 324 | | | 1362 | YGSLRTDNAFPVWEHIKCQM |
| 46 | 97 | 38 | 21 | 55 | 110 | 39 | 26 | 55 | 377 | | | 1371 | YGDSNRWATLPHFEVQCKIM |
| 47 | 25 | 54 | 9 | 44 | 54 | 34 | 32 | 122 | 292 | | 2 | 1373 | GYAWPSFRLHTVNDIEKCMQX |
| 48 | 8 | 22 | 7 | 6 | 28 | 10 | 25 | 16 | 23 | | 1 | 1377 | FMLISGVYPAWTDNQREKCHX |
| 49 | 15 | 6 | 13 | 4 | 13 | 5 | 9 | 2 | 11 | 2 | 1 | 1377 | DGEAHNQSYVLPTIRCKW\|FMX |
| 50 | 23 | 122 | 3 | 3 | 67 | 9 | 350 | 3 | 480 | 1 | 6 | 1383 | YVIPSLFHNDTACXMGKQRW\| |
| 50 | 495 | 769 | 270 | 876 | 1518 | 741 | 1104 | 540 | 2572 | 10 | 17 | 18621 | |

TABLE 11P

Tallies of AA frequencies in all CDR3 by length

Tally of sequences of length 7 # = 38

| | A | C | D | E | F | G | H | I | K | L | M | # | |
|---|---|---|---|---|---|---|---|---|---|---|---|---|---|
| 1 | 1 | | 8 | 1 | 1 | 14 | 1 | | 1 | 5 | | 38 | GDLRWAEFHKS |
| 2 | 1 | | 1 | | 2 | 6 | 3 | | 2 | 1 | 1 | 38 | RGNHVFKTYADLMW |
| 3 | 1 | | 4 | | 1 | 5 | 1 | 2 | | 2 | | 38 | GSDWYPVILTAFHN |
| 4 | 3 | | 1 | | 1 | 12 | 1 | 1 | | 1 | | 38 | GYSANRVDFHILPT |
| 5 | 2 | | | 1 | 14 | 3 | | 4 | 1 | 3 | 3 | 38 | FIGLMARVYEKP |

TABLE 11P-continued

Tallies of AA frequencies in all CDR3 by length

|   | A | C | D | E | F | G | H | I | K | L | M | # |         |
|---|---|---|---|---|---|---|---|---|---|---|---|---|---------|
| 6 |   |   |   |   |   | 26|   |   | 1 | 1 |   | 38 | DVPTHISWY |
| 7 | 1 |   |   | 2 |   |   |   | 2 | 3 |   | 1 | 38 | YVINDHSALR |
|   |   |   | 9 | 42| 2 | 19| 40| 9 | 11| 4 | 13| 4 |   |

|   | N | P | Q | R | S | T | V | W | Y | \| | X | # |           |
|---|---|---|---|---|---|---|---|---|---|----|---|---|-----------|
| 1 |   |   |   | 3 | 1 |   |   | 2 |   |    |   | 38 | GDLRWAEFHKS |
| 2 | 6 |   | 7 |   | 2 | 3 | 1 | 2 |   |    |   | 38 | RGNHVFKTYADLMW |
| 3 | 1 | 3 |   | 5 | 2 | 3 | 4 |   | 4 |    |   | 38 | GSDWYPVILTAFHN |
| 4 | 2 | 1 |   | 2 | 4 | 1 | 2 |   | 6 |    |   | 38 | GYSANRVDFHILPT |
| 5 |   | 1 | 2 |   |   | 2 |   | 2 |   |    |   | 38 | FIGLMARVYEKP |
| 6 |   | 2 |   | 1 | 2 | 3 | 1 | 1 |   |    |   | 38 | DVPTHISWY |
| 7 | 3 |   | 1 | 2 |   | 7 |   | 16|   |    |   | 38 | YVINDHSALR |
|   | 12| 7 | 15| 13| 7 | 20| 8 | 31|   |    |   | 266 |      |

Tally of sequences of length 8 # = 61

|   | A | C | D | E | F | G | H | I | K | L | M | # |           |
|---|---|---|---|---|---|---|---|---|---|---|---|---|-----------|
| 1 | 3 |   | 7 | 3 |   | 14| 2 | 2 |   | 5 |   | 61 | GDLTVRSAEHINWPQY |
| 2 | 1 |   | 9 | 1 | 1 | 15|   | 1 | 2 | 1 |   | 61 | GDTNRSVKWYAEFILPQ |
| 3 | 2 |   | 3 |   | 1 | 10| 1 | 1 |   | 7 | 1 | 61 | GLSTYVDPRAFHIMNQW |
| 4 | 4 | 1 | 3 | 1 | 1 | 15| 1 |   |   | 4 |   | 61 | GYRALQDSWVCEFHNPT |
| 5 | 10|   | 2 | 1 |   | 9 | 5 |   | 1 | 5 | 1 | 61 | AGYHLTPRVDSEKMW |
| 6 | 5 | 1 |   |   | 24| 2 |   | 7 |   | 5 | 2 | 61 | FIALPSVYGMCQRW |
| 7 | 5 |   | 37| 2 |   |   | 4 | 1 |   | 2 |   | 61 | DAHSELNVIP\| |
| 8 | 1 |   | 2 |   | 3 |   | 1 | 12|   | 3 |   | 61 | YISFLVDNAHPRT |
|   | 31| 2 | 63| 8 | 30| 65| 14| 24| 3 | 32| 4 |   |           |

|   | N | P | Q | R | S | T | V | W | Y | \| | X | # |           |
|---|---|---|---|---|---|---|---|---|---|----|---|---|-----------|
| 1 | 2 | 1 | 1 | 4 | 4 | 5 | 5 | 2 | 1 |    |   | 61 | GDLTVRSAEHINWPQY |
| 2 | 6 | 1 | 1 | 4 | 3 | 8 | 3 | 2 | 2 |    |   | 61 | GDTNRSVKWYAEFILPQ |
| 3 | 1 | 3 | 1 | 3 | 7 | 7 | 5 | 1 | 7 |    |   | 61 | GLSTYVDPRAFHIMNQW |
| 4 | 1 | 1 | 4 | 5 | 3 | 1 | 2 | 3 | 11|    |   | 61 | GYRALQDSWVCEFHNPT |
| 5 |   | 4 |   | 4 | 2 | 5 | 4 | 1 | 7 |    |   | 61 | AGYHLTPRVDSEKMW |
| 6 |   | 3 | 1 | 1 | 3 |   | 3 | 1 | 3 |    |   | 61 | FIALPSVYGMCQRW |
| 7 | 2 | 1 |   |   | 4 |   | 2 |   |   | 1  |   | 61 | DAHSELNVIP\| |
| 8 | 2 | 1 |   | 1 | 7 | 1 | 3 |   | 24|    |   | 61 | YISFLVDNAHPRT |
|   | 14| 15| 8 | 22| 33| 27| 27| 10| 55| 1  |   | 488 |        |

Tally of sequences of length 9 # = 88

|   | A | C | D | E | F | G | H | I | K | L | M | # |           |
|---|---|---|---|---|---|---|---|---|---|---|---|---|-----------|
| 1 | 9 |   | 12| 4 |   | 21| 1 | 1 | 2 | 5 |   | 88 | GDARNVLEQTKWHIPSY |
| 2 | 2 |   | 2 | 3 | 3 | 13| 4 |   | 3 | 7 | 2 | 88 | GPSRLNTHEFKYADMQW |

TABLE 11P-continued

Tallies of AA frequencies in all CDR3 by length

| | A | C | D | E | F | G | H | I | K | L | M | # | |
|---|---|---|---|---|---|---|---|---|---|---|---|---|---|
| 3 | 4 | 2 | 3 | 3 | 3 | 15 | | | 1 | 1 | | 88 | GTPSQNRVWYADEFCLM |
| 4 | 5 | 1 | 6 | 3 | 6 | 22 | 2 | 4 | 1 | 6 | 1 | 88 | GSDFLARITYENPWHVCKM |
| 5 | 7 | 1 | 4 | 3 | 4 | 14 | 2 | | | 7 | 2 | 88 | GSYALNDFVERWHMQTCP |
| 6 | 13 | | 2 | 1 | 3 | 13 | 6 | 2 | 1 | 4 | 1 | 88 | YAGHNLPSVFTWDIEKMQR |
| 7 | 4 | | | 2 | | 41 | 2 | | 3 | 1 | 14 | 5 | 88 FLMAPWIDGSVKNQTY |
| 8 | 1 | 1 | 73 | 2 | | 2 | 1 | | | 2 | | 88 | DEGLSACHNQRV |
| 9 | | 1 | 1 | | 4 | 1 | 3 | 8 | | 2 | | 88 | YVISFHPLNTCDGR |
| | 45 | 6 | 105 | 19 | 64 | 103 | 19 | 18 | 8 | 48 | 12 | | |

| | N | P | Q | R | S | T | V | W | Y | \| | X | # | |
|---|---|---|---|---|---|---|---|---|---|---|---|---|---|
| 1 | 7 | 1 | 3 | 8 | 1 | 3 | 7 | 2 | 1 | | | 88 | GDARNVLEQTKWHIPSY |
| 2 | 5 | 11 | 2 | 10 | 11 | 5 | | 2 | 3 | | | 88 | GPSRLNTHEFKYADMQW |
| 3 | 5 | 7 | 6 | 5 | 7 | 11 | 5 | 5 | 5 | | | 88 | GTPSQNRVWYADEFCLM |
| 4 | 3 | 3 | | 5 | 7 | 4 | 2 | 3 | 4 | | | 88 | GSDFLARITYENPWHVCKM |
| 5 | 6 | 1 | 2 | 3 | 12 | 2 | 4 | 3 | 11 | | | 88 | GSYALNDFVERWHMQTCP |
| 6 | 5 | 4 | 1 | 1 | 4 | 3 | 4 | 3 | 17 | | | 88 | YAGHNLPSVFTWDIEKMQR |
| 7 | 1 | 4 | 1 | | 2 | 1 | 2 | 4 | 1 | | | 88 | FLMAPWIDGSVKNQTY |
| 8 | 1 | | 1 | 1 | 2 | | 1 | | | | | 88 | DEGLSACHNQRV |
| 9 | 2 | 3 | | 1 | 8 | 2 | 9 | | 43 | | | 88 | YVISFHPLNTCDGR |
| | 35 | 34 | 16 | 34 | 54 | 31 | 34 | 22 | 85 | | | 792 | |

Tally of sequences of length 10 # = 101

| | A | C | D | E | F | G | H | I | K | L | M | # | |
|---|---|---|---|---|---|---|---|---|---|---|---|---|---|
| 1 | 8 | 1 | 19 | 7 | 1 | 16 | 3 | | 2 | 3 | 2 | 101 | DGNAERTSQVHLWKMYCF |
| 2 | 3 | | 8 | 3 | 5 | 13 | | 5 | | 15 | 2 | 101 | LGRDSPVFINTAEQYMW |
| 3 | 6 | | 9 | | 1 | 26 | 1 | 3 | 1 | 4 | 1 | 101 | GSYDAVTLNRIPWFHKMQ |
| 4 | 7 | | 6 | | 1 | 25 | 1 | 5 | | 4 | 1 | 101 | GSYARDINPLTVWQFHM |
| 5 | 6 | | 5 | 9 | 4 | 16 | 1 | | 3 | 4 | | 101 | GYTESANDPRFLVKQWH |
| 6 | 6 | 1 | 6 | 5 | 4 | 23 | 2 | 4 | 3 | 3 | 1 | 101 | GYRSWADEFINKLTHCMQV |
| 7 | 13 | | 3 | 1 | 5 | 9 | 3 | 1 | | 4 | 1 | 101 | YASGPRWFTVLDHNEIMQ |
| 8 | 2 | 1 | | 1 | 57 | 3 | | 4 | | 15 | 4 | 101 | FLIMSGWANPVCEY |
| 9 | 3 | | 78 | 2 | | 6 | | 1 | 1 | 1 | | 101 | DGAQENIKLPRSW |
| 10 | | | 3 | | 4 | | 4 | 13 | | 1 | | 101 | YIPSVFHNDL |
| | 54 | 3 | 137 | 28 | 82 | 137 | 15 | 36 | 10 | 54 | 12 | | |

| | N | P | Q | R | S | T | V | W | Y | \| | X | # | |
|---|---|---|---|---|---|---|---|---|---|---|---|---|---|
| 1 | 9 | | 4 | 6 | 5 | 6 | 4 | 3 | 2 | | | 101 | DGNAERTSQVHLWKMYCF |
| 2 | 5 | 6 | 3 | 11 | 8 | 4 | 6 | 1 | 3 | | | 101 | LGRDSPVFINTAEQYMW |
| 3 | 4 | 3 | 1 | 4 | 14 | 5 | 6 | 2 | 10 | | | 101 | GSYDAVTLNRIPWFHKMQ |
| 4 | 5 | 5 | 3 | 7 | 11 | 4 | 4 | 4 | 8 | | | 101 | GSYARDINPLTVWQFHM |

TABLE 11P-continued

Tallies of AA frequencies in all CDR3 by length

| | | | | | | | | | | | | |
|---|---|---|---|---|---|---|---|---|---|---|---|---|
| 5 | 6 | 5 | | 2 | 5 | 8 | 10 | 4 | 2 | 11 | | 101 GYTESANDPRFLVKQWH |
| 6 | 4 | | 1 | 8 | 7 | 3 | 1 | 7 | | 12 | | 101 GYRSWADEFINKLTHCMQV |
| 7 | 2 | 7 | 1 | 7 | 11 | 5 | 5 | 6 | | 17 | | 101 YASGPRWFTVLDHNEIMQ |
| 8 | 2 | 2 | | | 4 | | 2 | 3 | | 1 | | 101 FLIMSGWANPVCEY |
| 9 | 2 | 1 | 3 | 1 | 1 | | | 1 | | | | 101 DGAQENIKLPRSW |
| 10 | 4 | 8 | | | | 7 | | 5 | | 52 | | 101 YIPSVFHNDL |
| | 43 | 37 | 18 | 49 | 76 | 37 | 37 | 29 | | 116 | | 1010 |

Tally of sequences of length 11 # = 118

| | A | C | D | E | F | G | H | I | K | L | M | # |
|---|---|---|---|---|---|---|---|---|---|---|---|---|
| 1 | 7 | 1 | 21 | 11 | | 23 | 5 | 2 | | 7 | | 118 GDEVRALQHSPTINCWY |
| 2 | 1 | 2 | 9 | 1 | 1 | 24 | 5 | 6 | 2 | 7 | 3 | 118 GSRDYLPIVHQTMNCKWAEFX |
| 3 | 4 | | 4 | 2 | 4 | 13 | 2 | 3 | 1 | 7 | 2 | 118 SGTVRLYWADFNQIEHMKP |
| 4 | 10 | | 3 | 3 | 2 | 25 | 1 | 2 | | 4 | 3 | 118 SGARTWYLVDEMQFINPH |
| 5 | 5 | 2 | 10 | 1 | 4 | 24 | 2 | | 1 | 5 | 1 | 118 GSVYDTNALRFWCHQEKM |
| 6 | 6 | | 4 | 2 | 7 | 19 | 2 | 3 | 1 | 5 | 1 | 118 GSYWTFAVLRDINEHQKMP |
| 7 | 4 | 1 | 8 | 5 | 2 | 20 | 4 | 1 | | 2 | 1 | 118 GYSNRDWTEPAHFLQVCIM |
| 8 | 13 | 2 | 6 | 1 | 8 | 12 | 4 | | 2 | 7 | | 118 YAGWFLDPRSTHCKVE |
| 9 | 2 | | 2 | 68 | 2 | | 5 | | | 14 | 7 | 118 FLMYVITADGP |
| 10 | 2 | 1 | 100 | 5 | | 3 | 2 | | | 1 | 1 | 118 DEGAHCLMNPQ |
| 11 | | | 2 | | 6 | | 1 | 7 | 1 | 6 | 1 | 118 YPVISFLNDHKM |
| | 54 | 9 | 169 | 31 | 102 | 165 | 28 | 29 | 8 | 65 | 20 | |

| | N | P | Q | R | S | T | V | W | Y | | X | # |
|---|---|---|---|---|---|---|---|---|---|---|---|---|
| 1 | 2 | 4 | 7 | 8 | 5 | 3 | 10 | 1 | 1 | | | 118 GDEVRALQHSPTINCWY |
| 2 | 3 | 7 | 4 | 10 | 11 | 4 | 6 | 2 | 9 | | 1 | 118 GSRDYLPIVHQTMNCKWAEFX |
| 3 | 4 | 1 | 4 | 8 | 25 | 12 | 9 | 6 | 7 | | | 118 SGTVRLYWADFNQIEHMKP |
| 4 | 2 | 2 | 3 | 9 | 26 | 8 | 4 | 6 | 5 | | | 118 SGARTWYLVDEMQFINPH |
| 5 | 6 | | 2 | 5 | 15 | 9 | 11 | 4 | 11 | | | 118 GSVYDTNALRFWCHQEKM |
| 6 | 3 | 1 | 2 | 5 | 16 | 9 | 6 | 11 | 15 | | | 118 GSYWTFAVLRDINEHQKMP |
| 7 | 9 | 5 | 2 | 9 | 11 | 6 | 2 | 7 | 19 | | | 118 GYSNRDWTEPAHFLQVCIM |
| 8 | | 6 | | 5 | 5 | 5 | 2 | 11 | 29 | | | 118 YAGWFLDPRSTHCKVE |
| 9 | | 1 | | | | 4 | 6 | | 7 | | | 118 FLMYVITADGP |
| 10 | 1 | 1 | 1 | | | | | | | | | 118 DEGAHCLMNPQ |
| 11 | 3 | 13 | | | 7 | | 11 | | 60 | | | 118 YPVISFLNDHKM |
| | 33 | 41 | 25 | 59 | 121 | 60 | 67 | 48 | 163 | | 1 | 1298 |

Tally of sequences of length 12 # = 154

| | A | C | D | E | F | G | H | I | K | L | M | # |
|---|---|---|---|---|---|---|---|---|---|---|---|---|
| 1 | 5 | | 31 | 12 | | 37 | 6 | 1 | 1 | 7 | 3 | 154 GDRESVLHAPMNQTWYIK |
| 2 | 5 | 1 | 7 | 6 | 1 | 25 | 3 | 7 | 3 | 13 | 2 | 154 GSRLPDIQEAVYHKNTMWCF |

TABLE 11P-continued

Tallies of AA frequencies in all CDR3 by length

| | | | | | | | | | | | | |
|---|---|---|---|---|---|---|---|---|---|---|---|---|
| 3 | 10 | 2 | 7 | 5 | 1 | 19 | | 5 | 4 | 12 | 2 | 154 GRSYLATVPDQEIKWCMNF |
| 4 | 8 | | 9 | 6 | 8 | 27 | | 6 | 5 | 6 | 1 | 154 GVSDNAFRTYEILKWPQM |
| 5 | 18 | 1 | 8 | 5 | 6 | 42 | 1 | 9 | 1 | 7 | 3 | 154 GSAIDYLFPTEQVMNWCHK |
| 6 | 13 | | 12 | 4 | 10 | 23 | 1 | 7 | | 8 | 1 | 154 GAVDSFYTLPRWINEQHM |
| 7 | 11 | 2 | 4 | 3 | 10 | 15 | 1 | 4 | | 12 | | 154 YGSPLRAFWTNVDIECQH |
| 8 | 3 | 2 | 18 | 3 | 3 | 25 | 4 | 2 | 5 | 6 | | 154 YGDSNLTKRWHPAEFCIQV |
| 9 | 15 | 1 | 2 | | 8 | 33 | 4 | 7 | 1 | 5 | 1 | 154 GYWARFISPLHTDQCKMN |
| 10 | 1 | 1 | 2 | 1 | 79 | 1 | 2 | 5 | 1 | 19 | 26 | 154 FMLIPYDHVWACEGKNQRST |
| 11 | 2 | | 135 | 2 | | 4 | 2 | | | | | 154 DGYAEHSVNR |
| 12 | | 1 | 1 | | 6 | 1 | 9 | 16 | | 4 | | 154 YVPIHFSLNCDGW |
| | 91 | 11 | 236 | 47 | 132 | 252 | 33 | 69 | 21 | 99 | 39 | |

| | N | P | Q | R | S | T | V | W | Y | \| | X | # |
|---|---|---|---|---|---|---|---|---|---|---|---|---|
| 1 | 3 | 4 | | 3 | 14 | 10 | 3 | 10 | 2 | | 2 | 154 GDRESVLHAPMNQTWYIK |
| 2 | 3 | 11 | | 7 | 22 | 24 | 3 | 5 | 2 | | 4 | 154 GSRLPDIQEAVYHKNTMWCF |
| 3 | 2 | 8 | | 6 | 17 | 17 | 9 | 9 | 4 | | 15 | 154 GRSYLATVPDQEIKWCMNF |
| 4 | 9 | 4 | | 4 | 7 | 17 | 7 | 18 | 5 | | 7 | 154 GVSDNAFRTYEILKWPQM |
| 5 | 3 | 6 | | 4 | | 20 | 6 | 4 | 2 | | 8 | 154 GSAIDYLFPTEQVMNWCHK |
| 6 | 5 | 8 | | 3 | 8 | 11 | 9 | 13 | 8 | | 10 | 154 GAVDSFYTLPRWINEQHM |
| 7 | 5 | 14 | | 2 | 12 | 15 | 6 | 5 | 9 | | 24 | 154 YGSPLRAFWTNVDIECQH |
| 8 | 10 | 4 | | 2 | 5 | 15 | 6 | 2 | 5 | | 34 | 154 YGDSNLTKRWHPAEFCIQV |
| 9 | 1 | 6 | | 2 | 10 | 7 | 3 | | 18 | | 30 | 154 GYWARFISPLHTDQCKMN |
| 10 | 1 | 4 | | 1 | 1 | 1 | 1 | 2 | 2 | | 3 | 154 FMLIPYDHVWACEGKNQRST |
| 11 | 1 | | | | 1 | 2 | | 2 | | | 3 | 154 DGYAEHSVNR |
| 12 | 2 | 18 | | | | 5 | | 32 | 1 | | 58 | 154 YVPIHFSLNCDGW |
| | 45 | 87 | | 34 | 97 | 144 | 53 | 102 | 58 | | 198 | 1848 |

Tally of sequences of length 13 # = 150

| | A | C | D | E | F | G | H | I | K | L | M | # |
|---|---|---|---|---|---|---|---|---|---|---|---|---|
| 1 | 4 | 2 | 28 | 9 | 3 | 37 | 8 | 3 | 3 | 5 | | 150 GDTESHRVLPAQFIKCNW |
| 2 | 11 | 4 | 4 | 1 | 2 | 32 | 3 | 1 | 5 | 11 | 3 | 150 GRSPALTKVCDYHMQWFEIN |
| 3 | 7 | 2 | 8 | 4 | 4 | 23 | 11 | 1 | 4 | 6 | 2 | 150 GSYHQTDPRAVLEFKNCMWI |
| 4 | 6 | 2 | 6 | 4 | 6 | 30 | 1 | 8 | | 6 | 1 | 150 GSWYTIADFLPVEQRCHMNX |
| 5 | 8 | | 10 | 4 | 2 | 28 | 1 | 2 | | 22 | 3 | 150 GLSYDATWPREQMNVFIH |
| 6 | 10 | 2 | 11 | 1 | 6 | 21 | | 2 | 2 | 5 | 1 | 150 GYSPTDAQVFRLNWCIKEM |
| 7 | 5 | 1 | 8 | 1 | 4 | 19 | 1 | 6 | 5 | 21 | 2 | 150 LGYSTDPIRVAKFNWMQCEH |
| 8 | 7 | 5 | 22 | 5 | 3 | 12 | 3 | 3 | 3 | 8 | 1 | 150 YDSGLARTCEQVNPFHIKWM |
| 9 | 1 | 2 | 12 | 3 | 1 | 26 | 7 | 2 | 4 | 7 | 2 | 150 NGYDSWHLPRKETVCIMAFQ |
| 10 | 19 | 1 | 2 | 2 | 17 | 24 | 5 | 2 | | 5 | 1 | 150 YGAFWHLPTNSVDEIQRCM |
| 11 | 1 | | | 1 | 105 | 2 | | 2 | 1 | 13 | 14 | 150 FMLYGIVAEKPQRSWX |

TABLE 11P-continued

Tallies of AA frequencies in all CDR3 by length

|    | A | C | D | E | F | G | H | I | K | L | M | # | |
|----|---|---|---|---|---|---|---|---|---|---|---|---|---|
| 12 |   |   | 130 | 3 |   | 5 | 1 |   |   |   |   | 150 | DGYEQNHT |
| 13 | 1 |   | 2 |   | 5 | 5 | 14 |   | 18 | 1 |   | 150 | YVLIPSFHTDAMN |
|    | 80 | 21 | 243 | 38 | 158 | 259 | 46 | 46 | 27 | 127 | 31 | | |

|    | N | P | Q | R | S | T | V | W | Y | \| | X | # | |
|----|---|---|---|---|---|---|---|---|---|---|---|---|---|
| 1 | 2 | 5 | 4 | 8 | 9 | 11 | 8 | 1 |   |   |   | 150 | GDTESHRVLPAQFIKCNW |
| 2 | 1 | 13 | 3 | 20 | 17 | 7 | 5 | 3 | 4 |   |   | 150 | GRSPALTKVCDYHMQWFEIN |
| 3 | 3 | 8 | 11 | 8 | 16 | 11 | 7 | 2 | 12 |   |   | 150 | GSYHQTDPRAVLEFKNCMWI |
| 4 | 1 | 6 | 4 | 4 | 18 | 10 | 6 | 16 | 14 |   | 1 | 150 | GSWYTIADFLPVEQRCHMNX |
| 5 | 3 | 6 | 4 | 5 | 19 | 8 | 3 | 7 | 15 |   |   | 150 | GLSYDATWPREQMNVFIH |
| 6 | 3 | 15 | 8 | 6 | 16 | 13 | 8 | 3 | 17 |   |   | 150 | GYSPTDAQVFRLNWCIKEM |
| 7 | 4 | 7 | 2 | 6 | 15 | 14 | 6 | 4 | 19 |   |   | 150 | LGYSTDPIRVAKFNWMQCEH |
| 8 | 4 | 4 | 5 | 7 | 15 | 7 | 5 | 2 | 29 |   |   | 150 | YDSGLARTCEQVNPFHIKWM |
| 9 | 31 | 5 | 1 | 5 | 10 | 3 | 3 | 9 | 16 |   |   | 150 | NGYDSWHLPRKETVCIMAFQ |
| 10 | 3 | 5 | 2 | 2 | 3 | 4 | 3 | 15 | 35 |   |   | 150 | YGAFWHLPTNSVDEIQRCM |
| 11 |   | 1 | 1 | 1 | 1 |   | 2 | 1 | 3 |   | 1 | 150 | FMLYGIVAEKPQRSWX |
| 12 | 2 |   | 3 |   |   | 1 |   |   | 5 |   |   | 150 | DGYEQNHT |
| 13 | 1 | 14 |   |   | 13 | 4 | 21 |   | 51 |   |   | 150 | YVLIPSFHTDAMN |
|    | 58 | 89 | 48 | 72 | 152 | 93 | 77 | 63 | 220 |   | 2 | 1950 | |

Tally of sequences of length 14 # = 118

|    | A | C | D | E | F | G | H | I | K | L | M | # | |
|----|---|---|---|---|---|---|---|---|---|---|---|---|---|
| 1 | 6 |   | 29 | 7 | 2 | 32 | 8 | 1 | 1 | 2 |   | 118 | GDVHERTAFLPSIKNQ |
| 2 | 4 |   | 10 | 1 | 5 | 22 | 7 | 3 | 4 | 7 |   | 118 | GPDRYSVHLFAKIQTENW |
| 3 | 11 | 2 | 7 | 2 | 3 | 25 |   | 5 | 1 | 9 | 2 | 118 | GVARYLSDITFWCEMPK |
| 4 | 5 | 2 | 7 | 7 | 3 | 12 | 4 | 4 | 3 | 6 |   | 118 | SGVYPDELRTANHIFKWC |
| 5 | 6 | 5 | 12 |   | 2 | 18 | 2 | 2 | 2 | 4 | 1 | 118 | GYSDTVARCLPFHIKNWMQ |
| 6 | 6 |   | 10 | 5 | 4 | 16 |   | 5 | 3 | 2 | 1 | 118 | YGSTDRAEIFVKWLPQMN |
| 7 | 4 |   | 4 | 1 | 4 | 32 | 2 | 2 | 2 |   | 1 | 118 | GSVTYNADFHIKPQRWEM |
| 8 | 6 | 1 | 5 | 1 | 4 | 18 | 2 | 5 |   | 3 | 2 | 118 | GSYTWAPRDIFNVLHMCE |
| 9 | 5 | 2 | 4 | 1 | 2 | 11 | 2 | 1 | 5 | 9 | 1 | 118 | YSGTLVAKNRDWCFHPEIM |
| 10 | 2 | 5 | 9 | 2 | 3 | 21 |   | 2 | 2 | 4 |   | 118 | YGSDNTCQLRFWAEIKPV |
| 11 | 12 |   | 1 | 3 | 5 | 25 | 2 |   |   | 2 | 1 | 118 | YGWAPVFNEHLTDMQR |
| 12 | 1 |   |   |   | 64 | 5 | 1 | 5 |   | 12 | 16 | 118 | FMLGIPSVAHQTY |
| 13 | 3 |   | 97 | 4 |   | 5 | 1 | 1 | 1 | 1 |   | 118 | DGEANQHIKLV |
| 14 | 2 |   |   |   | 3 |   | 4 | 12 |   | 6 |   | 118 | YVPILHFANS |
|    | 73 | 17 | 195 | 34 | 104 | 242 | 35 | 48 | 24 | 67 | 25 | | |

TABLE 11P-continued

Tallies of AA frequencies in all CDR3 by length

|    | N  | P  | Q  | R  | S   | T  | V   | W  | Y   | \| | X | # |         |
|----|----|----|----|----|-----|----|-----|----|-----|----|---|---|---------|
| 1  | 1  | 2  |    | 1  | 7   | 2  | 7   | 10 |     |    |   | 118 | GDVHERTAFLPSIKNQ |
| 2  | 1  | 13 | 2  | 10 | 8   | 2  | 8   | 1  | 10  |    |   | 118 | GPDRYSVHLFAKIQTENW |
| 3  |    | 2  |    | 11 | 8   | 4  | 13  | 3  | 10  |    |   | 118 | GVARYLSDITFWCEMPK |
| 4  | 5  | 8  |    | 6  | 13  | 6  | 12  | 3  | 12  |    |   | 118 | SGVYPDELRTANHIFKWC |
| 5  | 2  | 3  | 1  | 6  | 15  | 10 | 7   | 2  | 18  |    |   | 118 | GYSDTVARCLPFHIKNWMQ |
| 6  | 1  | 2  | 2  | 7  | 16  | 12 | 4   | 3  | 19  |    |   | 118 | YGSTDRAEIFVKWLPQMN |
| 7  | 5  | 2  | 2  | 2  | 18  | 12 | 13  | 2  | 10  |    |   | 118 | GSVTYNADFHIKPQRWEM |
| 8  | 4  | 6  |    | 6  | 16  | 12 | 4   | 9  | 14  |    |   | 118 | GSYTWAPRDIFNVLHMCE |
| 9  | 5  | 2  |    | 5  | 14  | 10 | 8   | 4  | 27  |    |   | 118 | YSGTLVAKNRDWCFHPEIM |
| 10 | 6  | 2  | 5  | 4  | 13  | 6  | 2   | 3  | 27  |    |   | 118 | YGSDNTCQLRFWAEIKPV |
| 11 | 4  | 7  | 1  | 1  |     | 2  | 6   | 14 | 32  |    |   | 118 | YGWAPVFNEHLTDMQR |
| 12 |    | 4  | 1  |    | 4   | 1  | 3   |    | 1   |    |   | 118 | FMLGIPSVAHQTY |
| 13 | 2  |    | 2  |    |     | 1  |     |    |     |    |   | 118 | DGEANQHIKLV |
| 14 | 2  | 14 |    |    | 2   |    | 20  |    | 53  |    |   | 118 | YVPILHFANS |
|    | 38 | 67 | 17 | 65 | 129 | 84 | 111 | 44 | 233 |    |   | 1652 |  |

Tally of sequences of length 15 # = 125

|    | A  | C  | D   | E  | F   | G   | H  | I  | K  | L  | M  | # |         |
|----|----|----|-----|----|-----|-----|----|----|----|----|----|---|---------|
| 1  | 7  |    | 26  | 8  | 3   | 29  | 1  | 3  |    | 10 |    | 125 | GDLREASTVNFIPYH |
| 2  | 6  |    | 2   | 3  |     | 22  | 3  | 4  | 1  | 9  |    | 125 | RGPLNSTYAVIQEHWDK |
| 3  | 4  | 4  | 5   | 7  | 2   | 19  | 2  | 6  | 2  | 9  | 2  | 125 | GRYLSVEPIDTACQWFHKMN |
| 4  | 7  | 4  | 14  | 6  | 6   | 15  | 2  | 7  | 5  | 7  | 4  | 125 | GDYAILVEFRKSTCMNPWHQ |
| 5  | 6  | 3  | 10  | 2  | 5   | 18  |    | 4  | 2  | 3  | 2  | 125 | GSYVDRWAFTICLNEKMP |
| 6  | 6  | 2  | 7   | 2  | 5   | 10  | 1  | 5  |    | 7  | 1  | 125 | SRYGTDLWAPFIVNCEQHM |
| 7  | 8  | 4  | 14  | 2  | 2   | 22  | 3  | 3  | 1  | 9  | 1  | 125 | GSDLAVRPYCTHIWEFNKM |
| 8  | 6  | 2  | 4   |    |     | 22  |    | 2  | 2  | 3  |    | 125 | GYSVWRATDNPLCIKQ |
| 9  | 4  | 3  | 8   |    | 4   | 20  | 4  | 3  | 1  | 6  |    | 125 | YGSDLPTRVAFHQCINKW |
| 10 | 3  | 4  | 5   | 8  | 8   | 17  | 1  | 3  |    | 7  |    | 125 | YGEFNTLSRDVCPAIWH |
| 11 | 4  | 2  | 15  | 3  | 3   | 17  | 1  | 1  | 1  |    |    | 125 | YGDSNPAWEFRTCQHIKV |
| 12 | 22 | 3  |     |    | 2   | 31  | 3  | 1  |    | 3  | 3  | 125 | GYAWPSNCHLMFQRVITX |
| 13 |    |    |     |    | 71  | 1   |    | 4  |    | 6  | 30 | 125 | FMLISQTVGPRY |
| 14 |    |    | 115 | 2  | 1   | 1   | 1  |    |    |    |    | 125 | DNEFGHPQ |
| 15 |    | 3  |     |    | 5   | 1   | 1  | 20 |    | 7  | 1  | 125 | YVILPFSCNGHMQ |
|    | 83 | 34 | 225 | 43 | 117 | 245 | 23 | 66 | 15 | 86 | 44 |   |  |

|    | N  | P  | Q  | R  | S  | T | V | W | Y  | \| | X | # |         |
|----|----|----|----|----|----|---|---|---|----|----|---|---|---------|
| 1  | 4  | 3  |    | 10 | 7  | 6 | 6 |   | 2  |    |   | 125 | GDLREASTVNFIPYH |
| 2  | 8  | 11 | 4  | 23 | 7  | 7 | 5 | 3 | 7  |    |   | 125 | RGPLNSTYAVIQEHWDK |
| 3  | 2  | 7  | 3  | 13 | 9  | 5 | 8 | 3 | 13 |    |   | 125 | GRYLSVEPIDTACQWFHKMN |

TABLE 11P-continued

Tallies of AA frequencies in all CDR3 by length

| | | | | | | | | | | | | |
|---|---|---|---|---|---|---|---|---|---|---|---|---|
| 4 | 4 | 4 | 1 | 6 | 5 | 5 | 7 | 3 | 13 | | 125 | GDYAILVEFRKSTCMNPWHQ |
| 5 | 3 | 2 | | 8 | 18 | 5 | 11 | 8 | 15 | | 125 | GSYVDRWAFTICLNEKMP |
| 6 | 3 | 6 | 2 | 12 | 24 | 9 | 4 | 7 | 12 | | 125 | SRYGTDLWAPFIVNCEQHM |
| 7 | 2 | 6 | | 7 | 21 | 4 | 8 | 3 | 5 | | 125 | GSDLAVRPYCTHIWEFNKM |
| 8 | 4 | 4 | 2 | 7 | 19 | 5 | 12 | 10 | 21 | | 125 | GYSVWRATDNPLCIKQ |
| 9 | 3 | 6 | 4 | 5 | 19 | 6 | 5 | 1 | 23 | | 125 | YGSDLPTRVAFHQCINKW |
| 10 | 8 | 4 | | 6 | 7 | 8 | 5 | 2 | 29 | | 125 | YGEFNTLSRDVCPAIWH |
| 11 | 7 | 5 | 2 | 3 | 14 | 3 | 1 | 4 | 39 | | 125 | YGDSNPAWEFRTCQHIKV |
| 12 | 4 | 7 | 2 | 2 | 6 | 1 | 2 | 8 | 24 | 1 | 125 | GYAWPSNCHLMFQRVITX |
| 13 | | 1 | 2 | 1 | 4 | 2 | 2 | | 1 | | 125 | FMLISQTVGPRY |
| 14 | 3 | 1 | 1 | | | | | | | | 125 | DNEFGHPQ |
| 15 | 2 | 7 | 1 | | 5 | | 33 | | 39 | | 125 | YVILPFSCNGHMQ |
| | 57 | 74 | 24 | 103 | 165 | 66 | 109 | 52 | 243 | 1 | 1875 | |

Distribution of D-JH with number of cys's

| 0 | 1 | 2 | 3 | 4 |
|---|---|---|---|---|
| 1248 | 53 | 80 | 1 | 1 |

Tally of AAs in the YYCar motif

| | A | C | D | E | F | G | H | I | K | L | M | # | |
|---|---|---|---|---|---|---|---|---|---|---|---|---|---|
| 1 | | | 1 | 1 | 14 | | 1 | | | | | 1383 | YFDEH |
| 2 | | 4 | 1 | | 92 | | 11 | | | 4 | | 1383 | YFHCLSWDR |
| 3 | | 1379 | | | | | | | | | | 1383 | CRS |
| 4 | 1207 | | | 3 | | 2 | 12 | 2 | | 2 | | 1383 | AVTSGNDFILRQX |
| 5 | 14 | | | 1 | 4 | 18 | 17 | 9 | 187 | 4 | 1 | 1383 | RKTSGHAIVNFLQYPEM| |
| | 1221 | 1383 | 5 | 2 | 112 | 30 | 29 | 11 | 187 | 10 | 1 | | |

| | N | P | Q | R | S | T | V | W | Y | \| | X | # | |
|---|---|---|---|---|---|---|---|---|---|---|---|---|---|
| 1 | | | | | | | | | 1366 | | | 1383 | YFDEH |
| 2 | | | | 1 | 3 | | | 2 | 1265 | | | 1383 | YFHCLSWDR |
| 3 | | | | 2 | 2 | | | | | | | 1383 | CRS |
| 4 | 4 | | 1 | 2 | 17 | 51 | 79 | | | | 1 | 1383 | AVTSGNDFILRQX |
| 5 | 7 | 2 | 3 | 992 | 55 | 56 | 9 | | 3 | 1 | | 1383 | RKTSGHAIVNFLQYPEM| |
| | 11 | 2 | 4 | 997 | 77 | 107 | 88 | 2 | 2634 | 1 | 1 | 6915 | |

TABLE 12P

Alignment and tabulation of sequences having 3-22 D segments
D3:3-22_Phz0 YYYDSSGYYY = GLG

| Entry | Seq1 | L1 | Seq2 | L2 | JH | P | Score |
|---|---|---|---|---|---|---|---|
| 1 hs3d6hcv | GRDYYDSGGYFT (SEQ ID NO: 334) | 12 | GRDYYDSGGYFTVAFDI (SEQ ID NO: 335) | 17 | 3 | 6 | 1.76D+13 |

TABLE 12P-continued

| | | | | | | | |
|---|---|---|---|---|---|---|---|
| 2 | hs6d4xb7 | DRHNYYDSSGSYS (SEQ ID NO: 336) | 13 | DRHNYYDSSGSYSDY (SEQ ID NO: 337) | 15 | 4 | 9 4.40D+12 |
| 3 | hs6d4xg3 | DCPAPAKMYYYGSGICT (SEQ ID NO: 338) | 17 | DCPAPAKMYYYGSGICTFDY (SEQ ID NO: 339) | 20 | 4 | 3 6.55D+04 |
| 4 | hs83x6f2 | AFYDSAD (SEQ ID NO: 340) | 7 | AFYDSADDY (SEQ ID NO: 341) | 9 | 4 | -4 2.62D+05 |
| 5 | hsa230644 | RDYYDSSGPEAG (SEQ ID NO: 342) | 12 | RDYYDSSGPEAGFDI (SEQ ID NO: 343) | 15 | 3 | 3 6.87D+10 |
| 6 | hsa239386 | DGTLIDTSAYYYL (SEQ ID NO: 344) | 13 | DGTLIDTSAYYYLY (SEQ ID NO: 345) | 14 | 4 | 6 6.87D+10 |
| 7 | hsa234232 | NSSDSS (SEQ ID NO: 346) | 6 | NSSDSSVLDV (SEQ ID NO: 347) | 10 | 6 | -4 6.55D+04 |
| 8 | hsa239378 | DQVFDSGGYNHR (SEQ ID NO: 348) | 12 | DQVFDSGGYNHRFDS (SEQ ID NO: 349) | 15 | 4 | 3 1.07D+09 |
| 9 | hsa239367 | DLEYYYDSGGHYSP (SEQ ID NO: 350) | 14 | DLEYYYDSGGHYSPFHY (SEQ ID NO: 351) | 17 | 4 | 9 1.10D+12 |
| 10 | hsa239339 | DDSSGY (SEQ ID NO: 352) | 6 | DDSSGYYYIDY (SEQ ID NO: 353) | 11 | 4 | -10 1.72D+10 |
| 11 | hsa245311 | GHYYDSPGQYSYS (SEQ ID NO: 354) | 13 | GHYYDSPGQYSYSEY (SEQ ID NO: 355) | 15 | 4 | 3 1.07D+09 |
| 12 | hsa240578 | GGFRPPPYDYESSAYRTYR (SEQ ID NO: 356) | 19 | GGFRPPPYDYESSAYRTYRLDF (SEQ ID NO: 357) | 22 | 4 | 21 2.75D+11 |
| 13 | hsa245359 | DSDTRAY (SEQ ID NO: 358) | 7 | DSDTRAYYWYFDL (SEQ ID NO: 359) | 13 | 2 | -7 1.68D+07 |
| 14 | hsa245028 | GRHYYDSSGYYSTPE (SEQ ID NO: 360) | 15 | GRHYYDSSGYYSTPENYFDY (SEQ ID NO: 361) | 20 | 4 | 6 1.80D+16 |
| 15 | hsa245019 | DPSYYYDSSGLPL (SEQ ID NO: 362) | 13 | DPSYYYDSSGLPLHGMDV (SEQ ID NO: 363) | 18 | 6 | 9 4.40D+12 |
| 16 | hsa244991 | TYYYDSSGYLLTR (SEQ ID NO: 364) | 13 | TYYYDSSGYLLTRYFQH (SEQ ID NO: 365) | 17 | 1 | 3 4.50D+15 |
| 17 | hsa244945 | NAPHYDSSGYYQT (SEQ ID NO: 366) | 13 | NAPHYDSSGYYQTFDY (SEQ ID NO: 367) | 16 | 4 | 6 7.04D+13 |
| 18 | hsa244943 | GYHSSSYA (SEQ ID NO: 368) | 8 | GYHSSSYADAFDI (SEQ ID NO: 369) | 13 | 3 | -7 6.71D+07 |
| 19 | hsa245289 | PIGYCSGGSC (SEQ ID NO: 370) | 10 | PIGYCSGGSCYSFDY (SEQ ID NO: 371) | 15 | 4 | -4 2.62D+05 |
| 20 | hsa240554 | THGTYVTSGYYPKI (SEQ ID NO: 372) | 14 | THGTYVTSGYYPKI (SEQ ID NO: 373) | 14 | 4 | 6 2.68D+08 |
| 21 | hsa279533 | GATYYYESSGNYP (SEQ ID NO: 374) | 13 | GATYYYESSGNYPDY (SEQ ID NO: 375) | 15 | 4 | 9 7.04D+13 |
| 22 | hsa389177 | AFYHYDSTGYPNRRY (SEQ ID NO: 376) | 15 | AFYHYDSTGYPNRRYYFDY (SEQ ID NO: 377) | 19 | 4 | 6 4.29D+09 |
| 23 | hsa7321 | SYSYYYDSSGYWGG (SEQ ID NO: 378) | 14 | SYSYYYDSSGYWGGYFDY (SEQ ID NO: 379) | 18 | 4 | 9 4.50D+15 |
| 24 | hsaj2772 | LSPYYYDSSSYH (SEQ ID NO: 380) | 12 | LSPYYYDSSSYHDAFDI (SEQ ID NO: 381) | 17 | 3 | 6 2.62D+05 |
| 25 | hsb7g4f08 | EEDYYDSSGQAS (SEQ ID NO: 382) | 12 | EEDYYDSSGQASYNWFXP (SEQ ID NO: 383) | 18 | 5 | 6 2.75D+11 |
| 26 | hsb7g3b02 | ETNYYDSGGYPG (SEQ ID NO: 384) | 12 | ETNYYDSGGYPGFDF (SEQ ID NO: 385) | 15 | 4 | 6 4.40D+12 |
| 27 | hsb7g3c12 | GDHYYDRSGYRH (SEQ ID NO: 386) | 12 | GDHYYDRSGYRHSYYYYAMDV (SEQ ID NO: 387) | 21 | 6 | 6 2.75D+11 |
| 28 | hsb8g3b07 | DRSSGN (SEQ ID NO: 388) | 6 | DRSSGNYFDGMDV (SEQ ID NO: 389) | 13 | 6 | -10 6.55D+04 |

TABLE 12P-continued

| | | | | | | | | |
|---|---|---|---|---|---|---|---|---|
| 29 | hsfog1h | GRSRYSGYG (SEQ ID NO: 390) | 9 | GRSRYSGYGFYSGMDV (SEQ ID NO: 391) | 16 | 6 | -4 | 2.62D+05 |
| 30 | hsgvh0209 | DDTSGYGP (SEQ ID NO: 392) | 8 | DDTSGYGPYYFYYGMDV (SEQ ID NO: 393) | 17 | 6 | -10 | 2.68D+08 |
| 31 | hsgvh55 | RAYYDTSFYFEY (SEQ ID NO: 394) | 12 | RAYYDTSFYFEYY (SEQ ID NO: 395) | 13 | 4 | 3 | 1.72D+10 |
| 32 | hsgvh0304 | DRIDYYKSGYYLGSA (SEQ ID NO: 396) | 15 | DRIDYYKSGYYLGSADS (SEQ ID NO: 397) | 17 | 4 | 6 | 1.68D+07 |
| 33 | hsgvh0332 | DTDSSSHYG (SEQ ID NO: 398) | 9 | DTDSSSHYGRFDP (SEQ ID NO:399 ) | 13 | 5 | -7 | 1.68D+07 |
| 34 | hsgvh0328 | VSISHYDSSGRPQRVF (SEQ ID NO: 400) | 16 | VSISHYDSSGRPQRVFYGMDV (SEQ ID NO: 401) | 21 | 6 | 9 | 1.07D+09 |
| 35 | hsgvh536 | QARENVFYDSSGPTAP (SEQ ID NO: 402) | 16 | QARENVFYDSSGPTAPFDH (SEQ ID NO: 403) | 19 | 4 | 15 | 1.72D+10 |
| 36 | hshcmg42 | VPAGNYYDTSGPDN (SEQ ID NO: 404) | 14 | VPAGNYYDTSGPDNAD (SEQ ID NO: 405) | 16 | 4 | 12 | 1.72D+10 |
| 37 | hsig001vh | WYYFDTSGYYPRNFYYMDV (SEQ ID NO: 406) | 19 | WYYFDTSGYYPRNFYYMDV (SEQ ID NO: 407) | 19 | 4 | 3 | 2.81D+14 |
| 38 | hsig13g10 | GYYYDSGGNYNG (SEQ ID NO: 408) | 12 | GYYYDSGGNYNGDY (SEQ ID NO: 409) | 14 | 4 | 3 | 1.10D+12 |
| 39 | hsighpat3 | DLRSYDPSGYYN (SEQ ID NO: 410) | 12 | DLRSYDPSGYYNDGFDI (SEQ ID NO: 411) | 17 | 3 | 6 | 2.75D+11 |
| 40 | hsigh13g7 | GYYYDRGGNCNG (SEQ ID NO: 412) | 12 | GYYYDRGGNCNGDY (SEQ ID NO: 413) | 14 | 4 | 3 | 6.87D+10 |
| 41 | hsigh13g1 | GYYYDRGGNYNG (SEQ ID NO: 414) | 12 | GYYYDRGGNYNGDY (SEQ ID NO: 415) | 14 | 4 | 3 | 1.10D+12 |
| 42 | hsighxx20 | THYDSSGL (SEQ ID NO: 416) | 8 | THYDSSGLDAFDI (SEQ ID NO: 417) | 13 | 3 | -4 | 1.72D+10 |
| 43 | hsihr9 | DDSSGS (SEQ ID NO: 418) | 6 | DDSSGSYYFDY (SEQ ID NO: 419) | 11 | 4 | -10 | 1.07D+09 |
| 44 | hsihv11 | LSGGYYS (SEQ ID NO: 420) | 7 | LSGGYYSDFDY (SEQ ID NO: 421) | 11 | 4 | -13 | 2.68D+08 |
| 45 | hs ej1f | GDYSDSSDSYI (SEQ ID NO: 422) | 11 | GDYSDSSDSYIDAFV (SEQ ID NO: 423) | 16 | 3 | 3 | 1.10D+12 |
| 46 | hsmvh51 | GETYYYDSRGYA (SEQ ID NO: 424) | 12 | GETYYYDSRGYAFDH (SEQ ID NO: 425) | 15 | 4 | 6 | 2.62D+05 |
| 47 | hsmvh517 | PTRDSSGY (SEQ ID NO: 426) | 8 | PTRDSSGYYVGY (SEQ ID NO: 427) | 12 | 4 | -4 | 1.07D+09 |
| 48 | hsmvh0406 | GSFYYDSSGYPP (SEQ ID NO: 428) | 12 | GSFYYDSSGYPPFDC (SEQ ID NO: 429) | 15 | 4 | 6 | 6.87D+10 |
| 49 | hst14x14 | GPYYYDSSGYYL (SEQ ID NO: 430) | 12 | GPYYYDSSGYYLLDY (SEQ ID NO: 431) | 15 | 4 | 6 | 1.80D+16 |
| 50 | hsvhig2 | EEGYYDSSGYYSLGA (SEQ ID NO: 432) | 15 | EEGYYDSSGYYSLGASDY (SEQ ID NO: 433) | 18 | 4 | 6 | 4.50D+15 |
| 51 | hsvhia2 | RPDSSGSRW (SEQ ID NO: 434) | 9 | RPDSSGSRWYFDY (SEQ ID NO: 435) | 13 | 4 | -7 | 6.71D+07 |
| 52 | hsy14936 | GYYDISGYYF (SEQ ID NO: 436) | 10 | GYYDISGYYFDAFNI (SEQ ID NO: 437) | 15 | 3 | -4 | 2.81D+14 |
| 53 | hsy14934 | DRGYDSSGYYGN (SEQ ID NO: 438) | 12 | DRGYDSSGYYGNLDC (SEQ ID NO: 439) | 15 | 4 | 3 | 1.76D+13 |
| 54 | hsy14935 | DRGYDSIGYYGN (SEQ ID NO: 440) | 12 | DRGYDSIGYYGNLDC (SEQ ID NO: 441) | 15 | 4 | 3 | 1.10D+12 |

TABLE 12P-continued

| | | | | | | | |
|---|---|---|---|---|---|---|---|
| 55 | hsz80519 | AEDLTYYYDRSGWGVHGLL (SEQ ID NO: 442) | 19 | AEDLTYYYDRSGWGVHGLLYYFDY (SEQ ID NO: 443) | 24 | 4 | 15 4.40D+12 |
| 56 | hsz80429 | LYPHYDSSGYYYV (SEQ ID NO: 444) | 13 | LYPHYDSSGYYYVLDY (SEQ ID NO: 445) | 16 | 4 | 6 4.50D+15 |
| 57 | hsz80461 | DRVGYYDSSGYPPGSP (SEQ ID NO: 446) | 16 | DRVGYYDSSGYPPGSPLDY (SEQ ID NO: 447) | 19 | 4 | 9 1.76D+13 |

Frequency of each AA type at each position in 57 Sequences having D3-22 segments

| Pos | A | C | D | E | F | G | H | I | K | L | M | N | P | Q | R | S | T | V | W | Y | \| | X | # |
|---|---|---|---|---|---|---|---|---|---|---|---|---|---|---|---|---|---|---|---|---|---|---|---|
| 1 | | | | | | 1 | | | | | | | | | | | | | | | | 1 | |
| 2 | | | | | | 1 | | | | | | | | | | | | | | | | 1 | |
| 3 | 1 | | | | 1 | | | | | | | | | 1 | | | | | | | | 3 | |
| 4 | 1 | | | 1 | | | | | | | | | | | 1 | | 1 | | | | | 4 | |
| 5 | | | 5 | | | 1 | | | | 1 | | | 2 | | 1 | 1 | 1 | | | | | 12 | |
| 6 | 3 | | 3 | 4 | | 6 | | | | 3 | | 1 | 2 | | 2 | 2 | 1 | | | 1 | | 28 | x |
| 7 | 1 | | 5 | 4 | 1 | 7 | 2 | 1 | | 1 | | 1 | 3 | | 5 | 3 | 4 | 1 | 1 | 1 | | 41 | x |
| 8 | 2 | 1 | 4 | | 1 | 5 | 3 | 1 | | | | 4 | 4 | 1 | 3 | 1 | 3 | 1 | | 14 | | 48 | x |
| 9 | | | 4 | | | 2 | 3 | 5 | 1 | 1 | | | 1 | | 2 | 2 | 2 | 1 | | 28 | | 52 | Y |
| 10 | 1 | | 4 | | 2 | 1 | | 1 | | | | | 1 | | 1 | 4 | 1 | | | 40 | | 56 | Y |
| 11 | | | 46 | 2 | | | 1 | | | 1 | | | | | 1 | 2 | | 1 | | 3 | | 57 | D |
| 12 | 1 | 1 | 1 | | | | | 1 | 1 | | | | 1 | | 4 | 39 | 7 | | | 1 | | 57 | S |
| 13 | 1 | | | | | 8 | | 1 | 1 | | | | 1 | | 1 | 43 | 1 | | | | | 57 | S |
| 14 | 3 | | 2 | | 1 | 45 | | | 1 | | | | | | 1 | 3 | | | | | | 56 | G |
| 15 | | | | | 2 | 2 | | | 2 | 5 | 3 | 2 | 1 | 4 | | | | 1 | 33 | | | 55 | Y |
| 16 | 2 | 1 | 1 | 1 | 2 | 3 | 1 | | 1 | 1 | 6 | | | 3 | 1 | 1 | | 1 | 24 | | | 49 | x |
| 17 | 3 | 1 | | 1 | 1 | 5 | 2 | 1 | 4 | 6 | 6 | 2 | | | 7 | 2 | 1 | 1 | 3 | | | 46 | x |
| 18 | | | | | | 8 | 1 | | 1 | 2 | | 2 | 2 | | 4 | | 3 | 1 | | 3 | | 27 | |
| 19 | | | | 2 | | 1 | | | | 1 | 1 | | | | 3 | 4 | 1 | | | | | 13 | |
| 20 | 2 | | | 1 | 2 | 1 | | | | 1 | | 1 | | | | | | | | 1 | | 9 | |
| 21 | | | | | | | | | 1 | 1 | | | | | | | | | | 1 | | 3 | |
| 22 | | 1 | | | | | | | | | | | | | | | | | | 1 | | 2 | |
| 23 | | | | | | | | | | 1 | | | | | | | | 1 | | | | 2 | |
| 24 | | | 1 | | | | | | | | | | | | | | | | | | | 1 | |
| 25 | | | | | | | | | | | | | | | | | | | | 1 | | 1 | |

Average Dseg = 11.9 Average DJ = 15.7
Median D = 12 12 Shortest 6 Longest 19
Median DJ = 15 15 Shortest 9 Longest 24

TABLE 13P

Frequency of D-segments. "|" stands for a stop codon.

| D seg | "0" | % | C % | GLG | "1" | % | C % | GLG | "2" | % | C % | GLG |
|---|---|---|---|---|---|---|---|---|---|---|---|---|
| 1-01 | 1 | 0.13 | 0 | VQLERX (SEQ ID NO: 132) | 4 | 0.53 | 0.22 | GTTGTX (SEQ ID NO: 133) | 5 | 0.66 | 0.34 | YNWND (SEQ ID NO: 134) |

TABLE 13P-continued

Frequency of D-segments. "|" stands for a stop codon.

| D seg | "0" | % | C % | GLG | "1" | % | C % | GLG | "2" | % | C % | GLG |
|---|---|---|---|---|---|---|---|---|---|---|---|---|
| 1-07 | 0 | 0 | 0 | V\|LELX (SEQ ID NO: 135) | 3 | 0.4 | 0.11 | GITGTX (SEQ ID NO: 136) | 9 | 1.19 | 0.34 | YNWNY (SEQ ID NO: 137) |
| 1-20 | 0 | 0 | 0 | V\|LERX (SEQ ID NO: 138) | 1 | 0.13 | 0.22 | GITGTX (SEQ ID NO: 139) | 4 | 0.53 | 0.45 | YNWND (SEQ ID NO: 140) |
| 1-26 | 4 | 0.53 | 0 | V\|WELLX (SEQ ID NO: 141) | 13 | 1.72 | 0.90 | GIVGATX (SEQ ID NO: 142) | 36 | 4.76 | 0.78 | YSGSYY (SEQ ID NO: 143) |
| 2-02 | 31 | 4.1 | 2.47 | GYCSSTSCYT (SEQ ID NO: 144) | 4 | 0.53 | 0.22 | RIL\|\|YQLLYX (SEQ ID NO: 145) | 9 | 1.19 | 2.47 | DIVVVPAAIX (SEQ ID NO: 146) |
| 2-08 | 5 | 0.66 | 0.56 | GYCTNGVCYT (SEQ ID NO: 147) | 0 | 0 | 0 | RILY\|WCMLYX (SEQ ID NO: 148) | 3 | 0.4 | 0.56 | DIVLMVYAIX (SEQ ID NO: 149) |
| 2-15 | 29 | 3.83 | 1.57 | GYCSGGSCYS (SEQ ID NO: 150) | 2 | 0.26 | 0.11 | RIL\|WW\|LLLX (SEQ ID NO: 151) | 7 | 0.92 | 1.57 | DIVVVAATX (SEQ ID NO: 152) |
| 2-21 | 16 | 2.11 | 0.67 | AYCGGDCYS (SEQ ID NO: 153) | 0 | 0 | 0 | SILWW\|LLFX (SEQ ID NO: 154) | 7 | 0.92 | 0.67 | HIVVVTAIX (SEQ ID NO: 155) |
| 3-03 | 32 | 4.23 | 2.80 | YYDFWSGYYT (SEQ ID NO: 156) | 7 | 0.92 | 0.90 | VLRFLEWLLYX (SEQ ID NO: 157) | 27 | 3.57 | 1.12 | ITIFGVVIIX (SEQ ID NO: 158) |
| 3-09 | 13 | 1.72 | 1.35 | YYDILTGYYN (SEQ ID NO: 159) | 5 | 0.66 | 0.78 | VLRYFDWLL\|X (SEQ ID NO: 160) | 0 | 0 | 0 | ITIF\|LVIIX (SEQ ID NO: 161) |
| 3-10 | 42 | 5.55 | 4.26 | YYYGSGSYYN (SEQ ID NO: 162) | 13 | 1.72 | 0.89 | VLLWFGELL\|X (SEQ ID NO: 163) | 11 | 1.45 | 2.91 | ITMVRGVIIX (SEQ ID NO: 164) |
| 3-16 | 18 | 2.38 | 0.67 | YYDYVWGSYRYT (SEQ ID NO: 165) | 8 | 1.06 | 0 | VL\|LRLGELSLYX (SEQ ID NO: 166) | 5 | 0.66 | 0.34 | IMITFGGVIVIX (SEQ ID NO: 167) |
| 3-22 | 57 | 7.53 | 3.36 | YYYDSSGYYY (SEQ ID NO: 168) | 1 | 0.13 | 0.11 | VLL\|\|\|WLLLX (SEQ ID NO: 169) | 6 | 0.79 | 0.34 | ITMIVVVITX (SEQ ID NO: 170) |
| 4-04 | 5 | 0.66 | 0.28 | DYSNY (SEQ ID NO: 171) | 2 | 0.26 | 0 | \|LQ\|LX (SEQ ID NO: 172) | 2 | 0.26 | 0.06 | TTVTX (SEQ ID NO: 173) |
| 4-17 | 29 | 3.83 | 1.45 | DYGDY (SEQ ID NO: 174) | 0 | 0 | 0 | \|LR\|LX (SEQ ID NO: 175) | 20 | 2.64 | 0.90 | TTVTX (SEQ ID NO: 176) |
| 4-23 | 10 | 1.32 | 0.56 | DYGGNS (SEQ ID NO: 177) | 1 | 0.13 | 0 | \|LRW\|LX (SEQ ID NO: 178) | 4 | 0.53 | 0.56 | TTVVTX (SEQ ID NO: 179) |
| 5-05 | 3 | 0.4 | 0.06 | WIQLWLX (SEQ ID NO: 180) | 10 | 1.32 | 0.39 | VDTAMVX (SEQ ID NO: 181) | 31 | 4.1 | 0.73 | GYSYGY (SEQ ID NO: 182) |
| 5-12 | 0 | 0 | 0 | WI\|WLRLX (SEQ ID NO: 183) | 8 | 1.06 | 0.45 | VDIVATIX (SEQ ID NO: 184) | 14 | 1.85 | 1.12 | GYSGYDY (SEQ ID NO: 185) |
| 5-24 | 11 | 1.45 | 0 | \|RWLQLX (SEQ ID NO: 186) | 5 | 0.66 | 0.34 | VEMATIX (SEQ ID NO: 187) | 13 | 1.72 | 0.44 | RDGYNY (SEQ ID NO: 188) |
| 6-06 | 11 | 1.45 | 0.78 | SIAARX (SEQ ID NO: 189) | 9 | 1.19 | 0.48 | EYSSSS (SEQ ID NO: 190) | 1 | 0.13 | 0.11 | V\|QLVX (SEQ ID NO: 191) |

TABLE 13P-continued

Frequency of D-segments. "|" stands for a stop codon.

| D seg | "0" | % | C % | GLG | "1" | % | C % | GLG | "2" | % | C % | GLG |
|---|---|---|---|---|---|---|---|---|---|---|---|---|
| 6-13 | 19 | 2.51 | 1.01 | GIAAAGX (SEQ ID NO: 192) | 35 | 4.62 | 2.13 | GYSSSWY (SEQ ID NO: 193) | 2 | 0.26 | 0.31 | V\|QQLVX (SEQ ID NO: 194) |
| 6-19 | 14 | 1.85 | 2.12 | GIAVAGX (SEQ ID NO: 195) | 48 | 6.34 | 2.02 | GYSSGWY (SEQ ID NO: 196) | 4 | 0.53 | 0.56 | V\|QWLVX (SEQ ID NO: 197) |
| D7: 7-27 | 1 | 0.13 | 0 | \|LGX | 2 | 0.26 | 0.68 | LTGX (SEQ ID NO: 198) | 2 | 0.26 | 0.22 | NWG |

Total = 757

TABLE 14P

Possible library components.

| Component | | L | f | |
|---|---|---|---|---|
| D2_2-02_Phz0 | xxxYCSSTSCxxx | 13, | 31, | (SEQ ID NO: 199) |
| D3_3-16_Phz0 | xxxxYVWGSYxxxx | 13, | 18, | (SEQ ID NO: 200) |
| D5_5-12_Phz2 | xxxxxxxSGYxxx | 13, | 14, | (SEQ ID NO: 201) |
| D3_3-09_Phz0 | xxxYDILTGYYxx | 13, | 13, | (SEQ ID NO: 202) |
| D2_2-02_Phz2 | xxxVVVPAAxxxx | 13, | 9, | (SEQ ID NO: 203) |
| D3_3-22_Phz0 | xxxYYDSSGYxxx | 12, | 57, | (SEQ ID NO: 204) |
| D3_3-03_Phz0 | xxxDFWSGxxxx | 12, | 32, | (SEQ ID NO: 205) |
| D3_3-03_Phz2 | xxxTIFGVxxxx | 12, | 27, | (SEQ ID NO: 206) |
| D5_5-12_Phz1 | xxxxIVATxxxx | 12, | 8, | (SEQ ID NO: 207) |
| D3_3-10_Phz0 | xxxYGSGSYYx | 11, | 42, | ! could add one x at either end (SEQ ID NO: 208) |
| D5_5-05_Phz2 | xxxxYSYGxxx | 11, | 31, | (SEQ ID NO: 209) |
| D2_2-15_Phz0 | xxxCSGxxCYx | 11, | 29, | (SEQ ID NO: 210) |
| D6_6-13_Phz0 | xxxxAAAGxxx | 11, | 19, | (SEQ ID NO: 211) |
| D4_4-23_Phz0 | xGxxxGGNxxx | 11, | 10, | (SEQ ID NO: 212) |
| D1_1-26_Phz2 | xxxSGSYxxx | 10, | 35, | (SEQ ID NO: 213) |
| D6_6-13_Phz1 | xxxSSSWxxx | 10, | 35, | (SEQ ID NO: 214) |
| D4_4-17_Phz2 | xxxxTTVTTx | 10, | 20, | (SEQ ID NO: 215) |
| D2_2-21_Phz0 | xxxC(SG)GDxCx | 10, | 16, | (SEQ ID NO: 216) |
| D6_6-19_Phz0 | xxx(IV)AVAGxx | 10, | 14, | (SEQ ID NO: 217) |
| D3_3-10_Phz1 | xxLWFGELxx | 10, | 13, | (SEQ ID NO: 218) |
| D5_5-24_Phz0 | GxxWLxxxxF | 10, | 11, | (SEQ ID NO: 219) |
| D5_5-05_Phz1 | xxxDTxMVxx | 10, | 10, | (SEQ ID NO: 220) |
| D3_3-16_Phz2 | xxxxxGExxx | 10, | 8, | (SEQ ID NO: 221) |
| D6_6-19_Phz1 | xxxxSGWxx | 9, | 48, | (SEQ ID NO: 222) |
| D5_5-24_Phz2 | xxxxGYNxx | 9, | 13, | (SEQ ID NO: 223) |
| D3_3-10_Phz2 | xxxVRGVxx | 9, | 11, | (SEQ ID NO: 224) |
| D6_6-06_Phz0 | xxxIAAxxx | 9, | 11, | (SEQ ID NO: 225) |
| D1_1-07_Phz2 | xxYxWNxxx | 9, | 9, | (SEQ ID NO: 226) |
| D4_4-17_Phz0 | xxxYGDxx | 8, | 29, | (SEQ ID NO: 227) |
| D1_1-26_Phz1 | xxVGATxx | 8, | 13, | (SEQ ID NO: 228) |
| D6_6-06_Phz1 | xxxXSSSx | 8, | 9, | (SEQ ID NO: 229) |

TABLE 15P

Lengths of CDRs: 1095 actual VH domains and 51 VH GLGs.

| Length | 0 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| CDR1 | 0 | 0 | 10 | 0 | 1 | 820 | 38 | 175 | 1 | 1 | 5 | 1 | 11 | 0 | 23 | 1 | 7 | 0 |
| GLG | 0 | 0 | 0 | 0 | 0 | 38 | 3 | 10 | 0 | 0... | | | | | | | | |
| CDR2 | 0 | 0 | 0 | 0 | 0 | 2 | 0 | 0 | 0 | 0 | 0 | 0 | 0 | 0 | 0 | 0 | 464 | 579 |
| GLG | 0 | 0 | 0 | 0 | 0 | 0 | 0 | 0 | 0 | 0 | 0 | 0 | 0 | 0 | 0 | 1 | 17 | 28 |
| CDR3 | 0 | 0 | 0 | 4 | 2 | 8 | 6 | 28 | 40 | 65 | 77 | 90 | 117 | 117 | 88 | 105 | 86 | 81 |

| Length | 18 | 19 | 20 | 21 | 22 | 23 | 24 | 25 | 26 | 27 | 28 | 29 | 30 | 31 | 32 | (33 or more) |
|---|---|---|---|---|---|---|---|---|---|---|---|---|---|---|---|---|
| CDR2 | 9 | 31 | 1 | 3 | 3 | 1 | 0 | 0 | 0 | 0 | 2 | 0 | 0... | | | |
| GLG | 1 | 4 | 0 | 0... | | | | | | | | | | | | |
| CDR3 | 45 | 36 | 36 | 16 | 16 | 8 | 8 | 2 | 3 | 0 | 2 | 1 | 0 | 0 | 1 | 5 |

TABLE 16P

Library of HC_CDR3

| Bomponent | Fraction of | Length | #X | Complexity | library | Adjusted |
|---|---|---|---|---|---|---|
| 1: | YYCA21111YFDYWG. (2 = KR) (SEQ ID NO: 6) | 8 | 4 | 2.6E5 | .10 (0-8) | .02 |
| 2: | YYCA2111111YFDYWG. (2 = KR) (SEQ ID NO: 7) | 10 | 6 | 9.4E7 | .14 (9-10) | .14 |
| 3: | YYCA211111111YFDYTG. (2 = KR) (SEQ ID NO: 8) | 12 | 8 | 3.4E10 | .25 (11 + 12 + 13/2) | .25 |
| 4: | YYCAR111S2S3111YFDYWG. (2 = SG 3 = YW) (SEQ ID NO: 9) | 14 | 6 | 1.9E8 | .13 (14 + 13/2) | .14 |
| 5: | YYCA2111CSG11CY1YFDYWG. (2 = KR) (SEQ ID NO: 10) | 15 | 6 | 9.4E7 | .13 (15 + 16/2) | .14 |
| 6: | YYCA211S1TIFG11111YFDYWG. (2 = KR) (SEQ ID NO: 11) | 17 | 8 | 1.7E10 | .11 (17 + 16/2) | .12 |
| 7: | YYCAR111YY2S33YY111YFDYWG. (2 = D\|G; 3 = S\|G) (SEQ ID NO: 12) | 18 | 6 | 3.8E8 | .04 (18) | .08 |
| 8: | YYCAR1111YC2231CY111YFDYWG. (2 = S\|G; 3 = T\|D\|G) (SEQ ID NO: 13) | 19 | 8 | 2.0E11 | .10 (19 on) | .11 |

Allowed lengths: 8, 10, 12, 14, 15, 17, 18, & 19

TABLE 17P vgDNA encoding the CDR3 elements of the library

```
! CDR3 library components
(Ctop25) 5'-gctctggtcaa C|TTA|AGg|gct|gag|g-3' (SEQ ID NO: 40)

(CtprmA) 5'-gctctggtcaa C|TTA|AGg|gct|gag|gac-
!                      AflII...
!        |acc|gct|gtc|tac|tac|tgc|gcc-3' (SEQ ID NO: 41)
!
(CBprmB) [RC] 5'-|tac|ttc|gat|tac|ttg|ggc|caa|GGT|ACC|ctG|GTC|ACC|tcgctccacc-3' (SEQ ID NO: 42)
!                                                  BstEII...
!
(CBot25) [RC]                                5'-|GGT|ACC|ctG|GTC|ACC|tcgctccacc-3' (SEQ ID NO: 43)
!
! N.B. [RC] means the the actual oligonucleotide is the reverse complement
! of the one shown.
! N.B. The 20 bases at 3' end of CtprmA are identical to the most 5' 20 bases
! of each of the vgDNA molecules.
! N.B. Ctop25 is identical to the most 5' 25 bases of CtprmA.
! N.B. The 23 most 3' bases of CBprmB are the reverse complement of the
! most 3' 23 bases of each of the vgDNA molecules.
! N.B. CBot25 is identical to the 25 bases at the 5' end of CBprmB.
!
(C1t08) 5'-cc|gct|gtc|tac|tac|tgc|gcc|-
       <2>|<1>|<1>|<1>|<1>-
       |tac|ttc|gat|tac|ttg|ggc|caa|GG-3' (SEQ ID NO: 44)
! 2 = KR, 1 = 0.27Y + 0.27G + 0.027{ADEFHIKLMNPQRSTVW} no C
!
(C2t10) 5'-cc|gct|gtc|tac|tac|tgc|gcc|-
       <2>|<1>|<1>|<1>|<1>|<1>|<1>|-
       tac|ttc|gat|tac|ttg|ggc|caa|GG-3' (SEQ ID NO: 45)
! 2 = KR, 1 = 0.27Y + 0.27G + 0.027{ADEFHIKLMNPQRSTVW} no C
!
(C3t12) 5'-cc|gct|gtc|tac|tac|tgc|gcc|-
       <2>|<1>|<1>|<1>|<1>|<1>|<1>|<1>|<1>|-
       tac|ttc|gat|tac|ttg|ggc|caa|GG-3' (SEQ ID NO: 46)
! 2 = KR, 1 = 0.27Y + 0.27G + 0.027{ADEFHIKLMNPQRSTVW} no C
!
(C4t14) 5'-cc|gct|gtc|tac|tac|tgc|gcc|cgt|-
       |<1>|<1>|<1>|tct|<2>|tct|<3>|<1>|<1>|<1>|-
       tac|ttc|gat|tac|ttg|ggc|caa|GG-3' (SEQ ID NO: 47)
! 2 = SG, 1 = 0.27Y + 0.27G + 0.027{ADEFHIKLMNPQRSTVW} no C, 3 = YW
!
```

TABLE 17P-continued vgDNA encoding the CDR3 elements of the library

```
(C5t15)  5'-cc|gct|gtc|tac|tac|tgc|gcc|-
             <2>|<1>|<1>|<1>|tgc|tct|ggt|<1>|<1>|tgc|tat|<1>|-
             tac|ttc|gat|tac|ttg|ggc|caa|GG-3' (SEQ ID NO: 48)
! 2 = KR, 1 = 0.27Y + 0.27G + 0.027{ADEFHIKLMNPQRSTVW} no C
!
(C6t17)  5'-cc|gct|gtc|tac|tac|tgc|gcc|-
             <2>|<1>|<1>|tct|<1>|act|atc|ttc|ggt|<1>|<1>|<1>|<1>|<1>|-
             tac|ttc|gat|tac|ttg|ggc|caa|GG-3' (SEQ ID NO: 49)
! 2 = KR, 1 = 0.27Y + 0.27G + 0.027{ADEFHIKLMNPQRSTVW} no C
!
(C7t18)  5'-cc|gct|gtc|tac|tac|tgc|gcc|cgt|-
             |<1>|<1>|<1>|tat|tac|<2>|tct|<3>|<3>|tac|tat|<1>|<1>|<1>|-
             tac|ttc|gat|tac|ttg|ggc|caa|GG-3' (SEQ ID NO: 50)
! 2 = DG, 1 = 0.27Y + 0.27G + 0.027{ADEFHIKLMNPQRSTVW} no C, 3 = SG
!
(c8t19)  5'-cc|gct|gtc|tac|tac|tgc|gcc|cgt|-
             |<1>|<2>|<1>|tat|tgc|<2>|<2>|<3>|<1>|tgc|tat|<1>|<1>|<1>|-
             tac|ttc|gat|tac|ttg|ggc|caa|GG-3' (SEQ ID NO: 51)
! 2 = SG, 1 = 0.27Y + 0.27G + 0.027{ADEFHIKLMNPQRSTVW} no C, 3 = TDG
!
```

TABLE 19

Names of 1398 GeneBank entries examined

| | | | | | |
|---|---|---|---|---|---|
| haj10335 | hsa006167 | hsa234193 | hsa234294 | hsa239370 | hsa241345 | hsa244970 |
| hs201e3 | hsa006169 | hsa234194 | hsa234296 | hsa239371 | hsa241346 | hsa244971 |
| hs201g1 | hsa006171 | hsa234196 | hsa234298 | hsa239372 | hsa241347 | hsa244972 |
| hs201m2 | hsa006173 | hsa234197 | hsa235649 | hsa239373 | hsa241348 | hsa244973 |
| hs202e2 | hsa131921 | hsa234199 | hsa235658 | hsa239375 | hsa241349 | hsa244974 |
| hs202g3 | hsa132847 | hsa234202 | hsa235662 | hsa239376 | hsa241350 | hsa244975 |
| hs202g9 | hsa132849 | hsa234203 | hsa235664 | hsa239377 | hsa241351 | hsa244976 |
| hs202m3 | hsa132850 | hsa234205 | hsa235665 | hsa239378 | hsa241353 | hsa244977 |
| hs203e1 | hsa132851 | hsa234206 | hsa235667 | hsa239379 | hsa241354 | hsa244978 |
| hs203g1 | hsa132852 | hsa234207 | hsa235671 | hsa239380 | hsa241355 | hsa244979 |
| hs203m5 | hsa224746 | hsa234208 | hsa235675 | hsa239381 | hsa241356 | hsa244980 |
| hs204e1 | hsa225092 | hsa234209 | hsa235677 | hsa239382 | hsa241357 | hsa244981 |
| hs204g1 | hsa225093 | hsa234211 | hsa238036 | hsa239383 | hsa241420 | hsa244982 |
| hs3d6hcv | hsa230634 | hsa234212 | hsa238037 | hsa239384 | hsa241421 | hsa244983 |
| hs6d4xa7 | hsa230635 | hsa234214 | hsa238038 | hsa239385 | hsa242555 | hsa244984 |
| hs6d4xb7 | hsa230636 | hsa234217 | hsa238039 | hsa239386 | hsa242556 | hsa244985 |
| hs6d4xf1 | hsa230637 | hsa234221 | hsa238040 | hsa239387 | hsa243108 | hsa244986 |
| hs6d4xf2 | hsa230638 | hsa234224 | hsa238326 | hsa239388 | hsa243110 | hsa244987 |
| hs6d4xg3 | hsa230639 | hsa234227 | hsa238327 | hsa239390 | hsa244928 | hsa244988 |
| hs6d4xh5 | hsa230640 | hsa234229 | hsa238328 | hsa239391 | hsa244929 | hsa244989 |
| hs83x6b2 | hsa230641 | hsa234230 | hsa239330 | hsa240553 | hsa244930 | hsa244990 |
| hs83x6b5 | hsa230643 | hsa234232 | hsa239331 | hsa240554 | hsa244931 | hsa244991 |
| hs83x6c3 | hsa230644 | hsa234235 | hsa239332 | hsa240555 | hsa244932 | hsa244992 |
| hs83x6c4 | hsa230645 | hsa234238 | hsa239333 | hsa240556 | hsa244933 | hsa244993 |
| hs83x6c5 | hsa230646 | hsa234239 | hsa239334 | hsa240557 | hsa244934 | hsa244994 |
| hs83x6d4 | hsa230647 | hsa234242 | hsa239335 | hsa240558 | hsa244935 | hsa244995 |
| hs83x6f1 | hsa230648 | hsa234245 | hsa239336 | hsa240559 | hsa244936 | hsa244996 |
| hs83x6f2 | hsa230649 | hsa234248 | hsa239337 | hsa240560 | hsa244937 | hsa244997 |
| hs83x6f3 | hsa230650 | hsa234249 | hsa239338 | hsa240561 | hsa244938 | hsa244998 |
| hs83x6f5 | hsa230651 | hsa234251 | hsa239339 | hsa240562 | hsa244939 | hsa244999 |
| hs83x6h3 | hsa230652 | hsa234252 | hsa239340 | hsa240563 | hsa244940 | hsa245000 |
| hs83x9a6 | hsa230653 | hsa234255 | hsa239341 | hsa240564 | hsa244941 | hsa245001 |
| hs83x9b6 | hsa230654 | hsa234256 | hsa239342 | hsa240565 | hsa244942 | hsa245002 |
| hs83x9b9 | hsa230655 | hsa234257 | hsa239343 | hsa240566 | hsa244943 | hsa245003 |
| hs83x9c8 | hsa230656 | hsa234258 | hsa239344 | hsa240567 | hsa244944 | hsa245004 |
| hs83x9d6 | hsa230657 | hsa234259 | hsa239345 | hsa240568 | hsa244945 | hsa245005 |
| hs83x9d7 | hsa230658 | hsa234260 | hsa239346 | hsa240569 | hsa244946 | hsa245006 |
| hs83x9e6 | hsa234156 | hsa234262 | hsa239347 | hsa240570 | hsa244947 | hsa245007 |
| hs83x9e8 | hsa234158 | hsa234263 | hsa239348 | hsa240571 | hsa244948 | hsa245008 |
| hs83x9e9 | hsa234160 | hsa234264 | hsa239349 | hsa240572 | hsa244949 | hsa245009 |
| hs83x9f6 | hsa234161 | hsa234266 | hsa239350 | hsa240573 | hsa244950 | hsa245010 |
| hs83x9g6 | hsa234163 | hsa234268 | hsa239351 | hsa240575 | hsa244951 | hsa245011 |
| hs9d4x10 | hsa234164 | hsa234269 | hsa239353 | hsa240576 | hsa244952 | hsa245012 |
| hs9d4x7 | hsa234166 | hsa234270 | hsa239354 | hsa240578 | hsa244953 | hsa245013 |
| hs9d4x8 | hsa234168 | hsa234272 | hsa239355 | hsa240580 | hsa244954 | hsa245014 |
| hs9d4x9 | hsa234169 | hsa234273 | hsa239356 | hsa240581 | hsa244955 | hsa245015 |
| hs9d4xa6 | hsa234171 | hsa234274 | hsa239357 | hsa240582 | hsa244956 | hsa245016 |
| hs9d4xa7 | hsa234172 | hsa234276 | hsa239358 | hsa240585 | hsa244957 | hsa245017 |
| hs9d4xb6 | hsa234175 | hsa234277 | hsa239359 | hsa240586 | hsa244958 | hsa245018 |
| hs9d4xc2 | hsa234178 | hsa234279 | hsa239360 | hsa240588 | hsa244959 | hsa245019 |

TABLE 19-continued

Names of 1398 GeneBank entries examined

| | | | | | |
|---|---|---|---|---|---|
| hs9d4xd6 | hsa234180 | hsa234281 | hsa239361 | hsa240589 | hsa244960 | hsa245020 |
| hs9d4xe6 | hsa234181 | hsa234282 | hsa239362 | hsa240590 | hsa244961 | hsa245021 |
| hs9d4xf3 | hsa234183 | hsa234283 | hsa239363 | hsa240592 | hsa244962 | hsa245022 |
| hs9d4xh4 | hsa234184 | hsa234284 | hsa239364 | hsa240593 | hsa244963 | hsa245023 |
| hs9d4xh5 | hsa234186 | hsa234286 | hsa239365 | hsa240594 | hsa244965 | hsa245024 |
| hsa005975 | hsa234187 | hsa234287 | hsa239366 | hsa240595 | hsa244966 | hsa245025 |
| hsa005977 | hsa234189 | hsa234288 | hsa239367 | hsa240599 | hsa244967 | hsa245026 |
| hsa006161 | hsa234190 | hsa234290 | hsa239368 | hsa240604 | hsa244968 | hsa245027 |
| hsa006165 | hsa234191 | hsa234291 | hsa239369 | hsa241344 | hsa244969 | hsa245028 |
| hsa245029 | hsa245225 | hsa245319 | hsa279536 | hsasighc | hsb8g3g01 | hsfs11hc |
| hsa245030 | hsa245226 | hsa245320 | hsa279537 | hsavh510 | hsb8g3g03 | hsfs9whc |
| hsa245031 | hsa245228 | hsa245321 | hsa279543 | hsavh512 | hsb8g3g05 | hsgad2h |
| hsa245032 | hsa245229 | hsa245322 | hsa279544 | hsavh513 | hsb8g3g10 | hsgvh0117 |
| hsa245033 | hsa245230 | hsa245323 | hsa279545 | hsavh514 | hsb8g3h01 | hsgvh0118 |
| hsa245034 | hsa245231 | hsa245325 | hsa279552 | hsavh515 | hsb8g4c02 | hsgvh0119 |
| hsa245035 | hsa245232 | hsa245326 | hsa389169 | hsavh516 | hsb8g4e01 | hsgvh0120 |
| hsa245036 | hsa245233 | hsa245338 | hsa389170 | hsavh517 | hsb8g4e05 | hsgvh0121 |
| hsa245037 | hsa245234 | hsa245342 | hsa389171 | hsavh519 | hsb8g4f11 | hsgvh0122 |
| hsa245039 | hsa245235 | hsa245343 | hsa389172 | hsavh520 | hsb8g4h09 | hsgvh0123 |
| hsa245040 | hsa245236 | hsa245345 | hsa389173 | hsavh523 | hsb8g4h10 | hsgvh0124 |
| hsa245041 | hsa245237 | hsa245346 | hsa389174 | hsavh524 | hsb8g5d10 | hsgvh0201 |
| hsa245042 | hsa245238 | hsa245347 | hsa389175 | hsavh526 | hsb8g5h08 | hsgvh0202 |
| hsa245043 | hsa245239 | hsa245348 | hsa389176 | hsavh529 | hsbel1 | hsgvh0203 |
| hsa245044 | hsa245240 | hsa245349 | hsa389177 | hsavh53 | hsbel14 | hsgvh0204 |
| hsa245045 | hsa245241 | hsa245350 | hsa389178 | hsavh56 | hsbel28 | hsgvh0205 |
| hsa245046 | hsa245246 | hsa245352 | hsa389179 | hsb3g4a07 | hsbel29 | hsgvh0206 |
| hsa245047 | hsa245251 | hsa245353 | hsa389180 | hsb73g04n | hsbel3 | hsgvh0207 |
| hsa245048 | hsa245255 | hsa245355 | hsa389181 | hsb74a08n | hsbel34 | hsgvh0208 |
| hsa245049 | hsa245258 | hsa245356 | hsa389182 | hsb7g1a11 | hsbel43 | hsgvh0209 |
| hsa245050 | hsa245260 | hsa245357 | hsa389183 | hsb7g2b01 | hsbel45 | hsgvh0210 |
| hsa245051 | hsa245261 | hsa245358 | hsa389184 | hsb7g3a01 | hsbel5 | hsgvh0211 |
| hsa245052 | hsa245262 | hsa245359 | hsa389185 | hsb7g3a05 | hsbel54 | hsgvh0213 |
| hsa245053 | hsa245263 | hsa249378 | hsa389186 | hsb7g3a10 | hsbel69 | hsgvh0214 |
| hsa245054 | hsa245265 | hsa249628 | hsa389187 | hsb7g3b02 | hsbo1vhig | hsgvh0215 |
| hsa245055 | hsa245266 | hsa249629 | hsa389188 | hsb7g3b03 | hsbo3vhig | hsgvh0216 |
| hsa245056 | hsa245268 | hsa249630 | hsa389190 | hsb7g3b05 | hsbr1vhig | hsgvh0217 |
| hsa245057 | hsa245272 | hsa249631 | hsa389191 | hsb7g3c03 | hsbradh3 | hsgvh0218 |
| hsa245058 | hsa245273 | hsa249632 | hsa389192 | hsb7g3c12 | hscal4ghc | hsgvh0219 |
| hsa245059 | hsa245275 | hsa249633 | hsa389193 | hsb7g3d07 | hsd4xd10 | hsgvh0220 |
| hsa245060 | hsa245277 | hsa249634 | hsa389194 | hsb7g3e01 | hsd4xf21 | hsgvh0221 |
| hsa245061 | hsa245278 | hsa249635 | hsa389195 | hsb7g3f02 | hsd4xg2 | hsgvh0222 |
| hsa245062 | hsa245279 | hsa249636 | hsa389927 | hsb7g3f10 | hsd4xi10 | hsgvh0223 |
| hsa245063 | hsa245280 | hsa249637 | hsa389929 | hsb7g3g02 | hsd4xi4 | hsgvh0224 |
| hsa245064 | hsa245281 | hsa271600 | hsa6351 | hsb7g3g04 | hsd4xk9 | hsgvh0302 |
| hsa245065 | hsa245282 | hsa271601 | hsa7321 | hsb7g4a08 | hsd4xl3 | hsgvh0304 |
| hsa245066 | hsa245283 | hsa271602 | hsa7322 | hsb7g4c05 | hsd5hc | hsgvh0306 |
| hsa245067 | hsa245284 | hsa271603 | hsa7323 | hsb7g4d09 | hsdo1vhig | hsgvh0307 |
| hsa245068 | hsa245285 | hsa271604 | hsa7325 | hsb7g4f08 | hseliepa1 | hsgvh0308 |
| hsa245069 | hsa245286 | hsa279513 | hsa7326 | hsb7g4g07 | hseliepa3 | hsgvh0309 |
| hsa245071 | hsa245287 | hsa279514 | hsa7328 | hsb7g5g03 | hseliepa4 | hsgvh0310 |
| hsa245072 | hsa245288 | hsa279515 | hsa7438 | hsb8g1c04 | hseliepb2 | hsgvh0311 |
| hsa245073 | hsa245289 | hsa279516 | hsa7440 | hsb8g1e04 | hseliepd2 | hsgvh0312 |
| hsa245201 | hsa245290 | hsa279517 | hsa7441 | hsb8g1f03 | hselilpb1 | hsgvh0314 |
| hsa245203 | hsa245291 | hsa279519 | hsa7442 | hsb8g1g04 | hsevh51a1 | hsgvh0315 |
| hsa245204 | hsa245292 | hsa279520 | hsa7443 | hsb8g1h02 | hsevh51b1 | hsgvh0318 |
| hsa245208 | hsa245294 | hsa279521 | hsa7444 | hsb8g2f09 | hsevh52a1 | hsgvh0320 |
| hsa245209 | hsa245298 | hsa279522 | hsaarma1 | hsb8g2g08 | hsevh52a2 | hsgvh0321 |
| hsa245210 | hsa245299 | hsa279523 | hsabhiv8 | hsb8g3b07 | hsevh52a3 | hsgvh0322 |
| hsa245214 | hsa245301 | hsa279524 | hsadeigvh | hsb8g3c07 | hsevh52a4 | hsgvh0323 |
| hsa245215 | hsa245305 | hsa279526 | hsaj2768 | hsb8g3c08 | hsevh52a5 | hsgvh0324 |
| hsa245217 | hsa245307 | hsa279527 | hsaj2769 | hsb8g3c12 | hsevh52b1 | hsgvh0325 |
| hsa245218 | hsa245309 | hsa279528 | hsaj2771 | hsb8g3d03 | hsevh53a1 | hsgvh0326 |
| hsa245219 | hsa245311 | hsa279529 | hsaj2772 | hsb8g3d04 | hsevh53a2 | hsgvh0327 |
| hsa245220 | hsa245312 | hsa279530 | hsaj2773 | hsb8g3d07 | hsfog1h | hsgvh0328 |
| hsa245221 | hsa245313 | hsa279531 | hsaj2776 | hsb8g3d08 | hsfog3h | hsgvh0329 |
| hsa245222 | hsa245315 | hsa279532 | hsaj2777 | hsb8g3e02 | hsfogbh | hsgvh0330 |
| hsa245223 | hsa245317 | hsa279533 | hsaj4083 | hsb8g3e03 | hsfom1h | hsgvh0331 |
| hsa245224 | hsa245318 | hsa279535 | hsaj4899 | hsb8g3f03 | hsfs10hc | hsgvh0332 |
| hsgvh0333 | hsigathc | hsighxx10 | hsigvhc26 | hsld1117 | hsmvh51 | hst14x23 |
| hsgvh0334 | hsigdvrhc | hsighxx11 | hsigvhc27 | hsld152 | hsmvh510 | hst14x24 |
| hsgvh0335 | hsigg1kh | hsighxx12 | hsigvhc28 | hsld21 | hsmvh511 | hst14x25 |
| hsgvh0336 | hsigg1kl | hsighxx14 | hsigvhc29 | hsld217 | hsmvh512 | hst14x3 |
| hsgvh0419 | hsigg1lh | hsighxx16 | hsigvhc30 | hsld218 | hsmvh515 | hst14x6 |
| hsgvh0420 | hsigghc85 | hsighxx18 | hsigvhc31 | hsld25 | hsmvh516 | hst14x7 |
| hsgvh0421 | hsigghcv3 | hsighxx2 | hsigvhc32 | hsmad2h | hsmvh517 | hst14x8 |
| hsgvh0422 | hsigghevr | hsighxx20 | hsigvhc33 | hsmbcl5h4 | hsmvh53 | hst14x9 |
| hsgvh0423 | hsiggvdj1 | hsighxx21 | hsigvhc35 | hsmica1h | hsmvh54 | hst22x1 |
| hsgvh0424 | hsiggvdj2 | hsighxx22 | hsigvhc36 | hsmica3h | hsmvh55 | hst22x11 |

TABLE 19-continued

Names of 1398 GeneBank entries examined

| | | | | | | |
|---|---|---|---|---|---|---|
| hsgvh0428 | hsiggvhb | hsighxx23 | hsigvhc37 | hsmica4h | hsmvh56 | hst22x12 |
| hsgvh0429 | hsiggvhc | hsighxx25 | hsigvhc38 | hsmica5h | hsmvh57 | hst22x13 |
| hsgvh0430 | hsigh10g1 | hsighxx26 | hsigvhc39 | hsmica6h | hsmvh58 | hst22x14 |
| hsgvh0517 | hsigh10g2 | hsighxx28 | hsigvhc40 | hsmica7h | hsmvh59 | hst22x15 |
| hsgvh0519 | hsigh10g3 | hsighxx29 | hsigvhc41 | hsmt11ige | hsnamembo | hst22x18 |
| hsgvh0522 | hsigh10g4 | hsighxx3 | hsigvhc42 | hsmt12ige | hsnpb346e | hst22x20 |
| hsgvh0523 | hsigh10g5 | hsighxx30 | hsigvhc43 | hsmt13ige | hsoak3h | hst22x21 |
| hsgvh0526 | hsigh10g7 | hsighxx31 | hsigvhls | hsmt14ige | hsog31h | hst22x22 |
| hsgvh0527 | hsigh10g8 | hsighxx32 | hsigvhttd | hsmt15ige | hspag1h | hst22x23 |
| hsgvh0531 | hsigh10g9 | hsighxx34 | hsigvp151 | hsmt16ige | hsrael | hst22x25 |
| hsgvh511 | hsigh13g1 | hsighxx36 | hsigvp152 | hsmt17ige | hsregah | hst22x26 |
| hsgvh512 | hsigh13g7 | hsighxx37 | hsigvp153 | hsmt21ige | hsrfabh37 | hst22x27 |
| hsgvh513 | hsigh14g1 | hsighxx38 | hsigvp154 | hsmt22ige | hsrighvja | hst22x28 |
| hsgvh515 | hsigh14g2 | hsighxx5 | hsigvp155 | hsmt23ige | hsrighvjb | hst22x30 |
| hsgvh519 | hsigh2f2 | hsighxx6 | hsigvp156 | hsmt24ige | hsrou10 | hst22x9 |
| hsgvh521 | hsigh3135 | hsighxx7 | hsigvp157 | hsmt25ige | hsrou11 | hsu24687 |
| hsgvh526 | hsigh35 | hsighxx8 | hsigvp158 | hsmt26ige | hsrou111 | hsu24688 |
| hsgvh530 | hsigh44 | hsighxx9 | hsigvp251 | hsmt27ige | hsrou112 | hsu24690 |
| hsgvh533 | hsigh4c2 | hsigkrf | hsigvp255 | hsmutuiem | hsrou119 | hsu24691 |
| hsgvh534 | hsigh9e1 | hsigmhavh | hsigvp256 | hsmvh0001 | hsrou122 | hsv52a512 |
| hsgvh535 | hsighadi2 | hsigrhe15 | hsigvp257 | hsmvh0002 | hsrou126 | hsvdj10h |
| hsgvh536 | hsighadi3 | hsigtgk1h | hsigvp360 | hsmvh0003 | hsrou127 | hsvdj12h |
| hsgvh55 | hsighcvr | hsigtgk4h | hsigvp363 | hsmvh0004 | hsrou129 | hsvgcg1 |
| hsh217e | hsighcza | hsigtgl9h | hsigvp369 | hsmvh0005 | hsrou13 | hsvgcm1 |
| hsh241e | hsighczb | hsigvarh1 | hsigvp39 | hsmvh0006 | hsrou131 | hsvgcm1 |
| hsh28e | hsighczc | hsigvhc | hsihr8 | hsmvh0007 | hsrou18 | hsvh1djh6 |
| hsha3d1ig | hsighczd | hsigvhc01 | hsihr9 | hsmvh0009 | hsrou219 | hsvh3djh4 |
| hshambh | hsighczf | hsigvhc02 | hsihv1 | hsmvh0010 | hsrou221 | hsvh4dj |
| hshcmg42 | hsighczg | hsigvhc03 | hsihv11 | hsmvh0011 | hsrou222 | hsvh4djh6 |
| hshcmg43 | hsigheavy | hsigvhc04 | hsihv18 | hsmvh0012 | hsrou233 | hsvh4r |
| hshcmg44 | hsighpat2 | hsigvhc05 | hsim9vch | hsmvh0401 | hsrt792hc | hsvh52a43 |
| hshcmg46 | hsighpat3 | hsigvhc06 | hsimghc1 | hsmvh0403 | hsrt79hc | hsvh52a55 |
| hshcmt42 | hsighpat4 | hsigvhc07 | hsimghc2 | hsmvh0404 | hssm1vhig | hsvh5dj |
| hshcmt47 | hsighpat5 | hsigvhc08 | hsimghc3 | hsmvh0405 | hssp46a | hsvh5djh5 |
| hsig001vh | hsighpat6 | hsigvhc09 | hsimghc4 | hsmvh0406 | hst14vh | hsvh710p1 |
| hsig030vh | hsighpat7 | hsigvhc10 | hsimghc5 | hsmvh0501 | hst14x1 | hsvheg7 |
| hsig033vh | hsighpat8 | hsigvhc11 | hsin42p5 | hsmvh0502 | hst14x10 | hsvhfa2 |
| hsig039vh | hsighpat9 | hsigvhc12 | hsin51p7 | hsmvh0503 | hst14x11 | hsvhfa7 |
| hsig040vh | hsighpt11 | hsigvhc14 | hsin51p8 | hsmvh0504 | hst14x12 | hsvhfb5 |
| hsig055vh | hsighpt12 | hsigvhc16 | hsin78 | hsmvh0505 | hst14x13 | hsvhfc2 |
| hsig057vh | hsighpta1 | hsigvhc17 | hsin87 | hsmvh0506 | hst14x14 | hsvhfd7 |
| hsig1059 | hsighvb5 | hsigvhc18 | hsin89p2 | hsmvh0507 | hst14x15 | hsvhfe5 |
| hsig10610 | hsighvca | hsigvhc19 | hsin92 | hsmvh0508 | hst14x16 | hsvhfg9 |
| hsig13g10 | hsighvcb | hsigvhc20 | hsin98p1 | hsmvh0509 | hst14x17 | hsvhgd8 |
| hsig473 | hsighvcc | hsigvhc21 | hsjac10h | hsmvh0510 | hst14x18 | hsvhgd9 |
| hsig7sa11 | hsighvcd | hsigvhc22 | hsjhba1f | hsmvh0511 | hst14x19 | hsvhgh7 |
| hsigaehc | hsighvce | hsigvhc23 | hsjhbr2f | hsmvh0513 | hst14x20 | hsvhha10 |
| hsigaf2h2 | hsighvm | hsigvhc24 | hsjhej1f | hsmvh0515 | hst14x21 | hsvhia2 |
| hsigashc | hsighxx1 | hsigvhc25 | hsld1110 | hsmvh0529 | hst14x22 | hsvhia5 |
| hsvhib12 | hsvhp46 | hsx98948 | hsz74671 | hsz80393 | hsz80438 | hsz80489 |
| hsvhib6 | hsvhp48 | hsx98950 | hsz74672 | hsz80394 | hsz80439 | hsz80492 |
| hsvhib8 | hsvhp53 | hsx98951 | hsz74682 | hsz80397 | hsz80441 | hsz80495 |
| hsvhic1 | hsvhp7 | hsx98952 | hsz74688 | hsz80400 | hsz80442 | hsz80496 |
| hsvhic10 | hsvigd9 | hsx98953 | hsz74690 | hsz80403 | hsz80443 | hsz80499 |
| hsvhic11 | hswad35vh | hsx98954 | hsz74693 | hsz80406 | hsz80445 | hsz80500 |
| hsvhic2 | hswanembo | hsx98955 | hsz74695 | hsz80407 | hsz80458 | hsz80502 |
| hsvhic3 | hswo1vhig | hsx98956 | hsz80363 | hsz80409 | hsz80459 | hsz80504 |
| hsvhid1 | hsww1p10e | hsx98958 | hsz80364 | hsz80411 | hsz80460 | hsz80507 |
| hsvhid5 | hsx98932 | hsx98963 | hsz80365 | hsz80412 | hsz80461 | hsz80509 |
| hsvhid7 | hsx98933 | hsy14934 | hsz80367 | hsz80414 | hsz80462 | hsz80512 |
| hsvhid9 | hsx98934 | hsy14935 | hsz80368 | hsz80415 | hsz80463 | hsz80513 |
| hsvhie4 | hsx98935 | hsy14936 | hsz80372 | hsz80416 | hsz80465 | hsz80517 |
| hsvhif10 | hsx98936 | hsy14937 | hsz80375 | hsz80417 | hsz80466 | hsz80519 |
| hsvhif3 | hsx98938 | hsy14938 | hsz80377 | hsz80418 | hsz80473 | hsz80520 |
| hsvhif7 | hsx98939 | hsy14939 | hsz80378 | hsz80421 | hsz80474 | hsz80527 |
| hsvhig2 | hsx98940 | hsy14940 | hsz80383 | hsz80422 | hsz80475 | hsz80534 |
| hsvhp2 | hsx98941 | hsy14943 | hsz80385 | hsz80424 | hsz80476 | hsz80538 |
| hsvhp29 | hsx98943 | hsy14945 | hsz80386 | hsz80426 | hsz80477 | hsz80544 |
| hsvhp30 | hsx98944 | hsy18120 | hsz80388 | hsz80427 | hsz80480 | hsz80545 |
| hsvhp32 | hsx98945 | hsz74663 | hsz80390 | hsz80429 | hsz80482 | |
| hsvhp34 | hsx98946 | hsz74665 | hsz80391 | hsz80433 | hsz80483 | |
| hsvhp4 | hsx98947 | hsz74668 | hsz80392 | hsz80436 | hsz80487 | |

TABLE 20P

| | | Human GLG CDR1 & CDR2 AA seqs | |
|---|---|---|---|
| Name | CDR1<br>1234567 | CDR2<br>          1  1  1<br>1234567890123456789 | |
| 1-02 | GYY--MH | WINPNSGG--TNYAQKFQG | (SEQ ID NO: 231) |
| 1-03 | SYA--MH | WINAGNGN--TKYSQKFQG | (SEQ ID NO: 233) |
| 1-08 | SYD--IN | WMNPNSGN--TGYAQKFQG | (SEQ ID NO: 235) |
| 1-18 | SYG--IS | WISAYNGN--TNYAQKLQG | (SEQ ID NO: 237) |
| 1-24 | ELS--MH | GFDPEDGE--TIYAQKFQG | (SEQ ID NO: 239) |
| 1-45 | YRY--LH | WITPFNGN--TNYAQKFQD | (SEQ ID NO: 241) |
| 1-46 | SYY--MH | IINPSGGS--TSYAQKFQG | (SEQ ID NO: 243) |
| 1-58 | SSA--VQ | WIVVGSGN--TNYAQKFQE | (SEQ ID NO: 245) |
| 1-69 | SYA--IS | GIIPIFGT--ANYAQKFQG | (SEQ ID NO: 247) |
| 1-e | SYA--IS | GIIPIFGT--ANYAQKFQG | (SEQ ID NO: 249) |
| 1-f | DYY--MH | LVDPEDGE--TIYAEKFQG | (SEQ ID NO: 251) |
| 2-05 | TSGVGVG | LIYWNDDK---RYSPSLKS | (SEQ ID NO: 253) |
| 2-26 | NARMGVS | HIFSNDEK---SYSTSLKS | (SEQ ID NO: 255) |
| 2-70 | TSGMRVS | RIDWDDDK---FYSTSLKT | (SEQ ID NO: 257) |
| 3-07 | SYW--MS | NIKQDGSE--KYYVDSVKG | (SEQ ID NO: 259) |
| 3-09 | DYA--MH | GISWNSGS--IGYADSVKG | (SEQ ID NO: 261) |
| 3-11 | DYY--MS | YISSSGST--IYYADSVKG | (SEQ ID NO: 263) |
| 3-13 | SYD--MH | AIGTAGD---TYYPGSVKG | (SEQ ID NO: 265) |
| 3-15 | NAW--MS | RIKSKTDGGTTDYAAPVKG | (SEQ ID NO: 267) |
| 3-20 | DYG--MS | GINWNGGS--TGYADSVKG | (SEQ ID NO: 269) |
| 3-21 | SYS--MN | SISSSSSY--IYYADSVKG | (SEQ ID NO: 271) |
| 3-23 | SYA--MS | AISGSGGS--TYYADSVKG | (SEQ ID NO: 273) |
| 3-30 | SYG--MH | VISYDGSN--KYYADSVKG | (SEQ ID NO: 275) |
| 3303 | SYA--MH | VISYDGSN--KYYADSVKG | (SEQ ID NO: 277) |
| 3305 | SYG--MH | VISYDGSN--KYYADSVKG | (SEQ ID NO: 279) |
| 3-33 | SYG--MH | VIWYDGSN--KYYADSVKG | (SEQ ID NO: 281) |
| 3-43 | DYT--MH | LISWDGGS--TYYADSVKG | (SEQ ID NO: 283) |
| 3-48 | SYS--MN | YISSSSST--IYYADSVKG | (SEQ ID NO: 285) |
| 3-49 | DYA--MS | FIRSKAYGGTTEYTASVKG | (SEQ ID NO: 287) |
| 3-53 | SNY--MS | VIYSGGS---TYYADSVKG | (SEQ ID NO: 289) |
| 3-64 | SYA--MH | AISSNGGS--TYYANSVKG | (SEQ ID NO: 291) |
| 3-66 | SNY--MS | VIYSGGS---TYYADSVKG | (SEQ ID NO: 293) |
| 3-72 | DHY--MD | RTRNKANSYTTEYAASVKG | (SEQ ID NO: 295) |
| 3-73 | GSA--MH | RIRSKANSYATAYAASVKG | (SEQ ID NO: 297) |
| 3-74 | SYW--MH | RINSDGSS--TSYADSVKG | (SEQ ID NO: 299) |
| 3-d | SNE--MS | SISGGS----TYYADSRKG | (SEQ ID NO: 301) |
| 4-04 | SSNW-WS | EIYHSGS---TNYNPSLKS | (SEQ ID NO: 303) |

TABLE 20P-continued

| | | | |
|---|---|---|---|
| 4-28 | SSNW-WG | YIYYSGS---TYYNPSLKS | (SEQ ID NO: 305) |
| 4301 | SGGYYWS | YIYYSGS---TYYNPSLKS | (SEQ ID NO: 307) |
| 4302 | SGGYSWS | YIYHSGS---TYYNPSLKS | (SEQ ID NO: 309) |
| 4304 | SGDYYWS | YIYYSGS---TYYNPSLKS | (SEQ ID NO: 311) |
| 4-31 | SGGYYWS | YIYYSGS---TYYNPSLKS | (SEQ ID NO: 313) |
| 4-34 | GYY--WS | EINHSGS---TNYNPSLKS | (SEQ ID NO: 315) |
| 4-39 | SSSYYWG | SIYYSGS---TYYNPSLKS | (SEQ ID NO: 317) |
| 4-59 | SYY--WS | YIYYSGS---TNYNPSLKS | (SEQ ID NO: 319) |
| 4-61 | SGSYYWS | YIYYSGS---TNYNPSLKS | (SEQ ID NO: 321) |
| 4-b | SGYY-WG | SIYHSGS---TYYNPSLKS | (SEQ ID NO: 323) |
| 5-51 | SYW--IG | IIYPGDSD--TRYSPSFQG | (SEQ ID NO: 325) |
| 5-a | SYW--IS | RIDPSDSY--TNYSPSFQG | (SEQ ID NO: 327) |
| 6-1 | SNSAAWN | RTYYRSKWY-NDYAVSVKS | (SEQ ID NO: 329) |
| 74.1 | SYA--MN | WINTNTGN--PTYAQGFTG | (SEQ ID NO: 331) |

| | A | C | D | E | F | G | H | I | K | L | M | N | P | Q | R | S | T | V | W | Y | - | Consens. |
|---|---|---|---|---|---|---|---|---|---|---|---|---|---|---|---|---|---|---|---|---|---|---|
| CDR1 of human GLGs ||||||||||||||||||||||||
| 1 | | | 7 | 1 | | 3 | | | | | | 2 | | | | 35 | 2 | | | 1 | | Sd x |
| 2 | 2 | | | | | 6 | 1 | | 1 | | | 4 | | | 1 | 7 | | | | 29 | | Ysg x |
| 3 | 11 | | 3 | 1 | | 10 | | | | | | 2 | | | 1 | 6 | 1 | | 5 | 11 | | YAGS x |
| 4 | 1 | | | | | | | | | | | 2 | | | | | 1 | 2 | 7 | 38 | | — |
| 5 | 1 | | | | | | | | | 2 | | | | | | 1 | 1 | | 5 | 41 | | — |
| 6 | | | | | | | 6 | | 1 | 28 | | | | | | | | | 4 | 12 | | Mwi |
| 7 | | 1 | | | 5 | 16 | | | | 5 | | 1 | | 23 | | | | | | | | SHng |
| CDR2 of human GLGs ||||||||||||||||||||||||
| 1 | 3 | | | 2 | 1 | 5 | 1 | 2 | | 3 | | 1 | | | 7 | 4 | 6 | 7 | 9 | | | X |
| 2 | | | | 1 | | | | 46 | | 1 | | | | | 2 | 1 | | | | | | I |
| 3 | | 4 | | 1 | 1 | | 2 | 2 | | 8 | | 3 | 12 | 1 | 1 | 1 | 15 | | | | | ysn x |
| 4 | 2 | | | | 2 | 4 | | | | 1 | 10 | 1 | 11 | 2 | 1 | 5 | 12 | | | | | ysp x |
| 5 | 1 | 8 | 2 | 1 | 6 | | 2 | 4 | | 8 | | | 1 | 17 | | | 1 | | | | | sd x |
| 6 | 3 | 7 | | 2 | 26 | | | | | 3 | | | 8 | 2 | | | | | | | | Gsd x |
| 7 | | 4 | 1 | | 17 | | | 1 | | 2 | | | 24 | | | | | 1 | | 1 | | SG x |
| 8 | | 1 | 3 | | 3 | | | 3 | | 10 | | | 9 | 4 | | 1 | 2 | 15 | | | | -ns |
| 9 | | | | | 2 | | | | | | | | | | | | 3 | 46 | | | | — |
| 10 | 1 | | | | | | | | | | | | | | | 3 | | 47 | | | | — |
| 11 | 2 | | | | | 4 | 5 | | | 1 | 1 | | | 35 | | | | 3 | | | | T |
| 12 | 1 | | 2 | 2 | 1 | 3 | | 2 | 1 | 11 | | 2 | 3 | 1 | | | 22 | | | | | Yn x |
| 13 | | | | | | | | | | | | | | | | | 51 | | | | | Y |
| 14 | 31 | | | | | | | | 11 | 1 | | | 6 | 1 | 1 | | | | | | | An x |
| 15 | 4 | | 16 | 1 | | 1 | | | 1 | 14 | 11 | | | 2 | 1 | | | | | | | dpq x |
| 16 | | | | | | 1 | | | 11 | | | | 1 | | 38 | | | | | | | Sk |
| 17 | | | 13 | | | | | | | 15 | | | | 1 | | 22 | | | | | | Vlf |
| 18 | | | | | | | | | 37 | | | | | 13 | 1 | | | | | | | Kq |
| 19 | | 1 | 1 | | | 34 | | | | | | | | | 14 | 1 | | | | | | GS |

TABLE 21P

| Tallies of Amino-acid frequencies in mature CDR1 and CDR2 |||||||||||||||||||||
|---|---|---|---|---|---|---|---|---|---|---|---|---|---|---|---|---|---|---|---|---|
| | A | C | D | E | F | G | H | I | K | L | M | N | P | Q | R | S | T | V | W | Y | | X |
| Tally of 23 examples with length 14 ||||||||||||||||||||||
| 1 | | | 8 | | | | | | | | | 2 | | | | | | 13 | | | |
| 2 | 3 | | | | | | | | | | | | | | | 15 | 3 | 2 | | | |
| 3 | 2 | | | 1 | | 14 | | | | | | | | | | 1 | | 5 | | | |
| 4 | | | 2 | | 2 | 11 | | | | | | | | | | 5 | | | | 3 | |
| 5 | | | | | | 7 | | | | 1 | 1 | | | | | 13 | | | | | 1 |
| 6 | 1 | | | | 4 | 3 | | 12 | | 2 | | | | | | | 1 | | | | |
| 7 | | | | | 3 | | | 1 | 1 | | | 2 | 1 | | 5 | 10 | | | | | |
| 8 | | | | 6 | 1 | | | | 1 | | | 2 | | | 1 | 6 | 4 | 2 | | | |

TABLE 21P-continued

Tallies of Amino-acid frequencies in mature CDR1 and CDR2

| 9  |   |   | 1 | 5 |   | 1 |   |   | 3 | 1 |   | 4 | 7 | 1 |   |   |    |
|----|---|---|---|---|---|---|---|---|---|---|---|---|---|---|---|---|----|
| 10 | 1 | 8 |   | 3 |   |   |   |   | 1 | 2 |   | 1 | 4 | 1 |   |   | 2  |
| 11 | 1 |   | 1 |   | 1 | 1 |   |   |   |   |   |   | 2 |   | 1 |   | 16 |
| 12 | 1 | 2 | 1 |   | 1 | 1 |   |   | 1 |   |   |   | 1 |   |   | 1 | 14 |
| 13 |   |   |   |   |   |   |   | 4 |   |   |   |   |   |   | 2 | 17 |    |
| 14 | 4 | 1 |   | 5 |   |   |   |   | 4 |   |   |   | 5 | 4 |   |   |    |

Tally of 11 examples with length 12

| 1  |   |   |   | 4 |   |   |   |   |   |   |   |   |   | 7 |   | 2 |
|----|---|---|---|---|---|---|---|---|---|---|---|---|---|---|---|---|
| 2  |   |   | 1 | 4 |   |   |   |   |   |   |   | 4 |   |   |   | 2 |
| 3  |   |   |   | 7 |   |   |   |   |   |   |   | 4 |   |   |   |   |
| 4  | 1 | 1 | 1 | 5 |   | 2 |   |   |   |   |   |   |   | 1 |   |   |
| 5  |   |   |   |   |   |   |   |   |   |   | 1 | 9 | 1 |   |   |   |
| 6  |   |   | 2 | 1 |   | 3 |   | 2 |   |   |   | 3 |   |   |   |   |
| 7  |   |   |   | 3 |   | 1 |   |   | 3 |   | 1 | 3 |   |   |   |   |
| 8  | 1 | 3 |   | 2 | 1 |   |   |   |   |   |   | 2 | 2 |   |   |   |
| 9  |   | 1 |   |   |   |   | 1 |   |   |   |   |   |   |   |   | 9 |
| 10 |   |   | 1 |   |   |   |   |   |   |   |   |   |   |   |   | 10|
| 11 |   |   |   |   |   |   |   |   |   |   |   |   |   |   | 11|   |
| 12 |   |   |   | 2 |   |   |   |   | 1 |   |   | 7 | 1 |   |   |   |

Tally of 175 examples with length 7

| 1 | 2 |    | 1 | 1 | 2  |   |   | 1 |   | 3  |   | 2 | 153 | 10  |    |     |     |
|---|---|----|---|---|----|---|---|---|---|----|---|---|-----|-----|----|-----|-----|
| 2 | 3 | 2  |   | 1 | 87 |   |   |   | 1 | 10 | 1 | 5 | 61  | 2   |    |     | 2   |
| 3 | 3 | 26 | 1 |   | 54 |   | 1 |   |   | 5  | 1 | 2 | 76  | 3   | 1  |     | 2   |
| 4 | 6 | 1  | 1 |   | 6  |   | 1 |   | 2 | 1  |   |   |     |     | 11 | 1   | 145 |
| 5 | 5 | 2  |   |   | 13 | 2 |   | 2 |   | 3  |   |   | 6   | 2   |    |     | 140 |
| 6 |   |    |   |   |    |   | 1 |   | 1 | 1  |   |   |     |     | 13 | 159 |     |
| 7 | 2 |    | 1 |   | 67 | 1 |   |   |   | 10 |   |   | 88  | 5   | 1  |     |     |

Tally of 38 examples with length 6

| 1 |   |   |   |   |    |   |   |   | 2  |   | 34 | 2 |    |   |
|---|---|---|---|---|----|---|---|---|----|---|----|---|----|---|
| 2 | 1 |   | 2 |   | 1  | 8 |   |   | 4  |   | 22 |   |    |   |
| 3 |   |   |   |   |    | 3 |   |   | 26 |   |    |   |    | 9 |
| 4 |   |   |   | 1 |    | 1 |   |   |    |   |    |   | 29 | 7 |
| 5 |   |   |   |   |    |   |   |   |    |   |    |   | 38 |   |
| 6 |   |   |   |   | 10 |   |   |   | 3  |   | 22 | 3 |    |   |

Tally of 820 examples with length 5

|   | A   | C | D  | E  | F  | G   | H   | I   | K | L | M   | N   | P | Q | R  | S   | T  | V  | W   | Y   | Seen  |   |
|---|-----|---|----|----|----|-----|-----|-----|---|---|-----|-----|---|---|----|-----|----|----|-----|-----|-------|---|
| 1 | 8   |   | 81 | 10 |    | 151 | 4   | 8   | 5 | 3 |     | 100 |   | 4 | 15 | 364 | 55 | 8  |     | 4   | SGNDT x | 15 |
| 2 | 7   | 5 | 12 |    | 24 | 1   |     | 30  | 1 | 1 | 5   | 26  |   | 1 | 1  | 23  | 2  |    | 681 | Y   | 15 |
| 3 | 202 | 4 | 24 | 13 | 13 | 133 | 10  |     |   | 2 |     | 7   | 5 | 2 | 3  | 32  | 14 | 13 | 112 | 231 | YAGW x | 17 |
| 4 |     |   |    |    | 6  |     |     | 172 | 2 | 7 | 409 |     |   |   |    |     | 3  | 16 | 205 |     | MWI | 8 |
| 5 | 8   |   | 6  | 1  | 1  | 49  | 241 | 2   |   |   |     | 79  | 1 | 3 |    | 367 | 56 | 2  |     | 4   | SHNT x | 14 |

CDR2

|    | A  | C  | D  | E | F | G  | H  | I  | K  | L | M | N |
|----|----|----|----|---|---|----|----|----|----|---|---|---|
|    |    |    |    |   |   |    |    |    |    |   |   |   |

Tally of 31 examples with CDR2 of length 19

| 1  |    |   |    |   |   | 11 |    |   |    | 1 |   | 1 |
|----|----|---|----|---|---|----|----|---|----|---|---|---|
| 2  | 1  |   |    |   |   |    |    |   | 28 |   |   |   |
| 3  |    |   |    |   |   |    |    |   |    | 9 | 1 |   |
| 4  |    |   |    |   |   | 1  |    |   |    | 2 |   | 6 |
| 5  |    |   | 1  | 1 |   | 1  |    |   |    | 22 |   | 1 |
| 6  | 16 |   | 1  |   |   | 1  |    | 1 |    | 1 |   |   |
| 7  | 1  |   |    | 9 |   |    |    |   |    |   |   | 7 |
| 8  |    |   |    |   |   |    | 23 |   |    |   |   | 1 |
| 9  | 2  |   |    |   |   |    | 18 |   |    |   |   |   |
| 10 | 4  |   |    |   |   |    | 1  |   | 1  | 1 |   | 1 |
| 11 | 1  |   |    |   |   |    |    |   | 3  |   | 1 |   |
| 12 | 2  |   |    | 11 | 9 |    | 1  |   | 1  | 1 | 1 |   |
| 13 |    |   |    |   |   |    |    |   | 1  |   | 1 |   |
| 14 | 29 |   |    |   |   |    |    |   |    |   |   |   |
| 15 | 25 |   |    | 3 | 1 |    |    |   |    |   |   |   |
| 16 |    |   |    |   |   |    |    |   |    | 1 |   |   |
| 17 |    |   |    |   |   |    |    |   |    |   | 1 | 1 |
| 18 |    |   |    |   | 1 |    |    |   |    | 27 |   |   |
| 19 |    |   |    |   |   | 1  |    |   | 30 |   |   |   |

TABLE 21P-continued

Tallies of Amino-acid frequencies in mature CDR1 and CDR2

Tally of 579 (n > 50, bold; over 400, underscored) examples with length 17

| | A | C | D | E | F | G | H | I | K | L | M | N |
|---|---|---|---|---|---|---|---|---|---|---|---|---|
| 1 | 44 | 1 | 1 | 2 | 11 | 81 | 5 | 69 | 1 | 14 | 6 | 41 |
| 2 | | | | | 7 | | | _522_ | 1 | 10 | 17 | 1 |
| 3 | 3 | 1 | 22 | | 5 | 7 | 6 | 51 | 25 | 1 | | 76 |
| 4 | 39 | 2 | 8 | 6 | 16 | 64 | 9 | 3 | 2 | 3 | | 15 |
| 5 | 3 | | 194 | 6 | 1 | 70 | 6 | 44 | 6 | 4 | 1 | 55 |
| 6 | 3 | 1 | 75 | 4 | 45 | 326 | 1 | | | 6 | | 43 |
| 7 | 8 | | 24 | 5 | | 226 | 3 | 3 | 3 | 4 | | 24 |
| 8 | 4 | 2 | 57 | 37 | 5 | 22 | 4 | 18 | 18 | 2 | 2 | 161 |
| 9 | 56 | | | 11 | | 2 | | 63 | 157 | 1 | 3 | 3 |
| 10 | 1 | | 14 | 2 | 13 | 30 | 23 | 6 | 29 | 2 | 3 | 110 |
| 11 | | 1 | 2 | | 7 | | 5 | | 1 | 4 | | 3 |
| 12 | _405_ | | | 2 | | 18 | | 1 | | 6 | | 2 |
| 13 | 7 | | 323 | 22 | | 7 | 4 | | | 1 | | 4 |
| 14 | 2 | | | 5 | 6 | 3 | | | 123 | | 1 | 4 |
| 15 | 1 | | | 1 | 188 | 2 | | 1 | | 22 | 3 | |
| 16 | 1 | | | 13 | | 1 | 1 | | 332 | 3 | 2 | 1 |
| 17 | | | 11 | 1 | _565_ | | | | | | | |

Tally of 464 (over 50, bold; over 400, underscored)

| | A | C | D | E | F | G | H | I | K | L | M | N |
|---|---|---|---|---|---|---|---|---|---|---|---|---|
| 1 | 5 | | 13 | 184 | 8 | 1 | 7 | 1 | 2 | 15 | | 6 |
| 2 | | | | | 6 | | | _429_ | | 3 | 4 | |
| 3 | | 1 | 13 | | 13 | 4 | 10 | 5 | | | | 154 |
| 4 | 1 | | 12 | 2 | 6 | | 199 | 2 | | 1 | | 3 |
| 5 | 5 | | 20 | 1 | 1 | 18 | | 4 | | | | 9 |
| 6 | | | 13 | 8 | | _439_ | | | | | | 1 |
| 7 | | | 20 | 2 | | 14 | 2 | 4 | 2 | | | 26 |
| 8 | 13 | | | | | 2 | | 4 | 8 | 1 | 2 | |
| 9 | | | 10 | | 4 | 1 | 10 | 1 | 8 | 1 | | 245 |
| 10 | | 6 | | | 2 | | 2 | | | | | 2 |
| 11 | 14 | | 3 | | | | 1 | 1 | 8 | | | _408_ |
| 12 | 4 | | 13 | | | 4 | | | | 2 | | 1 |
| 13 | 2 | | | | | 2 | | | | | | |
| 14 | | | | | 2 | | | 2 | | _441_ | | |
| 15 | | | | 18 | | | | | | 413 | 3 | 5 |
| 16 | | 1 | | 1 | | 31 | | 2 | | | | 2 |

Tally of 31 examples with CDR2 of length 19

| | P | Q | R | S | T | V | W | Y | X | |
|---|---|---|---|---|---|---|---|---|---|---|
| 1 | | 1 | 15 | 1 | 1 | | | | | RF x |
| 2 | | | | | 2 | | | | | I |
| 3 | | | 18 | 1 | 1 | | | 1 | | Rk |
| 4 | | | | 21 | 1 | | | | | S |
| 5 | | 1 | 1 | 1 | 1 | | | 1 | | K x |
| 6 | 3 | | | 1 | 6 | 1 | | | | A x |
| 7 | | | | 3 | 1 | | | 10 | | y x |
| 8 | | 1 | | 5 | 1 | | | | | G |
| 9 | | | 1 | 1 | | 1 | | 7 | 1 | G |
| 10 | | | | 1 | 21 | | | 1 | | T |
| 11 | | | | | 26 | | | | | T |
| 12 | | | | 2 | 1 | | | 2 | | x |
| 13 | | | | | | | | 29 | | Y |
| 14 | 1 | | | | 1 | | | | | A |
| 15 | | 1 | | | 1 | | | | | A |
| 16 | 10 | | | 20 | | | | | | Sp |
| 17 | | | | | | | 29 | | | V |
| 18 | | 1 | 2 | | | | | | | K |
| 19 | | | | | | | | | | G |

Tally of 579 (n > 50, bold; over 400, underscored) examples with length 17

| | P | Q | R | S | T | V | W | Y | X | |
|---|---|---|---|---|---|---|---|---|---|---|
| 1 | 1 | 4 | 34 | 30 | 19 | 118 | 66 | 31 | | VGIW x |
| 2 | | | | 3 | 8 | 10 | | | | I |
| 3 | | | 8 | 262 | 19 | 1 | 46 | 46 | | SNI x |
| 4 | 178 | 23 | 6 | 50 | 11 | 8 | 16 | 120 | | PYG x |
| 5 | | 4 | 8 | 133 | 9 | 7 | 1 | 27 | | DSGN x |
| 6 | | | 1 | 63 | 8 | 1 | | 2 | | GDS x |
| 7 | | 2 | 11 | 245 | 14 | 6 | | 1 | | SG x |
| 8 | 1 | 4 | 11 | 106 | 90 | 2 | 1 | 32 | | NST X |
| 9 | | 11 | 5 | 13 | 4 | 242 | 8 | | | TKIA x |
| 10 | | 3 | 52 | 20 | 10 | 1 | 1 | 259 | | YNR x |
| 11 | | | | 5 | | | | _551_ | | Y |
| 12 | 3 | | 1 | | 89 | 8 | 44 | | | A |
| 13 | 66 | 138 | 3 | | | | 1 | | 3 | DQP x |
| 14 | | 2 | 7 | _421_ | 1 | | 2 | 2 | | SK x |

TABLE 21P-continued

Tallies of Amino-acid frequencies in mature CDR1 and CDR2

|    |     |   |     |    |    |    | 357 |    |   |     |      |
|----|-----|---|-----|----|----|----|-----|----|---|-----|------|
| 15 |     |   |     |    | 1  |    | 357 | 2  | 1 |     | VF   |
| 16 |     | 1 | 199 | 21 |    | 4  |     |    |   |     | KQ x |
| 17 |     |   |     |    |    |    |     | 1  | 1 |     | G    |

Tally of 464 (over 50, bold; over 400, underscored)

| 1  |     |   | 3  | 26 | 65  | 9  | 14 |   | 105 |   | EYSL x |
|----|-----|---|----|----|-----|----|----|---|-----|---|--------|
| 2  |     |   |    |    | 1   | 2  | 19 |   |     |   | I      |
| 3  |     |   |    | 1  | 12  | 1  |    |   | 250 |   | YN x   |
| 4  | 4   |   | 5  | 2  | 19  | 28 |    | 15 | 165 |   | YH x   |
| 5  |     | 1 |    | 22 | 365 | 16 | 1  |   | 1   |   | S x    |
| 6  |     |   |    |    |     | 1  | 1  | 1 |     |   | G      |
| 7  |     | 1 |    | 12 | 357 | 20 | 1  |   | 2   | 1 | S x    |
| 8  |     | 4 |    | 3  | 6   | 420 |   |   |     | 1 | T      |
| 9  |     |   |    | 13 | 9   | 3  | 1  | 1 | 157 |   | NY x   |
| 10 |     |   | 1  |    | 7   |    |    |   | 444 |   | Y      |
| 11 |     | 4 |    |    | 21  | 2  |    |   | 2   |   | N      |
| 12 | 418 |   |    |    | 14  | 7  | 1  |   |     |   | P      |
| 13 | 6   |   |    |    | 452 | 1  |    |   | 1   |   | S      |
| 14 |     |   | 1  |    |     |    | 18 |   |     |   | L      |
| 15 |     |   | 11 | 10 | 1   | 2  | 1  |   |     |   | K      |
| 16 |     |   |    | 3  | 419 | 5  |    |   |     |   | S      |

TABLE 22P

Tally of VH types

| 1-02 | 16 | 1-03 | 16 | 1-08 | 13 | 1-18 | 27 | 1-24 | 5  |
| 1-45 | 0  | 1-46 | 14 | 1-58 | 1  | 1-69 | 37 | 1-e  | 16 |
| 1-f  | 1  | 2-05 | 13 | 2-26 | 1  | 2-70 | 2  | 3-07 | 33 |
| 3-09 | 13 | 3-11 | 15 | 3-13 | 4  | 3-15 | 10 | 3-20 | 4  |
| 3-21 | 25 | 3-23 | 85 | 3-30 | 55 | 3303 | 59 | 3305 | 0  |
| 3-33 | 42 | 3-43 | 1  | 3-48 | 24 | 3-49 | 11 | 3-53 | 12 |

TABLE 22P-continued

Tally of VH types

| 3-64 | 4  | 3-66 | 4  | 3-72 | 3   | 3-73 | 3  | 3-74 | 12 |
| 3-d  | 0  | 4-04 | 29 | 4-28 | 3   | 4301 | 46 | 4302 | 7  |
| 4304 | 37 | 4-31 | 0  | 4-34 | 184 | 4-39 | 65 | 4-59 | 45 |
| 4-61 | 9  | 4-b  | 11 | 5-51 | 55  | 5-a  | 13 | 6-1  | 7  |
| 74.1 | 3  |      |    |      |     |      |    |      |    |

TABLE 23P

Oligonucleotides used to variegate CDR1 and CDR2 of human HC

```
(name)  5'-....DNA sequence....-3'
everything to right of an exclamation point is commentary
[RC] means "reverse complement" of sequence shown
If last non-comment and non-blank character is "-", then continue
on next line.
Ignore case, "a" = "A", "c" = "C", etc.
Ignore "|" and blanks.
<number> means incorporate trinucleotide mixtue of given number.
```

CDR1

```
(ON-R1V1vg)  5'-ct|TCC|GGA|ttc|act|ttc|tct|-
             <1>|tac|<1>|atg|<1>|-!  CDR1 of length 5, ON = 55 bases tgg|gtt|cgC|CAa|gct|ccT|GG-3'
<1> =        ADEFGHIKLMNPQRSTVWY no C
(ON-R1top)   5'-cctactgtct |TCC|GGA|ttc|act|ttc|tct-3'

(ON-R1bot)   [RC] 5'-tgg|gtt|cgC|CAa|gct|ccT|GG ttgctcactc-3'

(ON-R1V2vg)  5'-ct|TCC|GGA|ttc|act|ttc|tct|-
             <6>|<7>|<7>|tac|tac|tgg|<7>|-!  CDR1 of length 7, ON = 61 bases
             tgg|gtt|cgC|CAa|gct|ccT|GG-3'
<6> =        ST, 1:1
<7> =        0.2025(SG) + 0.035(ADEFHIKLMNPQRTVWY) no C
(ON-R1V3vg)  5'-ct|TCC|GGA|ttc|act|ttc|tct|-
             |atc|agc|ggt|ggt|tct|atc|tcc|<1>|<1>|<1>|tac|tac|tgg|<1>|-!  CDR1, L = 14
             tgg|gtt|cgC|CAa|gct|ccT|GG-3' !  ON = 82 bases
```

CDR2

```
(ON-R2V1vg)  5'-ggt|ttg|gag|tgg|gtt|tct|-
             <2>|atc|<2>|<3>|tct|ggt|ggc|<1>|act|<1>|-
             tat|gct|gac|tcc|gtt|aaa|gg-3' !  ON = 68 bases, CDR2 = 17 AA (ON-R2top)   5'-ct|tgg|gtt|cgC|CAa|gct|ccT|GGt|aaa|ggt|ttg|gag|tgg|gtt|tct-
```

TABLE 23P-continued

Oligonucleotides used to variegate CDR1 and CDR2 of human HC

```
(ON-R2bot)  [RC] 5'-tat|gct|gac|tcc|gtt|aaa|ggt|-
                 cgc|ttc|act|atc|TCT|AGA|ttcctgtcac-3' ! XbaI plus 10 bases of scab (ON-R2V2vg) 5'-ggt|ttg|gag|tgg|gtt|tct|-
               <1>|atc|<4>|<1>|<1>|ggt|<5>|<1>|<1>|<1>|-
               tat|gct|gac|tcc|gtt|aaa|gg-3' ! ON = 68 bases, CDR2 = 17 AA <4> = DINSWY, equimolar
<5> = SGDN, equimolar
(ON-R2V3vg) 5'-ggt|ttg|gag|tgg|gtt|tct|-
               <1>|atc|<4>|<1>|<1>|ggt|<5>|<1>|<1>|-
               tat|aac|cct|tcc|ctt|aag|gg-3' ! ON = 65 bases, CDR2 = 16 AA (ON-R2bo3)  [RC] 5'-tat|aac|cct|tcc|ctt|aag|ggt|-
                 cgc|ttc|act|atc|TCT|AGA|ttcctgtcac-3' ! XbaI plus 10 bases of scab (ON-R2V4vg) 5'-ggt|ttg|gag|tgg|gtt|tct|-
               <1>|atc|<8>|agt|<1>|<1>|<1>|ggt|ggt|act|act|<1>
               tat|gcc|gct|tcc|gtt|aag|gg-3' ! ON = 74 bases, CDR2 = 19 AA (ON-R2bo4)  [RC] 5'-tat|gcc|gct|tcc|gtt|aag|ggt|-
                 cgc|ttc|act|atc|TCT|AGA|ttcctgtcac-3' ! XbaI plus 10 bases of scab
```

TABLE 25P

Lengths of CDRs in 285 human kappa chains

| | 0 | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| CDR1 | 0 | 0 | 0 | 0 | 0 | 0 | 0 | 0 | 0 | 0 | 0 | 154 | 73 | 3 | 0 | 0 | 28 | 27 | 0 | 0 |
| CDR2 | 0 | 0 | 0 | 0 | 0 | 0 | 0 | 285 | 0 | 0 | 0 | 0 | 0 | 0 | 0 | 0 | 0 | 0 | 0 | 0 |
| CDR3 | 0 | 5 | 0 | 0 | 1 | 0 | 3 | 2 | 28 | 166 | 63 | 12 | 1 | 1 | 0 | 0 | 0 | 0 | 0 | 1 |

TABLE 26P

Tally of kappa types: V and J

V genes:

| | | | | | | | | |
|---|---|---|---|---|---|---|---|---|
| O12 | 59 | O2 | 0 | O18 | 0 | O8 | A20 | 0 |
| A30 | 0 | L14 | 0 | L1 | 2 | L15 | 0 | L4 | 2 |
| L18 | 0 | L5 | 4 | L19 | 0 | L8 | 4 | L23 | 0 |
| L9 | 1 | L24 | 0 | L11 | 4 | L12 | 8 | O11 | 10 |
| O1 | 0 | A17 | 5 | A1 | 0 | A18 | 3 | A2 | 0 |
| A19 | 13 | A3 | 0 | A23 | 4 | A27 | 79 | A11 | 26 |
| L2 | 28 | L16 | 0 | L6 | 11 | L20 | 0 | L25 | 0 |
| B3 | 22 | B2 | 0 | A26 | 0 | A10 | 0 | A14 | 0 |
| JH# | 1 | 2 | 3 | 4 | 5 | | | |
| tally | 105 | 64 | 29 | 78 | 9 | | | |

TABLE 27P

Names of Kappa chains analyzed

AB022651
AB022653
AB022654
AB022656
AF007572
AF021036
AF103499
AF103500
AF103527
AF103873
AF107244
AF107245
AF107246
AF107247
AF115361
AF165099
AF165101
AF165103
AF165108
AF165110
AF165111
AF184763
AF184767
hsa004955
hsa004956
hsa011133
HSA241367
HSA241375
HSA388639
HSA388640
HSA388641
HSA388642
HSA388643
HSA388644
HSA388645
HSA388646
HSA388647
HSA388648
HSA388650
HSA388651
HSA388652
HSA388653
HSA388654
HSA388655
HSA388656
HSA388657
hsew1vk
hsew3vk
hsew4vk
hsigdpk13
hsigg1kl
HSIGGVKA
hsigk123
hsigk319

TABLE 27P-continued

Names of Kappa chains analyzed

| | |
|---|---|
| hsigklc14 | hsigkvc27 |
| hsigklc28 | hsigkvc29 |
| hsigklc5 | hsigrklc |
| hsigklg31 | hsikcvjp1 |
| hsigklv01 | hsikcvjp2 |
| hsigklv02 | hsikcvjp3 |
| hsigklv03 | hsikcvjp6 |
| hsigklv04 | hsikcvjp7 |
| hsigklv05 | hsld110vl |
| hsigklv06 | hsld117vl |
| hsigklv07 | hsld128vl |
| hsigklv09 | hsld140vl |
| hsigklv10 | hsld152vl |
| hsigklv12 | hsld184vl |
| hsigklv13 | hsld198vl |
| hsigklv14 | hsld24vl |
| hsigklv15 | hsmbcl1k1 |
| hsigklv16 | hsmbcl1k2 |
| hsigklv17 | hsmbcl2k2 |
| hsigklv18 | hsmbcl5k4 |
| hsigklv19 | hssl0avl |
| hsigklv20 | hss17bvl |
| hsigklv21 | hss1a15vl |
| hsigklv22 | HSU44792 |
| hsigklv23 | HSU44794 |
| hsigklv24 | HSU94422 |
| hsigklv25 | hsz84852 |
| hsigklv27 | hsz84853 |
| hsigklv28 | humigk1dm |
| hsigklv29 | humigk3am |
| hsigklv31 | humigk3bm |
| hsigklv32 | humigk3cm |
| hsigklv33 | humigkacoa |
| hsigklv34 | humigkacob |
| hsigklv35 | humigkacoc |
| hsigklv36 | humigkacoe |
| hsigklv37 | humigkacof |
| hsigklv38 | humigkb1aa |
| hsigklv39 | humigkb1ab |
| hsigklv40 | humigkb1ac |
| hsigklv41 | humigkvra |
| hsigklv42 | humigkvrb |
| hsigklv43 | humigkvrc |
| hsigklv44 | humigkvrd |
| hsigklv45 | humigkvre |
| hsigklv46 | humigkvrg |
| hsigklv49 | humigkvrh |
| hsigklv50 | humigkvri |
| hsigklv51 | humigkx |
| hsigklv52 | humigky1 |
| hsigklv53 | humigky2 |
| hsigklv54a | humigky4 |
| hsigklv56 | humigky5 |
| hsigklv57 | humigky6 |
| hsigklv58 | humigl3ac |
| hsigklv59 | humikc |
| hsigklv60 | humikca |
| hsigklv61 | humikcad |
| hsigklv62 | humikcaf |
| hsigklv63 | humikcag |
| hsigklv65 | humikcah |
| hsigklv66 | humikcai |
| hsigklv68 | humikcaj |
| hsigklv69 | humikcal |
| hsigklv71 | humikcam |
| hsigkvba | humikcan |
| hsigkvbb | humikcas |
| hsigkvbc | humikcau |
| hsigkvbd | humikcav |
| hsigkvbe | humikcaw |
| hsigkvbf | humikcax |
| hsigkvc01 | humikcay |
| hsigkvc03 | humikcaz |
| hsigkvc06 | humikcb |
| hsigkvc11 | humikcba |
| hsigkvc12 | humikcbb |
| hsigkvc20 | humikcbc |
| hsigkvc23 | humikcbd |

TABLE 27P-continued

Names of Kappa chains analyzed

| |
|---|
| humikcbe |
| humikcbf |
| humikcbg |
| humikcbh |
| humikcbi |
| humikcbj |
| humikcbl |
| humikcbm |
| humikcbn |
| humikcbo |
| humikcbp |
| humikcbq |
| humikcbs |
| humikcbt |
| humikcbu |
| humikcbv |
| humikcbw |
| humikcbx |
| humikcbz |
| humikcc |
| humikcca |
| humikccb |
| humikccc |
| humikccd |
| humikcce |
| humikccf |
| humikccg |
| humikcch |
| humikcci |
| humi kccj |
| humikcck |
| humikcco |
| humikccp |
| humikccq |
| humikccr |
| humikccs |
| humikcct |
| humikccu |
| humikccv |
| humikccw |
| humikcd |
| humikcf |
| humikcg |
| humikch |
| humikci |
| humikck |
| humikcm |
| humikcn |
| humikco |
| humikcp |
| humikcq |
| humikcr |
| humikcs |
| humikct |
| humikcu |
| humikcv |
| humikcva |
| humikcvb |
| humikcvc |
| humikcvd |
| humikcve |
| humikcvf |
| humikcvg |
| humikcvh |
| humikcvi |
| humikcvj |
| humikcw |
| humikcx |
| humikcy |
| humikcz |
| S46248 |
| S82746 |
| S82747 |
| SU96396 |
| SU96397 |

TABLE 28P

AA types seen in 154 kappa sequences having CDR1 of length 11
Tally

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 1 | | | | | | | | | | | | | | 11 | 143 | | | | | | R |
| 2 | 148 | | | | | | | | | 1 | | | | | | 2 | 2 | 1 | | | A |
| 3 | | | | | | | | | | | | | | | | 152 | 2 | | | | S |
| 4 | | | 1 | 3 | | 3 | | | | | | | | 147 | | | | | | | Q |
| 5 | | 12 | 1 | | | 27 | | | | | | 7 | | | 3 | 99 | 4 | 1 | | | S |
| 6 | 1 | | | | | | | 81 | | 1 | | | | | | | | 71 | | | V |
| 7 | 2 | | 4 | | | 18 | | 5 | 1 | 2 | | 9 | | | 12 | 97 | 3 | | | 1 | S |
| 8 | | 3 | | | 5 | 1 | 2 | 1 | | | | 31 | 1 | | 10 | 87 | 12 | | | 1 | S |
| 9 | 2 | | 7 | | 10 | 1 | 6 | | | | | 29 | | | 1 | 8 | | | 13 | 77 | Y |
| 10 | | | | 2 | | | | | | 150 | | | | | | 1 | | 1 | | | L |
| 11 | 96 | | | | 4 | 2 | | | | | | 46 | | | | 2 | 1 | 3 | | | A |

TABLE 30P

Synthetic Kappa light chain gene

```
!
!
! A27::JH1 with all CDRs replaced by stuffers.
! Each stuffer contains at least one stop codon and a
! restriction site that will be unique within the diversity vector.
!
      1 GAGGACCATt GGGCCCC               ctccgagact
!        Scab...... EcoO109I
!                   ApaI.
!----------------------------------
!
     28        CTCGAG     cgca
```

TABLE 30P-continued

Synthetic Kappa light chain gene

```
!              XhoI..
!----------------------------------
!
!   38 acgcaatTAA TGTgagttag ctcactcatt aggcacccca ggcTTTACAc tttatgcttc
!            ..-35..          Plac                      ..-10.
!----------------------------------
!
!   98 cggctcgtat gttgtgtgga attgtgagcg gataacaatt tc
!----------------------------------
!
!  140 acacagga aacagctatgac
!----------------------------------
!
!  160 catgatta cgCCAAGCTT TGGagcctttt tttttggaga ttttcaac
!              PflMI.......
!              Hind3.
!----------------------------------
!
!          M13 III signal sequence (AA seq)--------------------------->
!           1   2   3   4   5   6   7   8   9  10  11  12  13  14  15
!           M   K   K   L   L   F   A   I   P   L   V   V   P   F   Y
!  206     gtg aag aag ctc cta ttt gct atc ccg ctt gtc gtt ccg ttt tac
!----------------------------------
!
!          --Signal-->  FR1---------------------------------------------->
!          16  17  18  19  20  21  22  23  24  25  26  27  28  29  30
!           S   H   S   A   Q   S   V   L   T   Q   S   P   G   T   L
!  251     |agc|cat|aGT|GCA|Caa|tcc|gtc|ctt|act|caa|tct|cct|ggc|act|ctt|
!                      ApaLI...
!----------------------------------
!
!          ----- FR1 ------------------------------------>| CDR1------>
!          31  32  33  34  35  36  37  38  39  40  41  42  43  44  45
!           S   L   S   P   G   E   R   A   T   L   S   C   R   A   S
!          |tcG|CTA|AGC|CCG|GGt|gaa|cgt|gct|acC|TTA|AGt|tgc|cgt|gct|tcc|
!           EspI.....                        AflII...
!                    XmaI....
!
!----------------------------------
! For CDR1:

! <1> ADEFGHIKLMNPQRSTVWY equimolar
! <2> S(0.2) ADEFGHIKLMNPQRTVWY (0.044 each)
! <3> Y(0.2) ADEFGHIKLMNPQRSTVW (0.044 each)
! In a preferred embodiment, we omit codon 52 in vgDNA for CDR1.
!
!          ------- CDR1 --------------------->|--- FR2 ---------------->
!           <1>        <2> <2> xxx <3>
!          46  47  48  49  50  51  52  53  54  55  56  57  58  59  60
!           Q   S   V   S   S   S   Y   L   A   W   Y   Q   Q   K   P
!          |cag|tct|gtt|tcc|tct|tct|tat|ctt|gct|tgg|tat|caa|cag|aaA|CCT|
!                                                                SexAI...
!----------------------------------
! For CDR2:

! <1> ADEFGHIKLMNPQRSTVWY equimolar
! <2> S(0.2) ADEFGHIKLMNPQRTVWY (0.044 each)
! <4> A(0.2) DEFGHIKLMNPQRSTVWY (0.044 each)
!          ----- FR2 ----------------------->|------- CDR2 ---------->
!                                             <1>          <2>       <4>
!          61  62  63  64  65  66  67  68  69  70  71  72  73  74  75
!           G   Q   A   P   R   L   L   I   Y   G   A   S   S   R   A
!          |GGT|caG|GCG|CCg|cgt|tta|ctt|att|tat|ggt|gct|tct|tcc|cgc|gct|
!     SexAI....  KasI.... (CDR1 installed as AflII-(SexAI or KasI) cas-
sette.)
!
!----------------------------------
!
!          CDR2-->|--- FR3 -------------------------------------------->
!           <1>
!          76  77  78  79  80  81  82  83  84  85  86  87  88  89  90
!           T   G   I   P   D   R   F   S   G   S   G   S   G   T   D
!          |act|gGG|ATC|CCG|GAC|CGt|ttc|tct|ggc|tct|ggt|tca|ggt|act|gac|
!                  BamHI...
!                          RsrII.....
! (CDR2 installed as (SexAI or KasI) to (BamHI or RsrII) cassette.)
!----------------------------------
!
```

TABLE 30P-continued

Synthetic Kappa light chain gene

```
!         ------ FR3 ------------------------------------------------->
!          91  92  93  94  95  96  97  98  99 100 101 102 103 104 105
!           F   T   L   T   I   S   R   L   E   P   E   D   F   A   V
  477     |ttt|acc|ctt|act|att|TCT|AGA|ttg|gaa|cct|gaa|gac|ttc|gct|gtt|
!                                 XbaI...
!
!-----------------------------------
!
!          ----------->|----CDR3-------------------------->|-----FR4--->
!                                 <3> <1> <1> <1>     <1>
!         106 107 108 109 110 111 112 113 114 115 116 117 118 119 120
!           Y   Y   C   Q   Q   Y   G   S   S   P   E   T   F   G   Q
!         |tat|tat|tgC|CAa|cag|taT|GGt|tct|tct|cct|gaa|act|ttc|ggt|caa|
!                         BstXI...........
!
!-----------------------------------
!
!         -----FR4------------------>|   <------- Ckappa ------------
!         121 122 123 124 125 126 127    128 129 130 131 132 133 134
!           G   T   K   V   E   I   K      R   T   V   A   A   P   S
  510     |ggt|aCC|AAG|Gtt|gaa|atc|aag|   |CGT|ACG|gtt|gcc|gct|cct|agt|
!                 StyI....                 BsiWI..
!
! (CDR3 installed as XbaI to (StyI or BsiWI) cassette.)
!
!         135 136 137 138 139 140 141 142 143 144 145 146 147 148 149
!           V   F   I   F   P   P   S   D   E   Q   L   K   S   G   T
  552     |gtg|ttt|atc|ttt|cct|cct|tct|gac|gaa|CAA|TTG|aag|tca|ggt|act|
!                                             MfeI...
!
!         150 151 152 153 154 155 156 157 158 159 160 161 162 163 164
!           A   S   V   V   C   L   L   N   N   F   Y   P   R   E   A
  597     |gct|tct|gtc|gta|tgt|ttg|ctc|aac|aat|ttc|tac|cCT|CGT|Gaa|gct|
!                                                         BssSI...
!
!         165 166 167 168 169 170 171 172 173 174 175 176 177 178 179
!           K   V   Q   W   K   V   D   N   A   L   Q   S   G   N   S
  642     |aaa|gtt|cag|tgg|aaa|gtc|gat|aAC|GCG|Ttg|cag|tcg|ggt|aac|agt|
!                                         MluI....
!
!         180 181 182 183 184 185 186 187 188 189 190 191 192 193 194
!           Q   E   S   V   T   E   Q   D   S   K   D   S   T   Y   S
  687     |caa|gaa|tcc|gtc|act|gaa|cag|gat|agt|aag|gac|tct|acc|tac|tct|
!
!         195 196 197 198 199 200 201 202 203 204 205 206 207 208 209
!           L   S   S   T   L   T   L   S   K   A   D   Y   E   K   H
  732     |ttg|tcc|tct|act|ctt|act|tta|tca|aag|gct|gat|tat|gag|aag|cat|
!
!         210 211 212 213 214 215 216 217 218 219 220 221 222 223 224
!           K   V   Y   A   C   E   V   T   H   Q   G   L   S   S   P
  777     |aag|gtc|tat|GCt|TGC|gaa|gtt|acc|cac|cag|ggt|ctG|AGC|TCc|cct|
!                         SacI....
!
!     225 226 227 228 229 230 231 232 233 234
!       V   T   K   S   F   N   R   G   E   C    .   . (SEQ ID NO: 332)
  822 |gtt|acc|aaa|agt|ttc|aaC|CGT|GGt|gaa|tgc|taa|tag GGCGCGCC
!                             DsaI....                  AscI....
!                                                       BssHII
!
  866    acgcatctctaa GCGGCCGC aacaggaggag             (SEQ ID NO: 333)
!                     NotI....
!                     EagI..
```

TABLE 31P

Tally of 285 CDR2s of length 7 in human kappa

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 1 | 51 | | 62 | 7 | | 95 | 1 | | 11 | 15 | 2 | 1 | | | 2 | 6 | 6 | 3 | 22 | 1 | x |
| 2 | 225 | | | | | | | 18 | | 5 | | 5 | | 2 | 1 | 1 | 3 | 16 | 9 | | | A |
| 3 | 2 | | | | 9 | | | 1 | | | | 2 | | | | 267 | 2 | | 1 | 1 | S |
| 4 | 2 | | 1 | | | 5 | 4 | 9 | 1 | 77 | | | | | 4 | 93 | 80 | | 2 | 7 | Sx |
| 5 | | 1 | | 2 | | | | | | 80 | | | | | 200 | 2 | | | | | R |

TABLE 31P-continued

Tally of 285 CDR2s of length 7 in human kappa

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 6 | 162 | | 7 | 36 | 4 | | 4 | | 1 | 3 | | | | 3 | 63 | | | 2 | | | Ax |
| 7 | 5 | | 1 | | | 3 | | 1 | 1 | | | 2 | 2 | | 1 | 125 | 144 | | | | x |

TABLE 32P

Tally of 166 CDR3s of length 9 from human kappa.

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 1 | | | | | | | 4 | | | 8 | 21 | | | 131 | 1 | | 1 | | | | Q |
| 2 | | | 1 | | | | 9 | | 2 | 1 | | | | 153 | | | | | | | Q |
| 3 | 14 | 4 | 4 | | 3 | 6 | 4 | | | 1 | | 1 | 3 | | 21 | 16 | 3 | 4 | | 82 | Yx |
| 4 | 1 | | 9 | 1 | 2 | 37 | 4 | 2 | 2 | 15 | 1 | 33 | | | 2 | 20 | 7 | 1 | | 29 | x |
| 5 | 2 | | 2 | 6 | | 3 | 4 | 5 | 3 | | | 28 | | 17 | 7 | 65 | 19 | 1 | 1 | 3 | x |
| 6 | 7 | | 1 | | 11 | 2 | | 3 | | 8 | | 1 | 4 | | 3 | 41 | 33 | 5 | 28 | 19 | x |
| 7 | | | | | 1 | 2 | | | | 6 | | | 146 | 2 | 2 | 5 | | 2 | | | P |
| 8 | 2 | 4 | 1 | 2 | 21 | 7 | 3 | 5 | 1 | 38 | | | 7 | 4 | 25 | 1 | 3 | 1 | 16 | 25 | x |
| 9 | 3 | | | | | | 2 | 1 | | | | 1 | | | | 2 | 157 | | | | T |

TABLE 33P lengths of CDRs in 93 human lambda chains

| | 0 | 1 | 2 | 3 | 4 | 5 | 6 | 7 | 8 | 9 | 10 | 11 | 12 | 13 | 14 | 15 | 16 | 17 | 18+ |
|---|---|---|---|---|---|---|---|---|---|---|---|---|---|---|---|---|---|---|---|
| CDR1 | 0 | 0 | 0 | 0 | 0 | 0 | 0 | 0 | 0 | 0 | 0 | 23 | 7 | 15 | 46 | 0 | 0 | 0 | 2 |
| CDR2 | 5 | 0 | 0 | 1 | 0 | 0 | 0 | 80 | 2 | 0 | 0 | 1 | 4 | 0 | 0 | 0 | 0 | 0 | 1 |
| CDR3 | 0 | 0 | 0 | 0 | 0 | 0 | 0 | 0 | 1 | 16 | 28 | 27 | 6 | 1 | 0 | 4 | 6 | 4 | 0 |

TABLE 34P

Tally of 46 CDR1s of length 14 from human lambda chains

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 1 | 2 | | | | 2 | | | | | | | | | | 1 | 41 | | | | | T |
| 2 | | | | | 43 | | | | | 3 | | | | | | | | | | | G |
| 3 | 2 | | | | | | | | | | | | | | 1 | 6 | 36 | | | | TGx |
| 4 | | | | | | | | | | 1 | | | | | | 45 | | | | | S |
| 5 | | | | | 5 | | | | | 1 | | | | | | 40 | | | | | S |
| 6 | | 39 | | | | | | 1 | | 4 | | | | | | 2 | | | | | DNx |
| 7 | | | | | | | | 8 | | 1 | | | | | | | 37 | | | | V |
| 8 | | 1 | | | 42 | | | | | | | | | | 2 | | 1 | | | | G |
| 9 | 4 | 1 | | | 35 | | | | | | | | | | 1 | 2 | 3 | | | | TGx |
| 10 | 1 | | | 1 | 3 | | | | | | | | | | 1 | 2 | | | | 38 | Yx |
| 11 | | 4 | | | | | | 1 | | | 35 | | | | | | | | | 6 | DNx |
| 12 | | 3 | 1 | | 2 | | | 1 | | | | | | | 1 | 2 | | | | 36 | Yx |
| 13 | | | | | | | 1 | | | | | 2 | | | | | 43 | | | | V |
| 14 | | | | | 1 | 4 | | | | | | | | | | 41 | | | | | S |

TABLE 35P

Synthtic human lambda-chain gene

```
! Lambda 14-7(A) 2a2 ::JH2::Clambda
! AA sequence tested
!
!                      !   1 GAGGACCATt GGGCCCC   ttactccgtgac
!      Scab...... EcoO109I
!                   ApaI..
!----------------------------------------------
!
!             -----------FR1---------------------------------------->
!             1   2   3   4   5   6   7   8   9  10  11  12  13  14  15
```

TABLE 35P-continued

Syntthic human lambda-chain gene

```
!        S   A   Q   S   A   L   T   Q   P   A   S   V   S   G   S   P   G
!     30 aGT|GCA|Caa|tcc|gct|ctc|act|cag|cct|GCT|AGC|gtt|tcc|gGG|TcA|CCt|GGT|
!        ApaLI...                    NheI...           BstEII...
!                                                              SexAI....
!-----------------------------------------------
!
! For CDR1,
! <1> = 0.27 T, 0.27 G, 0.027 {ADEFHIKLMNPQRSVWY} no C
! <2> = 0.27 D, 0.27 N, 0.027 {AEFGHIKLMPQRSTVWY} no C
! <3> = 0.36 Y, 0.0355{ADEFGHIKLMNPQRSTVW}        no C
!                            T   G  <1>  S   S  <2>  V   G
!        ------FR1----------------->  |-----CDR1----------------------
!        16  17  18  19  20  21  22  23  24  25  26  27  28  29  30
!        Q   S   I   T   I   S   C   T   G   T   S   S-
!    D   V   G
!       |caa|agt|atc|act|att|tct|TGT|ACA|ggt|act|tct|tct|gat|gtt|ggc|
!                                BsrGI..
!
! a second vg scheme for CDR1 gives segments of length 11:
! G23<2><4>L<4><4><4><3><4><4> where
! <4> = equimolar {ADEFGHIKLMNPQRSTVWY} no C
!-----------------------------------------------
!
!       <1> <3> <2> <3>  V   S  = vg Scheme #1, length = 14
!        -----CDR1-------------->|--------FR2-----------------------
!        31  32  33  34  35  36  37  38  39  40  41  42  43  44  45
!        G   Y   N   Y   V   S   W   Y   Q   Q   H   P   G   K   A
!       |ggt|tac|aat|tac|gtt|tct|tgg|tat|caa|caa|caC|CCG|GGc|aaG|GCG|
!                                                XmaI....    KasI.....
!                                                AvaI....
!-----------------------------------------------------------------
!
!                            <4> <4> <4> <2>  R   P   S
!       --FR2----------------->  |------CDR2-------------->|-----FR3--
!        46  47  48  49  50  51  52  53  54  55  56  57  58  59  60
!        P   K   L   M   I   Y   E   V   S   N   R   P   S   G   V
!       |CCg|aag|ttg|atg|atc|tac|gaa|gtt|tcc|aat|cgt|cct|tct|ggt|gtt|
! KasI....
!-----------------------------------------------------------------
!
!       --------FR3-------------------------------------------
!        61  62  63  64  65  66  67  68  69  70  71  72  73  74  75
!        S   N   R   F   S   G   S   K   S   G   N   T   A   S   L
!       |agc|aat|cgt|ttc|TCC|GGA|tct|aaa|tcc|ggt|aat|acc|gCA|AGC|TTa|
!                         BspEI..       |                    HindIII.
!                         BsaBI........(blunt)
!-----------------------------------------------------------------
!
!       --------FR3--------------------------------------------->|
!        76  77  78  79  80  81  82  83  84  85  86  87  88  89  90
!        T   I   S   G   L   Q   A   E   D   E   A   D   Y   Y   C
!       |act|atc|tct|ggt|CTG|CAG|gct|gaa|gac|gag|gct|gac|tac|tat|tgt|
!                         PstI...
!
!-----------------------------------------------------------------
!
! <5> = 0.36 S, 0.0355{ADEFGHIKLMNPQRTVWY} no C
!
!       <4> <5> <4> <2> <4>  S  <4> <4> <4> <4>  V
!        -----CDR3------------------------------>|---FR4---------
!        91  92  93  94  95  96  97  98  99 100 101 102 103 104 105
!        S   S   Y   T   S   S   T   L   V   V   F   G   G   G
!       |tct|tct|tac|act|tct|tct|agt|acc|ctt|gtt|gtc|ttc|ggc|ggt|GGT|
!                                                                KpnI...
!
!-----------------------------------------------------------------
!
!       -------FR4--------------->
!        106 107 108 109 110 111 112 113 114 115 116 117 118 119 120
!        T   K   L   T   V   L   G   Q   P   K   A   A   P   S   V
!     279 |ACC|aaa|ctt|act|gtc|ctc|gGT|CAA|CCT|aAG|Gct|gct|cct|tcc|gtt|
!     KpnI...                         HincII..
!                                      Bsu36I...
!
!        121 122 123 124 125 126 127 128 129 130 131 132 133 134 135
!        T   L   F   P   P   S   S   E   E   L   Q   A   N   K   A
!     324 |act|ctc|ttc|cct|cct|agt|tct|GAA|GAG|Ctt|caa|gct|aac|aag|gct|
!                                     SapI.....
```

TABLE 35P-continued

Synthtic human lambda-chain gene

```
!
!       136 137 138 139 140 141 142 143 144 145 146 147 148 149 150
!        T   L   V   C   L   I   S   D   F   Y   P   G   A   V   T
        369 |act|ctt|gtt|tgc|tTG|ATC|Agt|gac|ttt|tat|cct|ggt|gct|gtt|act|
                                BclI....
!
!       151 152 153 154 155 156 157 158 159 160 161 162 163 164 165
!        V   A   W   K   A   D   S   S   P   V   K   A   G   V   E
        414 |gtc|gct|tgg|aaa|gcc|gat|tct|tct|cct|gtt|aaa|gct|ggt|gtt|GAG|
                                                                BsmBI...
!
!       166 167 168 169 170 171 172 173 174 175 176 177 178 179 180
!        T   T   T   P   S   K   Q   S   N   N   K   Y   A   A   S
        459 |ACG|acc|act|cct|tct|aaa|caa|tct|aac|aat|aag|tac|gct|gcG|AGC|
! BsmBI....                                                     SacI....
!
!       181 182 183 184 185 186 187 188 189 190 191 192 193 194 195
!        S   Y   L   S   T   P   E   Q   W   K   S   H   K   S
        504 |TCt|tat|ctt|tct|ctc|acc|cct|gaa|caa|tgg|aag|tct|cat|aaa|tcc|
! SacI...
!
!       196 197 198 199 200 201 202 203 204 205 206 207 208 209 210
!        Y   S   C   Q   V   T   H   E   G   S   T   V   E   K   T
        549 |tat|tcc|tgt|caa|gtt|acT|CAT|GAa|ggt|tct|acc|gtt|gaa|aag|act|
                                    BspHI...
!
!       211 212 213 214 215 216 217 218 219
!        V   A   P   T   E   C   S   .   .                    (SEQ ID NO:
 57)
                594 |gtt|gcc|cct|act|gag|tgt|tct|tag|tga|GGCGCGCC
!                                               AscI....
!                                               BssHII
!
    629 aacgatgttc aag GCGGCCGC aacaggaggag                     (SEQ ID NO:
                                                                    56)
!                   NotI.... Scab.......
```

TABLE 36P

Tally of 23 CDR1s of length 11 from human lambda chains
Tally

|    | A  | C | D  | E | F | G | H  | I | K  | L | M | N | P  | Q | R | S  | T | V | W  | Y   |
|----|----|---|----|---|---|---|----|---|----|---|---|---|----|---|---|----|---|---|----|-----|
| 1  | 1  |   |    |   |   | 6 |    |   |    |   |   |   | 10 |   |   | 6  |   |   |    | x   |
| 2  | 1  |   |    | 1 |   | 21|    |   |    |   |   |   |    |   |   |    |   |   |    | G   |
| 3  |    |   | 15 |   |   | 1 |    |   |    |   |   | 7 |    |   |   |    |   |   |    | DNx |
| 4  | 2  |   |    | 1 |   | 1 |    | 3 |    |   |   | 7 |    |   | 1 | 8  |   |   |    | X   |
| 5  |    |   |    |   |   |   |    | 7 |    | 16|   |   |    |   |   |    |   |   |    | L   |
| 6  |    |   |    |   |   |   | 11 |   | 1  |   |   | 2 |    |   | 8 |    | 1 |   |    | X   |
| 7  |    | 1 | 1  |   |   | 1 |    |   | 2  |   |   | 2 |    |   | 1 | 14 | 1 |   |    | X   |
| 8  |    |   |    | 1 |   |   |    |   | 10 |   |   | 1 |    |   | 1 | 1  | 2 |   |    | 7 X |
| 9  |    |   |    |   |   |   |    |   |    |   |   | 2 |    |   |   | 6  |   |   | 15 | Yx  |
| 10 | 11 |   |    |   |   |   |    |   |    |   |   | 1 |    |   |   |    |   |   | 11 | X   |
| 11 |    | 3 |    |   |   | 7 |    |   |    |   |   |   |    |   |   | 9  | 2 |   |    | 2 X |

TABLE 37P

Tally of 80 CDR2s of length 7 from human lambda chains
Tally

|   | A | C | D  | E  | F | G  | H | I | K  | L | M | N  | P | Q | R | S  | T  | V | W | Y    |
|---|---|---|----|----|---|----|---|---|----|---|---|----|---|---|---|----|----|---|---|------|
| 1 | 1 |   | 14 | 32 | 1 | 13 |   |   | 3  |   |   | 1  |   | 4 | 5 | 1  | 2  |   |   | 3 X  |
| 2 |   |   | 18 | 2  |   |    |   |   | 8  |   |   | 16 |   |   |   |    | 2  | 34|   | X    |
| 3 | 1 |   | 2  |    |   |    | 1 |   |    |   |   | 31 |   |   |   | 39 | 4  |   |   | 2 X  |
| 4 |   |   | 6  | 4  |   |    |   | 1 | 14 | 1 |   | 41 |   |   | 8 | 1  | 1  | 2 |   | 1 DNx|
| 5 |   |   |    |    |   |    |   |   | 1  | 1 |   |    |   |   |   | 78 |    |   |   | R    |
| 6 |   |   |    |    |   |    |   |   | 1  |   |   |    |   | 77|   | 2  |    |   |   | P    |
| 7 | 2 |   |    |    |   |    |   |   |    |   |   |    |   |   |   |    | 78 |   |   | S    |

TABLE 38P

Tally of 27 CDR3s of length 11 from human lambda chains

Tally

| | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| 1 | 4 | | | | | 5 | | | | | | 6 | | 5 | | 4 | 3 | | | | X |
| 2 | 3 | | | | | 1 | | | | | | | 2 | | | 14 | 5 | 2 | | | Sx |
| 3 | | | 1 | | | | | | | | | | | | 7 | | | | 13 | 6 | X |
| 4 | | 19 | | | 2 | | | | | | | 1 | | | | 1 | 4 | | | | DNx |
| 5 | 1 | | 4 | | 2 | | | 2 | | | | 2 | | | 1 | 13 | 2 | | | | X |
| 6 | | | | | | | 1 | | | | | 3 | | | 1 | 21 | 1 | | | | S |
| 7 | | | 1 | | 7 | | | | | 12 | | 1 | | | | 4 | 2 | | | | X |
| 8 | | | 2 | | 1 | | | | | 10 | 1 | | | | | 6 | 6 | 1 | | | X |
| 9 | 3 | | | | 1 | 8 | 10 | | 3 | | | 1 | | | 1 | | | | | | X |
| 10 | 1 | | | | 4 | 1 | | 1 | 1 | | | 3 | | | 1 | 1 | | 6 | 5 | 3 | X |
| 11 | | | | | | | | | | 2 | | | | | | 25 | | | | | V |

TABLE 40P

Synthetic Kappa light chain gene with stuffers

```
!
! A27::JH1 with all CDRs replaced by stuffers.
! Each stuffer contains at least one stop codon and a restriction
! site that will be unique within the diversity vector.
     1 GAGGACCATt GGGCCCC               ctccgagact
!      Scab...... EcoO109I
!                 ApaI.
!----------------------------------
!
                         28           CTCGAG     cgca
!                        XhoI..
!----------------------------------
!
    38 acgcaatTAA TGTgagttag ctcactcatt aggcacccca ggcTTTACAc tttatgcttc
!        ..-35..            Plac                              ..-10.
!----------------------------------
!
                 98 cggctcgtat gttgtgtgga attgtgagcg gataacaatt tc
                     !----------------------------------
!
                        140 acacagga aacagctatgac
                             !----------------------------------
!
             160 catgatta cgCCAAGCTT TGGagcctttt tttttggaga ttttcaac
                  PflMI.......
!                 Hind3.
                        !----------------------------------
!
!      M13 III signal sequence (AA seq)---------------------------->
!       1   2   3   4   5   6   7   8   9  10  11  12  13  14  15
!       M   K   K   L   L   F   A   I   P   L   V   V   P   F   Y
         206    gtg aag aag ctc cta ttt gct atc ccg ctt gtc gtt ccg ttt tac
                !----------------------------------
!
!       --Signal--> FR1---------------------------------------------->
!        16  17  18  19  20  21  22  23  24  25  26  27  28  29  30
!         S   H   S   A   Q   S   V   L   T   Q   S   P   G   T   L
         251   |agc|cat|aGT|GCA|Caa|tcc|gtc|ctt|act|caa|tct|cct|ggc|act|ctt|
!                        ApaLI...
                        !----------------------------------
!
!       ----- FR1 ---------------------------------->|--------Stuffer->
!        31  32  33  34  35  36  37  38  39  40  41  42  43
!         S   L   S   P   G   E   R   A   T   L   S   |   |
         296   |tcG|CTA|AGC|CCG|GGt|gaa|cgt|gct|acC|TTA|AGt|TAG|TAA|gct|ccc|
!             EspI.....                        AflII...
!                 XmaI....
                        !----------------------------------
!
!       ------- Stuffer for CDR1--------------------->|- FR2 -->
!                                                      59  60
!                                                       K   P
         341   |AGG|CCT|ctt|TGA|tct|                  g|aaA|CCT|
!              StuI...                                     SexAI...
                        !----------------------------------
!
```

TABLE 40P-continued

Synthetic Kappa light chain gene with stuffers

```
!          ----- FR2 ------|-----------Stuffer for CDR2---------------->
!          61  62  63  64  65  66
!          G   Q   A   P   R       |   |
        363    |GGT|caG|GCG|CCg|cgt|TAA|TGA|a AGCGCT aa TGGCCA aca gtg
!    SexAI.... KasI....              AfeI..    MscI..
!                                 !---------------------------------
!
! Stuffer-->|--- FR3 ----------------------------------------------->
!           <1>
!           76  77  78  79  80  81  82  83  84  85  86  87  88  89  90
!           T   G   I   P   D   R   F   S   G   S   G   S   G   T   D
        405    |act|gGG|ATC|CCG|GAC|CGt|ttc|tct|ggc|tct|ggt|tca|ggt|act|gac|
!              BamHI...
!                      RsrII.....
!                          !---------------------------------
!
!          ------ FR3 ---------------------STUFFER for CDR3------------------>
!          91  92  93  94  95  96  97
!          F   T   L   T   I   S   R       |   |
    450    |ttt|acc|ctt|act|att|TCT|AGA|TAA|TGA| GTTAAC TAG acc TACGTA acc tag
!                              XbaI...        HpaI..       SnaBI.
!                                !---------------------------------
!
!          ----------------CDR3 stuffer------------------>|-----FR4--->
!                                                        118 119 120
!                                                         F   G   Q
        501                                              |ttc|ggt|caa|
!                                !---------------------------------
!
!          -----FR4------------------->|       <------- Ckappa -----------
!          121 122 123 124 125 126 127         128 129 130 131 132 133 134
!          G   T   K   V   E   I   K           R   T   V   A   A   P   S
       510    |ggt|aCC|AAG|Gtt|gaa|atc|aag|    |CGT|ACG|gtt|gcc|gct|cct|agt|
!                 StyI....                      BsiWI..
!
! (CDR3 installed as XbaI to (StyI or BsiWI) cassette.)
!          135 136 137 138 139 140 141 142 143 144 145 146 147 148 149
!           V   F   I   F   P   P   S   D   E   Q   L   K   S   G   T
      552    |gtg|ttt|atc|ttt|cct|cct|tct|gac|gaa|CAA|TTG|aag|tca|ggt|act|
!                                             MfeI...
!
    866  acgcatctctaa GCGGCCGC aacaggaggag                   (SEQ ID NO:
                                                                   95)
!             NotI....
!             EagI..
```

TABLE 41P

Variegated DNA for kappa chains

```
!--------------------------------------------------------------
! Kappa chains
! For CDR1:
! <1> ADEFGHIKLMNPQRSTVWY equimolar
! <2> S(0.2) ADEFGHIKLMNPQRTVWY (0.044 each)
! <3> Y(0.2) ADEFGHIKLMNPQRSTVW (0.044 each)
! <4> A(0.2) DEFGHIKLMNPQRSTVWY (0.044 each)
(Ka1vg600)                            5'-gct|acC|TTA|AGt|tgc|cgt|gct|tcc|cag-
      |<1>|gtt|<2>|<2>|   <3>|ctt|gct|tgg|tat|caa|cag|aaA|CC-3'   (SEQ ID NO:
 66)
(Ka2vg650)      5'-caG|GCG|CCg|cgt|tta|ctt|att|tat|<1>|gct|tct|<2>|cgc|<4>|-
                  |<1>|gGG|ATC|CCG|GAC|CGt|ttc|tct|ggt|tctcacc-3'   (SEQ ID NO:
 71)
(Ka3vg670) 5'-                                        gac|ttc|gct|gtt|-
           |tat|tat|tgC|CAa|cag|<3>|<1>|<1>|<1>|cct|<1>|act|ttc|ggt|caa|-
           |ggt|aCC|AAG|Gtt|g-3'  (SEQ ID NO: 77)
```

TABLE 42P

Variegated DNA for lambda chains

```
!------------------------
! For CDR1,
! <1> = 0.27 T, 0.27 G, 0.027 {ADEFHIKLMNPQRSVWY} no C
```

TABLE 42P-continued

Variegated DNA for lambda chains

```
! <2> = 0.27 D, 0.27 N, 0.027 {AEFGHIKLMPQRSTVWY} no C
! <3> = 0.36 Y, 0.0355{ADEFGHIKLMNPQRSTVW} no C
! <4> = equimolar {ADEFGHIKLMNPQRSTVWY} no C
! <5> = 0.36 S, 0.0355{ADEFGHIKLMNPQRTVWY} no C
(Lm1vg710)  5'-gt|atc|act|att|tct|TGT|ACA|ggt|<1>|tct|tct|<2>|gtt|ggc|-
           |<1>|<3>|<2>|<3>|gtt|tct|tgg|tat|caa|caa|caC|CC-3'        (SEQ ID NO: 83)
!---------------------------------------
(Lm2vg750)                   5'-G|CCg|aag|ttg|atg|atc|tac|-
    <4>|<4>|<4>|<2>|cgt|cct|tct|ggt|gtc|agc|aat|c-3'                 (SEQ ID NO: 88)
(Lm3vg817)  5'-gac|gag|gct|gac|tac|tat|tgt|-
       |<4>|<5>|<4>|<2>|<4>|tct|<4>|<4>|<4>|<4>|gtc|ttc|ggc|ggt|GGT|-
       |ACC|aaa|ctt|ac-3'     (SEQ ID NO: 93)
!---------------------------------------
```

TABLE 43P

Constant DNA for Synthetic Library

```
!CDR3 library components
(Ctop25)  5'-gctctggtcaa C|TTA|AGg|gct|gag|g-3'   (SEQ ID NO: 58)
(CtprmA)  5'-gctctggtcaa C|TTA|AGg|gct|gag|gac-
!                   AflII...
           |acc|gct|gtc|tac|tac|tgc|gcc-3'       (SEQ ID NO: 59)
!
(CBprmB) [RC] 5'-|tac|ttc|gat|tac|ttg|ggc|caa|GGT|ACC|ctG|GTC|ACC|tcgctccacc-3' (SEQ ID NO: 60)
!                                              BstEII...
(CBot25) [RC]                 5'-|GGT|ACC|ctG|GTC|ACC|tcgctccacc-3'  (SEQ ID NO: 61)
!---------------------------------------
!Kappa chains
(Ka1Top610) 5'-ggtctcagtt-
           G|CTA|AGC|CCG|GGt|gaa|cgt|gct|acC|TTA|AGt|tgc|cgt|gct|tcc|cag-3'  (SEQ ID NO: 62)
(Ka1STp615) 5'-ggtctcagtt-
           G|CTA|AGC|CCG|GGt|g-3'  (SEQ ID NO: 63)
(Ka1Bot620) [RC]    5'-ctt|gct|tgg|tat|caa|cag|aaA|-
                  CCt|GGT|caG|GCG|CC aagtcgtgtc-3'  (SEQ ID NO: 64)
(Ka1SB625)  [RC] 5'-cct|GGT|caG|GCG|CC aagtcgtgtc-3'  (SEQ ID NO: 65)
(Ka2Tshort657) 5'-cacgagtcctA|CCT|GGT|-
!
               caG|GC-3'   (SEQ ID NO: 68)
(Ka2Tlong655)  5'-cacgagtcctA|CCT|GGT|-
               caG|GCG|CCg|cgt|tta|ctt|att|tat-3'   (SEQ ID NO: 69)
(Ka2Bshort660) [RC] 5'-      |GAC|CGt|ttc|tct|ggt|tctcacc-3'  (SEQ ID NO: 70)
!---------------------------------------
(Ka3Tlon672)   5'-   gacgagtcct TCT|AGA|ttg|gaa|cct|gaa|gac|ttc|gct|gtt|-
               |tat|tat|tgC|CAa|c-3'  (SEQ ID NO: 72)
(Ka3BotL682)                     [RC] 5'-act|ttc|ggt|caa|-
               |ggt|aCC|AAG|Gtt|gaa|atc|aag|  |CGT|ACG| tcacaggtgag-3'  (SEQ ID NO: 73)
(Ka3Bsho694) [RC] 5'-        gaa|atc|aag|  |CGT|ACG| tcacaggtgag-3'   (SEQ ID NO: 74)
!---------------------------------------
(Lm1TPri75)  5'-gacgagtcct GG|TcA|CCt|GGT|-3'   (SEQ ID NO: 78)
(Lm1TLo715)  5'-gacgagtcct GG|TcA|CCt|GGT|-
             caa|agt|atc|act|att|tct|TGT|ACA|ggt-3'   (SEQ ID NO: 79)
(Lm1BLo724) [RC] 5'-gtt|tct|tgg|tat|caa|caa|caC|CCG|GGc|aaG|GCG|-
             AGA TCT  tcacaggtgag-3'   (SEQ ID NO: 80)
(Lm1BSh737) [RC] 5'-                               Gc|aaG|GCG|-
             AGA TCT  tcacaggtgag-3'   (SEQ ID NO: 81)
!---------------------------------------
(Lm2TSh757) 5'-gagcagagga C|CCG|GGc|aaG|GC-3'   (SEQ ID NO: 84)
(Lm2TLo753) 5'-gagcagagga C|CCG|GGc|aaG|GCG|CCg|aag|ttg|atg|atc|tac|-3'  (SEQ ID NO: 85)
(Lm2BLo762) [RC] 5'-cgt|cct|tct|ggt|gtc|agc|aat|cgt|ttc|TCC|GGA|tcacaggtgag-3' (SEQ ID NO: 86)
(Lm2BSh765) [RC] 5'-                       cgt|ttc|TCC|GGA|tcacaggtgag-3'  (SEQ ID NO: 87)
!---------------------------------------
(Lm3TSh822)       5'-CTG|CAG|gct|gaa|gac|gag|gct|gac          -3'  (SEQ ID NO: 89)
(Lm3TLo819)       5'-CTG|CAG|gct|gaa|gac|gag|gct|gac|tac|tat|tgt|-3' (SEQ ID NO: 90)
(Lm3BLo825) [RC]                      5'-gtc|ttc|ggc|ggt|GGT|-
           |ACC|aaa|ctt|act|gtc|ctc|gGT|CAA|CCT|aAG|G acacaggtgag-3'  (SEQ ID NO: 91)

(Lm3BSh832) [RC]  5'-         c|gGT|CAA|CCT|aAG|G acacaggtgag-3'   (SEQ ID NO: 92)
!---------------------------------------
```

TABLE 48P

Synthtic human lambda-chain gene with stuffers in place of CDRs

```
! Lambda 14-7(A)    2a2 ::JH2::Clambda
! AA sequence tested
!
    1 GAGGACCATt GGGCCCC   ttactccgtgac
      Scab......  EcoO109I
!              ApaI..
!----------------------------------------------
!
!         -----------FR1------------------------------------------>
!          1   2   3   4   5   6   7   8   9  10  11  12  13  14  15
!          S   A   Q   S   A   L   T   Q   P   A   S   V   S   G   S   P   G
   !  30 aGT|GCA|Caa|tcc|gct|ctc|act|cag|cct|GCT|AGC|gtt|tcc|gGG|TcA|CCt|GGT|
!         ApaLI...                     NheI...          BstEII...
!                                                            SexAI....
!----------------------------------------------
!
!         ------FR1----------------->  |-----stuffer for CDR1---------
!         16  17  18  19  20  21  22  23
!          Q   S   I   T   I   S   C   T
!              81 |caa|agt|atc|act|att|tct|TGT|ACA|tct TAG TGA ctc
!                                         BsrGI..
!----------------------------------------------
!
!         -----Stuffer-------------------------->--------------------
!         31  32  33  34  35  36  37  38  39  40  41  42  43  44  45
!          R   S   |   |   P   |                   H   P   G   K   A
!             117  AGA TCT TAA TGA ccg tag             caC|CCG|GGc|aaG|GCG|
!         BglII                                      XmaI....   KasI.....
!                                                    AvaI....
!----------------------------------------------
!
!         --|-------------Stuffer ------------------------------------>
!          P
!             150 |CCg|TAA|TGA|atc tCG TAC G                ct|ggt|gtt|
! KasI....           BsiWI...
!----------------------------------------------
!
!         --------FR3----------------------------------------
!         61  62  63  64  65  66  67  68  69  70  71  72  73  74  75
!          S   N   R   F   S   G   S   K   S   G   N   T   A   S   L
!             177 |agc|aat|cgt|ttc|TCC|GGA|tct|aaa|tcc|ggt|aat|acc|gcA|AGC|TTa|
!                      BspEI..       |                  HindIII.
!                          BsaBI........(blunt)
!----------------------------------------------
!
!         --------FR3------------->|--Stuffer------------------------>|
!         76  77  78  79  80  81  82  83  84  85  86  87  88  89  90
!          T   I   S   G   L   Q
!             222 |act|atc|tct|ggt|CTG|CAG|gtt ctg tag ttc CAATTG ctt tag tga ccc
!                                  PstI...                MfeI..
!----------------------------------------------
!
!         -----Stuffer----------------------->|---FR4---------
!                                                      103 104 105
!                                                       G   G   G
!             270                                       |ggc|ggt|GGT|
!                                                                KpnI...
!----------------------------------------------
!         -------FR4-------------->
!         106 107 108 109 110 111 112 113 114 115 116 117 118 119 120
!          T   K   L   T   V   L   G   Q   P   K   A   A   P   S   V
!             279 |ACC|aaa|ctt|act|gtc|ctc|gGT|CAA|CCT|aAG|Gct|gct|cct|tcc|gtt|
! KpnI...                HincII..
!                                     Bsu36I...
!
!         121 122 123 124 125 126 127 128 129 130 131 132 133 134 135
!          T   L   F   P   P   S   S   E   E   L   Q   A   N   K   A
!             324 |act|ctc|ttc|cct|cct|agt|tct|GAA|GAG|Ctt|caa|gct|aac|aag|gct|
!                                              SapI.....
!
!         136 137 138 139 140 141 142 143 144 145 146 147 148 149 150
!          T   L   V   C   L   I   S   D   F   Y   P   G   A   V   T       (SEQ ID NO:
! 97)
!         369 |act|ctt|gtt|tgc|tTG|ATC|Agt|gac|ttt|tat|cct|ggt|gct|gtt|act|    (SEQ ID NO:
                                                    97)
!                     BclI....
```

TABLE 50P 3-23::CDR3::JH4 Stuffers in place of CDRs

```
                    FR1(DP47/V3-23)---------------
               20  21  22  23  24  25  26  27  28  29  30
                A   M   A   E   V   Q   L   L   E   S   G
ctgtctgaac  CC atg gcc gaa|gtt|CAA|TTG|tta|gag|tct|ggt|
Scab......  NcoI....            | MfeI |

---------------FR1-------------------------------------------
         31  32  33  34  35  36  37  38  39  40  41  42  43  44  45
          G   G   L   V   Q   P   G   G   S   L   R   L   S   C   A
        |ggc|ggt|ctt|gtt|cag|cct|ggt|ggt|tct|tta|cgt|ctt|tct|tgc|gct|

----FR1-------------------->|...CDR1 stuffer....|---FR2------
         46  47  48  49  50  51  52  53  54  55  56  57  58  59  60
          A   S   G   F   T   F   S   S   Y   A   |   |   W   V   R
        |gct|TCC|GGA|ttc|act|ttc|tct|tCG|TAC|Gct|TAG|TAA|tgg|gtt|cgC|
            | BspEI |                    | BsiWI|                  |BstXI.

-------FR2--------------------------->|...CDR2 stuffer.
         61  62  63  64  65  66  67  68  69  70  71  72  73  74  75
          Q   A   P   G   K   G   L   E   W   V   S   |   p   r   |
        |CAa|gct|ccT|GGt|aaa|ggt|ttg|gag|tgg|gtt|tct|TAA|CCT|AGG|TAG|
        ...BstXI      |                                    AvrII..

.....CDR2 stuffer....................................|---FR3---
        --------FR3---------------------------------------------
         91  92  93  94  95  96  97  98  99 100 101 102 103 104 105
          T   I   S   R   D   N   S   K   N   T   L   Y   L   Q   M
        |act|atc|TCT|AGA|gac|aac|tct|aag|aat|act|ctc|tac|ttg|cag|atg|
                | XbaI |

---FR3-----------..> Stuffer-------------->|
         106 107 108 109 110
          N   S   L   R   A                              (SEQ ID NO: 53)
        |aac|agC|TTA|AGg|gct|TAG TAA AGG cct TAA          (SEQ ID NO: 52)
              |AflII |        StuI...

|----- FR4 ---(JH4)-----------------------------------
          Y   F   D   Y   W   G   Q   G   T   L   V   T   V   S   S   (SEQ ID NO: 26)
        |tat|ttc|gat|tat|tgg|ggt|caa|GGT|ACC|ctG|GTC|ACC|gtc|tct|agt|... (SEQ ID NO: 25)
                                | KpnI  |  | BstEII |
```

The invention claimed is:

1. A focused library of vectors or genetic packages, comprising a first set of variegated DNAs each of which comprises a nucleotide sequence encoding an antibody heavy chain, which comprises a CDR1 region, a CDR2 region, and a CDR3 region, each nucleotide sequence in the first set of variegated DNAs being represented by the formula V::nz::JHn, or V::nz::D::ny::JHn, wherein V is a v gene, nz is a series of bases that are essentially random, D is a D segment, ny is a series of bases that are essentially random, and JHn is one of the six JH segments, wherein the CDR2s of the heavy chains encoded by the first set of variegated DNAs are seventeen amino acids in length, sixteen amino acids in length, and/or nineteen amino acids in length, and wherein the heavy chain CDR2s encoded by the first set of variegated DNAs are seventeen amino acids in length having the sequence:

<2>I<2><3>SGG<1>T<1>YADSVKG (SEQ ID NO:2), in which each <1> independently is selected from the group consisting of A, D, E, F, G, H, I, K, L, M, N, P, Q, R, S, T, V, W, and Y; each <2> independently is an amino acid selected from the group consisting of Y, R, W, V, G and S; and <3> is selected from the group consisting of P and S.

2. A focused library of vectors or genetic packages, comprising a first set of variegated DNAs each of which comprises a nucleotide sequence encoding an antibody heavy chain, which comprises a CDR1 region, a CDR2 region, and a CDR3 region, each nucleotide sequence in the first set of variegated DNAs being represented by the formula V::nz::JHn, or V::nz::D::ny::JHn, wherein V is a v gene, nz is a series of bases that are essentially random, D is a D segment, ny is a series of bases that are essentially random, and JHn is one of the six JH segments, wherein:

(a) nz encodes the sequence <1><1>1>, in which each <1> independently is any amino acid residue other than C; D encodes the sequence S<2>S<3> (SEQ ID NO:450), in which <2> is S or G and <3> is Y or W; ny encodes the sequence <1><1><1>, in which each <1> independently is any amino acid residue other than C; and JHn encodes the sequence YFDY (SEQ ID NO:449), (b) nz encodes the sequence <1><1><1>, in which each <1> independently is any amino acid residue other than C; D encodes the sequence CSG<1><1>CY (SEQ ID NO:451), in which each <1> independently is any amino acid residue other than C; ny encodes the sequence <1>, which is any amino acid residue other than C; and JHn encodes the sequence YFDY (SEQ ID NO:449), (c) nz encodes the sequence <1><1>S<1> (SEQ ID NO:452), in which each <1> independently is any amino acid residue other than C; D encodes the sequence TIFG (SEQ ID NO:453); ny encodes the sequence <1><1><1><1><1> (SEQ ID NO:454), in which each <1> independently is any amino acid residue other than C; and JHn encodes the sequence YFDY (SEQ ID NO:449), (d) nz encodes the sequence <1><1><1>, in which each <1> independently is any amino acid residue other than C; D encodes the sequence YY<2>S<3><3>YY (SEQ ID NO:455), in which <2> is D or G, and each <3> independently is S or G; ny encodes the sequence <1><1><1>, in which each <1> independently is any amino acid residue other than C; and JHn encodes the sequence YFDY (SEQ ID NO:449), or (e) nz encodes the sequence <1><1><1><1> (SEQ ID NO:456), in which each <1> independently is any amino acid residue other than C; D encodes the sequence YC<2><2><3><1>CY (SEQ ID NO:457), in which <1> is any amino acid residue other than Cys, each <2> independently is S or G, and <3> is T, D or G; ny encodes the sequence <1><1><1>, in which each <1> independently is any amino acid residue other than C; and JHn encodes YFDY (SEQ ID NO:449).

3. The focused library of claim 2 further comprising: a second set of variegated DNAs, each of which comprises a nucleotide sequence encoding an antibody light chain, which comprises CDR1, CDR2 and CDR3, wherein the second set of variegated DNAs collectively comprise nucleotide sequences encoding kappa light chains, wherein the kappa light chains further comprise a framework region of germ line sequence A-27.

4. The library of claim 3, wherein the kappa light chain further comprises a JK1 region or a JK4 region.

5. The focused library of claim 2 further comprising: a second set of variegated DNAs, each of which comprises a nucleotide sequence encoding an antibody light chain, which comprises CDR1, CDR2 and CDR3, wherein the second set of variegated DNAs collectively comprise nucleotide sequences encoding kappa light chains, wherein the CDR2 in the kappa light chain is seven amino acids in length.

6. The library of claim 1 or claim 2 wherein the second set of variegated DNAs collectively encode kappa light chains having CDR1 regions that are eleven and/or twelve amino acids in length.

7. The library of claim 1 or claim 2, wherein the JH segment is a JH4 segment.

8. The library of claim 1 or claim 2, wherein the JHn is one of the six JH segments having a base or bases edited from the N-terminus.

9. The library of claim 1 or claim 2 wherein the D is a D segment having a base or bases edited from its 5' end, 3' end, or both.

10. The library of claim 1 or claim 2 wherein the JHn encodes an amino acid sequence that includes the sequence DYWG (SEQ ID NO:448), wherein D and Y are part of heavy chain CDR3 and W and G are part of the framework 4 region of the heavy chain.

11. The library of claim 1 or claim 2 wherein the heavy chains further comprise one or more framework regions of germline sequences selected from the group consisting of 3-23, 4-34, 3-30, 3-30.3, and 4-30.1.

12. The library of claim 2, wherein the CDR1s of the heavy chains encoded by the first set of variegated DNAs are five amino acids in length, seven amino acids in length, and/or fourteen amino acids in length.

13. The library of claim 12, wherein the heavy chain CDR1s are five amino acids in length and variegated at positions 1, 3 and 5 and the amino acids at positions 1, 3, and 5 can not be C.

14. The library of claim 13, wherein the heavy chain CDR1s have Y at position 2 and M at position 4.

15. The library of claim 12, wherein the heavy chain CDR1s have the sequence:
X-Y-X-M-X (SEQ ID NO:100), in which X is any one of amino acids A, D, E, F, G, H, I, K, L, M, N, P, Q, R, S, T, V, W, and Y.

16. The library of claim 1 or claim 2, wherein the CDR2s of the heavy chains encoded by the first set of variegated DNAs are seventeen amino acids in length, sixteen amino acids in length, and/or nineteen amino acids in length.

17. The library of claim 1 or claim 2, wherein the first set of variegated DNAs collectively encode antibody heavy chains comprising CDR3 regions that comprises one or more of the following motifs:
xxxYCSSTSCxxx (SEQ ID NO:199), in which x is any amino acid or is absent;
xxxxxxxSGYxxx (SEQ ID NO:201), in which x is any amino acid or is absent;
xxxVVVPAAxxxx (SEQ ID NO:203), in which x is any amino acid or is absent;
xxxYYDSSGYxx (SEQ ID NO:204), in which x is any amino acid or is absent;
xxxTIFGVxxxx (SEQ ID NO:206), in which x is any amino acid or is absent;
xxxYGSGSYYx (SEQ ID NO:208), in which x is any amino acid or is absent;
xxxxYSYGxxx (SEQ ID NO:209), in which x is any amino acid or is absent;
xxxCSGxxCYxx (SEQ ID NO:210), in which x is any amino acid or is absent;
xxxxAAAGxxx (SEQ ID NO:211), in which x is any amino acid or is absent;
xxxSGSYxxx (SEQ ID NO:213), in which x is any amino acid or is absent;
xxxSSSWxxx (SEQ ID NO:214), in which x is any amino acid or is absent;
xxx(IV)AVAGxx (SEQ ID NO:217), in which x is any amino acid or is absent;
xxLWFGELxx (SEQ ID NO:218), in which x is any amino acid or is absent;
xxxxxGExxx (SEQ ID NO:221), in which x is any amino acid or is absent;
xxxxSGWxx (SEQ ID NO:222), in which x is any amino acid or is absent;
xxxVRGVxx (SEQ ID NO:224), in which x is any amino acid or is absent;
xxxIAAxxx (SEQ ID NO:225), in which x is any amino acid or is absent;
xxxYGDxx (SEQ ID NO:227), in which x is any amino acid or is absent;
xxVGATxx (SEQ ID NO:228), in which x is any amino acid or is absent;
xxxYSSSx (SEQ ID NO:229), in which x is any amino acid or is absent.

18. The library of claim 3 or claim 5, wherein the second set of variegated DNAs collectively encode kappa light chains having CDR3 regions that are eight, nine, and/or ten amino acids in length.

19. The library of claim 1 or claim 2, wherein the genetic packages are cells, spores, or viral particles.

20. The library of claim 1 or claim 2, wherein the genetic packages are phages or yeast cells.

21. The library of claim 1 or claim 2, wherein the genetic packages are yeast cells, which display the antibody heavy chains encoded by the first set of variegated DNAs.

22. The library of claim 1 or claim 2, wherein the vectors are yeast vectors.

* * * * *

UNITED STATES PATENT AND TRADEMARK OFFICE
CERTIFICATE OF CORRECTION

PATENT NO. : 8,466,091 B2  
APPLICATION NO. : 13/161445  
DATED : June 18, 2013  
INVENTOR(S) : Robert Charles Ladner Page 1 of 1

It is certified that error appears in the above-identified patent and that said Letters Patent is hereby corrected as shown below:

In the Claims

In Claim 2, at column 197, line 44 should read:

"(a) nz encodes the sequence <1><1><1>, in which each <1>"

Signed and Sealed this  
Sixth Day of August, 2013

Teresa Stanek Rea  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,466,091 B2 | Page 1 of 1 |
| APPLICATION NO. | : 13/161445 | |
| DATED | : June 18, 2013 | |
| INVENTOR(S) | : Robert Charles Ladner | |

It is certified that error appears in the above-identified patent and that said Letters Patent is hereby corrected as shown below:

In the Specification

At column 4, line 40 should read:
"(7) YYCAR111YY2S33YY111YFDYWG (SEQ ID"

In column 141, lines 2-5 should be deleted

In column 141, line 13 should read:
Tyr Tyr Cys Ala Arg Xaa Xaa Xaa Tyr Tyr Xaa Ser Xaa Xaa Tyr Tyr Signed and Sealed this
Twenty-fifth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,466,091 B2
APPLICATION NO. : 13/161445
DATED : June 18, 2013
INVENTOR(S) : Robert Charles Ladner It is certified that error appears in the above-identified patent and that said Letters Patent is hereby corrected as shown below:

In the Specification

At column 4, line 22 should read:

" (3)   YYCA211111111YFDYWG   (SEQ ID NO: 8), "

In Table 4, component 3 should read:

"   YYCA211111111YFDYWG
   (SEQ ID NO: 8)
 (1 = any amino acid residue, except C; 2 = K and R)  "

In Table 16P, in the first column, the first line should read:

"Component Fraction of"

In Table 16P, Component Fraction of 3 should read:

"   YYCA211111111YFDYWG
 (2 = KR; SEQ ID NO: 8)   "

In Table 17P, (C1t08) should read:

(C1t08) 5'-cc|gct|gtc|tac|tac|tgc|gcc|-
              <2>|<1>|<1>|<1>|<1>-
          |tac|ttc|gat|tac|tgg|ggc|caa|GG-3'   (SEQ ID NO: 44)
" 2= KR, 1 = 0.27Y + 0.27G + 0.027{ADEFHIKLMNPQRSTVW} no C   "

Signed and Sealed this
Thirty-first Day of May, 2016

Michelle K. Lee
*Director of the United States Patent and Trademark Office*

CERTIFICATE OF CORRECTION (continued)
U.S. Pat. No. 8,466,091 B2

Page 2 of 2

In Table 17P, (C2t10) should read:

" (C2t10) 5'-cc|gct|gtc|tac|tac|tgc|gcc|-
                      <2>|<1>|<1>|<1>|<1>|<1>|<1>|-
                      tac|ttc|gat|tac|tgg|ggc|caa|GG-3'      (SEQ ID NO: 45)
2= KR, 1 = 0.27Y + 0.27G + 0.027{ADEFHIKLMNPQRSTVW} no C "

In Table 17P, (C3t12) should read:

" (C3t12) 5'-cc|gct|gtc|tac|tac|tgc|gcc|-
                      <2>|<1>|<1>|<1>|<1>|<1>|<1>|<1>|<1>|-
                      tac|ttc|gat|tac|tgg|ggc|caa|GG-3'      (SEQ ID NO: 46)
2= KR, 1 = 0.27Y + 0.27G + 0.027{ADEFHIKLMNPQRSTVW} no C "

In Table 17P, (C4t14) should read:

" (C4t14) 5'-cc|gct|gtc|tac|tac|tgc|gcc|cgt|-
                      <1>|<1>|<1>|<tct>|<2>|<tct>|<3>|<1>|<1>|<1>|-
                      tac|ttc|gat|tac|tgg|ggc|caa|GG-3'      (SEQ ID NO: 47)
2= SG, 1 = 0.27Y + 0.27G + 0.027{ADEFHIKLMNPQRSTVW} no C, 3 = YW "

In Table 17P, (C5t15) should read:

" (C5t15) 5'-cc|gct|gtc|tac|tac|tgc|gcc| -
                      <2>|<1>|<1>|<1>|tgc|<tct>|ggt|<1>|<1>|tgc|tat|<1>|-
                      tac|ttc|gat|tac|tgg|ggc|caa|GG-3'      (SEQ ID NO: 48)
2= KR, 1 = 0.27Y + 0.27G + 0.027{ADEFHIKLMNPQRSTVW} no C "

In Table 17P, (C6t17) should read:

" (C6t17) 5'-cc|gct|gtc|tac|tac|tgc|gcc| -
                      <2>|<1>|<1>|tct|<1>|act|atc|ttc|ggt|<1>|<1>|<1>|<1>|<1>|-
                      tac|ttc|gat|tac|tgg|ggc|caa|GG-3'      (SEQ ID NO: 49)
2= KR, 1 = 0.27Y + 0.27G + 0.027{ADEFHIKLMNPQRSTVW} no C "

In Table 17P, (C7t18) should read:

" (C7t18) 5'-cc|gct|gtc|tac|tac|tgc|gcc|cgt| -
                      |<1>|<1>|<1>|tat|tac|<2>|tct|<3>|<3>|tac|tat|<1>|<1>|<1>|-
                      tac|ttc|gat|tac|tgg|ggc|caa|GG-3'      (SEQ ID NO: 50)
2= DG, 1 = 0.27Y + 0.27G + 0.027{ADEFHIKLMNPQRSTVW} no C, 3 = SG "

In Table 17P, (C8t19) should read:

" (C8t19) 5'-cc|gct|gtc|tac|tac|tgc|gcc|cgt| -
                      |<1>|<1>|<1>|<1>|tat|tgc|<2>|<2>|<3>|<1>|tgc|tat|<1>|<1>|<1>|-
                      tac|ttc|gat|tac|tgg|ggc|caa|GG-3'      (SEQ ID NO: 51)
2= SG, 1 = 0.27Y + 0.27G + 0.027{ADEFHIKLMNPQRSTVW} no C, 3=TDG "

SEQUENCE LISTING

<160> NUMBER OF SEQ ID NOS: 99

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      heavy chain CDR1 vector peptide
<220> FEATURE:
<221> NAME/KEY: MOD_RES
<222> LOCATION: (8)..(10)
<223> OTHER INFORMATION: Any amino acid except Cys
<220> FEATURE:
<221> NAME/KEY: MOD_RES
<222> LOCATION: (14)
<223> OTHER INFORMATION: Any amino acid except Cys

<400> SEQUENCE: 1

Val Ser Gly Gly Ser Ile Ser Xaa Xaa Xaa Tyr Tyr Trp Xaa
1               5                   10

<210> SEQ ID NO 2
<211> LENGTH: 17
<212> TYPE: PRT
<213> ORGANISM: Artificial Sequence
<220> FEATURE:

```
<223> OTHER INFORMATION: Description of Artificial Sequence: Synthetic
      heavy chain CDR2 vector peptide
<220> FEATURE:
<221> NAME/KEY: MOD_RES
<222> LOCATION: (1)
<223> OTHER INFORMATION: Tyr, Arg, Trp, Val, Gly or Ser
<220> FEATURE:
<221> NAME/KEY: MOD_RES
<222> LOCATION: (3)
<223> OTHER INFORMATION: Tyr, Arg, Trp, Val, Gly or Ser
<220> FEATURE:
<221> NAME/KEY: MOD_RES
<222> LOCATION: (4)
<223> OTHER INFORMATION: Pro, Ser or Gly
<220> FEATURE:
<221> NAME/KEY: MOD_RES
<222> LOCATION: (8)
<223> OTHER INFORMATION: Any amino acid except Cys
<220> FEATURE:
<221> NAME/KEY: MOD_RES
<222> LOCATION: (10)
<223> OTHER INFORMATION: Any amino acid except Cys

<400> SEQUENCE: 2

Xaa Ile Xaa Xaa Ser Gly Gly Xaa Thr Xaa Tyr Ala Asp Ser Val Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain CDR2 vector peptide
<220> FEATURE:
<221> NAME/KEY: MOD_RES
<222> LOCATION: (1)
<223> OTHER INFORMATION: Any amino acid except Cys
<220> FEATURE:
<221> NAME/KEY: MOD_RES
<222> LOCATION: (3)
<223> OTHER INFORMATION: Asp, Ile, Asn, Ser, Trp or Tyr
<220> FEATURE:
<221> NAME/KEY: MOD_RES
<222> LOCATION: (4)..(5)
<223> OTHER INFORMATION: Any amino acid except Cys
<220> FEATURE:
<221> NAME/KEY: MOD_RES
<222> LOCATION: (7)
<223> OTHER INFORMATION: Ser, Gly, Asp or Asn
<220> FEATURE:
<221> NAME/KEY: MOD_RES
<222> LOCATION: (8)..(10)
<223> OTHER INFORMATION: Any amino acid except Cys

<400> SEQUENCE: 3

Xaa Ile Xaa Xaa Xaa Gly Xaa Xaa Xaa Xaa Tyr Ala Asp Ser Val Lys
1               5                   10                  15

Gly

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain CDR2 vector peptide
<220> FEATURE:
<221> NAME/KEY: MOD_RES
<222> LOCATION: (1)
<223> OTHER INFORMATION: Any amino acid except Cys
<220> FEATURE:
<221> NAME/KEY: MOD_RES
```

```
<222> LOCATION: (3)
<223> OTHER INFORMATION: Asp, Ile, Asn, Ser, Trp or Tyr
<220> FEATURE:
<221> NAME/KEY: MOD_RES
<222> LOCATION: (4)..(5)
<223> OTHER INFORMATION: Any amino acid except Cys
<220> FEATURE:
<221> NAME/KEY: MOD_RES
<222> LOCATION: (7)
<223> OTHER INFORMATION: Ser, Gly, Asp or Asn
<220> FEATURE:
<221> NAME/KEY: MOD_RES
<222> LOCATION: (8)..(9)
<223> OTHER INFORMATION: Any amino acid except Cys

<400> SEQUENCE: 4

Xaa Ile Xaa Xaa Xaa Gly Xaa Xaa Xaa Tyr Asn Pro Ser Leu Lys Gly
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      heavy chain CDR2 vector peptide
<220> FEATURE:
<221> NAME/KEY: MOD_RES
<222> LOCATION: (1)
<223> OTHER INFORMATION: Any amino acid except Cys
<220> FEATURE:
<221> NAME/KEY: MOD_RES
<222> LOCATION: (3)
<223> OTHER INFORMATION: Any amino acid except Cys
<220> FEATURE:
<221> NAME/KEY: MOD_RES
<222> LOCATION: (5)..(7)
<223> OTHER INFORMATION: Any amino acid except Cys
<220> FEATURE:
<221> NAME/KEY: MOD_RES
<222> LOCATION: (12)
<223> OTHER INFORMATION: Any amino acid except Cys

<400> SEQUENCE: 5

Xaa Ile Xaa Ser Xaa Xaa Xaa Gly Gly Tyr Tyr Xaa Tyr Ala Ala Ser
1               5                   10                  15

Val Lys Gly

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (5)
<223> OTHER INFORMATION: Lys or Arg
<220> FEATURE:
<221> NAME/KEY: MOD_RES
<222> LOCATION: (6)..(9)
<223> OTHER INFORMATION: Any amino acid except Cys

<400> SEQUENCE: 6

Tyr Tyr Cys Ala Xaa Xaa Xaa Xaa Xaa Tyr Phe Asp Tyr Trp Gly
1               5                   10                  15

<210> SEQ ID NO 7
<211> LENGTH: 17
<212> TYPE: PRT
<213> ORGANISM: Artificial Sequence
<220> FEATURE:
```

-continued

```
<223> OTHER INFORMATION: Description of Artificial Sequence: Synthetic
      heavy chain CDR3 vector peptide
<220> FEATURE:
<221> NAME/KEY: MOD_RES
<222> LOCATION: (5)
<223> OTHER INFORMATION: Lys or Arg
<220> FEATURE:
<221> NAME/KEY: MOD_RES
<222> LOCATION: (6)..(11)
<223> OTHER INFORMATION: Any amino acid except Cys

<400> SEQUENCE: 7

Tyr Tyr Cys Ala Xaa Xaa Xaa Xaa Xaa Xaa Xaa Tyr Phe Asp Tyr Trp
1               5                   10                  15

Gly

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (5)
<223> OTHER INFORMATION: Lys or Arg
<220> FEATURE:
<221> NAME/KEY: MOD_RES
<222> LOCATION: (6)..(13)
<223> OTHER INFORMATION: Any amino acid except Cys

<400> SEQUENCE: 8

Tyr Tyr Cys Ala Xaa Xaa Xaa Xaa Xaa Xaa Xaa Xaa Xaa Tyr Phe Asp
1               5                   10                  15

Tyr Trp Gly

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (6)..(8)
<223> OTHER INFORMATION: Any amino acid except Cys
<220> FEATURE:
<221> NAME/KEY: MOD_RES
<222> LOCATION: (10)
<223> OTHER INFORMATION: Ser or Gly
<220> FEATURE:
<221> NAME/KEY: MOD_RES
<222> LOCATION: (12)
<223> OTHER INFORMATION: Tyr or Trp
<220> FEATURE:
<221> NAME/KEY: MOD_RES
<222> LOCATION: (13)..(15)
<223> OTHER INFORMATION: Any amino acid except Cys

<400> SEQUENCE: 9

Tyr Tyr Cys Ala Arg Xaa Xaa Xaa Ser Xaa Ser Xaa Xaa Xaa Xaa Tyr
1               5                   10                  15

Phe Asp Tyr Trp Gly
            20

<210> SEQ ID NO 10
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (5)
<223> OTHER INFORMATION: Lys or Arg
<220> FEATURE:
<221> NAME/KEY: MOD_RES
<222> LOCATION: (6)..(8)
<223> OTHER INFORMATION: Any amino acid except Cys
<220> FEATURE:
<221> NAME/KEY: MOD_RES
<222> LOCATION: (12)..(13)
<223> OTHER INFORMATION: Any amino acid except Cys
<220> FEATURE:
<221> NAME/KEY: MOD_RES
<222> LOCATION: (16)
<223> OTHER INFORMATION: Any amino acid except Cys

<400> SEQUENCE: 10

Tyr Tyr Cys Ala Xaa Xaa Xaa Xaa Cys Ser Gly Xaa Xaa Cys Tyr Xaa
1               5                   10                  15

Tyr Phe Asp Tyr Trp Gly
            20

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (5)
<223> OTHER INFORMATION: Lys or Arg
<220> FEATURE:
<221> NAME/KEY: MOD_RES
<222> LOCATION: (6)..(7)
<223> OTHER INFORMATION: Any amino acid except Cys
<220> FEATURE:
<221> NAME/KEY: MOD_RES
<222> LOCATION: (9)
<223> OTHER INFORMATION: Any amino acid except Cys
<220> FEATURE:
<221> NAME/KEY: MOD_RES
<222> LOCATION: (14)..(18)
<223> OTHER INFORMATION: Any amino acid except Cys

<400> SEQUENCE: 11

Tyr Tyr Cys Ala Xaa Xaa Xaa Ser Xaa Thr Ile Phe Gly Xaa Xaa Xaa
1               5                   10                  15

Xaa Xaa Tyr Phe Asp Tyr Trp Gly
            20

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (6)..(8)
<223> OTHER INFORMATION: Any amino acid except Cys
<220> FEATURE:
<221> NAME/KEY: MOD_RES
<222> LOCATION: (11)
<223> OTHER INFORMATION: Asp or Gly
<220> FEATURE:
<221> NAME/KEY: MOD_RES
<222> LOCATION: (13)..(14)
```

```
<223> OTHER INFORMATION: Ser or Gly
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (17)..(19)
<223> OTHER INFORMATION: Any amino acid except Cys

<400> SEQUENCE: 12

Tyr Tyr Cys Ala Arg Xaa Xaa Xaa Tyr Tyr Xaa Ser Xaa Xaa Xaa Xaa
1               5                   10                  15

Xaa Xaa Xaa Tyr Phe Asp Tyr Trp Gly
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence: Synthetic
      heavy chain CDR3 vector peptide
<220> FEATURE:
<221> NAME/KEY: MOD_RES
<222> LOCATION: (6)..(9)
<223> OTHER INFORMATION: Any amino acid except Cys
<220> FEATURE:
<221> NAME/KEY: MOD_RES
<222> LOCATION: (12)..(13)
<223> OTHER INFORMATION: Ser or Gly
<220> FEATURE:
<221> NAME/KEY: MOD_RES
<222> LOCATION: (14)
<223> OTHER INFORMATION: Thr, Asp or Gly
<220> FEATURE:
<221> NAME/KEY: MOD_RES
<222> LOCATION: (15)
<223> OTHER INFORMATION: Any amino acid except Cys
<220> FEATURE:
<221> NAME/KEY: MOD_RES
<222> LOCATION: (18)..(20)
<223> OTHER INFORMATION: Any amino acid except Cys

<400> SEQUENCE: 13

Tyr Tyr Cys Ala Arg Xaa Xaa Xaa Xaa Tyr Cys Xaa Xaa Xaa Xaa Cys
1               5                   10                  15

Tyr Xaa Xaa Xaa Tyr Phe Asp Tyr Trp Gly
            20                  25

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      kappa light chain CDR1 vector peptide
<220> FEATURE:
<221> NAME/KEY: MOD_RES
<222> LOCATION: (5)
<223> OTHER INFORMATION: Any amino acid except Cys
<220> FEATURE:
<221> NAME/KEY: MOD_RES
<222> LOCATION: (7)..(8)
<223> OTHER INFORMATION: Any amino acid except Cys
<220> FEATURE:
<221> NAME/KEY: MOD_RES
<222> LOCATION: (9)
<223> OTHER INFORMATION: Any amino acid except Cys and Ser

<400> SEQUENCE: 14

Arg Ala Ser Gln Xaa Val Xaa Xaa Xaa Leu Ala
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      kappa light chain CDR1 vector peptide
<220> FEATURE:
<221> NAME/KEY: MOD_RES
<222> LOCATION: (5)
<223> OTHER INFORMATION: Any amino acid except Cys
<220> FEATURE:
<221> NAME/KEY: MOD_RES
<222> LOCATION: (7)..(9)
<223> OTHER INFORMATION: Any amino acid except Cys
<220> FEATURE:
<221> NAME/KEY: MOD_RES
<222> LOCATION: (10)
<223> OTHER INFORMATION: Any amino acid except Cys and Ser

<400> SEQUENCE: 15

Arg Ala Ser Gln Xaa Val Xaa Xaa Xaa Xaa Leu Ala
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      kappa light chain CDR3 vector peptide
<220> FEATURE:
<221> NAME/KEY: MOD_RES
<222> LOCATION: (3)
<223> OTHER INFORMATION: Any amino acid except Cys or Ser
<220> FEATURE:
<221> NAME/KEY: MOD_RES
<222> LOCATION: (4)..(6)
<223> OTHER INFORMATION: Any amino acid except Cys
<220> FEATURE:
<221> NAME/KEY: MOD_RES
<222> LOCATION: (8)
<223> OTHER INFORMATION: Any amino acid except Cys

<400> SEQUENCE: 16

Gln Gln Xaa Xaa Xaa Xaa Pro Xaa Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      kappa light chain CDR3 vector peptide
<220> FEATURE:
<221> NAME/KEY: MOD_RES
<222> LOCATION: (3)
<223> OTHER INFORMATION: Any amino acid except Cys or Ser
<220> FEATURE:
<221> NAME/KEY: MOD_RES
<222> LOCATION: (4)
<223> OTHER INFORMATION: Any amino acid except Cys
<220> FEATURE:
<221> NAME/KEY: MOD_RES
<222> LOCATION: (5)..(6)
<223> OTHER INFORMATION: Any amino acid except Cys
<220> FEATURE:
<221> NAME/KEY: MOD_RES
<222> LOCATION: (9)
<223> OTHER INFORMATION: Any amino acid except Cys

<400> SEQUENCE: 17
```

```
Gln Gln Xaa Xaa Xaa Xaa Pro Pro Xaa Thr
1               5               10
```

```
<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      lambda light chain CDR1 vector peptide
<220> FEATURE:
<221> NAME/KEY: MOD_RES
<222> LOCATION: (3)
<223> OTHER INFORMATION: Any amino acid except Cys
<220> FEATURE:
<221> NAME/KEY: MOD_RES
<222> LOCATION: (6)
<223> OTHER INFORMATION: Any amino acid except Cys
<220> FEATURE:
<221> NAME/KEY: MOD_RES
<222> LOCATION: (9)..(12)
<223> OTHER INFORMATION: Any amino acid except Cys

<400> SEQUENCE: 18

Thr Gly Xaa Ser Ser Xaa Val Gly Xaa Xaa Xaa Xaa Val Ser
1               5                   10
```

```
<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      lambda light chain CDR3 vector peptide
<220> FEATURE:
<221> NAME/KEY: MOD_RES
<222> LOCATION: (1)
<223> OTHER INFORMATION: Any amino acid except Cys
<220> FEATURE:
<221> NAME/KEY: MOD_RES
<222> LOCATION: (4)..(5)
<223> OTHER INFORMATION: Any amino acid except Cys
<220> FEATURE:
<221> NAME/KEY: MOD_RES
<222> LOCATION: (7)..(8)
<223> OTHER INFORMATION: Any amino acid except Cys
<220> FEATURE:
<221> NAME/KEY: MOD_RES
<222> LOCATION: (9)
<223> OTHER INFORMATION: Any amino acid except Cys or Tyr

<400> SEQUENCE: 19

Xaa Ser Tyr Xaa Xaa Ser Xaa Xaa Xaa Val
1               5                   10
```

```
<210> SEQ ID NO 20
<211> LENGTH: 14
<212> TYPE: PRT
<213> ORGANISM: Homo sapiens

<400> SEQUENCE: 20

Tyr Phe Asp Tyr Trp Gly Gln Gly Thr Leu Val Thr Ser Ser
1               5                   10
```

```
<210> SEQ ID NO 21
<211> LENGTH: 15
<212> TYPE: PRT
<213> ORGANISM: Homo sapiens

<400> SEQUENCE: 21

Ala Phe Asp Ile Trp Gly Gln Gly Thr Met Val Thr Val Ser Ser
1               5                   10                  15
```

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Tyr Cys Ala Arg
1               5

<210> SEQ ID NO 23
<211> LENGTH: 323
<212> TYPE: DNA
<213> ORGANISM: Artificial Sequence
<220> FEATURE:
<223> OTHER INFORMATION: Description of Artificial Sequence: Synthetic
      3-23: JH4 vector with CDR1/2 diversity polynucleotide
<220> FEATURE:
<221> NAME/KEY: CDS
<222> LOCATION: (3)..(323)
<220> FEATURE:
<221> NAME/KEY: modified_base
<222> LOCATION: (99)..(101)
<223> OTHER INFORMATION: a, c, t, g, other or unknown
<220> FEATURE:
<221> NAME/KEY: modified_base
<222> LOCATION: (105)..(107)
<223> OTHER INFORMATION: a, c, t, g, other or unknown
<220> FEATURE:
<221> NAME/KEY: modified_base
<222> LOCATION: (111)..(113)
<223> OTHER INFORMATION: a, c, t, g, other or unknown
<220> FEATURE:
<221> NAME/KEY: modified_base
<222> LOCATION: (156)..(158)
<223> OTHER INFORMATION: a, c, t, g, other or unknown
<220> FEATURE:
<221> NAME/KEY: modified_base
<222> LOCATION: (162)..(167)
<223> OTHER INFORMATION: a, c, t, g, other or unknown
<220> FEATURE:
<221> NAME/KEY: modified_base
<222> LOCATION: (177)..(179)
<223> OTHER INFORMATION: a, c, t, g, other or unknown
<220> FEATURE:
<221> NAME/KEY: modified_base
<222> LOCATION: (183)..(185)
<223> OTHER INFORMATION: a, c, t, g, other or unknown

<400> SEQUENCE: 23 cc atg gcc gaa gtt caa ttg tta gag tct ggt ggc ggt ctt gtt cag        47
    Ala Met Ala Glu Val Gln Leu Leu Glu Ser Gly Gly Gly Leu Val Gln
    1               5                   10                  15 cct ggt ggt tct tta cgt ctt tct tgc gct gct tcc gga ttc act ttc        95
Pro Gly Gly Ser Leu Arg Leu Ser Cys Ala Ala Ser Gly Phe Thr Phe
                20                  25                  30 tct nnn tac nnn atg nnn tgg gtt cgc caa gct cct ggt aaa ggt ttg       143
Ser Xaa Tyr Xaa Met Xaa Trp Val Arg Gln Ala Pro Gly Lys Gly Leu
            35                  40                  45 gag tgg gtt tct nnn atc nnn nnn tct ggt ggc nnn act nnn tat gct       191
Glu Trp Val Ser Xaa Ile Xaa Xaa Ser Gly Gly Xaa Thr Xaa Tyr Ala
        50                  55                  60 gac tcc gtt aaa ggt cgc ttc act atc tct aga gac aac tct aag aat       239
Asp Ser Val Lys Gly Arg Phe Thr Ile Ser Arg Asp Asn Ser Lys Asn
65                  70                  75                  80 act ctc tac ttg cag atg aac agc tta agg gct gag gac acc gct gtc       287
Thr Leu Tyr Leu Gln Met Asn Ser Leu Arg Ala Glu Asp Thr Ala Val
                85                  90                  95
```

```
tac tac tgc gcc aaa gac tat gaa ggt act ggt tat                323
Tyr Tyr Cys Ala Lys Asp Tyr Glu Gly Thr Gly Tyr
                100                 105
```

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      3-23: JH4 vector with CDR1/2 diversity polypeptide
<220> FEATURE:
<221> NAME/KEY: MOD_RES
<222> LOCATION: (34)
<223> OTHER INFORMATION: Any amino acid
<220> FEATURE:
<221> NAME/KEY: MOD_RES
<222> LOCATION: (36)
<223> OTHER INFORMATION: Any amino acid
<220> FEATURE:
<221> NAME/KEY: MOD_RES
<222> LOCATION: (38)
<223> OTHER INFORMATION: Any amino acid
<220> FEATURE:
<221> NAME/KEY: MOD_RES
<222> LOCATION: (53)
<223> OTHER INFORMATION: Any amino acid
<220> FEATURE:
<221> NAME/KEY: MOD_RES
<222> LOCATION: (55)..(56)
<223> OTHER INFORMATION: Any amino acid
<220> FEATURE:
<221> NAME/KEY: MOD_RES
<222> LOCATION: (60)
<223> OTHER INFORMATION: Any amino acid
<220> FEATURE:
<221> NAME/KEY: MOD_RES
<222> LOCATION: (62)
<223> OTHER INFORMATION: Any amino acid

<400> SEQUENCE: 24

```
Ala Met Ala Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Xaa Tyr Xaa Met Xaa Trp Val Arg Gln Ala Pro Gly Lys Gly Leu
        35                  40                  45

Glu Trp Val Ser Xaa Ile Xaa Xaa Ser Gly Gly Xaa Thr Xaa Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Asp Tyr Glu Gly Thr Gly Tyr
                100                 105
```

<210> SEQ ID NO 25
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 25

```
tat ttc gat tat tgg ggt caa ggt acc ctg gtc acc gtc tct agt      45
Tyr Phe Asp Tyr Trp Gly Gln Gly Thr Leu Val Thr Val Ser Ser
1               5                   10                  15
```

<210> SEQ ID NO 26
<211> LENGTH: 15
<212> TYPE: PRT
<213> ORGANISM: Homo sapiens

<400> SEQUENCE: 26

Tyr Phe Asp Tyr Trp Gly Gln Gly Thr Leu Val Thr Val Ser Ser
1               5                   10                  15

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(23)
<223> OTHER INFORMATION: a, c, t or g
<220> FEATURE:
<221> NAME/KEY: modified_base
<222> LOCATION: (27)..(29)
<223> OTHER INFORMATION: a, c, t or g
<220> FEATURE:
<221> NAME/KEY: modified_base
<222> LOCATION: (33)..(35)
<223> OTHER INFORMATION: a, c, t or g

<400> SEQUENCE: 27
cttccggatt cactttctct nnntacnnna tgnnntgggt tcgccaagct cctgg          55

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cctactgtct tccggattca ctttctct                                       28

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgggttcgcc aagctcctgg ttgctcactc                                     30

<210> SEQ ID NO 30
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t or g
<220> FEATURE:
<221> NAME/KEY: modified_base
<222> LOCATION: (39)..(41)
<223> OTHER INFORMATION: a, c, t or g

<400> SEQUENCE: 30
cttccggatt cactttctct wsnnnnnnnt actactggnn ntgggttcgc caagctcctg    60
g                                                                   61

<210> SEQ ID NO 31
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(50)
<223> OTHER INFORMATION: a, c, t or g
<220> FEATURE:
<221> NAME/KEY: modified_base
<222> LOCATION: (60)..(62)
<223> OTHER INFORMATION: a, c, t or g

<400> SEQUENCE: 31
cttccggatt cactttctct atcagcggtg gttctatctc cnnnnnnnnn tactactggn    60
nntgggttcg ccaagctcct gg                                            82

<210> SEQ ID NO 32
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(28)
<223> OTHER INFORMATION: a, c, t or g
<220> FEATURE:
<221> NAME/KEY: modified_base
<222> LOCATION: (30)
<223> OTHER INFORMATION: a, c, t or g
<220> FEATURE:
<221> NAME/KEY: modified_base
<222> LOCATION: (40)..(42)
<223> OTHER INFORMATION: a, c, t or g
<220> FEATURE:
<221> NAME/KEY: modified_base
<222> LOCATION: (46)..(48)
<223> OTHER INFORMATION: a, c, t or g

<400> SEQUENCE: 32
ggtttggagt gggtttctnn natcnnnnsn tctggtggcn nnactnnnta tgctgactcc    60
gttaaagg                                                            68

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cttgggttcg ccaagctcct ggtaaaggtt tggagtgggt ttct                    44

<210> SEQ ID NO 34
<211> LENGTH: 49
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 34
tatgctgact ccgttaaagg tcgcttcact atctctagat tcctgtcac          49

<210> SEQ ID NO 35
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (26)..(33)
<223> OTHER INFORMATION: a, c, t or g
<220> FEATURE:
<221> NAME/KEY: modified_base
<222> LOCATION: (39)..(48)
<223> OTHER INFORMATION: a, c, t or g

<400> SEQUENCE: 35
ggtttggagt gggtttctnn natcdnnnnn nnnggtdvnn nnnnnnnnta tgctgactcc    60
gttaaagg                                                              68

<210> SEQ ID NO 36
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (26)..(33)
<223> OTHER INFORMATION: a, c, t or g
<220> FEATURE:
<221> NAME/KEY: modified_base
<222> LOCATION: (39)..(45)
<223> OTHER INFORMATION: a, c, t or g

<400> SEQUENCE: 36
ggtttggagt gggtttctnn natcdnnnnn nnnggtdvnn nnnnntataa cccttcccc    60 aaggg                                                                 65

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tataacccct cccttaaggg tcgcttcact atctctagat tcctgtcac              49

<210> SEQ ID NO 38
<211> LENGTH: 74
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t or g
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (31)..(39)
<223> OTHER INFORMATION: a, c, t or g
<220> FEATURE:
<221> NAME/KEY: modified_base
<222> LOCATION: (52)..(54)
<223> OTHER INFORMATION: a, c, t or g

<400> SEQUENCE: 38
ggtttggagt gggtttctnn natcnnnagt nnnnnnnnng gtggtactac tnnntatgcc      60
gcttccgtta aggg                                                       74

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tatgccgctt ccgttaaggg tcgcttcact atctctagat tcctgtcac                 49

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gctctggtca acttaagggc tgagg                                           25

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctctggtca acttaagggc tgaggacacc gctgtctact actgcgcc                  48

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tacttcgatt actggggcca aggtaccctg gtcacctcgc tccacc                    46
```

```
<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggtaccctgg tcacctcgct ccacc                                           25

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(35)
<223> OTHER INFORMATION: a, c, t or g

<400> SEQUENCE: 44
ccgctgtcta ctactgcgcc mrnnnnnnnn nnnnntactt cgattactgg ggccaagg       58

<210> SEQ ID NO 45
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(41)
<223> OTHER INFORMATION: a, c, t or g

<400> SEQUENCE: 45
ccgctgtcta ctactgcgcc mrnnnnnnnn nnnnnnnnnn ntacttcgat tactggggcc     60
aagg                                                                  64

<210> SEQ ID NO 46
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(47)
<223> OTHER INFORMATION: a, c, t or g

<400> SEQUENCE: 46
ccgctgtcta ctactgcgcc mrnnnnnnnn nnnnnnnnnn nnnnnntac ttcgattact      60 ggggccaagg                                                            70

<210> SEQ ID NO 47
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(32)
<223> OTHER INFORMATION: a, c, t or g
<220> FEATURE:
```

```
<221> NAME/KEY: modified_base
<222> LOCATION: (38)
<223> OTHER INFORMATION: a, c, t or g
<220> FEATURE:
<221> NAME/KEY: modified_base
<222> LOCATION: (45)..(53)
<223> OTHER INFORMATION: a, c, t or g

<400> SEQUENCE: 47
ccgctgtcta ctactgcgcc cgtnnnnnnn nntctdsntc ttrbnnnnnn nnntacttcg      60
attactgggg ccaagg                                                     76

<210> SEQ ID NO 48
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(32)
<223> OTHER INFORMATION: a, c, t or g
<220> FEATURE:
<221> NAME/KEY: modified_base
<222> LOCATION: (42)..(47)
<223> OTHER INFORMATION: a, c, t or g
<220> FEATURE:
<221> NAME/KEY: modified_base
<222> LOCATION: (54)..(56)
<223> OTHER INFORMATION: a, c, t or g

<400> SEQUENCE: 48
ccgctgtcta ctactgcgcc mrnnnnnnnn nntgctctgg tnnnnnntgc tatnnntact      60
tcgattactg gggccaagg                                                  79

<210> SEQ ID NO 49
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(29)
<223> OTHER INFORMATION: a, c, t or g
<220> FEATURE:
<221> NAME/KEY: modified_base
<222> LOCATION: (33)..(35)
<223> OTHER INFORMATION: a, c, t or g
<220> FEATURE:
<221> NAME/KEY: modified_base
<222> LOCATION: (48)..(62)
<223> OTHER INFORMATION: a, c, t or g

<400> SEQUENCE: 49
ccgctgtcta ctactgcgcc mrnnnnnnnt ctnnnactat cttcggtnnn nnnnnnnnn       60 nntacttcga ttactggggc caagg                                           85

<210> SEQ ID NO 50
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(32)
<223> OTHER INFORMATION: a, c, t or g
```

```
<220> FEATURE:
<221> NAME/KEY: modified_base
<222> LOCATION: (41)
<223> OTHER INFORMATION: a, c, t or g
<220> FEATURE:
<221> NAME/KEY: modified_base
<222> LOCATION: (47)
<223> OTHER INFORMATION: a, c, t or g
<220> FEATURE:
<221> NAME/KEY: modified_base
<222> LOCATION: (50)
<223> OTHER INFORMATION: a, c, t or g
<220> FEATURE:
<221> NAME/KEY: modified_base
<222> LOCATION: (57)..(65)
<223> OTHER INFORMATION: a, c, t or g

<400> SEQUENCE: 50
ccgctgtcta ctactgcgcc cgtnnnnnnn nntattacgr ntctdsndsn tactatnnnn      60
nnnnntactt cgattactgg ggccaagg                                        88

<210> SEQ ID NO 51
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(35)
<223> OTHER INFORMATION: a, c, t or g
<220> FEATURE:
<221> NAME/KEY: modified_base
<222> LOCATION: (44)
<223> OTHER INFORMATION: a, c, t or g
<220> FEATURE:
<221> NAME/KEY: modified_base
<222> LOCATION: (47)
<223> OTHER INFORMATION: a, c, t or g
<220> FEATURE:
<221> NAME/KEY: modified_base
<222> LOCATION: (50)..(53)
<223> OTHER INFORMATION: a, c, t or g
<220> FEATURE:
<221> NAME/KEY: modified_base
<222> LOCATION: (60)..(68)
<223> OTHER INFORMATION: a, c, t or g

<400> SEQUENCE: 51
ccgctgtcta ctactgcgcc cgtnnnnnnn nnnnntattg cdsndsnrvn nnntgctatn      60
nnnnnnnnta cttcgattac tggggccaag g                                    91

<210> SEQ ID NO 52
<211> LENGTH: 242
<212> TYPE: DNA
<213> ORGANISM: Artificial Sequence
<220> FEATURE:
<223> OTHER INFORMATION: Description of Artificial Sequence: Synthetic
      3-23: JH4 vector with stuffers polynucleotide
<220> FEATURE:
<221> NAME/KEY: CDS
<222> LOCATION: (3)..(107)
<220> FEATURE:
<221> NAME/KEY: CDS
<222> LOCATION: (114)..(155)
<220> FEATURE:
<221> NAME/KEY: CDS
<222> LOCATION: (159)..(164)
<220> FEATURE:
<221> NAME/KEY: CDS
<222> LOCATION: (168)..(227)

<400> SEQUENCE: 52
```

```
cc atg gcc gaa gtt caa ttg tta gag tct ggt ggt ggt ctt gtt cag        47
   Ala Met Ala Glu Val Gln Leu Leu Glu Ser Gly Gly Gly Leu Val Gln
   1               5                  10                  15 cct ggt ggt tct tta cgt ctt tct tgc gct gct tcc gga ttc act ttc        95
Pro Gly Gly Ser Leu Arg Leu Ser Cys Ala Ala Ser Gly Phe Thr Phe
             20                  25                  30 tct tcg tac gct tagtaa tgg gtt cgc caa gct cct ggt aaa ggt ttg        143
Ser Ser Tyr Ala        Trp Val Arg Gln Ala Pro Gly Lys Gly Leu
         35                     40                  45 gag tgg gtt tct taa cct agg tag act atc tct aga gac aac tct aag       191
Glu Trp Val Ser     Pro Arg     Thr Ile Ser Arg Asp Asn Ser Lys
             50                         55                  60 aat act ctc tac ttg cag atg aac agc tta agg gct tagtaaaggc cttaa      242
Asn Thr Leu Tyr Leu Gln Met Asn Ser Leu Arg Ala
             65                  70
```

<210> SEQ ID NO 53
<211> LENGTH: 72
<212> TYPE: PRT
<213> ORGANISM: Artificial Sequence
<220> FEATURE:
<223> OTHER INFORMATION: Description of Artificial Sequence: Synthetic
      3-23: JH4 vector with stuffers polypeptide

<400> SEQUENCE: 53

```
Ala Met Ala Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Trp Val Arg Gln Ala Pro Gly Lys Gly Leu Glu Trp
        35                  40                  45

Val Ser Pro Arg Thr Ile Ser Arg Asp Asn Ser Lys Asn Thr Leu Tyr
    50                  55                  60

Leu Gln Met Asn Ser Leu Arg Ala
65                  70
```

<210> SEQ ID NO 54
<211> LENGTH: 952
<212> TYPE: DNA
<213> ORGANISM: Homo sapiens
<220> FEATURE:
<221> NAME/KEY: CDS
<222> LOCATION: (206)..(907)
<220> FEATURE:
<221> NAME/KEY: modified_base
<222> LOCATION: (344)..(346)
<223> OTHER INFORMATION: a, c, t, g, other or unknown
<220> FEATURE:
<221> NAME/KEY: modified_base
<222> LOCATION: (350)..(361)
<223> OTHER INFORMATION: a, c, t, g, other or unknown
<220> FEATURE:
<221> NAME/KEY: modified_base
<222> LOCATION: (413)..(415)
<223> OTHER INFORMATION: a, c, t, g, other or unknown
<220> FEATURE:
<221> NAME/KEY: modified_base
<222> LOCATION: (422)..(424)
<223> OTHER INFORMATION: a, c, t, g, other or unknown
<220> FEATURE:
<221> NAME/KEY: modified_base
<222> LOCATION: (428)..(433)
<223> OTHER INFORMATION: a, c, t, g, other or unknown
<220> FEATURE:
<221> NAME/KEY: modified_base
<222> LOCATION: (536)..(547)
<223> OTHER INFORMATION: a, c, t, g, other or unknown
<220> FEATURE:

```
<221> NAME/KEY: modified_base
<222> LOCATION: (551)..(553)
<223> OTHER INFORMATION: a, c, t, g, other or unknown

<400> SEQUENCE: 54
gaggaccatt gggccccctc cgagactctc gagcgcaacg caattaatgt gagttagctc      60
actcattagg caccccaggc tttacacttt atgcttccgg ctcgtatgtt gtgtggaatt     120
gtgagcggat aacaatttca cacaggaaac agctatgacc atgattacgc caagctttgg     180 agccttttt ttggagattt tcaac gtg aag aag ctc cta ttt gct atc ccg        232
                              Met Lys Lys Leu Leu Phe Ala Ile Pro
                              1               5 ctt gtc gtt ccg ttt tac agc cat agt gca caa tcc gtc ctt act caa       280
Leu Val Val Pro Phe Tyr Ser His Ser Ala Gln Ser Val Leu Thr Gln
 10              15                  20                  25 tct cct ggc act ctt tcg cta agc ccg ggt gaa cgt gct acc tta agt       328
Ser Pro Gly Thr Leu Ser Leu Ser Pro Gly Glu Arg Ala Thr Leu Ser
             30                  35                  40 tgc cgt gct tcc cag nnn gtt nnn nnn nnn nnn ctt gct tgg tat caa       376
Cys Arg Ala Ser Gln Xaa Val Xaa Xaa Xaa Xaa Leu Ala Trp Tyr Gln
                 45                  50                  55 cag aaa cct ggt cag gcg ccg cgt tta ctt att tat nnn gct tct nnn       424
Gln Lys Pro Gly Gln Ala Pro Arg Leu Leu Ile Tyr Xaa Ala Ser Xaa
         60                  65                  70 cgc nnn nnn ggg atc ccg gac cgt ttc tct ggc tct ggt tca ggt act       472
Arg Xaa Xaa Gly Ile Pro Asp Arg Phe Ser Gly Ser Gly Ser Gly Thr
     75                  80                  85 gac ttt acc ctt act att tct aga ttg gaa cct gaa gac ttc gct gtt       520
Asp Phe Thr Leu Thr Ile Ser Arg Leu Glu Pro Glu Asp Phe Ala Val
 90              95                 100                 105 tat tat tgc caa cag nnn nnn nnn nnn cct nnn act ttc ggt caa ggt       568
Tyr Tyr Cys Gln Gln Xaa Xaa Xaa Xaa Pro Xaa Thr Phe Gly Gln Gly
            110                 115                 120 acc aag gtt gaa atc aag cgt acg gtt gcc gct cct agt gtg ttt atc       616
Thr Lys Val Glu Ile Lys Arg Thr Val Ala Ala Pro Ser Val Phe Ile
                125                 130                 135 ttt cct cct tct gac gaa caa ttg aag tca ggt act gct tct gtc gta       664
Phe Pro Pro Ser Asp Glu Gln Leu Lys Ser Gly Thr Ala Ser Val Val
        140                 145                 150 tgt ttg ctc aac aat ttc tac cct cgt gaa gct aaa gtt cag tgg aaa       712
Cys Leu Leu Asn Asn Phe Tyr Pro Arg Glu Ala Lys Val Gln Trp Lys
    155                 160                 165 gtc gat aac gcg ttg cag tcg ggt aac agt caa gaa tcc gtc act gaa       760
Val Asp Asn Ala Leu Gln Ser Gly Asn Ser Gln Glu Ser Val Thr Glu
170                 175                 180                 185 cag gat agt aag gac tct acc tac tct ttg tcc tct act ctt act tta       808
Gln Asp Ser Lys Asp Ser Thr Tyr Ser Leu Ser Ser Thr Leu Thr Leu
                190                 195                 200 tca aag gct gat tat gag aag cat aag gtc tat gct tgc gaa gtt acc       856
Ser Lys Ala Asp Tyr Glu Lys His Lys Val Tyr Ala Cys Glu Val Thr
        205                 210                 215 cac cag ggt ctg agc tcc cct gtt acc aaa agt ttc aac cgt ggt gaa       904
His Gln Gly Leu Ser Ser Pro Val Thr Lys Ser Phe Asn Arg Gly Glu
    220                 225                 230 tgc taatagggcg cgccacgcat ctctaagcgg ccgcaacagg aggag                 952
Cys

<210> SEQ ID NO 55
<211> LENGTH: 234
<212> TYPE: PRT
<213> ORGANISM: Homo sapiens
```

```
<220> FEATURE:
<221> NAME/KEY: MOD_RES
<222> LOCATION: (47)
<223> OTHER INFORMATION: Any amino acid
<220> FEATURE:
<221> NAME/KEY: MOD_RES
<222> LOCATION: (49)..(52)
<223> OTHER INFORMATION: Any amino acid
<220> FEATURE:
<221> NAME/KEY: MOD_RES
<222> LOCATION: (70)
<223> OTHER INFORMATION: Any amino acid
<220> FEATURE:
<221> NAME/KEY: MOD_RES
<222> LOCATION: (73)
<223> OTHER INFORMATION: Any amino acid
<220> FEATURE:
<221> NAME/KEY: MOD_RES
<222> LOCATION: (75)..(76)
<223> OTHER INFORMATION: Any amino acid
<220> FEATURE:
<221> NAME/KEY: MOD_RES
<222> LOCATION: (111)..(114)
<223> OTHER INFORMATION: Any amino acid
<220> FEATURE:
<221> NAME/KEY: MOD_RES
<222> LOCATION: (116)
<223> OTHER INFORMATION: Any amino acid

<400> SEQUENCE: 55

Met Lys Lys Leu Leu Phe Ala Ile Pro Leu Val Val Pro Phe Tyr Ser
1               5                   10                  15

His Ser Ala Gln Ser Val Leu Thr Gln Ser Pro Gly Thr Leu Ser Leu
            20                  25                  30

Ser Pro Gly Glu Arg Ala Thr Leu Ser Cys Arg Ala Ser Gln Xaa Val
        35                  40                  45

Xaa Xaa Xaa Xaa Leu Ala Trp Tyr Gln Gln Lys Pro Gly Gln Ala Pro
    50                  55                  60

Arg Leu Leu Ile Tyr Xaa Ala Ser Xaa Arg Xaa Xaa Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Xaa Xaa
            100                 105                 110

Xaa Xaa Pro Xaa Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 56
<211> LENGTH: 732
<212> TYPE: DNA
```

-continued

```
<213> ORGANISM: Homo sapiens
<220> FEATURE:
<221> NAME/KEY: CDS
<222> LOCATION: (30)..(686)
<220> FEATURE:
<221> NAME/KEY: modified_base
<222> LOCATION: (108)..(110)
<223> OTHER INFORMATION: a, c, t, g, other or unknown
<220> FEATURE:
<221> NAME/KEY: modified_base
<222> LOCATION: (117)..(119)
<223> OTHER INFORMATION: a, c, t, g, other or unknown
<220> FEATURE:
<221> NAME/KEY: modified_base
<222> LOCATION: (126)..(137)
<223> OTHER INFORMATION: a, c, t, g, other or unknown
<220> FEATURE:
<221> NAME/KEY: modified_base
<222> LOCATION: (189)..(200)
<223> OTHER INFORMATION: a, c, t, g, other or unknown
<220> FEATURE:
<221> NAME/KEY: modified_base
<222> LOCATION: (306)..(320)
<223> OTHER INFORMATION: a, c, t, g, other or unknown
<220> FEATURE:
<221> NAME/KEY: modified_base
<222> LOCATION: (324)..(335)
<223> OTHER INFORMATION: a, c, t, g, other or unknown

<400> SEQUENCE: 56
gaggaccatt gggccccttta ctccgtgac agt gca caa tcc gct ctc act cag        53
                                 Ser Ala Gln Ser Ala Leu Thr Gln
                                  1               5 cct gct agc gtt tcc ggg tca cct ggt caa agt atc act att tct tgt       101
Pro Ala Ser Val Ser Gly Ser Pro Gly Gln Ser Ile Thr Ile Ser Cys
 10              15                  20 aca ggt nnn tct tct nnn gtt ggc nnn nnn nnn nnn gtt tct tgg tat       149
Thr Gly Xaa Ser Ser Xaa Val Gly Xaa Xaa Xaa Xaa Val Ser Trp Tyr
 25              30                  35                  40 caa caa cac ccg ggc aag gcg ccg aag ttg atg atc tac nnn nnn nnn       197
Gln Gln His Pro Gly Lys Ala Pro Lys Leu Met Ile Tyr Xaa Xaa Xaa
                 45                  50                  55 nnn cgt cct tct ggt gtt agc aat cgt ttc tcc gga tct aaa tcc ggt       245
Xaa Arg Pro Ser Gly Val Ser Asn Arg Phe Ser Gly Ser Lys Ser Gly
             60                  65                  70 aat acc gca agc tta act atc tct ggt ctg cag gct gaa gac gag gct       293
Asn Thr Ala Ser Leu Thr Ile Ser Gly Leu Gln Ala Glu Asp Glu Ala
         75                  80                  85 gac tac tat tgt nnn nnn nnn nnn tct nnn nnn nnn nnn gtc ttc           341
Asp Tyr Tyr Cys Xaa Xaa Xaa Xaa Ser Xaa Xaa Xaa Xaa Val Phe
         90                  95                 100 ggc ggt ggt acc aaa ctt act gtc ctc ggt caa cct aag gct gct cct       389
Gly Gly Gly Thr Lys Leu Thr Val Leu Gly Gln Pro Lys Ala Ala Pro
105                 110                 115                 120 tcc gtt act ctc ttc cct cct agt tct gaa gag ctt caa gct aac aag       437
Ser Val Thr Leu Phe Pro Pro Ser Ser Glu Glu Leu Gln Ala Asn Lys
                125                 130                 135 gct act ctt gtt tgc ttg atc agt gac ttt tat cct ggt gct gtt act       485
Ala Thr Leu Val Cys Leu Ile Ser Asp Phe Tyr Pro Gly Ala Val Thr
            140                 145                 150 gtc gct tgg aaa gcc gat tct tct cct gtt aaa gct ggt gtt gag acg       533
Val Ala Trp Lys Ala Asp Ser Ser Pro Val Lys Ala Gly Val Glu Thr
        155                 160                 165 acc act cct tct aaa caa tct aac aat aag tac gct gcg agc tct tat       581
Thr Thr Pro Ser Lys Gln Ser Asn Asn Lys Tyr Ala Ala Ser Ser Tyr
    170                 175                 180 ctt tct ctc acc cct gaa caa tgg aag tct cat aaa tcc tat tcc tgt       629
```

```
Leu Ser Leu Thr Pro Glu Gln Trp Lys Ser His Lys Ser Tyr Ser Cys
185                 190                 195                 200 caa gtt act cat gaa ggt tct acc gtt gaa aag act gtt gcc cct act        677
Gln Val Thr His Glu Gly Ser Thr Val Glu Lys Thr Val Ala Pro Thr
                    205                 210                 215 gag tgt tct tagtgaggcg cgccaacgat gttcaaggcg ccgcaacag gaggag          732
Glu Cys Ser
```

<210> SEQ ID NO 57
<211> LENGTH: 219
<212> TYPE: PRT
<213> ORGANISM: Homo sapiens
<220> FEATURE:
<221> NAME/KEY: MOD_RES
<222> LOCATION: (27)
<223> OTHER INFORMATION: Any amino acid
<220> FEATURE:
<221> NAME/KEY: MOD_RES
<222> LOCATION: (30)
<223> OTHER INFORMATION: Any amino acid
<220> FEATURE:
<221> NAME/KEY: MOD_RES
<222> LOCATION: (33)..(36)
<223> OTHER INFORMATION: Any amino acid
<220> FEATURE:
<221> NAME/KEY: MOD_RES
<222> LOCATION: (54)..(57)
<223> OTHER INFORMATION: Any amino acid
<220> FEATURE:
<221> NAME/KEY: MOD_RES
<222> LOCATION: (93)..(97)
<223> OTHER INFORMATION: Any amino acid
<220> FEATURE:
<221> NAME/KEY: MOD_RES
<222> LOCATION: (99)..(102)
<223> OTHER INFORMATION: Any amino acid

<400> SEQUENCE: 57

```
Ser Ala Gln Ser Ala Leu Thr Gln Pro Ala Ser Val Ser Gly Ser Pro
1               5                   10                  15

Gly Gln Ser Ile Thr Ile Ser Cys Thr Gly Xaa Ser Ser Xaa Val Gly
                20                  25                  30

Xaa Xaa Xaa Xaa Val Ser Trp Tyr Gln Gln His Pro Gly Lys Ala Pro
            35                  40                  45

Lys Leu Met Ile Tyr Xaa Xaa Xaa Xaa Arg Pro Ser Gly Val Ser Asn
50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Xaa Xaa Xaa Xaa
                85                  90                  95

Xaa Ser Xaa Xaa Xaa Xaa Val Phe Gly Gly Gly Thr Lys Leu Thr Val
            100                 105                 110

Leu Gly Gln Pro Lys Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Lys Ser Tyr Ser Cys Gln Val Thr His Glu Gly Ser Thr
        195                 200                 205
```

Val Glu Lys Thr Val Ala Pro Thr Glu Cys Ser
    210                 215

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gctctggtca acttaagggc tgagg                                            25

<210> SEQ ID NO 59
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gctctggtca acttaagggc tgaggacacc gctgtctact actgcgcc                   48

<210> SEQ ID NO 60
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tacttcgatt acttgggcca aggtaccctg gtcacctcgc tccacc                     46

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggtaccctgg tcacctcgct ccacc                                            25

<210> SEQ ID NO 62
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggtctcagtt gctaagcccg ggtgaacgtg ctaccttaag ttgccgtgct tcccag          56

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ggtctcagtt gctaagcccg ggtg                                          24
```

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
cttgcttggt atcaacagaa acctggtcag gcgccaagtc gtgtc               45
```

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65

```
cctggtcagg cgccaagtcg tgtc                                          24
```

<210> SEQ ID NO 66
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(30)
<223> OTHER INFORMATION: a, c, t or g
<220> FEATURE:
<221> NAME/KEY: modified_base
<222> LOCATION: (34)..(42)
<223> OTHER INFORMATION: a, c, t or g

<400> SEQUENCE: 66

```
gctaccttaa gttgccgtgc ttcccagnnn gttnnnnnnn nncttgcttg gtatcaacag   60
aaacc                                                               65
```

<210> SEQ ID NO 67
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(30)
<223> OTHER INFORMATION: a, c, t or g
<220> FEATURE:
<221> NAME/KEY: modified_base
<222> LOCATION: (34)..(45)
<223> OTHER INFORMATION: a, c, t or g

<400> SEQUENCE: 67

```
gctaccttaa gttgccgtgc ttcccagnnn gttnnnnnnn nnnncttgc ttggtatcaa    60 cagaaacc                                                            68
```

<210> SEQ ID NO 68
<211> LENGTH: 22
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 68
cacgagtcct acctggtcag gc                                              22

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cacgagtcct acctggtcag gcgccgcgtt tacttattta t                         41

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaccgtttct ctggttctca cc                                              22

<210> SEQ ID NO 71
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (34)..(36)
<223> OTHER INFORMATION: a, c, t or g
<220> FEATURE:
<221> NAME/KEY: modified_base
<222> LOCATION: (40)..(45)
<223> OTHER INFORMATION: a, c, t or g

<400> SEQUENCE: 71
caggcgccgc gtttacttat ttatnnngct tctnnncgcn nnnngggat cccggaccgt       60 ttctctggtt ctcacc                                                     76

<210> SEQ ID NO 72
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gacgagtcct tctagattgg aacctgaaga cttcgctgtt tattattgcc aac            53

<210> SEQ ID NO 73
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 73
actttcggtc aaggtaccaa ggttgaaatc aagcgtacgt cacaggtgag                50

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gaaatcaagc gtacgtcaca ggtgag                                          26

<210> SEQ ID NO 75
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(39)
<223> OTHER INFORMATION: a, c, t or g
<220> FEATURE:
<221> NAME/KEY: modified_base
<222> LOCATION: (43)..(45)
<223> OTHER INFORMATION: a, c, t or g

<400> SEQUENCE: 75
gacttcgctg tttattattg ccaacagnnn nnnnnnnnnc ctnnnacttt cggtcaaggt      60
accaaggttg                                                            70

<210> SEQ ID NO 76
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(42)
<223> OTHER INFORMATION: a, c, t or g

<400> SEQUENCE: 76
gacttcgctg tttattattg ccaacagnnn nnnnnnnn nnccttttcgg tcaaggtacc       60 aaggttg                                                               67

<210> SEQ ID NO 77
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(39)
<223> OTHER INFORMATION: a, c, t or g
<220> FEATURE:
<221> NAME/KEY: modified_base
<222> LOCATION: (46)..(48)
<223> OTHER INFORMATION: a, c, t or g

<400> SEQUENCE: 77

```
gacttcgctg tttattattg ccaacagnnn nnnnnnnnnc ctcctnnnac tttcggtcaa    60
ggtaccaagg ttg                                                      73

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gacgagtcct ggtcacctgg t                                             21

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gacgagtcct ggtcacctgg tcaaagtatc actatttctt gtacaggt                48

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtttcttggt atcaacaaca cccgggcaag gcgagatctt cacaggtgag              50

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcaaggcgag atcttcacag gtgag                                         25

<210> SEQ ID NO 82
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(29)
<223> OTHER INFORMATION: a, c, t or g
<220> FEATURE:
<221> NAME/KEY: modified_base
<222> LOCATION: (33)..(50)
<223> OTHER INFORMATION: a, c, t or g

<400> SEQUENCE: 82
gtatcactat ttcttgtaca ggtnnnnnnc tcnnnnnnnn nnnnnnnnnn tggtatcaac    60
aacaccc                                                             67
```

```
<210> SEQ ID NO 83
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(26)
<223> OTHER INFORMATION: a, c, t or g
<220> FEATURE:
<221> NAME/KEY: modified_base
<222> LOCATION: (33)..(35)
<223> OTHER INFORMATION: a, c, t or g
<220> FEATURE:
<221> NAME/KEY: modified_base
<222> LOCATION: (42)..(53)
<223> OTHER INFORMATION: a, c, t or g

<400> SEQUENCE: 83
gtatcactat ttcttgtaca ggtnnntctt ctnnngttgg cnnnnnnnnn nnngtttctt      60
ggtatcaaca acaccc                                                     76

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gagcagagga cccgggcaag gc                                              22

<210> SEQ ID NO 85
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gagcagagga cccgggcaag gcgccgaagt tgatgatcta c                         41

<210> SEQ ID NO 86
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cgtccttctg gtgtcagcaa tcgtttctcc ggatcacagg tgag                      44

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgtttctccg gatcacaggt gag                                             23

<210> SEQ ID NO 88
```

```
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t or g

<400> SEQUENCE: 88
gccgaagttg atgatctacn nnnnnnnnnn ncgtccttct ggtgtcagca atc            53

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctgcaggctg aagacgaggc tgac                                            24

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ctgcaggctg aagacgaggc tgactactat tgt                                  33

<210> SEQ ID NO 91
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gtcttcggcg gtggtaccaa acttactgtc ctcggtcaac ctaaggacac aggtgag        57

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cggtcaacct aaggacacag gtgag                                           25

<210> SEQ ID NO 93
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(36)
<223> OTHER INFORMATION: a, c, t or g
<220> FEATURE:
```

```
<221> NAME/KEY: modified_base
<222> LOCATION: (40)..(51)
<223> OTHER INFORMATION: a, c, t or g

<400> SEQUENCE: 93
gacgaggctg actactattg tnnnnnnnnn nnnnnntctn nnnnnnnnnn ngtcttcggc      60
ggtggtacca aacttac                                                   77

<210> SEQ ID NO 94
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(24)
<223> OTHER INFORMATION: a, c, t or g
<220> FEATURE:
<221> NAME/KEY: modified_base
<222> LOCATION: (31)..(36)
<223> OTHER INFORMATION: a, c, t or g
<220> FEATURE:
<221> NAME/KEY: modified_base
<222> LOCATION: (40)..(48)
<223> OTHER INFORMATION: a, c, t or g

<400> SEQUENCE: 94
gacgaggctg actactattg tnnnagctat nnnnnntctn nnnnnnnngt cttcggcggt      60
ggtaccaaac ttac                                                      74

<210> SEQ ID NO 95
<211> LENGTH: 627
<212> TYPE: DNA
<213> ORGANISM: Artificial Sequence
<220> FEATURE:
<223> OTHER INFORMATION: Description of Artificial Sequence: Synthetic
      A27: JH1 Kappa light chain gene with stuffers polynucleotide
<220> FEATURE:
<221> NAME/KEY: CDS
<222> LOCATION: (206)..(328)
<220> FEATURE:
<221> NAME/KEY: CDS
<222> LOCATION: (357)..(377)
<220> FEATURE:
<221> NAME/KEY: CDS
<222> LOCATION: (405)..(470)
<220> FEATURE:
<221> NAME/KEY: CDS
<222> LOCATION: (501)..(596)

<400> SEQUENCE: 95
gaggaccatt gggcccctc cgagactctc gagcgcaacg caattaatgt gagttagctc        60
actcattagg cacccaggc tttacacttt atgcttccgg ctcgtatgtt gtgtggaatt      120
gtgagcggat aacaatttca cacaggaaac agctatgacc atgattacgc caagctttgg     180
agcctttttt ttggagattt tcaac gtg aag aag ctc cta ttt gct atc ccg       232
                          Met Lys Lys Leu Leu Phe Ala Ile Pro
                            1               5 ctt gtc gtt ccg ttt tac agc cat agt gca caa tcc gtc ctt act caa       280
Leu Val Val Pro Phe Tyr Ser His Ser Ala Gln Ser Val Leu Thr Gln
 10              15                  20                  25 tct cct ggc act ctt tcg cta agc ccg ggt gaa cgt gct acc tta agt       328
Ser Pro Gly Thr Leu Ser Leu Ser Pro Gly Glu Arg Ala Thr Leu Ser
             30                  35                  40 tagtaagctc ccaggcctct tgatctg aaa cct ggt cag gcg ccg cgt             377
                              Lys Pro Gly Gln Ala Pro Arg
```

```
taatgaaagc gctaatggcc aacagtg act ggg atc ccg gac cgt ttc tct ggc    431
                              Thr Gly Ile Pro Asp Arg Phe Ser Gly
                               50                  55 tct ggt tca ggt act gac ttt acc ctt act att tct aga taatgagtta       480
Ser Gly Ser Gly Thr Asp Phe Thr Leu Thr Ile Ser Arg
 60              65                  70 actagaccta cgtaacctag ttc ggt caa ggt acc aag gtt gaa atc aag cgt    533
                      Phe Gly Gln Gly Thr Lys Val Glu Ile Lys Arg
                                   75                  80 acg gtt gcc gct cct agt gtg ttt atc ttt cct cct tct gac gaa caa      581
Thr Val Ala Ala Pro Ser Val Phe Ile Phe Pro Pro Ser Asp Glu Gln
             85                  90                  95 ttg aag tca ggt act acgcatctct aagcggccgc aacaggagga g               627
Leu Lys Ser Gly Thr
            100
```

<210> SEQ ID NO 96
<211> LENGTH: 102
<212> TYPE: PRT
<213> ORGANISM: Artificial Sequence
<220> FEATURE:
<223> OTHER INFORMATION: Description of Artificial Sequence: Synthetic
      A27: JH1 Kappa light chain gene with stuffers polypeptide

<400> SEQUENCE: 96

```
Met Lys Lys Leu Leu Phe Ala Ile Pro Leu Val Val Pro Phe Tyr Ser
1               5                   10                  15

His Ser Ala Gln Ser Val Leu Thr Gln Ser Pro Gly Thr Leu Ser Leu
            20                  25                  30

Ser Pro Gly Glu Arg Ala Thr Leu Ser Lys Pro Gly Gln Ala Pro Arg
        35                  40                  45

Thr Gly Ile Pro Asp Arg Phe Ser Gly Ser Gly Ser Gly Thr Asp Phe
    50                  55                  60

Thr Leu Thr Ile Ser Arg Phe Gly Gln Gly Thr Lys Val Glu Ile Lys
65                  70                  75                  80

Arg Thr Val Ala Ala Pro Ser Val Phe Ile Phe Pro Pro Ser Asp Glu
                85                  90                  95

Gln Leu Lys Ser Gly Thr
            100
```

<210> SEQ ID NO 97
<211> LENGTH: 413
<212> TYPE: DNA
<213> ORGANISM: Artificial Sequence
<220> FEATURE:
<223> OTHER INFORMATION: Description of Artificial Sequence: Synthetic
      2a2: JH2 human lambda-chain gene polynucleotide
<220> FEATURE:
<221> NAME/KEY: CDS
<222> LOCATION: (30)..(104)
<220> FEATURE:
<221> NAME/KEY: CDS
<222> LOCATION: (117)..(122)
<220> FEATURE:
<221> NAME/KEY: CDS
<222> LOCATION: (177)..(239)
<220> FEATURE:
<221> NAME/KEY: CDS
<222> LOCATION: (270)..(413)
<220> FEATURE:
<221> NAME/KEY: CDS
<222> LOCATION: (129)..(131)
<220> FEATURE:
<221> NAME/KEY: CDS
<222> LOCATION: (135)..(152)

<400> SEQUENCE: 97

```
gaggaccatt gggcccctta ctccgtgac agt gca caa tcc gct ctc act cag      53
                                  Ser Ala Gln Ser Ala Leu Thr Gln
                                   1               5 cct gct agc gtt tcc ggg tca cct ggt caa agt atc act att tct tgt     101
Pro Ala Ser Val Ser Gly Ser Pro Gly Gln Ser Ile Thr Ile Ser Cys
 10              15                  20 aca tcttagtgac tc aga tct taatga ccg    tag cac ccg ggc aag gcg     149
Thr             Arg Ser        Pro         His Pro Gly Lys Ala
 25                                              30 ccg taatgaatct cgtacgctgg tgtt agc aat cgt ttc tcc gga tct aaa      200
Pro                            Ser Asn Arg Phe Ser Gly Ser Lys
                                35                  40 tcc ggt aat acc gca agc tta act atc tct ggt ctg cag gttctgtagt      249
Ser Gly Asn Thr Ala Ser Leu Thr Ile Ser Gly Leu Gln
         45                  50                  55 tccaattgct ttagtgaccc ggc ggt ggt acc aaa ctt act gtc ctc ggt caa   302
                      Gly Gly Gly Thr Lys Leu Thr Val Leu Gly Gln
                                      60                  65 cct aag gct gct cct tcc gtt act ctc ttc cct cct agt tct gaa gag     350
Pro Lys Ala Ala Pro Ser Val Thr Leu Phe Pro Pro Ser Ser Glu Glu
         70                  75                  80 ctt caa gct aac aag gct act ctt gtt tgc ttg atc agt gac ttt tat     398
Leu Gln Ala Asn Lys Ala Thr Leu Val Cys Leu Ile Ser Asp Phe Tyr
         85                  90                  95 cct ggt gct gtt act                                                 413
Pro Gly Ala Val Thr
    100
```

<210> SEQ ID NO 98
<211> LENGTH: 103
<212> TYPE: PRT
<213> ORGANISM: Artificial Sequence
<220> FEATURE:
<223> OTHER INFORMATION: Description of Artificial Sequence: Synthetic
       2a2: JH2 human lambda-chain gene polypeptide

<400> SEQUENCE: 98

```
Ser Ala Gln Ser Ala Leu Thr Gln Pro Ala Ser Val Ser Gly Ser Pro
 1               5                  10                  15

Gly Gln Ser Ile Thr Ile Ser Cys Thr Arg Ser Pro His Pro Gly Lys
             20                  25                  30

Ala Pro Ser Asn Arg Phe Ser Gly Ser Lys Ser Gly Asn Thr Ala Ser
         35                  40                  45

Leu Thr Ile Ser Gly Leu Gln Gly Gly Gly Thr Lys Leu Thr Val Leu
 50                  55                  60

Gly Gln Pro Lys Ala Ala Pro Ser Val Thr Leu Phe Pro Pro Ser Ser
 65                  70                  75                  80

Glu Glu Leu Gln Ala Asn Lys Ala Thr Leu Val Cys Leu Ile Ser Asp
                 85                  90                  95

Phe Tyr Pro Gly Ala Val Thr
            100
```

<210> SEQ ID NO 99
<211> LENGTH: 10
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 99
ctgtctgaac                                                          10